US012559536B2

(12) United States Patent
Shah et al.

(10) Patent No.:    US 12,559,536 B2
(45) Date of Patent:      Feb. 24, 2026

(54) CD33 SPECIFIC CHIMERIC ANTIGEN RECEPTORS

(71) Applicant: PRECIGEN, INC., Germantown, MD (US)

(72) Inventors: Rutul Shah, Germantown, MD (US); Tim Chan, Germantown, MD (US); Peter Emtage, Germantown, MD (US); Ramya Yarlagadda, Germantown, MD (US)

(73) Assignee: PRECIGEN, INC., Germantown, MD (US)

( * ) Notice: Subject to any disclaimer, the term of this patent is extended or adjusted under 35 U.S.C. 154(b) by 0 days.

(21) Appl. No.: 18/462,207

(22) Filed: Sep. 6, 2023

(65) Prior Publication Data

US 2024/0254188 A1      Aug. 1, 2024

Related U.S. Application Data

(63) Continuation of application No. 15/616,869, filed on Jun. 7, 2017, now Pat. No. 11,787,848.

(60) Provisional application No. 62/347,503, filed on Jun. 8, 2016.

(51) Int. Cl.
| | |
|---|---|
| *C07K 14/705* | (2006.01) |
| *A61K 40/11* | (2025.01) |
| *A61K 40/15* | (2025.01) |
| *A61K 40/31* | (2025.01) |
| *A61K 40/42* | (2025.01) |
| *C07K 14/71* | (2006.01) |
| *C07K 14/725* | (2006.01) |
| *C07K 16/28* | (2006.01) |
| *C12N 5/0783* | (2010.01) |
| *A61K 39/00* | (2006.01) |

(52) U.S. Cl.
CPC ........ *C07K 14/70503* (2013.01); *A61K 40/11* (2025.01); *A61K 40/15* (2025.01); *A61K 40/31* (2025.01); *A61K 40/4205* (2025.01); *A61K 40/4211* (2025.01); *A61K 40/4224* (2025.01); *C07K 14/7051* (2013.01); *C07K 14/70517* (2013.01); *C07K 14/70521* (2013.01); *C07K 14/70575* (2013.01); *C07K 14/70578* (2013.01); *C07K 14/70596* (2013.01); *C07K 14/71* (2013.01); *C07K 16/2803* (2013.01); *C12N 5/0636* (2013.01); *A61K 2039/505* (2013.01); *A61K 2039/57* (2013.01); *A61K 2239/29* (2023.05); *A61K 2239/31* (2023.05); *A61K 2239/38* (2023.05); *A61K 2239/48* (2023.05); *C07K 2317/24* (2013.01); *C07K 2317/622* (2013.01); *C07K 2317/73* (2013.01); *C07K 2319/00* (2013.01); *C07K 2319/02* (2013.01); *C07K 2319/03* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,693,761 | A | 12/1997 | Queen et al. |
| 5,714,350 | A | 2/1998 | Co et al. |
| 6,007,814 | A | 12/1999 | Scheinberg |
| 7,119,183 | B2 * | 10/2006 | Seed ..................... C12N 15/85 |
| | | | 536/23.1 |
| 7,985,559 | B2 | 7/2011 | Freeman et al. |
| 8,790,649 | B2 | 7/2014 | Setlady et al. |
| 8,802,374 | B2 | 8/2014 | Jensen |
| 9,447,194 | B2 | 9/2016 | Jensen |
| 9,580,685 | B2 | 2/2017 | Jensen |
| 10,570,186 | B2 | 2/2020 | Cooper et al. |
| 10,676,717 | B2 | 6/2020 | Brown et al. |
| 2009/0123944 | A1 | 5/2009 | Finney et al. |
| 2016/0096892 | A1 | 4/2016 | Brogdon et al. |
| 2016/0355590 | A1 * | 12/2016 | Epstein ................... A61P 35/00 |

FOREIGN PATENT DOCUMENTS

| | | | |
|---|---|---|---|
| EP | 0566647 | B1 | 10/2003 |
| WO | 2012079000 | A1 | 6/2012 |
| WO | 2014186469 | A2 | 11/2014 |
| WO | 2015/089344 | A1 | 6/2015 |
| WO | 2015105522 | A1 | 7/2015 |
| WO | 2015123642 | A1 | 8/2015 |
| WO | 2015142675 | A2 | 9/2015 |
| WO | 2015150526 | A2 | 10/2015 |
| WO | 2015157391 | A1 | 10/2015 |
| WO | 2015179801 | A1 | 11/2015 |
| WO | 2016014576 | A1 | 1/2016 |
| WO | 2016120216 | A1 | 8/2016 |

(Continued)

OTHER PUBLICATIONS

Vogler et al, Molecular Therapy, vol. 18, No. 7, Jul. 2010. (Year: 2010).*

(Continued)

*Primary Examiner* — Gary B Nickol
*Assistant Examiner* — Cheom-Gil Cheong
(74) *Attorney, Agent, or Firm* — Gene J. Yao; Barnes & Thornburg LLP

(57)      ABSTRACT

Provided herein are chimeric antigen receptors (CARs) for cancer therapy, and more particularly, CARs containing a scFv from a CD33 monoclonal antibody. Provided are immune effector cells containing such CARs, and methods of treating proliferative disorders such as acute myeloid leukemia (AML), and relapsed or refractory AML.

11 Claims, 55 Drawing Sheets

Specification includes a Sequence Listing.

(56) References Cited

FOREIGN PATENT DOCUMENTS

| WO | 2016201304 A1 | 12/2016 |
|----|---------------|---------|
| WO | 2017214333 A1 | 12/2017 |

OTHER PUBLICATIONS

Rudikoff et al, PNAS USA 79: 1979-1983 (1982). (Year: 1982).*
Ng et al., Genome Research, 11:863-874 (2001).
Jonson et al., Protein Engineering, 14:397-402 (2001).
Bendig, Methods: A Companion to Methods in Enzymology , 8:83-93 (1995).
Kussie et al., Journal of Immunology, 152:146-152 (1994).
Chen et al, EMBO J., 14:2784-2794 (1995).
Jones et al., Front.Pharmacol., 5:254 (2014).
Hudecek et al., Blood, 118:643 (2011).
Wang et al., Blood, 122:4491 (2013).
Chan et al., "CD19-specific chimeric antigen receptor-modified T cells with safety switch produced under 'Point-of-Care' using the Sleeping Beauty system for the very rapid manufacture and treatment of B-cell malignancies," 59th American Society of Hematology (ASH) Annual Meeting and Exposition, Atlanta, Poster, Dec. 9, 2017.
Song et al., "Autologous T Cells Modified to Co-express CD33-Specific Chimeric Antigen Receptor and a Kill Switch for Treatment of CD33+ Acute Myeloid Leukemia," 59th American Society of Hematology (ASH) Annual Meeting and Exposition, Atlanta, Poster, Dec. 9, 2017.
Song et al., "Chimeric Antigen Receptor-Modified T cells for the Treatment of Acute Myeloid Leukemia Expressing CD33," American Society of Hematology 58th Annual Meeting (ASH), Poster, Dec. 5, 2016.
Dutour etal, Advances in Hematology, 2012, 10 pages.
Pizzitola et al., Leukemia, 28:1596-1605 (2014).
Figueroa et al. Chimeric Antigen Receptor Engineering: A Right Step in the Evolution of Adoptive Cellular Immunotherapy. International Reviews of immunology. 2015. 154-187.
International Search Report and Written Opinion dated Nov. 7, 2017 for International PCT Patent Application No. PCT/US2017/036440.
Ruella et al. Smart CARS: optimized development of a chimeric antigen receptor (CAR) T cell targeting epidermal growth factor receptor variant III (EGFRvIII) for glioblastoma. Ann Transl Med 4(1):13 (2016).
Paszkiewicz, Paulina Joanna. Development of a truncated EGFR marker as a safeguard for adoptive T cell therapy. Ph.D. Thesis Paper. 2014. 192 pages.
Jonnalagadda, et al., "Efficient selection of genetically modified human T cells using methotrexate-resistant human dihydrofolate reductase", Gene Therapy (2013) 20, 853-860.

Jonnalagadda, et al., "Engineering Human T Cells for Resistance to Methotrexate and Mycophenolate Mofetil as an In Vivo Cell Selection Strategy", PLOS One, Jun. 2013, vol. 8, Issue 6 pp. 1-10.
Paskiewicz, et al., "Targeted antibody-mediated depletion of murine CD19 Cart cells permanently reverses B cell aplasia", J Clin Invest (2016); 126(11):4262-4272.
Wang, et al. "A transgene-encoded cell surface polypeptide for selection, in vivo tracking, and ablation of engineered cells", Gene Therapy, Blood, Aug. 4, 2011, vol. 118, No. 5.
Huang, et al. Sleeping Beauty transposon-mediated engineering of human primary T cells for therapy of CD19+ lymphoid malignancies. Mol Ther. Mar. 2008;16(3):580-9.
O'Hear, et al. Anti-CD33 chimeric antigen receptor targeting of acute myeloid leukemia. Haematologica. Mar. 2015; 100(3):336-44. doi: 10.3324/haematol.2014.1127 48.
D.A. Einfeld et al., Molecular Cloning of the Human B Cell CD20 Receptor Predicts a Hydrophobic Protein with Multiple Transmembrane Domains, 7 EMBO J. 711 (1988).
Mascha Binder et al., The Epitope Recognized by Rituximab, 108 Blood 1975 (2006).
Jianzhi Zhang, Rates of Conservative and Radical Nonsynonymous Nucleotide Substitutions in Mammalian Nuclear Genes, 50 J. Mol. Evol. 56 (2000).
Pauline C. Ng & Steven Henikoff, Predicting Deleterious Amino Acid Substitutions, 11 Genome Res. 863 (2001).
Arvind Rajpal et al., A General Method for Greatly Improving the Affinity of Antibodies by Using Combinatorial Libraries, 102 Proc. Nat'l Acad. Sci. U.S. 8466 (2005).
Inbal Sela-Culang et al., The Structural Basis of Antibody-Antigen Recognition, 4 Front. Immunol. 302 (2013).
Kevin C. Entzminger et al., De Novo Design of Antibody Complementarity Determining Regions Binding a Flag Tetrapeptide, 7 Sci. Rep. 10295 (2017).
Julie P. Deans et al., CD20-Mediated Apoptosis: Signalling Through Lipid Rafts, 107 Immunology 176 (2002).
Martin McLaughlin & Koen Vandenbroeck, The Endoplasmic Reticulum Protein Folding Factory and its Chaperones: New Targets for Drug Discovery?, 162 Brit. J. Pharmacol. 328 (2011).
Ziqing Liu et al., Systematic Comparison of 2A Peptides for Cloning Multi-Genes in a Polycistronic Vector, 7 Sci. Rep. 2193 (2017).
Ekaterina Minskaia & Martin D. Ryan, Protein Coexpression Using FMDV 2A: Effect of "Linker" Residues, 2013 Biomed Res. Int., (2013).
Garry A. Luke, Translating 2A Research into Practice, in Innovations in Biotechnology 162 (M. Tank ed., InTech 2012).
Hiroyuki Mizuguchi et al., IRES-Dependent Second Gene Expression is Significantly Lower Than Cap-Dependent First Gene Expression in a Bicistronic Vector, 1 Mol. Therapy 376 (Apr. 2000).

* cited by examiner

FIGURE 1

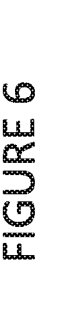
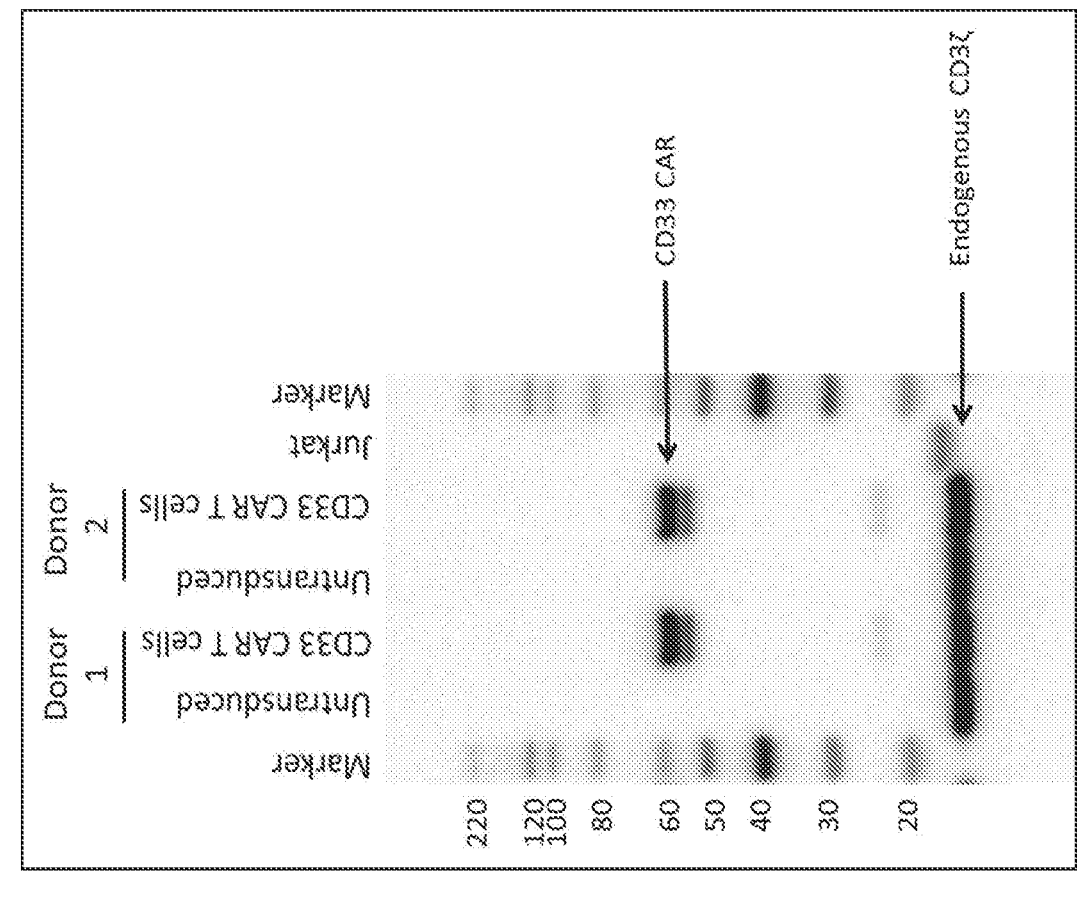
FIGURE 6

FIGURE 7
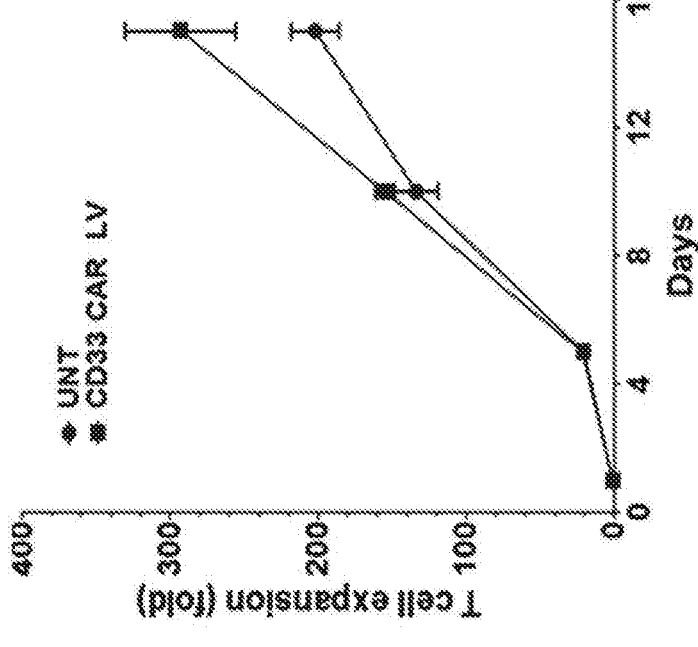
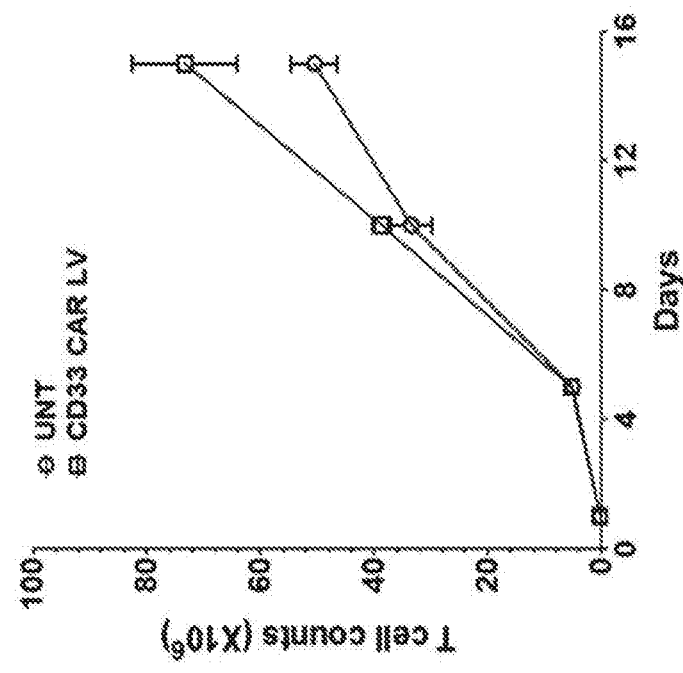

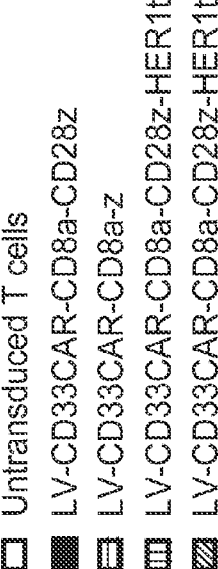
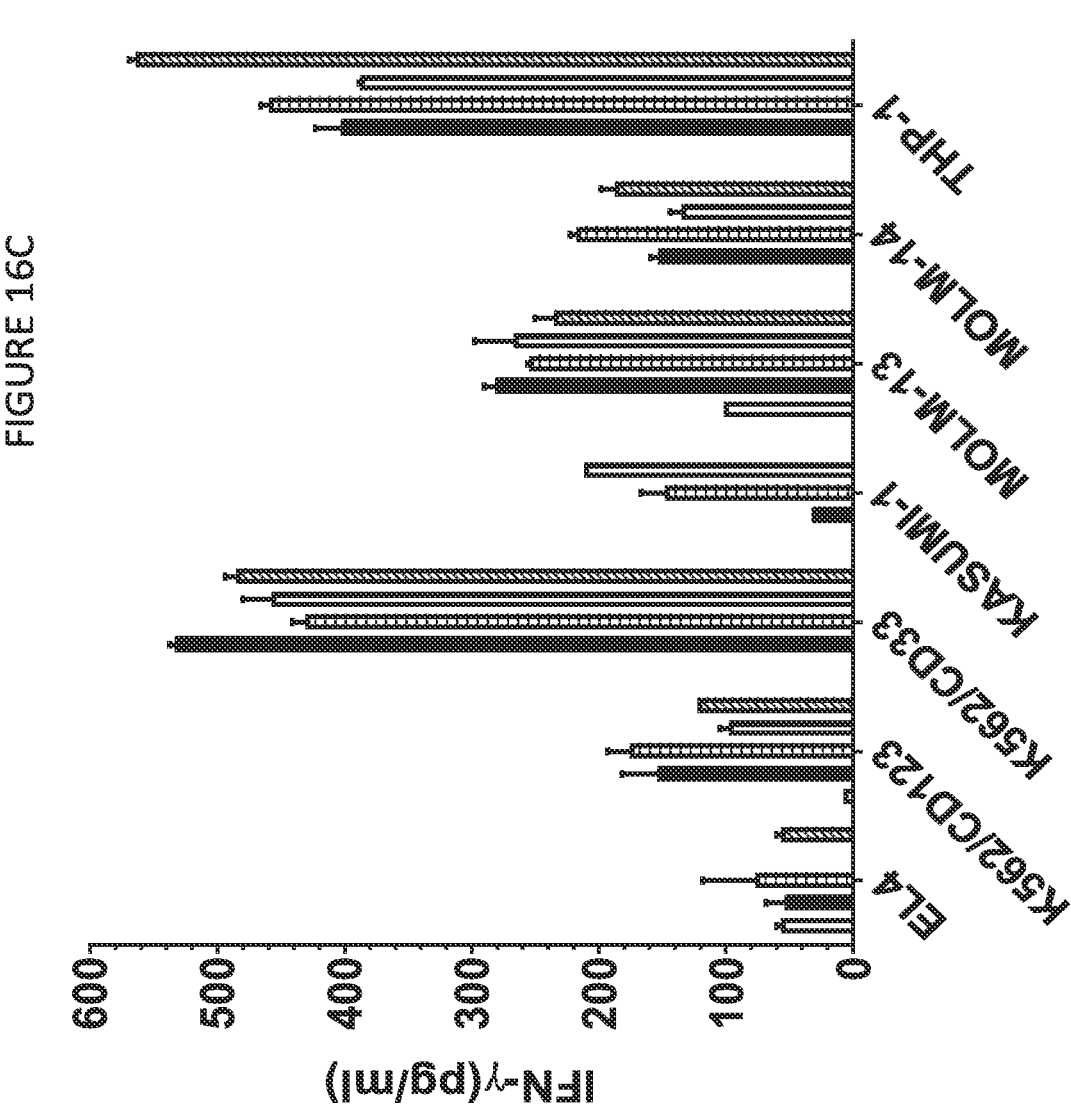
FIGURE 16C

Figure 21A

| Sequence Name | SEQ ID NO | Sequence |
|---|---|---|
| hM195 VL (aa) | 1 | DIQMTQSPSSLSASVGDRVTITCRASESVDNYGISFMNWFQQKPGKAPKL LIYAASNQGSGVPSRFSGSGSGTDFTLTISSLQPDDFATYYCQQSKEVPW TFGQGTKVEIK |
| hM195 VL (nt) | 2 | Gacattcagatgacccagtctccgagctctctgtccgcatcagtaggagacaggg tcaccatcacatgcagagccagcgaaagtgtcgacaattatggcattagctttat gaactggttccaacagaaacccgggaaggctcctaagcttctgatttacgctgca tccaaccaaggctccggggtaccctctcgcttctcaggcagtggatctgggacag acttcactctcaccatttcatctctgcagcctgatgacttcgcaacctattactg tcagcaaagtaaggaggttccgtggacgttcggtcaagggaccaaggtggagatc aaa |
| hM195 VH (aa) | 3 | QVQLVQSGAEVKKPGSSVKVSCKASGYTFTDYNMHWVRQAPGQGLEWIGY IYPYNGGTGYNQKFKSKATITADESTNTAYMELSSLRSEDTAVYYCARGR PAMDYWGQGTLVTVSS |
| hM195 VH (nt) | 4 | Caggttcagctggtgcagtctggagctgaggtgaagaagcctgggagctcagtga aggtttcctgcaaagcttctggctacaccttcactgactacaacatgcactgggt gaggcaggctcctggccaaggcctggaatggattggatatatttatccttacaat ggtggtaccggctacaaccagaagttcaagagcaaggccacaattacagcagacg agagtactaacacagcctacatggaactctccagcctgaggtctgaggacactgc agtctattactgcgcaagagggcgccccgctatggactactggggccaagggact ctggtcactgtctcttca |
| (G4S)3 Linker (nt) | 5 | Ggtggcggtggctcgggcggtggtgggtcgggtggcggcggatct |
| (G4S)3 Linker (aa) | 6 | GGGGSGGGGSGGGGS |
| hM195 scFv with linker (nt) | 7 | Gacattcagatgacccagtctccgagctctctgtccgcatcagtaggagacaggg tcaccatcacatgcagagccagcgaaagtgtcgacaattatggcattagctttat gaactggttccaacagaaacccgggaaggctcctaagcttctgatttacgctgca tccaaccaaggctccggggtaccctctcgcttctcaggcagtggatctgggacag acttcactctcaccatttcatctctgcagcctgatgacttcgcaacctattactg tcagcaaagtaaggaggttccgtggacgttcggtcaagggaccaaggtggagatc aaaGgtggcggtggctcgggcggtggtgggtcgggtggcggcggatctcaggttc agctggtgcagtctggagctgaggtgaagaagcctgggagctcagtgaaggtttc ctgcaaagcttctggctacaccttcactgactacaacatgcactgggtgaggcag gctcctggccaaggcctggaatggattggatatatttatccttacaatggtggta ccggctacaaccagaagttcaagagcaaggccacaattacagcagacgagagtac taacacagcctacatggaactctccagcctgaggtctgaggacactgcagtctat |

Figure 21B

| Sequence Name | SEQ ID NO | Sequence |
|---|---|---|
| | | tactgcgcaagagggcgccccgctatggactactggggccaagggactctggtca ctgtctcttca |
| hM195 scFv with linker (aa) | 8 | DIQMTQSPSSLSASVGDRVTITCRASESVDNYGISFMNWFQQKPGKAPKL LIYAASNQGSGVPSRFSGSGSGTDFTLTISSLQPDDFATYYCQQSKEVPW TFGQGTKVEIKGGGGSGGGGSGGGGSQVQLVQSGAEVKKPGSSVKVSCKA SGYTFTDYNMHWVRQAPGQGLEWIGYIYPYNGGTGYNQKFKSKATITADE STNTAYMELSSLRSEDTAVYYCARGRPAMDYWGQGTLVTVSS |
| M2H12 VH (aa) | 9 | QVQLQQSGPELVRPGTFVKISCKASGYTFTNYD INWVNQRPGQGLEWIGWIYPGDGSTKYNEKF KAKATLTADKSSSTAYLQLNNLTSENSAVYFCAS GYEDAMDYWGQGTSVTVSS |
| M2H12 VL (aa) | 10 | DIKMTQSPSSMYASLGERVIINCKASQDINSYLS WFQQKPGKSPKTLIYRANRLVDGVPSRFSGSG SGQDYSLTISSLEYEDMGIYYCLQYDEFPLTFGA GTKLELKR |
| DRB2 VH (aa) | 11 | EVKLQESGPELVKPGASVKMSCKASGYKFTDYV VHWLKQKPGQGLEWIGYINPYNDGTKYNEKF KGKATLTSDKSSSTAYMEVSSLTSEDSAVYYCA RDYRYEVYGMDYWGQGTSVTVSS |
| DRB2 VL (aa) | 12 | DIVLTQSPTIMSASPGERVTMTCTASSSVNYIH WYQQKSGDSPLRWIFDTSKVASGVPARFSGSG SGTSYSLTISTMEAEDAATYYCQQWRSYPLTFG DGTRLELKRADAAPTVS |
| My9-6 VH (aa) | 13 | QVQLQQPGAEVVKPGASVKMSCKASGYTFTS YYIHWIKQTPGQGLEWVGVIYPGNDDISYNQK FKGKATLTADKSSTTAYMQLSSLTSEDSAVYYC AREVRLRYFDVWGAGTTVTVSS |
| My9-6 VL (aa) | 14 | NIMLTQSPSSLAVSAGEKVTMSCKSSQSVFFSS SQKNYLAWYQQIPGQSPKLLIYWASTRESGVP DRFTGSGSGTDFTLTISSVQSEDLAIYYCHQYLS SRTFGGGTKLEIKR |
| GM-CSFRa signal peptide (nt) | 15 | Atgctgctgctggtgaccagcctgctgctgtgtgagctgccccacccgcctttc tgctgatcccc |
| GM-CSFRa signal peptide (aa) | 16 | MLLLVTSLLLCELPHPAFLLIP |
| CD8alpha TM (nt) | 17 | Atctacatctgggcccctctggccggcacctgtggcgtgctgctgctgagcctgg tcatcaccctgtactgcaaccaccggaat |

Figure 21C

| Sequence Name | SEQ ID NO | Sequence |
|---|---|---|
| CD8alpha TM (aa) | 18 | IYIWAPLAGTCGVLLLSLVITLYCNHRN |
| CD28 TM (nt) | 19 | Ttttgggtgctggtggtggttggtggagtcctggcttgctatagcttgctagtaa cagtggcctttattattttctgggtg |
| CD28 TM (aa) | 20 | FWVLVVVGGVLACYSLLVTVAFIIFWV |
| CD8alpha hinge (nt) | 21 | Aagcccaccaccacccctgcccctagacctccaaccccagcccctacaatcgcca gccagcccctgagcctgaggcccgaagcctgtagacctgccgctggcggagccgt gcacaccagaggcctggatttcgcctgcgac |
| CD8alpha hinge (aa) | 22 | KPTTTPAPRPPTPAPTIASQPLSLRPEACRPAAGGAVHTRGLDFACD |
| 4-1BB signaling domain (nt) | 23 | Aagagaggccggaagaaactgctgtacatcttcaagcagcccttcatgcggcccg tgcagaccacccaggaagaggacggctgcagctgccggttccccgaggaagagga aggcggctgcgaactg |
| 4-1BB signaling domain (aa) | 24 | KRGRKKLLYIFKQPFMRPVQTTQEEDGCSCRFPEEEEGGCEL |
| CD3ς signaling domain (nt) | 25 | Cgggtgaagttcagccggagcgccgacgcccctgcctaccagcagggccagaacc agctgtacaacgagctgaacctgggccggaggggaggagtacgacgtgctggacaa gcggagaggccgggaccctgagatgggcggcaagcccggagaaagaaccctcag gagggcctgtataacgaactgcagaaagacaagatggccgaggcctacagcgaga tcggcatgaagggcgagcggcggaggggcaagggccacgacggcctgtaccaggg cctgagcaccgccaccaaggatacctacgacgccctgcacatgcaggccctgccc cccaga |
| CD3ς signaling domain (aa) | 26 | RVKFSRSADAPAYQQGQNQLYNELNLGRREEYDVLDKRRGRDPEMGGKPR RKNPQEGLYNELQKDKMAEAYSEIGMKGERRRGKGHDGLYQGLSTATKDT YDALHMQALPPR |
| CD28 signaling domain(nt) | 27 | Aggagcaagcggagcagaggcggccacagcgactacatgaacatgacccccgga ggcctggcccccacccggaagcactaccagccctacgcccctcccagggacttcgc cgcctaccggagc |
| CD28 signaling domain (aa) | 28 | RSKRSRGGHSDYMNMTPRRPGPTRKHYQPYAPPRDFAAYRS |
| T2A (nt) | 29 | GAGGGCAGAGGAAGTCTTCTAACATGCGGTGACGTGGAGGAGAATCCCGGCCCT |
| T2A (aa) | 30 | EGRGSLLTCGDVEENPGP |

Figure 21D

| Sequence Name | SEQ ID NO | Sequence |
|---|---|---|
| HER1t (nt) | 31 | Cgcaaagtgtgtaacggaataggtattggtgaatttaaagactcactctccataaatgctacgaatattaaacacttcaaaaactgcacctccatcagtggcgatctccacatcctgccggtggcatttaggggtgactccttcacacatactcctcctctggatccacaggaactggatattctgaaaaccgtaaaggaaatcacagggttttttgctgattcaggcttggcctgaaaacaggacggacctccatgcctttgagaacctagaaatcatacgcggcaggaccaagcaacatggtcagttttctcttgcagtcgtcagcctgaacataacatccttgggattacgctccctcaaggagataagtgatggagatgtgataatttcaggaaacaaaaatttgtgctatgcaaatacaataaactggaaaaaactgtttgggacctccggtcagaaaaccaaaattataagcaacagaggtgaaaacagctgcaaggccacaggccaggtctgccatgccttgtgctcccccgagggctgctgggccccggagcccagggactgcgtctcttgccggaatgtcagccgaggcagggaatgcgtggacaagtgcaaccttctggagggtgagccaagggagtttgtggagaactctgagtgcatacagtgccacccagagtgcctgcctcaggccatgaacatcacctgcacaggacggggaccagacaactgtatccagtgtgcccactacattgacggcccccactgcgtcaagacctgcccggcaggagtcatgggagaaaacaacaccctggtctggaagtacgcagacgccggccatgtgtgccacctgtgccatccaaactgcacctacgatgcactgggccaggtcttgaaggctgtccaacgaatgggcctaagatcccgtccatcgccactgggatggtggggggccctcctcttgctgctggtggtggccctggggatcggcctcttcatg |
| HER1t (aa) | 32 | RKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQVCHALCSPEGCWGPEPRDCVSCRNVSRGRECVDKCNLLEGEPREFVENSECIQCHPECLPQAMNITCTGRGPDNCIQCAHYIDGPHCVKTCPAGVMGENNTLVWKYADAGHVCHLCHPNCTYGCTGPGLEGCPTNGPKIPSIATGMVGALLLLLVVALGIGLFM |
| IgK signal peptide (nt) | 33 | Atgaggctccctgctcagctcctggggctgctaatgctctgggtcccaggatccagtggg |
| IgK signal peptide (aa) | 34 | MRLPAQLLGLLMLWVPGSSG |
| FL CD20 (nt) | 35 | Atgacaacacccagaaattcagtaaatgggactttcccggcagagccaatgaaaggccctattgctatgcaatctggtccaaaaccactcttcaggaggatgtcttcactggtgggccccacgcaaagcttcttcatgagggaatctaagactttgggggctgtccagattatgaatgggctcttccacattgccctggggggtcttctgatgatcccagcagggatctatgcacccatctgtgtgactgtgtggtaccctctctggggaggcattatgtatattatttccggatcactcctggcagcaacggagaaaaactccaggaagtgtttggtcaaaggaaaaatgataatgaattcattgagcctcttgctgccatttctggaatgattctttcaatcatggacatacttaatattaaaatttcccattttttaaaaatggagagtctgaatttttattagagctcacacaccatatattaacatatac |

Figure 21E

| Sequence Name | SEQ ID NO | Sequence |
|---|---|---|
| | | aactgtgaaccagctaatccctctgagaaaaactccccatctacccaatactgtt acagcatacaatctctgttcttgggcattttgtcagtgatgctgatctttgcctt cttccaggaacttgtaatagctggcatcgttgagaatgaatggaaaagaacgtgc tccagacccaaatctaacatagttctcctgtcagcagaagaaaaaaaagaacaga ctattgaaataaaagaagaagtggttgggctaactgaaacatcttcccaaccaaa gaatgaagaagacattgaaattattccaatccaagaagaggaagaagaagaaaca gagacgaactttccagaacctcccccaagatcaggaatcctcaccaatagaaatg acagctctcct |
| FL CD20 (aa) | 36 | MTTPRNSVNGTFPAEPMKGPIAMQSGPKPLFRRMSSLVGPTQSFFMRESK TLGAVQIMNGLFHIALGGLLMIPAGIYAPICVTVWYPLWGGIMYIISGSL LAATEKNSRKCLVKGKMIMNSLSLFAAISGMILSIMDILNIKISHFLKME SLNFIRAHTPYINIYNCEPANPSEKNSPSTQYCYSIQSLFLGILSVMLIF AFFQELVIAGIVENEWKRTCSRPKSNIVLLSAEEKKEQTIEIKEEVVGLT ETSSQPKNEEDIEIIPIQEEEEEETETNFPEPPQDQESSPIENDSSP |
| mbIL-15 (aa) | 37 | MDWTWILFLVAAATRVHSNWVNVISDLKKIEDLIQSMHIDATLYTESDVHPSCKV TAMKC FLLELQVISLESGDASIHDTVENLIILANNSLSSNGNVTESGCKECEELEEKNIK EFLQS FVHIVQMFINTSSGGGSGGGGSGGGGSGGGGSGGGSLQITCPPPMSVEHADIWVK SYSLY SRERYICNSGFKRKAGTSSLTECVLNKATNVAHWTTPSLKCIRDPALVHQRPAPP STVTT AGVTPQPESLSPSGKEPAASSPSSNNTAATTAAIVPGSQLMPSKSPSTGTTEISS HESSH GTPSQTTAKNWELTASASHQPPGVYPQGHSDTTVAISTSTVLLCGLSAVSLLACY LKSRQ TPPLASVEMEAMEALPVTWGTSSRDEDLENCSHHL |
| hM195scFv-CD8a-CD28m-Z | 38 | atgctgctgctggtgaccagcctgctgctgtgtgagctgccccacccccgcctttc tgctgatccccgacattcagatgacccagtctccgagctctctgtccgcatcagt aggagacagggtcaccatcacatgcagagccagcgaaagtgtcgacaattatggc attagctttatgaactggttccaacagaaacccgggaaggctcctaagcttctga tttacgctgcatccaaccaaggctccggggtaccctctcgcttctcaggcagtgg atctgggacagacttcactctcaccatttcatctctgcagcctgatgacttcgca acctattactgtcagcaaagtaaggaggttccgtggacgttcggtcaagggacca aggtggagatcaaaggtggcggtggctcgggcggtggtgggtcgggtggcggcgg atctcaggttcagctggtgcagtctggagctgaggtgaagaagcctgggagctca gtgaaggtttcctgcaaagcttctggctacaccttcactgactacaacatgcact gggtgaggcaggctcctggccaaggcctggaatggattggatatatttatcctta caatggtggtaccggctacaaccagaagttcaagagcaaggccacaattacagca gacgagagtactaacacagcctacatggaactctccagcctgaggtctgaggaca ctgcagtctattactgcgcaagagggcgccccgctatggactactggggccaagg |

Figure 21F

| Sequence Name | SEQ ID NO | Sequence |
|---|---|---|
| | | gactctggtcactgtctcttcaaagcccaccaccaccctgcccctagacctcca acccagcccctacaatcgccagccagcccctgagcctgaggcccgaagcctgta gacctgccgctggcggagccgtgcacaccagaggcctggatttcgcctgcgacat ctacatctgggcccctctggccggcacctgtggcgtgctgctgctgagcctggtc atcaccctgtactgcaaccaccggaataggagcaagcggagcagaggcggccaca gcgactacatgaacatgacccccggaggcctggcccaccccggaagcactacca gccctacgcccctcccagggacttcgccgcctaccggagccgggtgaagttcagc cggagcgccgacgcccctgcctaccagcagggccagaaccagctgtacaacgagc tgaacctgggccggaggggaggagtacgacgtgctggacaagcggagaggccggga ccctgagatgggcggcaagcccggagaaagaacctcaggagggcctgtataac gaactgcagaaagacaagatggccgaggcctacagcgagatcggcatgaagggcg agcggcggagggggcaagggccacgacggcctgtaccagggcctgagcaccgccac caaggatacctacgacgccctgcacatgcaggccctgccccccaga |
| hM195scFv-CD8a-CD28m-Z | 39 | MLLLVTSLLLCELPHPAFLLIPDIQMTQSPSSLSASVGDRVTITCRASES VDNYGISFMNWFQQKPGKAPKLLIYAASNQGSGVPSRFSGSGSGTDFTLT ISSLQPDDFATYYCQQSKEVPWTFGQGTKVEIKGGGGSGGGGSGGGGSQV QLVQSGAEVKKPGSSVKVSCKASGYTFTDYNMHWVRQAPGQGLEWIGYIY PYNGGTGYNQKFKSKATITADESTNTAYMELSSLRSEDTAVYYCARGRPA MDYWGQGTLVTVSSKPTTTPAPRPPTPAPTIASQPLSLRPEACRPAAGGA VHTRGLDFACDIYIWAPLAGTCGVLLLSLVITLYCNHRNRSKRSRGGHSD YMNMTPRRPGPTRKHYQPYAPPRDFAAYRSRVKFSRSADAPAYQQGQNQL YNELNLGRREEYDVLDKRRGRDPEMGGKPRRKNPQEGLYNELQKDKMAEA YSEIGMKGERRRGKGHDGLYQGLSTATKDTYDALHMQALPPR |
| hM195scFv-CD8a-Z | 40 | atgctgctgctggtgaccagcctgctgctgtgtgagctgccccaccccgcctttc tgctgatccccgacattcagatgacccagtctccgagctctctgtccgcatcagt aggagacagggtcaccatcacatgcagagccagcgaaagtgtcgacaattatggc attagctttatgaactggttccaacagaaacccgggaaggctcctaagcttctga tttacgctgcatccaaccaaggctccggggtaccctctcgcttctcaggcagtgg atctgggacagacttcactctcaccatttcatctctgcagcctgatgacttcgca acctattactgtcagcaaagtaaggaggttccgtggacgttcggtcaagggacca aggtggagatcaaaggtggcggtggctcgggcggtggtgggtcgggtggcggcgg atctcaggttcagctggtgcagtctggagctgaggtgaagaagcctgggagctca gtgaaggtttcctgcaaagcttctggctacaccttcactgactacaacatgcact gggtgaggcaggctcctggccaaggcctggaatggattggatatatttatcctta caatggtggtaccggctacaaccagaagttcaagagcaaggccacaattacagca gacgagagtactaacacagcctacatggaactctccagcctgaggtctgaggaca ctgcagtctattactgcgcaagagggcgccccgctatggactactggggccaagg gactctggtcactgtctcttcaaagcccaccaccaccctgcccctagacctcca acccagcccctacaatcgccagccagcccctgagcctgaggcccgaagcctgta gacctgccgctggcggagccgtgcacaccagaggcctggatttcgcctgcgacat ctacatctgggcccctctggccggcacctgtggcgtgctgctgctgagcctggtc atcaccctgtactgcaaccaccggaatcgggtgaagttcagccggagcgccgacg |

Figure 21G

| Sequence Name | SEQ ID NO | Sequence |
|---|---|---|
| | | cccctgcctaccagcagggccagaaccagctgtacaacgagctgaacctgggccg gagggaggagtacgacgtgctggacaagcggagaggccgggaccctgagatgggc ggcaagccccggagaaagaaccctcaggagggcctgtataacgaactgcagaaag acaagatggccgaggcctacagcgagatcggcatgaagggcgagcggcggagggg caagggccacgacggcctgtaccagggcctgagcaccgccaccaaggatacctac gacgccctgcacatgcaggccctgcccccaga |
| hM195scFv-CD8a-Z | 41 | MLLLVTSLLLCELPHPAFLLIPDIQMTQSPSSLSASVGDRVTITCRASES VDNYGISFMNWFQQKPGKAPKLLIYAASNQGSGVPSRFSGSGSGTDFTLT ISSLQPDDFATYYCQQSKEVPWTFGQGTKVEIKGGGGSGGGGSGGGGSQV QLVQSGAEVKKPGSSVKVSCKASGYTFTDYNMHWVRQAPGQGLEWIGYIY PYNGGTGYNQKFKSKATITADESTNTAYMELSSLRSEDTAVYYCARGRPA MDYWGQGTLVTVSSKPTTTPAPRPPTPAPTIASQPLSLRPEACRPAAGGA VHTRGLDFACDIYIWAPLAGTCGVLLLSLVITLYCNHRNRVKFSRSADAP AYQQGQNQLYNELNLGRREEYDVLDKRRGRDPEMGGKPRRKNPQEGLYNE LQKDKMAEAYSEIGMKGERRRGKGHDGLYQGLSTATKDTYDALHMQALPP R |
| hM195scFv-CD8a-CD28m-Z-T2A-GM-CSFRasp.HE R1t | 42 | ATGCTGCTGCTGGTGACCAGCCTGCTGCTGTGTGAGCTGCCCCACCCCGCCTTTC TGCTGATCCCCGACATTCAGATGACCCAGTCTCCGAGCTCTCTGTCCGCATCAGT AGGAGACAGGGTCACCATCACATGCAGAGCCAGCGAAAGTGTCGACAATTATGGC ATTAGCTTTATGAACTGGTTCCAACAGAAACCCGGGAAGGCTCCTAAGCTTCTGA TTTACGCTGCATCCAACCAAGGCTCCGGGGTACCCTCTCGCTTCTCAGGCAGTGG ATCTGGGACAGACTTCACTCTCACCATTTCATCTCTGCAGCCTGATGACTTCGCA ACCTATTACTGTCAGCAAAGTAAGGAGGTTCCGTGGACGTTCGGTCAAGGGACCA AGGTGGAGATCAAAGGTGGCGGTGGCTCGGGCGGTGGTGGGTCGGGTGGCGGCGG ATCTCAGGTTCAGCTGGTGCAGTCTGGAGCTGAGGTGAAGAAGCCTGGGAGCTCA GTGAAGGTTTCCTGCAAAGCTTCTGGCTACACCTTCACTGACTACAACATGCACT GGGTGAGGCAGGCTCCTGGCCAAGGCCTGGAATGGATTGGATATATTTATCCTTA CAATGGTGGTACCGGCTACAACCAGAAGTTCAAGAGCAAGGCCACAATTACAGCA GACGAGAGTACTAACACAGCCTACATGGAACTCTCCAGCCTGAGGTCTGAGGACA CTGCAGTCTATTACTGCGCAAGAGGGCGCCCCGCTATGGACTACTGGGGCCAAGG GACTCTGGTCACTGTCTCTTCAAAGCCCACCACCACCCCTGCCCCTAGACCTCCA ACCCCAGCCCCTACAATCGCCAGCCAGCCCCTGAGCCTGAGGCCCGAAGCCTGTA GACCTGCCGCTGGCGGAGCCGTGCACACCAGAGGCCTGGATTTCGCCTGCGACAT CTACATCTGGGCCCCTCTGGCCGGCACCTGTGGCGTGCTGCTGCTGAGCCTGGTC ATCACCCTGTACTGCAACCACCGGAATAGGAGCAAGCGGAGCAGAGGCGGCCACA GCGACTACATGAACATGACCCCCCGGAGGCCTGGCCCCACCCGGAAGCACTACCA GCCCTACGCCCCTCCCAGGGACTTCGCCGCCTACCGGAGCCGGGTGAAGTTCAGC CGGAGCGCCGACGCCCCTGCCTACCAGCAGGGCCAGAACCAGCTGTACAACGAGC TGAACCTGGGCCGGAGGGAGGAGTACGACGTGCTGGACAAGCGGAGAGGCCGGGA CCCTGAGATGGGCGGCAAGCCCCGGAGAAAGAACCCTCAGGAGGGCCTGTATAAC GAACTGCAGAAAGACAAGATGGCCGAGGCCTACAGCGAGATCGGCATGAAGGGCG AGCGGCGGAGGGGCAAGGGCCACGACGGCCTGTACCAGGGCCTGAGCACCGCCAC |

Figure 21H

| Sequence Name | SEQ ID NO | Sequence |
|---|---|---|
|  |  | CAAGGATACCTACGACGCCCTGCACATGCAGGCCCTGCCCCCCAGACTCGAGGGC GGCGGAGAGGGCAGAGGAAGTCTTCTAACATGCGGTGACGTGGAGGAGAATCCCG GCCCTAGGATGCTTCTCCTGGTGACAAGCCTTCTGCTCTGTGAGTTACCACACCC AGCATTCCTCCTGATCCCACGCAAAGTGTGTAACGGAATAGGTATTGGTGAATTT AAAGACTCACTCTCCATAAATGCTACGAATATTAAACACTTCAAAAACTGCACCT CCATCAGTGGCGATCTCCACATCCTGCCGGTGGCATTTAGGGGTGACTCCTTCAC ACATACTCCTCCTCTGGATCCACAGGAACTGGATATTCTGAAAACCGTAAAGGAA ATCACAGGGTTTTTGCTGATTCAGGCTTGGCCTGAAAACAGGACGGACCTCCATG CCTTTGAGAACCTAGAAATCATACGCGGCAGGACCAAGCAACATGGTCAGTTTTC TCTTGCAGTCGTCAGCCTGAACATAACATCCTTGGGATTACGCTCCCTCAAGGAG ATAAGTGATGGAGATGTGATAATTTCAGGAAACAAAAATTTGTGCTATGCAAATA CAATAAACTGGAAAAAACTGTTTGGGACCTCCGGTCAGAAAACCAAAATTATAAG CAACAGAGGTGAAAACAGCTGCAAGGCCACAGGCCAGGTCTGCCATGCCTTGTGC TCCCCCGAGGGCTGCTGGGGCCCGGAGCCCAGGGACTGCGTCTCTTGCCGGAATG TCAGCCGAGGCAGGGAATGCGTGGACAAGTGCAACCTTCTGGAGGGTGAGCCAAG GGAGTTTGTGGAGAACTCTGAGTGCATACAGTGCCACCCAGAGTGCCTGCCTCAG GCCATGAACATCACCTGCACAGGACGGGGACCAGACAACTGTATCCAGTGTGCCC ACTACATTGACGGCCCCCACTGCGTCAAGACCTGCCCGGCAGGAGTCATGGGAGA AAACAACACCCTGGTCTGGAAGTACGCAGACGCCGGCCATGTGTGCCACCTGTGC CATCCAAACTGCACCTACGGATGCACTGGGCCAGGTCTTGAAGGCTGTCCAACGA ATGGGCCTAAGATCCCGTCCATCGCCACTGGGATGGTGGGGGCCCTCCTCTTGCT GCTGGTGGTGGCCCTGGGGATCGGCCTCTTCATG |
| hM195scFv-CD8a-CD28m-Z-T2A-GM-CSFRasp.HER1t | 43 | MLLLVTSLLLCELPHPAFLLIPDIQMTQSPSSLSASVGDRVTITCRASES VDNYGISFMNWFQQKPGKAPKLLIYAASNQGSGVPSRFSGSGSGTDFTLT ISSLQPDDFATYYCQQSKEVPWTFGQGTKVEIKGGGGSGGGGSGGGGSQV QLVQSGAEVKKPGSSVKVSCKASGYTFTDYNMHWVRQAPGQGLEWIGYIY PYNGGTGYNQKFKSKATITADESTNTAYMELSSLRSEDTAVYYCARGRPA MDYWGQGTLVTVSSKPTTTPAPRPPTPAPTIASQPLSLRPEACRPAAGGA VHTRGLDFACDIYIWAPLAGTCGVLLLSLVITLYCNHRNRSKRSRGGHSD YMNMTPRRPGPTRKHYQPYAPPRDFAAYRSRVKFSRSADAPAYQQGQNQL YNELNLGRREEYDVLDKRRGRDPEMGGKPRRKNPQEGLYNELQKDKMAEA YSEIGMKGERRRGKGHDGLYQGLSTATKDTYDALHMQALPPRLEGGGEGR GSLLTCGDVEENPGPRMLLLVTSLLLCELPHPAFLLIPRKVCNGIGIGEF KDSLSINATNIKHFKNCTSISGDLHILPVAFRGDSFTHTPPLDPQELDIL KTVKEITGFLLIQAWPENRTDLHAFENLEIIRGRTKQHGQFSLAVVSLNI TSLGLRSLKEISDGDVIISGNKNLCYANTINWKKLFGTSGQKTKIISNRG ENSCKATGQVCHALCSPEGCWGPEPRDCVSCRNVSRGRECVDKCNLLEGE PREFVENSECIQCHPECLPQAMNITCTGRGPDNCIQCAHYIDGPHCVKTC PAGVMGENNTLVWKYADAGHVCHLCHPNCTYGCTGPGLEGCPTNGPKIPS IATGMVGALLLLLVVALGIGLFM |
| hM195scFv | 44 | Atgctgctgctggtgaccagcctgctgctgtgtgagctgccccaccccgcctttc tgctgatccccgacattcagatgacccagtctccgagctctctgtccgcatcagt |

Figure 21I

| Sequence Name | SEQ ID NO | Sequence |
|---|---|---|
| | | aggagacagggtcaccatcacatgcagagccagcgaaagtgtcgacaattatggc<br>attagctttatgaactggttccaacagaaacccgggaaggctcctaagcttctga<br>tttacgctgcatccaaccaaggctccggggtaccctctcgcttctcaggcagtgg<br>atctgggacagacttcactctcaccatttcatctctgcagcctgatgacttcgca<br>acctattactgtcagcaaagtaaggaggttccgtggacgttcggtcaagggacca<br>aggtggagatcaaaggtggcggtggctcgggcggtggtgggtcgggtggcggcgg<br>atctcaggttcagctggtgcagtctggagctgaggtgaagaagcctgggagctca<br>gtgaaggtttcctgcaaagcttctggctacaccttcactgactacaacatgcact<br>gggtgaggcaggctcctggccaaggcctggaatggattggatatatttatcctta<br>caatggtggtaccggctacaaccagaagttcaagagcaaggccacaattacagca<br>gacgagagtactaacacagcctacatggaactctccagcctgaggtctgaggaca<br>ctgcagtctattactgcgcaagagggcgccccgctatggactactggggccaagg<br>gactctggtcactgtctcttca |
| hM195scFv | 45 | MLLLVTSLLLLCELPHPAFLLIPDIQMTQSPSSLSASVGDRVTITCRASES<br>VDNYGISFMNWFQQKPGKAPKLLIYAASNQGSGVPSRFSGSGSGTDFTLT<br>ISSLQPDDFATYYCQQSKEVPWTFGQGTKVEIKGGGGSGGGGSGGGGSQV<br>QLVQSGAEVKKPGSSVKVSCKASGYTFTDYNMHWVRQAPGQGLEWIGYIY<br>PYNGGTGYNQKFKSKATITADESTNTAYMELSSLRSEDTAVYYCARGRPA<br>MDYWGQGTLVTVSS |
| hM195scFv-CD8a-4-1BB-Z | 46 | atgctgctgctggtgaccagcctgctgctgtgtgagctgccccacccccgcctttc<br>tgctgatccccgacattcagatgacccagtctccgagctctctgtccgcatcagt<br>aggagacagggtcaccatcacatgcagagccagcgaaagtgtcgacaattatggc<br>attagctttatgaactggttccaacagaaacccgggaaggctcctaagcttctga<br>tttacgctgcatccaaccaaggctccggggtaccctctcgcttctcaggcagtgg<br>atctgggacagacttcactctcaccatttcatctctgcagcctgatgacttcgca<br>acctattactgtcagcaaagtaaggaggttccgtggacgttcggtcaagggacca<br>aggtggagatcaaaggtggcggtggctcgggcggtggtgggtcgggtggcggcgg<br>atctcaggttcagctggtgcagtctggagctgaggtgaagaagcctgggagctca<br>gtgaaggtttcctgcaaagcttctggctacaccttcactgactacaacatgcact<br>gggtgaggcaggctcctggccaaggcctggaatggattggatatatttatcctta<br>caatggtggtaccggctacaaccagaagttcaagagcaaggccacaattacagca<br>gacgagagtactaacacagcctacatggaactctccagcctgaggtctgaggaca<br>ctgcagtctattactgcgcaagagggcgccccgctatggactactggggccaagg<br>gactctggtcactgtctcttcaaagcccaccaccacccctgcccctagacctcca<br>accccagcccctacaatcgccagccagcccctgagcctgaggcccgaagcctgta<br>gacctgccgctggcggagccgtgcacaccagaggcctggatttcgcctgcgacat<br>ctacatctgggcccctctggccggcacctgtggcgtgctgctgctgagcctggtc<br>atcaccctgtactgcaaccaccggaataagagaggccggaagaaactgctgtaca<br>tcttcaagcagcccttcatgcggcccgtgcagaccacccaggaagaggacggctg<br>cagctgccggttccccgaggaagaggaaggcggctgcgaactgcgggtgaagttc<br>agccggagcgccgacgcccctgcctaccagcagggccagaaccagctgtacaacg<br>agctgaacctgggccggagggaggagtacgacgtgctggacaagcggagaggccg |

Figure 21J

| Sequence Name | SEQ ID NO | Sequence |
|---|---|---|
| | | ggaccctgagatgggcggcaagccccggagaaagaaccctcaggagggcctgtat aacgaactgcagaaagacaagatggccgaggcctacagcgagatcggcatgaagg gcgagcggcggaggggcaagggccacgacggcctgtaccagggcctgagcaccgc caccaaggatacctacgacgccctgcacatgcaggccctgcccccaga |
| hM195scFv-CD8a-4-1BB-Z | 47 | MLLLVTSLLLCELPHPAFLLIPDIQMTQSPSSLSASVGDRVTITCRASES VDNYGISFMNWFQQKPGKAPKLLIYAASNQGSGVPSRFSGSGSGTDFTLT ISSLQPDDFATYYCQQSKEVPWTFGQGTKVEIKGGGGSGGGGSGGGGSQV QLVQSGAEVKKPGSSVKVSCKASGYTFTDYNMHWVRQAPGQGLEWIGYIY PYNGGTGYNQKFKSKATITADESTNTAYMELSSLRSEDTAVYYCARGRPA MDYWGQGTLVTVSSKPTTTPAPRPPTPAPTIASQPLSLRPEACRPAAGGA VHTRGLDFACDIYIWAPLAGTCGVLLLSLVITLYCNHRNKRGRKKLLYIF KQPFMRPVQTTQEEDGCSCRFPEEEEGGCELRVKFSRSADAPAYQQGQNQ LYNELNLGRREEYDVLDKRRGRDPEMGGKPRRKNPQEGLYNELQKDKMAE AYSEIGMKGERRRGKGHDGLYQGLSTATKDTYDALHMQALPPR |
| hM195scFv-CD8a-4-1BB-Z-T2A-GM-CSFRasp.HER1t | 48 | atgctgctgctggtgaccagcctgctgctgtgtgagctgccccaccccgcctttc tgctgatccccgacattcagatgacccagtctccgagctctctgtccgcatcagt aggagacagggtcaccatcacatgcagagccagcgaaagtgtcgacaattatggc attagctttatgaactggttccaacagaaacccgggaaggctcctaagcttctga tttacgctgcatccaaccaaggctccggggtaccctctcgcttctcaggcagtgg atctgggacagacttcactctcaccatttcatctctgcagcctgatgacttcgca acctattactgtcagcaaagtaaggaggttccgtggacgttcggtcaagggacca aggtggagatcaaaggtggcggtggctcgggcggtggtgggtcgggtggcggcgg atctcaggttcagctggtgcagtctggagctgaggtgaagaagcctgggagctca gtgaaggtttcctgcaaagcttctggctacaccttcactgactacaacatgcact gggtgaggcaggctcctggccaaggcctggaatggattggatatatttatcctta caatggtggtaccggctacaaccagaagttcaagagcaaggccacaattacagca gacgagagtactaacacagcctacatggaactctccagcctgaggtctgaggaca ctgcagtctattactgcgcaagagggcgccccgctatggactactggggccaagg gactctggtcactgtctcttcaaagcccaccaccacccctgcccctagacctcca accccagcccctacaatcgccagccagcccctgagcctgaggcccgaagcctgta gacctgccgctggcggagccgtgcacaccagaggcctggatttcgcctgcgacat ctacatctgggcccctctggccggcacctgtggcgtgctgctgctgagcctggtc atcaccctgtactgcaaccaccggaataagagaggccggaagaaactgctgtaca tcttcaagcagcccttcatgcggcccgtgcagaccacccaggaagaggacggctg cagctgccggttccccgaggaagaggaaggcggctgcgaactgcgggtgaagttc agccggagcgccgacgcccctgcctaccagcagggccagaaccagctgtacaacg agctgaacctgggccggaggggaggagtacgacgtgctggacaagcggagaggccg ggaccctgagatgggcggcaagccccggagaaagaaccctcaggagggcctgtat aacgaactgcagaaagacaagatggccgaggcctacagcgagatcggcatgaagg gcgagcggcggaggggcaagggccacgacggcctgtaccagggcctgagcaccgc caccaaggatacctacgacgccctgcacatgcaggccctgccccccagactcgag ggcggcggagagggcagaggaagtcttctaacatgcggtgacgtggaggagaatc |

Figure 21K

| Sequence Name | SEQ ID NO | Sequence |
|---|---|---|
| | | ccggccctaggatgcttctcctggtgacaagccttctgctctgtgagttaccaca cccagcattcctcctgatcccacgcaaagtgtgtaacggaataggtattggtgaa tttaaagactcactctccataaatgctacgaatattaaacacttcaaaaactgca cctccatcagtggcgatctccacatcctgccggtggcatttaggggtgactcctt cacacatactcctcctctggatccacaggaactggatattctgaaaaccgtaaag gaaatcacagggttttgctgattcaggcttggcctgaaaacaggacggacctcc atgcctttgagaacctagaaatcatacgcggcaggaccaagcaacatggtcagtt ttctcttgcagtcgtcagcctgaacataacatccttgggattacgctccctcaag gagataagtgatggagatgtgataatttcaggaaacaaaaatttgtgctatgcaa atacaataaactggaaaaaactgtttgggacctccggtcagaaaaccaaaattat aagcaacagaggtgaaaacagctgcaaggccacaggccaggtctgccatgccttg tgctcccccgagggctgctggggcccggagcccaggactgcgtctcttgccgga atgtcagccgaggcagggaatgcgtggacaagtgcaaccttctggagggtgagcc aagggagtttgtggagaactctgagtgcatacagtgccacccagagtgcctgcct caggccatgaacatcacctgcacaggacggggaccagacaactgtatccagtgtg cccactacattgacggcccccactgcgtcaagacctgcccggcaggagtcatggg agaaaacaacaccctggtctggaagtacgcagacgccggccatgtgtgccacctg tgccatccaaactgcacctacggatgcactgggccaggtcttgaaggctgtccaa cgaatgggcctaagatcccgtccatcgccactgggatggtggggggccctcctctt gctgctggtggtggccctggggatcggcctcttcatg |
| hM195scFv-CD8a-4-1BB-Z-T2A-GM-CSFRasp.HER1t | 49 | MLLLVTSLLLCELPHPAFLLIPDIQMTQSPSSLSASVGDRVTITCRASES VDNYGISFMNWFQQKPGKAPKLLIYAASNQGSGVPSRFSGSGSGTDFTLT ISSLQPDDFATYYCQQSKEVPWTFGQGTKVEIKGGGGSGGGGSGGGGSQV QLVQSGAEVKKPGSSVKVSCKASGYTFTDYNMHWVRQAPGQGLEWIGYIY PYNGGTGYNQKFKSKATITADESTNTAYMELSSLRSEDTAVYYCARGRPA MDYWGQGTLVTVSSKPTTTPAPRPPTPAPTIASQPLSLRPEACRPAAGGA VHTRGLDFACDIYIWAPLAGTCGVLLLSLVITLYCNHRNKRGRKKLLYIF KQPFMRPVQTTQEEDGCSCRFPEEEEGGCELRVKFSRSADAPAYQQGQNQ LYNELNLGRREEYDVLDKRRGRDPEMGGKPRRKNPQEGLYNELQKDKMAE AYSEIGMKGERRRGKGHDGLYQGLSTATKDTYDALHMQALPPRLEGGGEG RGSLLTCGDVEENPGPRMLLLVTSLLLCELPHPAFLLIPRKVCNGIGIGE FKDSLSINATNIKHFKNCTSISGDLHILPVAFRGDSFTHTPPLDPQELDI LKTVKEITGFLLIQAWPENRTDLHAFENLEIIRGRTKQHGQFSLAVVSLN ITSLGLRSLKEISDGDVIISGNKNLCYANTINWKKLFGTSGQKTKIISNR GENSCKATGQVCHALCSPEGCWGPEPRDCVSCRNVSRGRECVDKCNLLEG EPREFVENSECIQCHPECLPQAMNITCTGRGPDNCIQCAHYIDGPHCVKT CPAGVMGENNTLVWKYADAGHVCHLCHPNCTYGCTGPGLEGCPTNGPKIP SIATGMVGALLLLLVVALGIGLFM |
| hM195scFv-CD8a-4-1BB-Z-T2A.FL | 50 | ATGCTGCTGCTGGTGACCAGCCTGCTGCTGTGTGAGCTGCCCCACCCCGCCTTTC TGCTGATCCCCGACATTCAGATGACCCAGTCTCCGAGCTCTCTGTCCGCATCAGT AGGAGACAGGGTCACCATCACATGCAGAGCCAGCGAAAGTGTCGACAATTATGGC ATTAGCTTTATGAACTGGTTCCAACAGAAACCCGGGAAGGCTCCTAAGCTTCTGA |

Figure 21L

| Sequence Name | SEQ ID NO | Sequence |
|---|---|---|
| CD20 | | TTTACGCTGCATCCAACCAAGGCTCCGGGGTACCCTCTCGCTTCTCAGGCAGTGG ATCTGGGACAGACTTCACTCTCACCATTTCATCTCTGCAGCCTGATGACTTCGCA ACCTATTACTGTCAGCAAAGTAAGGAGGTTCCGTGGACGTTCGGTCAAGGGACCA AGGTGGAGATCAAAGGTGGCGGTGGCTCGGGCGGTGGTGGGTCGGGTGGCGGCGG ATCTCAGGTTCAGCTGGTGCAGTCTGGAGCTGAGGTGAAGAAGCCTGGGAGCTCA GTGAAGGTTTCCTGCAAAGCTTCTGGCTACACCTTCACTGACTACAACATGCACT GGGTGAGGCAGGCTCCTGGCCAAGGCCTGGAATGGATTGGATATATTTATCCTTA CAATGGTGGTACCGGCTACAACCAGAAGTTCAAGAGCAAGGCCACAATTACAGCA GACGAGAGTACTAACACAGCCTACATGGAACTCTCCAGCCTGAGGTCTGAGGACA CTGCAGTCTATTACTGCGCAAGAGGGCGCCCCGCTATGGACTACTGGGGCCAAGG GACTCTGGTCACTGTCTCTTCAAAGCCCACCACCACCCCTGCCCCTAGACCTCCA ACCCCAGCCCCTACAATCGCCAGCCAGCCCCTGAGCCTGAGGCCCGAAGCCTGTA GACCTGCCGCTGGCGGAGCCGTGCACACCAGAGGCCTGGATTTCGCCTGCGACAT CTACATCTGGGCCCCTCTGGCCGGCACCTGTGGCGTGCTGCTGCTGAGCCTGGTC ATCACCCTGTACTGCAACCACCGGAATAAGAGAGGCCGGAAGAAACTGCTGTACA TCTTCAAGCAGCCCTTCATGCGGCCCGTGCAGACCACCCAGGAAGAGGACGGCTG CAGCTGCCGGTTCCCCGAGGAAGAGGAAGGCGGCTGCGAACTGCGGGTGAAGTTC AGCCGGAGCGCCGACGCCCCTGCCTACCAGCAGGGCCAGAACCAGCTGTACAACG AGCTGAACCTGGGCCGGAGGGAGGAGTACGACGTGCTGGACAAGCGGAGAGGCCG GGACCCTGAGATGGGCGGCAAGCCCCGGAGAAAGAACCCTCAGGAGGGCCTGTAT AACGAACTGCAGAAAGACAAGATGGCCGAGGCCTACAGCGAGATCGGCATGAAGG GCGAGCGGCGGAGGGGCAAGGGCCACGACGGCCTGTACCAGGGCCTGAGCACCGC CACCAAGGATACCTACGACGCCCTGCACATGCAGGCCCTGCCCCCCAGACTCGAG GGCGGCGGAGAGGGCAGAGGAAGTCTTCTAACATGCGGTGACGTGGAGGAGAATC CCGGCCCTAGGATGACAACACCCAGAAATTCAGTAAATGGGACTTTCCCGGCAGA GCCAATGAAAGGCCCTATTGCTATGCAATCTGGTCCAAAACCACTCTTCAGGAGG ATGTCTTCACTGGTGGGCCCCACGCAAAGCTTCTTCATGAGGGAATCTAAGACTT TGGGGGCTGTCCAGATTATGAATGGGCTCTTCCACATTGCCCTGGGGGGTCTTCT GATGATCCCAGCAGGGATCTATGCACCCATCTGTGTGACTGTGTGGTACCCTCTC TGGGGAGGCATTATGTATATTATTTCCGGATCACTCCTGGCAGCAACGGAGAAAA ACTCCAGGAAGTGTTTGGTCAAAGGAAAAATGATAATGAATTCATTGAGCCTCTT TGCTGCCATTTCTGGAATGATTCTTTCAATCATGGACATACTTAATATTAAAATT TCCCATTTTTTTAAAAATGGAGAGTCTGAATTTTATTAGAGCTCACACACCATATA TTAACATATACAACTGTGAACCAGCTAATCCCTCTGAGAAAAACTCCCCATCTAC CCAATACTGTTACAGCATACAATCTCTGTTCTTGGGCATTTTGTCAGTGATGCTG ATCTTTGCCTTCTTCCAGGAACTTGTAATAGCTGGCATCGTTGAGAATGAATGGA AAAGAACGTGCTCCAGACCCAAATCTAACATAGTTCTCCTGTCAGCAGAAGAAAA AAAAGAACAGACTATTGAAATAAAAGAAGAAGTGGTTGGGCTAACTGAAACATCT TCCCAACCAAAGAATGAAGAAGACATTGAAATTATTCCAATCCAAGAAGAGGAAG AAGAAGAAACAGAGACGAACTTTCCAGAACCTCCCCAAGATCAGGAATCCTCACC AATAGAAAATGACAGCTCTCCT |
| hM195scFv-CD8a-4- | 51 | MLLLVTSLLLCELPHPAFLLIPDIQMTQSPSSLSASVGDRVTITCRASES VDNYGISFMNWFQQKPGKAPKLLIYAASNQGSGVPSRFSGSGSGTDFTLT |

Figure 21M

| Sequence Name | SEQ ID NO | Sequence |
|---|---|---|
| 1BB-Z-T2A.FL CD20 | | ISSLQPDDFATYYCQQSKEVPWTFGQGTKVEIKGGGGSGGGGSGGGGSQV QLVQSGAEVKKPGSSVKVSCKASGYTFTDYNMHWVRQAPGQGLEWIGYIY PYNGGTGYNQKFKSKATITADESTNTAYMELSSLRSEDTAVYYCARGRPA MDYWGQGTLVTVSSKPTTTPAPRPPTPAPTIASQPLSLRPEACRPAAGGA VHTRGLDFACDIYIWAPLAGTCGVLLLSLVITLYCNHRNKRGRKKLLYIF KQPFMRPVQTTQEEDGCSCRFPEEEEGGCELRVKFSRSADAPAYQQGQNQ LYNELNLGRREEYDVLDKRRGRDPEMGGKPRRKNPQEGLYNELQKDKMAE AYSEIGMKGERRRGKGHDGLYQGLSTATKDTYDALHMQALPPRLEGGGEG RGSLLTCGDVEENPGPRMTTPRNSVNGTFPAEPMKGPIAMQSGPKPLFR RMSSLVGPTQSFFMRESKTLGAVQIMNGLFHIALGGLLMIPAGIYAPICV TVWYPLWGGIMYIISGSLLAATEKNSRKCLVKGKMIMNSLSLFAAISGMI LSIMDILNIKISHFLKMESLNFIRAHTPYINIYNCEPANPSEKNSPSTQY CYSIQSLFLGILSVMLIFAFFQELVIAGIVENEWKRTCSRPKSNIVLLSA EEKKEQTIEIKEEVVGLTETSSQPKNEEDIEIIPIQEEEEEETETNFPEP PQDQESSPIENDSSP |
| human CD33(M1-R287) | 52 | Atgccgctgctgctactgctgcccctgctgtgggcaggggccctggctatggatc caaatttctggctgcaagtgcaggagtcagtgacggtacaggagggtttgtgcgt cctcgtgccctgcactttcttccatcccataccctactacgacaagaactcccca gttcatggttactggttccgggaaggagccattatatccagggactctccagtgg ccacaaacaagctagatcaagaagtacaggaggagactcagggcagattccgcct ccttggggatcccagtaggaacaactgctccctgagcatcgtagacgccaggagg agggataatggttcatacttctttcggatggagagaggaagtaccaaatacagtt acaaatctccccagctctctgtgcatgtgacagacttgacccacaggcccaaaat cctcatccctggcactctagaacccggccactccaaaaacctgacctgctctgtg tcctggggcctgtgagcagggaacaccccgatcttctcctggttgtcagctgccc ccacctccctgggccccaggactactcactcctcggtgctcataatcacccacg gccccaggaccacggcaccaacctgacctgtcaggtgaagttcgctggagctggt gtgactacggagagaaccatccagctcaacgtcacctatgttccacagaacccaa caactggtatctttccaggagatggctcagggaaacaagagaccagagcaggagt ggttcatggggccattggaggagctggtgttacagccctgctcgctctttgtctc tgcctcatcttcttcatagtgaagacccacaggagg |
| human CD33(M1-R287) | 53 | MPLLLLLLPLLWAGALAMDPNFWLQVQESVTVQEGLCVLVPCTFFHPIPYY DKNSPVHGYWFREGAIISRDSPVATNKLDQEVQEETQGRFRLLGDPSRNN CSLSIVDARRRDNGSYFFRMERGSTKYSYKSPQLSVHVTDLTHRPKILIP GTLEPGHSKNLTCSVSWACEQGTPPIFSWLSAAPTSLGPRTTHSSVLIIT PRPQDHGTNLTCQVKFAGAGVTTERTIQLNVTYVPQNPTTGIFPGDGSGK QETRAGVVHGAIGGAGVTALLALCLCLIFFIVKTHRR |
| HER1t-1 | 54 | RKVCNGIGIGEFKDSLSINATNIKHFKNCTSISGDLHILPVAFRGDSFTH TPPLDPQELDILKTVKEITGFLLIQAWPENRTDLHAFENLEIIRGRTKQH GQFSLAVVSLNITSLGLRSLKEISDGDVIISGNKNLCYANTINWKKLFGT SGQKTKIISNRGENSCKATGQVCHALCSPEGCWGPEPRDCVSGGGGSGGG |

Figure 21N

| Sequence Name | SEQ ID NO | Sequence |
|---|---|---|
| | | GSGGGGSGGGGSFWVLVVVGGVLACYSLLVTVAFIIFWVRSKRS |
| HER1t-1 | 55 | cgcaaagtgtgtaacggaataggtattggtgaatttaaagactcactctccataa atgctacgaatattaaacacttcaaaaactgcacctccatcagtggcgatctcca catcctgccggtggcatttaggggtgactccttcacacatactcctcctctggat ccacaggaactggatattctgaaaaccgtaaaggaaatcacagggttttgctga ttcaggcttggcctgaaaacaggacggacctccatgcctttgagaacctagaaat catacgcggcaggaccaagcaacatggtcagttttctcttgcagtcgtcagcctg aacataacatccttgggattacgctccctcaaggagataagtgatggagatgtga taatttcaggaaacaaaaatttgtgctatgcaaatacaataaactggaaaaaact gtttgggacctccggtcagaaaaccaaaattataagcaacagaggtgaaaacagc tgcaaggccacaggccaggtctgccatgccttgtgctcccccgagggctgctggg gcccggagcccagggactgcgtctctggtggcggtggctcgggcggtggtgggtc gggtggcggcggatctggtggcggtggctcgttttgggtgctggtggtggttggt ggagtcctggcttgctatagcttgctagtaacagtggcctttattattttctggg tgaggagtaagaggagc |
| CD20t-1 | 56 | MTTPRNSVNGTFPAEPMKGPIAMQSGPKPLFRRMSSLVGPTQSFFMRESK TLGAVQIMNGLFHIALGGLLMIPAGIYAPICVTVWYPLWGGIMYIISGSL LAATEKNSRKCLVKGKMIMNSLSLFAAISGMILSIMDILNIKISHFLKME SLNFIRAHTPYINIYNCEPANPSEKNSPSTQYCYSIQSLFLGILSVMLIF AFFQELVIAGIVENEWKRTCSRPKSNIVLLSAEEKKEQTIEIKEEVVGLT ETSSQPKNEEDIE |
| Cd20t-1 | 57 | atgaccacaccacggaactctgtgaatggcaccttcccagcagagccaatgaagg gaccaatcgcaatgcagagcggacccaagcctctgtttcggagaatgagctccct ggtgggccccaacccagtccttctttatgagagagtctaagacactgggcgccgtg cagatcatgaacggactgttccacatcgccctgggaggactgctgatgatcccag ccggcatctacgcccctatctgcgtgaccgtgtggtacctctgtggggcggcat catgtatatcatctccggctctctgctggccgccacagagaagaacagcaggaag tgtctggtgaagggcaagatgatcatgaatagcctgtccctgtttgccgccatct ctggcatgatcctgagcatcatggacatcctgaacatcaagatcagccacttcct gaagatggagagcctgaacttcatcagagcccacacccccttacatcaacatctat aattgcgagcctgccaacccatccgagaagaattctccaagcacacagtactgtt attccatccagtctctgttcctgggcatcctgtctgtgatgctgatctttgcctt ctttcaggagctggtcatcgccggcatcgtggagaacgagtggaagaggacctgc agccgcccccaagtccaatatcgtgctgctgtccgccgaggagaagaaggagcaga caatcgagatcaaggaggaggtggtgggcctgaccgagacatctagccagcctaa gaatgaggaggatatcgag |
| DNAX-activation protein 10 (DAP 10) | 58 | ctgtgcgcacgcccacgccgcagccccgcccaagaagatggcaaagtctacatca acatgccaggcaggggc |

Figure 21O

| Sequence Name | SEQ ID NO | Sequence |
|---|---|---|
| Signaling Domain | | |
| DNAX-activation protein 10 (DAP10) Signaling Domain | 59 | LCARPRRSPAQEDGKVYINMPGRG |
| DNAX-activation protein 12 (DAP12) Signaling Domain | 60 | tacttcctgggccggctggtccctcgggggcgaggggctgcggaggcagcgaccc ggaaacagcgtatcactgagaccgagtcgccttatcaggagctccagggtcagag gtcggatgtctacagcgacctcaacacacagaggccgtattacaaa |
| DNAX-activation protein 12 (DAP12) Signaling Domain | 61 | YFLGRLVPRGRGAAEAATRKQRITETESPYQELQGQRSDVYSDLNTQRPYYK |

FIGURE 22B
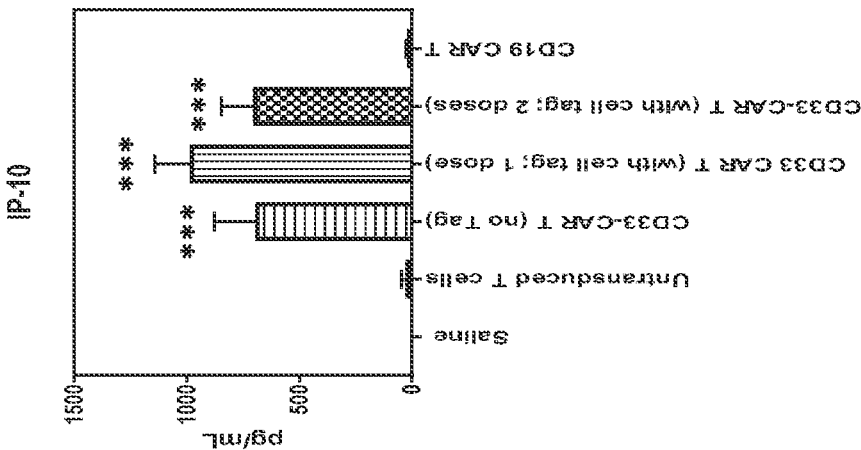
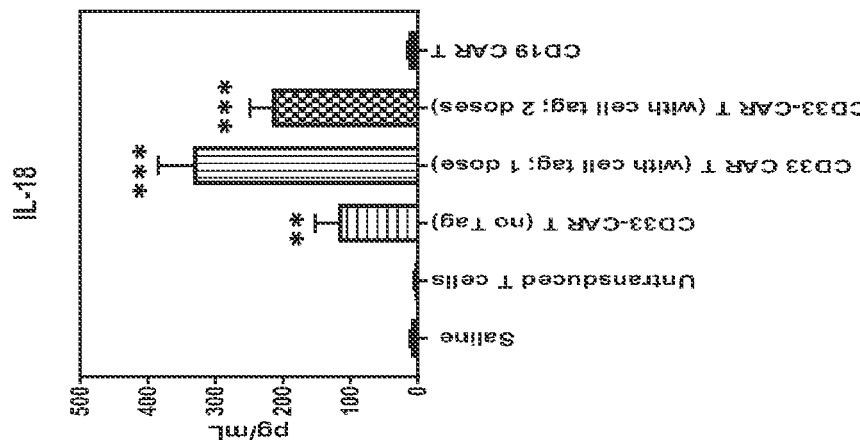
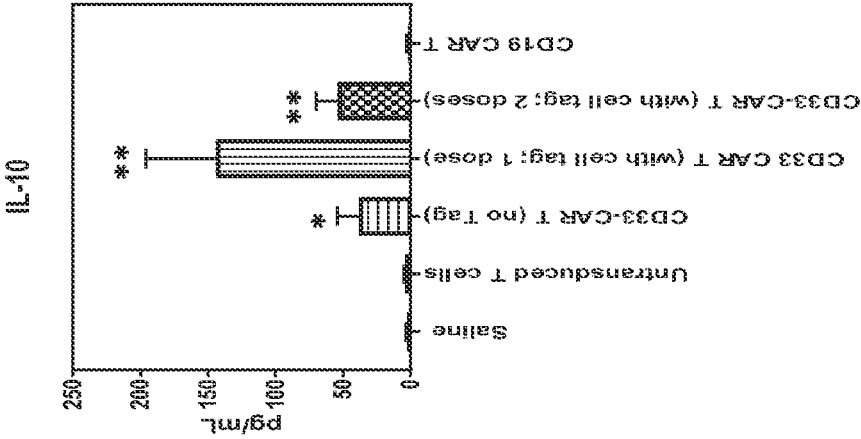

SEQUENCE LISTING

Sequence total quantity: 62
SEQ ID NO: 1                  moltype = AA   length = 111
FEATURE                       Location/Qualifiers
REGION                        1..111
                              note = source = /note="Description of Artificial Sequence:
                              Syntheticpolypeptide"
source                        1..111
                              mol_type = protein
                              organism = synthetic construct
SEQUENCE: 1
DIQMTQSPSS LSASVGDRVT ITCRASESVD NYGISFMNWF QQKPGKAPKL LIYAASNQGS   60
GVPSRFSGSG SGTDFTLTIS SLQPDDFATY YCQQSKEVPW TFGQGTKVEI K            111

SEQ ID NO: 2                  moltype = DNA   length = 333
FEATURE                       Location/Qualifiers
misc_feature                  1..333
                              note = source = /note="Description of Artificial Sequence:
                              Syntheticpolynucleotide"
source                        1..333
                              mol_type = other DNA
                              organism = synthetic construct
SEQUENCE: 2
gacattcaga tgacccagtc tccgagctct ctgtccgcat cagtaggaga cagggtcacc   60
atcacatgca gagccagcga aagtgtcgac aattatggca ttagctttat gaactggttc   120
caacagaaac ccgggaaggc tcctaagctt ctgatttacg ctgcatccaa ccaaggctcc   180
ggggtaccct ctcgcttctc aggcagtgga tctgggacag acttcactct caccatttca   240
tctctgcagc ctgatgactt cgcaacctat tactgtcagc aaagtaagga ggttccgtgg   300
acgttcggtc aagggaccaa ggtggagatc aaa                               333

SEQ ID NO: 3                  moltype = AA   length = 116
FEATURE                       Location/Qualifiers
REGION                        1..116
                              note = source = /note="Description of Artificial Sequence:
                              Syntheticpolypeptide"
source                        1..116
                              mol_type = protein
                              organism = synthetic construct
SEQUENCE: 3
QVQLVQSGAE VKKPGSSVKV SCKASGYTFT DYNMHWVRQA PGQGLEWIGY IYPYNGGTGY   60
NQKFKSKATI TADESTNTAY MELSSLRSED TAVYYCARGR PAMDYWGQGT LVTVSS       116

SEQ ID NO: 4                  moltype = DNA   length = 348
FEATURE                       Location/Qualifiers
misc_feature                  1..348
                              note = source = /note="Description of Artificial Sequence:
                              Syntheticpolynucleotide"
source                        1..348
                              mol_type = other DNA
                              organism = synthetic construct
SEQUENCE: 4
caggttcagc tggtgcagtc tggagctgag gtgaagaagc ctgggagctc agtgaaggtt   60
tcctgcaaag cttctggcta caccttcact gactacaaca tgcactgggt gaggcaggct   120
cctggccaag gcctggaatg gattggatat atttatcctt acaatggtgg taccggctac   180
aaccagaagt tcaagagcaa ggccacaatt acagcagacg agagtactaa cacagcctac   240
atggaactct ccagcctgag gtctgaggac actgcagtct attactgcgc aagagggcgc   300
cccgctatgg actactgggg ccaagggact ctggtcactg tctcttca              348

SEQ ID NO: 5                  moltype = DNA   length = 45
FEATURE                       Location/Qualifiers
misc_feature                  1..45
                              note = source = /note="Description of Artificial Sequence:
                              Syntheticoligonucleotide"
source                        1..45
                              mol_type = other DNA
                              organism = synthetic construct
SEQUENCE: 5
ggtggcggtg gctcgggcgg tggtgggtcg ggtggcggcg gatct                           45

SEQ ID NO: 6                  moltype = AA   length = 15
FEATURE                       Location/Qualifiers
REGION                        1..15
                              note = source = /note="Description of Artificial Sequence:
                              Syntheticpeptide"
source                        1..15
                              mol_type = protein
                              organism = synthetic construct
SEQUENCE: 6
GGGGSGGGGS GGGGS                                                            15

```
SEQ ID NO: 7              moltype = DNA  length = 726
FEATURE                  Location/Qualifiers
misc_feature             1..726
                         note = source = /note="Description of Artificial Sequence:
                         Syntheticpolynucleotide"
source                   1..726
                         mol_type = other DNA
                         organism = synthetic construct
SEQUENCE: 7
gacattcaga tgacccagtc tccgagctct ctgtccgcat cagtaggaga cagggtcacc   60
atcacatgca gagccagcga aagtgtcgac aattatggca ttagctttat gaactggttc  120
caacagaaac ccgggaaggc tcctaagctt ctgatttacg ctgcatccaa ccaaggctcc  180
ggggtaccct ctcgcttctc aggcagtgga tctgggacag acttcactct caccatttca  240
tctctgcagc ctgatgactt cgcaacctat tactgtcagc aaagtaagga ggttccgtgg  300
acgttcggtc aagggaccaa ggtggagatc aaaggtggcg gtggctcggg cggtggtggg  360
tcgggtggcg gcggatctca ggttcagctg gtgcagtctg gagctgaggt gaagaagcct  420
gggagctcag tgaaggtttc ctgcaaagct tctggctacg cctcactgga ctacaacatg  480
cactgggtga ggcaggctcc tggccaaggc ctggaatgga ttggatatat ttatccttac  540
aatggtggta ccggctacaa ccagaagttc aagagcaagg ccacaattac agcagacgag  600
agtactaaca cagcctacat ggaactctcc agcctgaggt ctgaggacac tgcagtctat  660
tactgcgcaa gagggcgccc cgctatggac tactggggcc aagggactct ggtcactgtc  720
tcttca                                                             726

SEQ ID NO: 8              moltype = AA  length = 242
FEATURE                  Location/Qualifiers
REGION                   1..242
                         note = source = /note="Description of Artificial Sequence:
                         Syntheticpolypeptide"
source                   1..242
                         mol_type = protein
                         organism = synthetic construct
SEQUENCE: 8
DIQMTQSPSS LSASVGDRVT ITCRASESVD NYGISFMNWF QQKPGKAPKL LIYAASNQGS   60
GVPSRFSGSG SGTDFTLTIS SLQPDDFATY YCQQSKEVPW TFGQGTKVEI KGGGGSGGGG  120
SGGGGSQVQL VQSGAEVKKP GSSVKVSCKA SGYTFTDYNM HWVRQAPGQG LEWIGYIYPY  180
NGGTGYNQKF KSKATITADE STNTAYMELS SLRSEDTAVY YCARGRPAMD YWGQGTLVTV  240
SS                                                                 242

SEQ ID NO: 9              moltype = AA  length = 117
FEATURE                  Location/Qualifiers
REGION                   1..117
                         note = source = /note="Description of Artificial Sequence:
                         Syntheticpolypeptide"
source                   1..117
                         mol_type = protein
                         organism = synthetic construct
SEQUENCE: 9
QVQLQQSGPE LVRPGTFVKI SCKASGYTFT NYDINWVNQR PGQGLEWIGW IYPGDGSTKY   60
NEKFKAKATL TADKSSSTAY LQLNNLTSEN SAVYFCASGY EDAMDYWGQG TSVTVSS     117

SEQ ID NO: 10             moltype = AA  length = 108
FEATURE                  Location/Qualifiers
REGION                   1..108
                         note = source = /note="Description of Artificial Sequence:
                         Syntheticpolypeptide"
source                   1..108
                         mol_type = protein
                         organism = synthetic construct
SEQUENCE: 10
DIKMTQSPSS MYASLGERVI INCKASQDIN SYLSWFQQKP GKSPKTLIYR ANRLVDGVPS   60
RFSGSGSGQD YSLTISSLEY EDMGIYYCLQ YDEFPLTFGA GTKLELKR              108

SEQ ID NO: 11             moltype = AA  length = 120
FEATURE                  Location/Qualifiers
REGION                   1..120
                         note = source = /note="Description of Artificial Sequence:
                         Syntheticpolypeptide"
source                   1..120
                         mol_type = protein
                         organism = synthetic construct
SEQUENCE: 11
EVKLQESGPE LVKPGASVKM SCKASGYKFT DYVVHWLKQK PGQGLEWIGY INPYNDGTKY   60
NEKFKGKATL TSDKSSSTAY MEVSSLTSED SAVYYCARDY RYEVYGMDYW GQGTSVTVSS  120

SEQ ID NO: 12             moltype = AA  length = 115
FEATURE                  Location/Qualifiers
REGION                   1..115
                         note = source = /note="Description of Artificial Sequence:
```

-continued

```
                            Syntheticpolypeptide"
source                      1..115
                            mol_type = protein
                            organism = synthetic construct
SEQUENCE: 12
DIVLTQSPTI MSASPGERVT MTCTASSSVN YIHWYQQKSG DSPLRWIFDT SKVASGVPAR  60
FSGSGSGTSY SLTISTMEAE DAATYYCQQW RSYPLTFGDG TRLELKRADA APTVS        115

SEQ ID NO: 13               moltype = AA  length = 118
FEATURE                     Location/Qualifiers
REGION                      1..118
                            note = source = /note="Description of Artificial Sequence:
                            Syntheticpolypeptide"
source                      1..118
                            mol_type = protein
                            organism = synthetic construct
SEQUENCE: 13
QVQLQQPGAE VVKPGASVKM SCKASGYTFT SYYIHWIKQT PGQGLEWVGV IYPGNDDISY  60
NQKFKGKATL TADKSSTTAY MQLSSLTSED SAVYYCAREV RLRYFDVWGA GTTVTVSS    118

SEQ ID NO: 14               moltype = AA  length = 113
FEATURE                     Location/Qualifiers
REGION                      1..113
                            note = source = /note="Description of Artificial Sequence:
                            Syntheticpolypeptide"
source                      1..113
                            mol_type = protein
                            organism = synthetic construct
SEQUENCE: 14
NIMLTQSPSS LAVSAGEKVT MSCKSSQSVF FSSSQKNYLA WYQQIPGQSP KLLIYWASTR  60
ESGVPDRFTG SGSGTDFTLT ISSVQSEDLA IYYCHQYLSS RTFGGGTKLE IKR         113

SEQ ID NO: 15               moltype = DNA  length = 66
FEATURE                     Location/Qualifiers
misc_feature                1..66
                            note = source = /note="Description of Artificial Sequence:
                            Syntheticoligonucleotide"
source                      1..66
                            mol_type = other DNA
                            organism = synthetic construct
SEQUENCE: 15
atgctgctgc tggtgaccag cctgctgctg tgtgagctgc cccacccgc ctttctgctg   60
atcccc                                                             66

SEQ ID NO: 16               moltype = AA  length = 22
FEATURE                     Location/Qualifiers
REGION                      1..22
                            note = source = /note="Description of Artificial Sequence:
                            Syntheticpeptide"
source                      1..22
                            mol_type = protein
                            organism = synthetic construct
SEQUENCE: 16
MLLLVTSLLL CELPHPAFLL IP                                            22

SEQ ID NO: 17               moltype = DNA  length = 84
FEATURE                     Location/Qualifiers
misc_feature                1..84
                            note = source = /note="Description of Artificial Sequence:
                            Syntheticoligonucleotide"
source                      1..84
                            mol_type = other DNA
                            organism = synthetic construct
SEQUENCE: 17
atctacatct gggccctct ggccggcacc tgtggcgtgc tgctgctgag cctggtcatc    60
accctgtact gcaaccaccg gaat                                         84

SEQ ID NO: 18               moltype = AA  length = 28
FEATURE                     Location/Qualifiers
REGION                      1..28
                            note = source = /note="Description of Artificial Sequence:
                            Syntheticpeptide"
source                      1..28
                            mol_type = protein
                            organism = synthetic construct
SEQUENCE: 18
IYIWAPLAGT CGVLLLSLVI TLYCNHRN                                      28

SEQ ID NO: 19               moltype = DNA  length = 81
```

-continued

```
FEATURE              Location/Qualifiers
misc_feature         1..81
                     note = source = /note="Description of Artificial Sequence:
                     Syntheticoligonucleotide"
source               1..81
                     mol_type = other DNA
                     organism = synthetic construct
SEQUENCE: 19
ttttgggtgc tggtggtggt tggtggagtc ctggcttgct atagcttgct agtaacagtg   60
gcctttatta ttttctgggt g                                             81

SEQ ID NO: 20        moltype = AA  length = 27
FEATURE              Location/Qualifiers
REGION               1..27
                     note = source = /note="Description of Artificial Sequence:
                     Syntheticpeptide"
source               1..27
                     mol_type = protein
                     organism = synthetic construct
SEQUENCE: 20
FWVLVVVGGV LACYSLLVTV AFIIFWV                                        27

SEQ ID NO: 21        moltype = DNA  length = 141
FEATURE              Location/Qualifiers
misc_feature         1..141
                     note = source = /note="Description of Artificial Sequence:
                     Syntheticpolynucleotide"
source               1..141
                     mol_type = other DNA
                     organism = synthetic construct
SEQUENCE: 21
aagcccacca ccacccctgc ccctagacct ccaaccccag cccctacaat cgccagccag   60
cccctgagcc tgaggcccga agcctgtaga cctgccgctg gcggagccgt gcacaccaga  120
ggcctggatt tcgcctgcga c                                            141

SEQ ID NO: 22        moltype = AA  length = 47
FEATURE              Location/Qualifiers
REGION               1..47
                     note = source = /note="Description of Artificial Sequence:
                     Syntheticpolypeptide"
source               1..47
                     mol_type = protein
                     organism = synthetic construct
SEQUENCE: 22
KPTTTPAPRP PTPAPTIASQ PLSLRPEACR PAAGGAVHTR GLDFACD                 47

SEQ ID NO: 23        moltype = DNA  length = 126
FEATURE              Location/Qualifiers
misc_feature         1..126
                     note = source = /note="Description of Artificial Sequence:
                     Syntheticpolynucleotide"
source               1..126
                     mol_type = other DNA
                     organism = synthetic construct
SEQUENCE: 23
aagagaggcc ggaagaaact gctgtacatc ttcaagcagc ccttcatgcg gcccgtgcag   60
accacccagg aagaggacgg ctgcagctgc cggttccccg aggaagagga aggcggctgc  120
gaactg                                                             126

SEQ ID NO: 24        moltype = AA  length = 42
FEATURE              Location/Qualifiers
REGION               1..42
                     note = source = /note="Description of Artificial Sequence:
                     Syntheticpolypeptide"
source               1..42
                     mol_type = protein
                     organism = synthetic construct
SEQUENCE: 24
KRGRKKLLYI FKQPFMRPVQ TTQEEDGCSC RFPEEEEGGC EL                      42

SEQ ID NO: 25        moltype = DNA  length = 336
FEATURE              Location/Qualifiers
misc_feature         1..336
                     note = source = /note="Description of Artificial Sequence:
                     Syntheticpolynucleotide"
source               1..336
                     mol_type = other DNA
                     organism = synthetic construct
SEQUENCE: 25
```

-continued

```
cgggtgaagt tcagccggag cgccgacgcc cctgcctacc agcagggcca gaaccagctg   60
tacaacgagc tgaacctggg ccggagggag gagtacgacg tgctggacaa gcggagaggc   120
cgggaccctg agatgggcgg caagccccgg agaaagaacc ctcaggaggg cctgtataac   180
gaactgcaga aagacaagat ggccgaggcc tacagcgaga tcggcatgaa gggcgagcgg   240
cggaggggca agggccacga cggcctgtac cagggcctga gcaccgccac caaggatacc   300
tacgacgccc tgcacatgca ggccctgccc cccaga                             336

SEQ ID NO: 26            moltype = AA  length = 112
FEATURE                  Location/Qualifiers
REGION                   1..112
                         note = source = /note="Description of Artificial Sequence:
                          Syntheticpolypeptide"
source                   1..112
                         mol_type = protein
                         organism = synthetic construct
SEQUENCE: 26
RVKFSRSADA PAYQQGQNQL YNELNLGRRE EYDVLDKRRG RDPEMGGKPR RKNPQEGLYN   60
ELQKDKMAEA YSEIGMKGER RRGKGHDGLY QGLSTATKDT YDALHMQALP PR          112

SEQ ID NO: 27            moltype = DNA  length = 123
FEATURE                  Location/Qualifiers
misc_feature             1..123
                         note = source = /note="Description of Artificial Sequence:
                          Syntheticpolynucleotide"
source                   1..123
                         mol_type = other DNA
                         organism = synthetic construct
SEQUENCE: 27
aggagcaagc ggagcagagg cggccacagc gactacatga acatgacccc ccggaggcct   60
ggccccaccc ggaagcacta ccagccctac gcccctccca gggacttcgc cgcctaccgg   120
agc                                                                 123

SEQ ID NO: 28            moltype = AA  length = 41
FEATURE                  Location/Qualifiers
REGION                   1..41
                         note = source = /note="Description of Artificial Sequence:
                          Syntheticpolypeptide"
source                   1..41
                         mol_type = protein
                         organism = synthetic construct
SEQUENCE: 28
RSKRSRGGHS DYMNMTPRRP GPTRKHYQPY APPRDFAAYR S                        41

SEQ ID NO: 29            moltype = DNA  length = 54
FEATURE                  Location/Qualifiers
source                   1..54
                         mol_type = other DNA
                         organism = Thosea asigna virus
SEQUENCE: 29
gagggcagag gaagtcttct aacatgcggt gacgtggagg agaatcccgg ccct          54

SEQ ID NO: 30            moltype = AA  length = 18
FEATURE                  Location/Qualifiers
source                   1..18
                         mol_type = protein
                         organism = Thosea asigna virus
SEQUENCE: 30
EGRGSLLTCG DVEENPGP                                                  18

SEQ ID NO: 31            moltype = DNA  length = 1005
FEATURE                  Location/Qualifiers
misc_feature             1..1005
                         note = source = /note="Description of Artificial Sequence:
                          Syntheticpolynucleotide"
source                   1..1005
                         mol_type = other DNA
                         organism = synthetic construct
SEQUENCE: 31
cgcaaagtgt gtaacggaat aggtattggt gaatttaaag actcactctc cataaatgct   60
acgaatatta aacacttcaa aaactgcacc tccatcagtg gcgatctcca catcctgccg   120
gtggcattta ggggtgactc cttcacacat actcctcctc tggatccaca ggaactggat   180
attctgaaaa ccgtaaagga aatcacaggg tttttgctga ttcaggcttg gcctgaaaac   240
aggacggacc tccatgcctt tgagaaccta gaaatcatac gcggcaggac caagcaacat   300
ggtcagtttt ctcttgcagt cgtcagcctg aacataacat ccttgggatt acgctccctc   360
aaggagataa gtgatggaga tgtgataatt tcaggaaaca aaaatttgtg ctatgcaaat   420
acaataaact ggaaaaaact gtttgggacc tccggtcaga aaaccaaaat tataagcaac   480
agaggtgaaa acagctgcaa ggccacaggc caggtctgcc atgccttgtg ctcccccgag   540
ggctgctggg gccggagcc cagggactgc gtctcttgcc ggaatgtcag ccgaggcagg   600
gaatgcgtgg acaagtgcaa ccttctggag ggtgagccaa gggagtttgt ggagaactct   660
```

```
gagtgcatac agtgccaccc agagtgcctg cctcaggcca tgaacatcac ctgcacagga  720
cggggaccag acaactgtat ccagtgtgcc cactacattg acggccccca ctgcgtcaag  780
acctgcccgg caggagtcat gggagaaaac aacaccctgg tctggaagta cgcagacgcc  840
ggccatgtgt gccacctgtg ccatccaaac tgcacctacg gatgcactgg gccaggtctt  900
gaaggctgtc caacgaatgg gcctaagatc ccgtccatcg ccactgggat ggtgggggcc  960
ctcctcttgc tgctggtggt ggccctgggg atcggcctct tcatg        1005

SEQ ID NO: 32            moltype = AA  length = 335
FEATURE                  Location/Qualifiers
REGION                   1..335
                         note = source = /note="Description of Artificial Sequence:
                          Syntheticpolypeptide"
source                   1..335
                         mol_type = protein
                         organism = synthetic construct
SEQUENCE: 32
RKVCNGIGIG EFKDSLSINA TNIKHFKNCT SISGDLHILP VAFRGDSFTH TPPLDPQELD  60
ILKTVKEITG FLLIQAWPEN RTDLHAFENL EIIRGRTKQH GQFSLAVVSL NITSLGLRSL  120
KEISDGDVII SGNKNLCYAN TINWKKLFGT SGQKTKIISN RGENSCKATG QVCHALCSPE  180
GCWGPEPRDC VSCRNVSRGR ECVDKCNLLE GEPREFVENS ECIQCHPECL PQAMNITCTG  240
RGPDNCIQCA HYIDGPHCVK TCPAGVMGEN NTLVWKYADA GHVCHLCHPN CTYGCTGPGL  300
EGCPTNGPKI PSIATGMVGA LLLLLVVALG IGLFM                           335

SEQ ID NO: 33            moltype = DNA  length = 60
FEATURE                  Location/Qualifiers
misc_feature             1..60
                         note = source = /note="Description of Artificial Sequence:
                          Syntheticoligonucleotide"
source                   1..60
                         mol_type = other DNA
                         organism = synthetic construct
SEQUENCE: 33
atgaggctcc ctgctcagct cctggggctg ctaatgctct gggtcccagg atccagtggg  60

SEQ ID NO: 34            moltype = AA  length = 20
FEATURE                  Location/Qualifiers
REGION                   1..20
                         note = source = /note="Description of Artificial Sequence:
                          Syntheticpeptide"
source                   1..20
                         mol_type = protein
                         organism = synthetic construct
SEQUENCE: 34
MRLPAQLLGL LMLWVPGSSG                                            20

SEQ ID NO: 35            moltype = DNA  length = 891
FEATURE                  Location/Qualifiers
misc_feature             1..891
                         note = source = /note="Description of Artificial Sequence:
                          Syntheticpolynucleotide"
source                   1..891
                         mol_type = other DNA
                         organism = synthetic construct
SEQUENCE: 35
atgacaacac ccagaaattc agtaaatggg actttcccgg cagagccaat gaaaggccct  60
attgctatgc aatctggtcc aaaaccactc ttcaggagga tgtcttcact ggtgggcccc  120
acgcaaagct tcttcatgag ggaatctaag actttggggg ctgtccagat tatgaatggg  180
ctcttccaca ttgccctggg gggtcttctg atgatcccag cagggatcta tgcacccatc  240
tgtgtgactg tgtggtaccc tctctgggga ggcattatgt atattatttc cggatcactc  300
ctggcagcaa cggagaaaaa ctccaggaag tgtttggtca aaggaaaaat gataatgaat  360
tcattgagcc tctttgctgc catttctgga atgattcttt caatcatgga catacttaat  420
attaaaattt cccattttt aaaaatggag agtctgaatt ttattagagc tcacacacca  480
tatattaaca tatacaactg tgaaccagct aatccctctg agaaaaactc cccatctacc  540
caatactgtt acagcataca atctctgttc ttgggcattt tgtcagtgat gctgatcttt  600
gccttcttcc aggaacttgt aatagctggc atcgttgaga tgaatggaa aagaacgtgc  660
tccagaccca aatctaacat agttctcctg tcagcagaag aaaaaaaaga acagactatt  720
gaaataaaag aagaagtggt tgggctaact gaaacatctt cccaaccaaa gaatgaagaa  780
gacattgaaa ttattccaat ccaagaagag gaagaagaag aaacagagac gaactttcca  840
gaacctcccc aagatcagga atcctcacca atagaaaatg acagctctcc t         891

SEQ ID NO: 36            moltype = AA  length = 297
FEATURE                  Location/Qualifiers
REGION                   1..297
                         note = source = /note="Description of Artificial Sequence:
                          Syntheticpolypeptide"
source                   1..297
                         mol_type = protein
                         organism = synthetic construct
SEQUENCE: 36
```

```
MTTPRNSVNG TFPAEPMKGP IAMQSGPKPL FRRMSSLVGP TQSFFMRESK TLGAVQIMNG  60
LFHIALGGLL MIPAGIYAPI CVTVWYPLWG GIMYIISGSL LAATEKNSRK CLVKGKMIMN  120
SLSLFAAISG MILSIMDILN IKISHFLKME SLNFIRAHTP YINIYNCEPA NPSEKNSPST  180
QYCYSIQSLF LGILSVMLIF AFFQELVIAG IVENEWKRTC SRPKSNIVLL SAEEKKEQTI  240
EIKEEVVGLT ETSSQPKNEE DIEIIPIQEE EEEETETNFP EPPQDQESSP IENDSSP     297

SEQ ID NO: 37          moltype = AA  length = 395
FEATURE                Location/Qualifiers
REGION                 1..395
                       note = source = /note="Description of Artificial Sequence:
                       Syntheticpolypeptide"
source                 1..395
                       mol_type = protein
                       organism = synthetic construct
SEQUENCE: 37
MDWTWILFLV AAATRVHSNW VNVISDLKKI EDLIQSMHID ATLYTESDVH PSCKVTAMKC  60
FLLELQVISL ESGDASIHDT VENLIILANN SLSSNGNVTE SGCKECEELE EKNIKEFLQS  120
FVHIVQMFIN TSSGGGSGGG GSGGGGSGGG GSGGGSLQIT CPPPMSVEHA DIWVKSYSLY  180
SRERYICNSG FKRKAGTSSL TECVLNKATN VAHWTTPSLK CIRDPALVHQ RPAPPSTVTT  240
AGVTPQPESL SPSGKEPAAS SPSSNNTAAT TAAIVPGSQL MPSKSPSTGT TEISSHESSH  300
GTPSQTTAKN WELTASASHQ PPGVYPQGHS DTTVAISTST VLLCGLSAVS LLACYLKSRQ  360
TPPLASVEME AMEALPVTWG TSSRDEDLEN CSHHL                            395

SEQ ID NO: 38          moltype = DNA  length = 1476
FEATURE                Location/Qualifiers
misc_feature           1..1476
                       note = source = /note="Description of Artificial Sequence:
                       Syntheticpolynucleotide"
source                 1..1476
                       mol_type = other DNA
                       organism = synthetic construct
SEQUENCE: 38
atgctgctgc tggtgaccag cctgctgctg tgtgagctgc cccaccccgc ctttctgctg  60
atccccgaca ttcagatgac ccagtctccg agctctctgt ccgcatcagt aggagacagg  120
gtcaccatca catgcagagc cagcgaaagt gtcgacaatt atggcattag ctttatgaac  180
tggttccaac agaaacccgg gaaggctcct aagcttctga tttacgctgc atccaaccaa  240
ggctccgggg taccctctcg cttctcaggc agtggatctg ggacagactt cactctcacc  300
atttcatctc tgcagcctga tgacttcgca acctattact gtcagcaaag taaggaggtt  360
ccgtggacgt tcggtcaagg gaccaaggtg gagatcaaag gtggcggtag ctcgggcgtt  420
ggtgggtcgg gtggcggcgg atctcaggtt cagctggtgc agtctggagc tgaggtgaag  480
aagcctggga gctcagtgaa ggtttcctgc aaagcttctg gctacacctt cactgactac  540
aacatgcact gggtgaggca ggctcctggc caaggcctgg aatggattgg atatatttat  600
ccttacaatg gtggtaccgg ctacaaccag aagttcaaga aggccgccac aattacagca  660
gacgagagta ctaacacagc ctacatggaa ctctccagcc tgaggtctga ggacactgca  720
gtctattact gcgcaagagg gcgcccgct atggactact ggggccaagg gactctggtc  780
actgtctctt caaagcccac caccaccctg cccctagac tccaacccc agcccctaca  840
atcgccagcc agccctgag cctgaggccc gaagcctgca gacctgcgc tggcggagcc  900
gtgcacacca gaggcctgga tttcgcctgc gacatctaca tctggcccc tctggccggc  960
acctgtggcg tgctgctgct gagcctggtc atcaccctgt actgcaacca ccggaatagg  1020
agcaagcgga gcagaggcgg ccacagcgac tacatgaaca tgacccccg gaggcctggc  1080
cccaccgga agcactacca gcctacgcc cctcccaggg acttcgccgc ctaccggagc  1140
cgggtgaagt tcagccggag cgccgacgcc cctgcctacc agcagggcca gaaccagctg  1200
tacaacgagc tgaacctggg ccggaggag gagtacgacg tgctggacaa gcggagaggc  1260
cgggaccctg agatgggcgg caagcccgg agaaagaacc ctcaggaggg cctgtataac  1320
gaactgcaga aagacaagat ggccgaggcc tacagcgaga tcggcatgaa gggcgagcgg  1380
cggaggggca agggccacga cggcctgtac cagggcctga gcaccgccac caaggatacc  1440
tacgacgccc tgcacatgca ggccctgccc cccaga                          1476

SEQ ID NO: 39          moltype = AA  length = 492
FEATURE                Location/Qualifiers
REGION                 1..492
                       note = source = /note="Description of Artificial Sequence:
                       Syntheticpolypeptide"
source                 1..492
                       mol_type = protein
                       organism = synthetic construct
SEQUENCE: 39
MLLLVTSLLL CELPHPAFLL IPDIQMTQSP SSLSASVGDR VTITCRASES VDNYGISFMN  60
WFQQKPGKAP KLLIYAASNQ GSGVPSRFSG SGSGTDFTLT ISSLQPDDFA TYYCQQSKEV  120
PWTFGQGTKV EIKGGGGSGG GGSGGGGSQV QLVQSGAEVK KPGSSVKVSC KASGYTFTDY  180
NMHWVRQAPG QGLEWIGYIY PYNGGTGYNQ KFKSKATITA DESTNTAYME LSSLRSEDTA  240
VYYCARGRPA MDYWGQGTLV TVSSKPTTTP APRPPTPAPT IASQPLSLRP EACRPAAGGA  300
VHTRGLDFAC DIYIWAPLAG TCGVLLLSLV ITLYCNHRNR SKRSRGGHSD YMNMTPRRPG  360
PTRKHYQPYA PPRDFAAYRS RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                    492

SEQ ID NO: 40          moltype = DNA  length = 1353
FEATURE                Location/Qualifiers
```

```
misc_feature          1..1353
                      note = source = /note="Description of Artificial Sequence:
                      Syntheticpolynucleotide"
source                1..1353
                      mol_type = other DNA
                      organism = synthetic construct
SEQUENCE: 40
atgctgctgc tggtgaccag cctgctgctg tgtgagctgc cccacccccgc ctttctgctg   60
atccccgaca ttcagatgac ccagtctccg agctctctgt ccgcatcagt aggagacagg  120
gtcaccatca catgcagagc cagcgaaagt gtcgacaatt atggcattag ctttatgaac  180
tggttccaac agaaacccgg gaaggctcct aagcttctga tttacgctgc atccaaccaa  240
ggctccgggg tacctctcg cttctcaggc agtggatctg ggacagactt cactctcacc  300
atttcatctc tgcagcctga tgacttcgca acctattact gtcagcaaag taaggaggtt  360
ccgtggacgt tcggtcaagg gaccaaggtg gagatcaaag gtggcggtgg ctcgggcggt  420
ggtgggtcgg gtggcggcgg atctcaggtt cagctggtgc agtctggagc tgaggtgaag  480
aagcctggga gctcagtgaa ggtttcctgc aaagcttctg gctacacctt cactgactac  540
aacatgcact gggtgaggca ggctcctggc caaggcctgg aatggattgg atatatttat  600
ccttacaatg gtggtaccgg ctacaaccag aagttcaaga gcaaggccac aattacagca  660
gacgagagta ctaacacagc ctacatggaa ctctccagcc tgaggtctga ggacactgca  720
gtctattact gcgcaagagg gcgcccccgct atggactact ggggccaagg gactctggtc  780
actgtctctt caaagcccac caccacccct gcccctagac tccaacccc agcccctaca  840
atcgccagcc agccctgag cctgaggccc gaagcctgta gacctgccgc tggcggagcc  900
gtgcacacca gaggcctgga tttcgcctgc gacatctaca tctgggcccc tctggccggc  960
acctgtggcg tgctgctgct gagcctggtc atcaccctgt actgcaacca ccggaatcgg 1020
gtgaagttca gccggagcgc cgacgcccct gcctaccagc agggccagaa ccagctgtac 1080
aacgagctga acctgggccg gagggaggag tacgacgtgc tggacaagcg gagaggccgg 1140
gaccctgaga tgggcggcaa gccccggaga aagaaccctc aggagggcct gtataacgaa 1200
ctgcagaaag acaagatggc cgaggcctac agcgagatcg gcatgaaggg cgagcggcgg 1260
aggggcaagg gccacgacgg cctgtaccag ggcctgagca ccgccaccaa ggataccac 1320
gacgccctgc acatgcaggc cctgcccccc aga                             1353

SEQ ID NO: 41           moltype = AA   length = 451
FEATURE                 Location/Qualifiers
REGION                  1..451
                        note = source = /note="Description of Artificial Sequence:
                        Syntheticpolypeptide"
source                  1..451
                        mol_type = protein
                        organism = synthetic construct
SEQUENCE: 41
MLLLVTSLLL CELPHPAFLL IPDIQMTQSP SSLSASVGDR VTITCRASES VDNYGISFMN   60
WFQQKPGKAP KLLIYAASNQ GSGVPSRFSG SGSGTDFTLT ISSLQPDDFA TYYCQQSKEV  120
PWTFGQGTKV EIKGGGGSGG GGSGGGGSQV QLVQSGAEVK KPGSSVKVSC KASGYTFTDY  180
NMHWVRQAPG QGLEWIGYIY PYNGGTGYNQ KFKSKATITA DESTNTAYME LSSLRSEDTA  240
VYYCARGRPA MDYWGQGTLV TVSSKPTTTP APRPPTPAPT IASQPLSLRP EACRPAAGGA  300
VHTRGLDFAC DIYIWAPLAG TCGVLLLSLV ITLYCNHRNR VKFSRSADAP AYQQGQNQLY  360
NELNLGRREE YDVLDKRRGR DPEMGGKPRR KNPQEGLYNE LQKDKMAEAY SEIGMKGERR  420
RGKGHDGLYQ GLSTATKDTY DALHMQALPP R                               451

SEQ ID NO: 42           moltype = DNA   length = 2619
FEATURE                 Location/Qualifiers
misc_feature            1..2619
                        note = source = /note="Description of Artificial Sequence:
                        Syntheticpolynucleotide"
source                  1..2619
                        mol_type = other DNA
                        organism = synthetic construct
SEQUENCE: 42
atgctgctgc tggtgaccag cctgctgctg tgtgagctgc cccacccccgc ctttctgctg   60
atccccgaca ttcagatgac ccagtctccg agctctctgt ccgcatcagt aggagacagg  120
gtcaccatca catgcagagc cagcgaaagt gtcgacaatt atggcattag ctttatgaac  180
tggttccaac agaaacccgg gaaggctcct aagcttctga tttacgctgc atccaaccaa  240
ggctccgggg tacctctcg cttctcaggc agtggatctg ggacagactt cactctcacc  300
atttcatctc tgcagcctga tgacttcgca acctattact gtcagcaaag taaggaggtt  360
ccgtggacgt tcggtcaagg gaccaaggtg gagatcaaag gtggcggtgg ctcgggcggt  420
ggtgggtcgg gtggcggcgg atctcaggtt cagctggtgc agtctggagc tgaggtgaag  480
aagcctggga gctcagtgaa ggtttcctgc aaagcttctg gctacacctt cactgactac  540
aacatgcact gggtgaggca ggctcctggc caaggcctgg aatggattgg atatatttat  600
ccttacaatg gtggtaccgg ctacaaccag aagttcaaga gcaaggccac aattacagca  660
gacgagagta ctaacacagc ctacatggaa ctctccagcc tgaggtctga ggacactgca  720
gtctattact gcgcaagagg gcgcccccgct atggactact ggggccaagg gactctggtc  780
actgtctctt caaagcccac caccacccct gcccctagac tccaacccc agcccctaca  840
atcgccagcc agccctgag cctgaggccc gaagcctgta gacctgccgc tggcggagcc  900
gtgcacacca gaggcctgga tttcgcctgc gacatctaca tctgggcccc tctggccggc  960
acctgtggcg tgctgctgct gagcctggtc atcaccctgt actgcaacca ccggaatagg 1020
agcaagcgga gcagaggcgg ccacagcgac tacatgaaca tgacccccg gaggcctggc 1080
cccaccggaa gcactacca gccctacgcc cctcccaggg acttcgccgc ctaccggagc 1140
cgggtgaagt tcagccggag cgccgacgcc cctgcctacc agcagggcca gaaccagctg 1200
tacaacgagc tgaacctggg ccggagggag gagtacgacg tgctggacaa gcggagaggc 1260
```

```
cgggaccctg agatgggcgg caagccccgg agaaagaacc ctcaggaggg cctgtataac  1320
gaactgcaga aagacaagat ggccgaggcc tacagcgaga tcggcatgaa gggcgagcgg  1380
cggaggggca agggccacga cggcctgtac cagggcctga gcaccgccac caaggatacc  1440
tacgacgccc tgcacatgca ggccctgccc cccagactcg agggcggcgg agagggcaga  1500
ggaagtcttc taacatgcgg tgacgtggag gagaatcccg gccctaggat gcttctcctg  1560
gtgacaagcc ttctgctctg tgagttacca cacccagcat tcctcctgat cccacgcaaa  1620
gtgtgtaacg gaataggtat tggtgaattt aaagactcac tctccataaa tgctacgaat  1680
attaaacact tcaaaaactg cacctccatc agtggcgatc tccacatcct gccggtggca  1740
tttaggggtg actccttcac acatactcct cctctggatc cacaggaact ggatattctg  1800
aaaaccgtaa aggaaatcac aggggttttg ctgattcagg cttggcctga aaacaggacg  1860
gacctccatg cctttgagaa cctagaaatc atacgcggca ggaccaagca acatggtcag  1920
ttttctcttg cagtcgtcag cctgaacata acatccttgg gattacgctc cctcaaggag  1980
ataagtgatg gagatgtgat aatttcagga aacaaaaatt tgtgctatgc aaatacaata  2040
aactggaaaa aactgtttgg gacctccggt cagaaaacca aaattataag caacagaggt  2100
gaaaacagct gcaaggccac aggccaggtc tgccatgcct tgtgctcccc cgagggctgc  2160
tggggccgg  agcccaggga ctgcgtctct tgccggaatg tcagccgagg cagggaatgc  2220
gtggacaagt gcaaccttct ggagggtgag ccaagggagt tgtgtgagaa ctctgagtgc  2280
atacagtgcc acccagagtg cctgcctcag gccatgaaca tcacctgcac aggacgggga  2340
ccagacaact gtatccagtg tgcccactac attgacgacc cccactgcgt caagacctgc  2400
ccggcaggag tcatgggaga aaacaacacc ctggtctgga gtacgcaga cgccggccat  2460
gtgtgccacc tgtgccatcc aaactgcacc tacgatgca ctgggccagg tcttgaaggc  2520
tgtccaacga atgggcctaa gatcccgtcc atcgccactg ggatggtggg ggccctcctc  2580
ttgctgctgg tggtggccct ggggatcggc ctcttcatg                        2619
```

```
SEQ ID NO: 43            moltype = AA  length = 873
FEATURE                  Location/Qualifiers
REGION                   1..873
                         note = source = /note="Description of Artificial Sequence:
                         Syntheticpolypeptide"
source                   1..873
                         mol_type = protein
                         organism = synthetic construct
SEQUENCE: 43
MLLLVTSLLL CELPHPAFLL IPDIQMTQSP SSLSASVGDR VTITCRASES VDNYGISFMN   60
WFQQKPGKAP KLLIYAASNQ GSGVPSRFSG SGSGTDFTLT ISSLQPDDFA TYYCQQSKEV  120
PWTFGQGTKV EIKGGGGSGG GGSGGGGSQV QLVQSGAEVK KPGSSVKVSC KASGYTFTDY  180
NMHWVRQAPG QGLEWIGYIY PYNGGTGYNQ KFKSKATITA DESTNTAYME LSSLRSEDTA  240
VYYCARGRPA MDYWGQGTLV TVSSKPTTTP APRPPTPAPT IASQPLSLRP EACRPAAGGA  300
VHTRGLDFAC DIYIWAPLAG TCGVLLLSLV ITLYCNHRNR SKRSRGGHSD YMNMTPRRPG  360
PTRKHYQPYA PPRDFAAYRS RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PRLEGGGEGR GSLLTCGDVE ENPGPRMLLL VTSLLLCELP HPAFLLIPRK  540
VCNGIGIGEF KDSLSINATN IKHFKNCTSI SGDLHILPVA FRGDSFTHTP PLDPQELDIL  600
KTVKEITGFL LIQAWPENRT DLHAFENLEI IRGRTKQHGQ FSLAVVSLNI TSLGLRSLKE  660
ISDGDVIISG NKNLCYANTI NWKKLFGTSG QKTKIISNRG ENSCKATGQV CHALCSPEGC  720
WGPEPRDCVS CRNVSRGREC VDKCNLLEGE PREFVENSEC IQCHPECLPQ AMNITCTGRG  780
PDNCIQCAHY IDGPHCVKTC PAGVMGENNT LVWKYADAGH VCHLCHPNCT YGCTGPGLEG  840
CPTNGPKIPS IATGMVGALL LLLVVALGIG LFM                               873
```

```
SEQ ID NO: 44            moltype = DNA  length = 792
FEATURE                  Location/Qualifiers
misc_feature             1..792
                         note = source = /note="Description of Artificial Sequence:
                         Syntheticpolynucleotide"
source                   1..792
                         mol_type = other DNA
                         organism = synthetic construct
SEQUENCE: 44
atgctgctgc tggtgaccag cctgctgctg tgtgagctgc cccacccgc ctttctgctg   60
atccccgaca ttcagatgac ccagtctccg agctctctgt ccgcatcagt aggagacagg  120
gtcaccatca catgcagagc cagcgaaagt gtcgacaatt atggcattag ctttatgaac  180
tggttccaac agaaacccgg gaaggctcct aagcttctga tttacgctgc atccaaccaa  240
ggctccgggg taccctctcg cttctcaggc agtggatctg ggacagactt cactctcacc  300
atttcatctc tgcagcctga tgacttcgca acctattact gtcagcaaag taaggaggtt  360
ccgtggacgt tcggtcaagg gaccaaggtg gagatcaaag gtggcggtgg ctcgggcggt  420
ggtgggtcgg gtggcggcgg atctcaggtt cagctggtgc agtctggagc tgaggtgaag  480
aagcctggga gctcagtgaa ggtttcctgc aaagcttctg ctacacctt cactgactac  540
aacatgcact gggtgaggca ggctcctggc caaggcctgg aatggattgg atatatttat  600
ccttacaatg gtggtaccgg ctacaaccag aagttcaaga gcaaggccac aattacagca  660
gacgagagta ctaacacagc ctacatggaa ctctccagcc tgaggtctga ggacactgca  720
gtctattact gcgcaagagg cgcccccgct atggactact ggggccaagg gactctggtc  780
actgtctctt ca                                                      792
```

```
SEQ ID NO: 45            moltype = AA  length = 264
FEATURE                  Location/Qualifiers
REGION                   1..264
                         note = source = /note="Description of Artificial Sequence:
                         Syntheticpolypeptide"
source                   1..264
```

```
                         mol_type = protein
                         organism = synthetic construct
SEQUENCE: 45
MLLLVTSLLL CELPHPAFLL IPDIQMTQSP SSLSASVGDR VTITCRASES VDNYGISFMN    60
WFQQKPGKAP KLLIYAASNQ GSGVPSRFSG SGSGTDFTLT ISSLQPDDFA TYYCQQSKEV   120
PWTFGQGTKV EIKGGGGSGG GGSGGGGSQV QLVQSGAEVK KPGSSVKVSC KASGYTFTDY   180
NMHWVRQAPG QGLEWIGYIY PYNGGTGYNQ KFKSKATITA DESTNTAYME LSSLRSEDTA   240
VYYCARGRPA MDYWGQGTLV TVSS                                          264

SEQ ID NO: 46            moltype = DNA   length = 1479
FEATURE                  Location/Qualifiers
misc_feature             1..1479
                         note = source = /note="Description of Artificial Sequence:
                          Syntheticpolynucleotide"
source                   1..1479
                         mol_type = other DNA
                         organism = synthetic construct
SEQUENCE: 46
atgctgctgc tggtgaccag cctgctgctg tgtgagctgc cccacccgc ctttctgctg     60
atccccgaca ttcagatgac ccagtctccg agctctctgt ccgcatcagt aggagacagg   120
gtcaccatca catgcagagc cagcgaaagt gtcgacaatt atggcattag ctttatgaac   180
tggttccaac agaaacccgg gaaggctcct aagcttctga tttacgctgc atccaaccaa   240
ggctccgggg tacctctcg cttctcaggc agtggatctg ggacagactt cactctcacc    300
atttcatctc tgcagcctga tgacttcgca acctattact gtcagcaaag taaggaggtt   360
ccgtggacgt tcggtcaagg gaccaaggtg gagatcaaag gtggcggtgg ctcgggcggt   420
ggtgggtcgg gtggcggcgg atctcaggtt cagctggtgc agtctggagc tgaggtgaag   480
aagcctggga gctcagtgaa ggtttcctgc aaagcttctg gctacacctt cactgactac   540
aacatgcact gggtgaggca ggctcctggc caaggcctgg aatggattgg atatatttat   600
ccttacaatg gtggtaccgg ctacaaccag aagttcaaga gcaaggccac aattacagca   660
gacgagagta ctaacacagc ctacatggaa ctctccagcc tgaggtctga ggacactgca   720
gtctattact gcgcaagagg gcgccccgct atggactact ggggccaagg gactctggtc   780
actgtctctt caaagcccac caccacccct gccctagac ctccaacccc agcccctaca    840
atcgccagcc agcccctgag cctgaggccc gaagcctgta gacctgccgc tggcggagcc   900
gtgcacacca gaggcctgga tttcgcctgc gacatctaca tctgggcccc tctggccggc   960
acctgtggcg tgctgctgct gagcctggtc atcacctgt actgcaacca ccggaataag  1020
agaggccgga gaaactgct gtacatcttc aagcagccct tcatgcggcc cgtgcagacc  1080
acccaggaag aggacggctg cagctgccgg ttccccgagg aagaggaagg cggctgcgaa  1140
ctgcgggtga agttcagccg gagcgccgac gcccctgcct accagcaggg ccagaaccag  1200
ctgtacaacg agctgaacct gggccggagg gaggagtacg acgtgctgga caagcggaga  1260
ggccgggacc ctgagatggg cggcaagccc cggagaaaga accctcagga gggcctgtat  1320
aacgaactgc agaaagacaa gatggccgag gcctacagcg agatcggcat gaagggcgag  1380
cggcggaggg gcaagggcca cgacggcctg taccagggcc tgagcaccgc caccaaggat  1440
acctacgacg ccctgcacat gcaggccctg cccccaga                          1479

SEQ ID NO: 47            moltype = AA   length = 493
FEATURE                  Location/Qualifiers
REGION                   1..493
                         note = source = /note="Description of Artificial Sequence:
                          Syntheticpolypeptide"
source                   1..493
                         mol_type = protein
                         organism = synthetic construct
SEQUENCE: 47
MLLLVTSLLL CELPHPAFLL IPDIQMTQSP SSLSASVGDR VTITCRASES VDNYGISFMN    60
WFQQKPGKAP KLLIYAASNQ GSGVPSRFSG SGSGTDFTLT ISSLQPDDFA TYYCQQSKEV   120
PWTFGQGTKV EIKGGGGSGG GGSGGGGSQV QLVQSGAEVK KPGSSVKVSC KASGYTFTDY   180
NMHWVRQAPG QGLEWIGYIY PYNGGTGYNQ KFKSKATITA DESTNTAYME LSSLRSEDTA   240
VYYCARGRPA MDYWGQGTLV TVSSKPTTTP APRPPTPAPT IASQPLSLRP EACRPAAGGA   300
VHTRGLDFAC DIYIWAPLAG TCGVLLLSLV ITLYCNHRNK RGRKKLLYIF KQPFMRPVQT   360
TQEEDGCSCR FPEEEEGGCE LRVKFSRSAD APAYQQGQNQ LYNELNLGRR EEYDVLDKRR   420
GRDPEMGGKP RRKNPQEGLY NELQKDKMAE AYSEIGMKGE RRRGKGHDGL YQGLSTATKD   480
TYDALHMQAL PPR                                                      493

SEQ ID NO: 48            moltype = DNA   length = 2622
FEATURE                  Location/Qualifiers
misc_feature             1..2622
                         note = source = /note="Description of Artificial Sequence:
                          Syntheticpolynucleotide"
source                   1..2622
                         mol_type = other DNA
                         organism = synthetic construct
SEQUENCE: 48
atgctgctgc tggtgaccag cctgctgctg tgtgagctgc cccacccgc ctttctgctg     60
atccccgaca ttcagatgac ccagtctccg agctctctgt ccgcatcagt aggagacagg   120
gtcaccatca catgcagagc cagcgaaagt gtcgacaatt atggcattag ctttatgaac   180
tggttccaac agaaacccgg gaaggctcct aagcttctga tttacgctgc atccaaccaa   240
ggctccgggg tacctctcg cttctcaggc agtggatctg ggacagactt cactctcacc    300
atttcatctc tgcagcctga tgacttcgca acctattact gtcagcaaag taaggaggtt   360
ccgtggacgt tcggtcaagg gaccaaggtg gagatcaaag gtggcggtgg ctcgggcggt   420
```

-continued

```
ggtgggtcgg gtggcggcgg atctcaggtt cagctggtgc agtctggagc tgaggtgaag    480
aagcctggga gctcagtgaa ggtttcctgc aaagcttctg gctacacctt cactgactac    540
aacatgcact gggtgaggca ggctcctggc caaggcctgg aatggattgg atatatttat    600
ccttacaatg gtggtaccgg ctacaaccag aagttcaaga gcaaggccac aattacagca    660
gacgagagta ctaacacagc ctacatggaa ctctccagcc tgaggtctga ggacactgca    720
gtctattact gcgcaagagg cgcccccgct atggactact ggggccaagg gactctggtc    780
actgtctctt caaagcccac caccacccct gcccctagac ctccaacccc agcccctaca    840
atcgccagcc agcccctgag cctgaggccc gaagcctgta gacctgccgc tggcggagcc    900
gtgcacacca gaggcctgga tttcgcctgc gacatctaca tctgggcccc tctggccggc    960
acctgtggcg tgctgctgct gagcctggtc atcacctgt actgcaacca ccggaataag   1020
agaggccgga agaaactgct gtacatcttc aagcagccct catcgcggcc cgtgcagacc   1080
acccaggaag aggacggctg cagctgccgg ttccccgagg aagaggaagg cggctgcgaa   1140
ctgcgggtga agttcagccg gagcgccgac gcccctgcct accagcaggg ccagaaccag   1200
ctgtacaacg agctgaacct gggccggagc gaggagtacg acgtgctgga caagcggaga   1260
ggccgggacc ctgagatggg cggcaagccc cggagaaaga accctcagga gggcctgtat   1320
aacgaactgc agaaagacaa gatggccgag gcctacagcg agatcggcat gaagggcgag   1380
cggcggaggg gcaagggcca cgacggcctg taccagggct gagcaccgc caccaaggat   1440
acctacgacg ccctgcacat gcaggccctg ccccccaagc tcgaggggcg cggagaggc    1500
agaggaagtc ttctaacatg cggtgacgtg gaggagaatc ccggccctag gatgcttctc   1560
ctggtgacaa gccttctgct ctgtgagtta ccacacccag cattcctcct gatcccacgc   1620
aaagtgtgta acggaatagg tattggtgaa tttaaagact cactctccat aaatgctacg   1680
aatattaaac acttcaaaaa ctgcacctcc atcagtggcg atctccacat cctgccggtg   1740
gcatttaggg gtgactcctt cacacatact cctcctctgg atccacagga actggatatt   1800
ctgaaaaccg taaggaaat cacagggttt ttgctgattc aggcttggcc tgaaaacagg   1860
acggacctcc atgcctttga gaacctagaa atcatacgcg gcaggaccaa gcaacatggt   1920
cagttttctc ttgcagtcgt cagcctgaac ataacatct tgggattacg ctccctcaag   1980
gagataagtg atggagatgt gataatttca ggaaacaaaa atttgtgcta tgcaaataca   2040
ataaactgga aaaaactgtt tgggacctcc ggtcagaaaa ccaaaattat aagcaacaga   2100
ggtgaaaaca gctgcaaggc cacaggccag gtctgccatg ccttgtgctc ccccgagggc   2160
tgctggggcc cggagcccag ggactgcgtc tcttgccgga atgtcagccg aggcagggaa   2220
tgcgtggaca agtgcaacct tctggagggt gagccaaggg agtttgtgga gaactctgag   2280
tgcatacagt gccacccaga gtgcctgcct caggccatga acatcacctg cacaggacgg   2340
ggaccagaca actgtatcca gtgtgcccac tacattgacg gcccccactg cgtcaagacc   2400
tgcccggcag gagtcatggg agaaaacaac accctggtct ggaagtacgc agacgccggc   2460
catgtgtgcc acctgtgcca tccaaactgc acctacggat gcactgggcc aggtcttgaa   2520
ggctgtccaa cgaatgggcc taagatcccg tccatcgcca ctgggatggt gggggccctc   2580
ctcttgctgc tggtggtggc cctggggatc ggcctcttca tg                      2622
```

```
SEQ ID NO: 49          moltype = AA   length = 874
FEATURE                Location/Qualifiers
REGION                 1..874
                       note = source = /note="Description of Artificial Sequence:
                       Syntheticpolypeptide"
source                 1..874
                       mol_type = protein
                       organism = synthetic construct
SEQUENCE: 49
MLLLVTSLLL CELPHPAFLL IPDIQMTQSP SSLSASVGDR VTITCRASES VDNYGISFMN    60
WFQQKPGKAP KLLIYAASNQ GSGVPSRFSG SGSGTDFTLT ISSLQPDDFA TYYCQQSKEV   120
PWTFGQGTKV EIKGGGGSGG GGSGGGGSQV QLVQSGAEVK KPGSSVKVSC KASGYTFTDY   180
NMHWVRQAPG QGLEWIGYIY PYNGGTGYNQ KFKSKATITA DESTNTAYME LSSLRSEDTA   240
VYYCARGRPA MDYWGQGTLV TVSSKPTTTP APRPPTPAPT IASQPLSLRP EACRPAAGGA   300
VHTRGLDFAC DIYIWAPLAG TCGVLLLSLV ITLYCNHRNK RGRKKLLYIF KQPFMRPVQT   360
TQEEDGCSCR FPEEEEGGCE LRVKFSRSAD APAYQQGQNQ LYNELNLGRR EEYDVLDKRR   420
GRDPEMGGKP RRKNPQEGLY NELQKDKMAE AYSEIGMKGE RRRGKGHDGL YQGLSTATKD   480
TYDALHMQAL PPRLEGGGEG RGSLLTCGDV EENPGPRMLL LVTSLLLCEL PHPAFLLIPR   540
KVCNGIGIGE FKDSLSINAT NIKHFKNCTS ISGDLHILPV AFRGDSFTHT PPLDPQELDI   600
LKTVKEITGF LLIQAWPENR TDLHAFENLE IIRGRTKQHG QFSLAVVSLN ITSLGLRSLK   660
EISDGDVIIS GNKNLCYANT INWKKLFGTS GQKTKIISNR GENSCKATGQ VCHALCSPEG   720
CWGPEPRDCV SCRNVSRGRE CVDKCNLLEG EPREFVENSE CIQCHPECLP QAMNITCTGR   780
GPDNCIQCAH YIDGPHCVKT CPAGVMGENN TLVWKYADAG HVCHLCHPNC TYGCTGPGLE   840
GCPTNGPKIP SIATGMVGAL LLLLVVALGI GLFM                              874
```

```
SEQ ID NO: 50          moltype = DNA   length = 2442
FEATURE                Location/Qualifiers
misc_feature           1..2442
                       note = source = /note="Description of Artificial Sequence:
                       Syntheticpolynucleotide"
source                 1..2442
                       mol_type = other DNA
                       organism = synthetic construct
SEQUENCE: 50
atgctgctgc tggtgaccag cctgctgctg tgtgagctgc cccacccgc ctttctgctg     60
atccccgaca ttcagatgac ccagtctccg agctctccgt ccgcatcagt aggagacagg    120
gtcaccatca catgcagagc cagcgaaagt gtcgacaatt atggcattag ctttatgaac    180
tggttccaac agaaacccgg gaaggctcct aagcttctga tttacgctgc atccaaccaa    240
ggctccgggg tacctctcg cttctcaggc agtggatctg gacagactt cactctcacc    300
atttcatctc tgcagcctga tgacttcgca acctattact gtcagcaaag taaggaggtt    360
ccgtggacgt tcggtcaagg gaccaaggtg gagatcaaag tggcggtgg ctcgggcggt    420
```

-continued

```
ggtgggtcgg gtggcggcgg atctcaggtt cagctggtgc agtctggagc tgaggtgaag  480
aagcctggga gctcagtgaa ggtttcctgc aaagcttctg gctacacctt cactgactac  540
aacatgcact gggtgaggca ggctcctggc caaggcctgg aatggattgg atatatttat  600
ccttacaatg gtggtaccgg ctacaaccag aagttcaaga gcaaggccac aattacagca  660
gacgagagta ctaacacagc ctacatggaa ctctccagcc tgaggtctga ggacactgca  720
gtctattact gcgcaagagg gcgcccccgct atggactact ggggccaagg gactctggtc  780
actgtctctt caaagcccac caccacccct gccctagac ctccaacccc agccctaca  840
atcgccagcc agccctgag cctgaggccc gaagcctgta gacctgccgc tggcggagcc  900
gtgcacacca gaggcctgga tttcgcctgc gacatctaca tctgggcccc tctggccggc  960
acctgtggcg tgctgctgct gagcctggtc atcaccctgt actgcaacca ccggaataag  1020
agaggccgga agaaactgct gtacatcttc aagcagcct tcatgcggcc cgtgcagacc  1080
acccaggaag aggacggctg cagctgccgg ttccccgagg aagaggaagg cggctgcgaa  1140
ctgcgggtga agttcagccg gagcgccgac gcccctgcct accagcaggg ccagaaccag  1200
ctgtacaacg agctgaacct gggccggagg gaggagtacg acgtgctgga caagcggaga  1260
ggccgggacc ctgagatggg cggcaagccc cggagaaaga accctcagga gggcctgtat  1320
aacgaactgc agaaagacaa gatggccgag gcctacagcg agatcggcat gaagggcgag  1380
cggcggaggg gcaagggcca cgacggcctg taccagggc tgagcaccgc caccaaggat  1440
acctacgacg ccctgcacat gcaggccctg ccccccagac tcgaggggcg cggagaggcc  1500
agaggaagtc ttctaacatg cggtgacgtg gaggagaatc ccggccctag gatgacaaca  1560
cccagaaatt cagtaaatgg gactttcccg gcagagccaa tgaaaggccc tattgctatg  1620
caatctggtc caaaaccact cttcaggagg atgtcttcac tggtgggccc cacgcaaagc  1680
ttcttcatga gggaatctaa gactttgggg gctgtccaga ttatgaatgg gctcttccac  1740
attgccctgg ggggtcttct gatgatccca gcagggatct atgcacccat ctgtgtgact  1800
gtgtggtacc ctctctgggg aggcattatg tatattattt ccggatcact cctggcagca  1860
acggagaaaa actccaggaa gtgtttggtc aaaggaaaaa tgataatgaa ttcattgagc  1920
ctctttgctg ccatttctgg aatgattctt tcaatcatgg acatacttaa tattaaaatt  1980
tcccattttt taaaaatgga gagtctgaat tttattagag ctcacacacc atatattaac  2040
atatacaact gtgaaccagc taatccctct gagaaaaact ccccatctac ccaatactgt  2100
tacagcatac aatctctgtt cttgggcatt ttgtcagtga tgctgatctt tgccttcttc  2160
caggaacttg taatagctgg catcgttgag aatgaatgga aagaacgtg ctccagaccc  2220
aaatctaaca tagttctcct gtcagcagaa gaaaaaaaag aacagactat tgaaataaaa  2280
gaagaagtgg ttgggctaac tgaaacatct tcccaaccaa agaatgaaga agacattgaa  2340
attattccaa tccaagaaga ggaagaagaa gaaacagaga cgaactttcc agaacctccc  2400
caagatcagg aatcctcacc aatagaaaat gacagctctc ct  2442
```

```
SEQ ID NO: 51          moltype = AA  length = 814
FEATURE                Location/Qualifiers
REGION                 1..814
                       note = source = /note="Description of Artificial Sequence:
                        Syntheticpolypeptide"
source                 1..814
                       mol_type = protein
                       organism = synthetic construct
SEQUENCE: 51
MLLLVTSLLL CELPHPAFLL IPDIQMTQSP SSLSASVGDR VTITCRASES VDNYGISFMN  60
WFQQKPGKAP KLLIYAASNQ GSGVPSRFSG SGSGTDFTLT ISSLQPDDFA TYYCQQSKEV  120
PWTFGQGTKV EIKGGGGSGG GGSGGGGSQV QLVQSGAEVK KPGSSVKVSC KASGYTFTDY  180
NMHWVRQAPG QGLEWIGYIY PYNGGTGYNQ KFKSKATITA DESTNTAYME LSSLRSEDTA  240
VYYCARGRPA MDYWGQGTLV TVSSKPTTTP APRPPTPAPT IASQPLSLRP EACRPAAGGA  300
VHTRGLDFAC DIYIWAPLAG TCGVLLLSLV ITLYCNHRNK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPRLEGGGEG RGSLLTCGDV EENPGPRMTT PRNSVNGTFP AEPMKGPIAM  540
QSGPKPLFRR MSSLVGPTQS FFMRESKTLG AVQIMNGLFH IALGGLLMIP AGIYAPICVT  600
VWYPLWGGIM YIISGSLLAA TEKNSRKCLV KGKMIMNSLS LFAAISGMIL SIMDILNIKI  660
SHFLKMESLN FIRAHTPYIN IYNCEPANPS EKNSPSTQYC YSIQSLFLGI LSVMLIFAFF  720
QELVIAGIVE NEWKRTCSRP KSNIVLLSAE EKKEQTIEIK EEVVGLTETS SQPKNEEDIE  780
IIPIQEEEEE ETETNFPEPP QDQESSPIEN DSSP  814
```

```
SEQ ID NO: 52          moltype = DNA  length = 861
FEATURE                Location/Qualifiers
source                 1..861
                       mol_type = other DNA
                       organism = Homo sapiens
SEQUENCE: 52
atgccgctgc tgctactgct gcccctgctg tgggcagggg ccctggctat ggatccaaat  60
ttctggctgc aagtgcagga gtcagtgacg gtacaggagg gtttgtgcgt cctcgtgccc  120
tgcactttct tccatcccat accctactac gacaagaact ccccagttca tggttactgg  180
ttccgggaag gagccattat atccagggac tctccagtcg ccacaaacaa ctagatcaa  240
gaagtacagg aggagactca gggcagattc cgcctccttg gggatcccag taggaacaac  300
tgctccctga gcatcgtaga cgccaggagg agggataatg gttcatactt ctttcggatg  360
gagagaggaa gtaccaaata cagttacaaa tctccccagc tctctgtgca tgtgacagac  420
ttgacccaca ggcccaaaat cctcatccct ggcactctag aacccggcca ctccaaaaac  480
ctgacctgct ctgtgtcctg ggctgtgag cagggaacac cccgatctt ctccgtgttg  540
tcagctgccc ccacctccct gggccccagg actactcact cctcggtgct cataatcacc  600
ccacggcccc aggaccacgg caccaacctg acctgtcagg tgaagttcgc tggagctggt  660
gtgactacgg agagaaccat ccagctcaac gtcacctatg ttccacagaa cccaacaact  720
ggtatctttc aggagatgg ctcagggaaa caagagacca gagcaggagt ggttcatggg  780
gccattggag gagctggtgt tacagccctg ctcgctcttt gtctctgcct catcttcttc  840
```

```
atagtgaaga cccacaggag g                                                  861

SEQ ID NO: 53              moltype = AA   length = 287
FEATURE                    Location/Qualifiers
source                     1..287
                           mol_type = protein
                           organism = Homo sapiens
SEQUENCE: 53
MPLLLLLPLL WAGALAMDPN FWLQVQESVT VQEGLCVLVP CTFFHPIPYY DKNSPVHGYW   60
FREGAIISRD SPVATNKLDQ EVQEETQGRF RLLGDPSRNN CSLSIVDARR RDNGSYFFRM  120
ERGSTKYSYK SPQLSVHVTD LTHRPKILIP GTLEPGHSKN LTCSVSWACE QGTPPIFSWL  180
SAAPTSLGPR TTHSSVLIIT PRPQDHGTNL TCQVKFAGAG VTTERTIQLN VTYVPQNPTT  240
GIFPGDGSGK QETRAGVVHG AIGGAGVTAL LALCLCLIFF IVKTHRR             287

SEQ ID NO: 54              moltype = AA   length = 244
FEATURE                    Location/Qualifiers
REGION                     1..244
                           note = source = /note="Description of Artificial Sequence:
                            Syntheticpolypeptide"
source                     1..244
                           mol_type = protein
                           organism = synthetic construct
SEQUENCE: 54
RKVCNGIGIG EFKDSLSINA TNIKHFKNCT SISGDLHILP VAFRGDSFTH TPPLDPQELD   60
ILKTVKEITG FLLIQAWPEN RTDLHAFENL EIIRGRTKQH GQFSLAVVSL NITSLGLRSL  120
KEISDGDVII SGNKNLCYAN TINWKKLFGT SGQKTKIISN RGENSCKATG QVCHALCSPE  180
GCWGPEPRDC VSGGGGSGGG GSGGGGSGGG GSFWVLVVVG GVLACYSLLV TVAFIIFWVR  240
SKRS                                                           244

SEQ ID NO: 55              moltype = DNA   length = 732
FEATURE                    Location/Qualifiers
misc_feature               1..732
                           note = source = /note="Description of Artificial Sequence:
                            Syntheticpolynucleotide"
source                     1..732
                           mol_type = other DNA
                           organism = synthetic construct
SEQUENCE: 55
cgcaaagtgt gtaacggaat aggtattggt gaatttaaag actcactctc cataaatgct   60
acgaatatta aacacttcaa aaactgcacc tccatcagtg gcgatctcca catcctgccg  120
gtggcattta ggggtgactc cttcacacat actcctcctc tggatccaca ggaactggat  180
attctgaaaa ccgtaaagga aatcacaggg tttttgctga ttcaggcttg gcctgaaaac  240
aggacggacc tccatgcctt tgagaaccta gaaatcatac gcggcaggac caagcaacat  300
ggtcagtttt ctcttgcagt cgtcagcctg aacataacat ccttgggatt acgctccctc  360
aaggagataa gtgatggaga tgtgataatt tcaggaaaca aaaatttgtg ctatgcaaat  420
acaataaact ggaaaaaact gtttgggacc tccggtcaga aaaccaaaat tataagcaac  480
agaggtgaaa acagctgcaa ggccacaggc caggtctgcc atgccttgtg ctcccccgag  540
ggctgctggg gcccggagcc cagggactgc gtctctggtg gcggtggctc gggcggtggt  600
gggtcgggtg gcggcggatc tggtggcggt ggctcgtttt gggtgctggt ggtgttggt  660
ggagtcctgg cttgctatag cttgctagta acagtggcct ttattatttt ctgggtgagg  720
agtaagagga gc                                                  732

SEQ ID NO: 56              moltype = AA   length = 263
FEATURE                    Location/Qualifiers
REGION                     1..263
                           note = source = /note="Description of Artificial Sequence:
                            Syntheticpolypeptide"
source                     1..263
                           mol_type = protein
                           organism = synthetic construct
SEQUENCE: 56
MTTPRNSVNG TFPAEPMKGP IAMQSGPKPL FRRMSSLVGP TQSFFMRESK TLGAVQIMNG   60
LPHIALGGLL MIPAGIYAPI CVTVWYPLWG GIMYIISGSL LAATEKNSRK CLVKGKMIMN  120
SLSLFAAISG MILSIMDILN IKISHFLKME SLNFIRAHTP YINIYNCEPA NPSEKNSPST  180
QYCYSIQSLF LGILSVMLIF AFFQELVIAG IVENEWKRTC SRPKSNIVLL SAEEKKEQTI  240
EIKEEVVGLT ETSSQPKNEE DIE                                      263

SEQ ID NO: 57              moltype = DNA   length = 789
FEATURE                    Location/Qualifiers
misc_feature               1..789
                           note = source = /note="Description of Artificial Sequence:
                            Syntheticpolynucleotide"
source                     1..789
                           mol_type = other DNA
                           organism = synthetic construct
SEQUENCE: 57
atgaccacac cacggaactc tgtgaatggc accttcccag cagagccaat gaagggacca   60
atcgcaatgc agagcggacc caagcctctg tttcggagaa tgagctccct ggtgggccca  120
acccagtcct tctttatgag agagtctaag acactgggcg ccgtgcagat catgaacgga  180
```

-continued

```
ctgttccaca tcgccctggg aggactgctg atgatcccag ccggcatcta cgcccctatc  240
tgcgtgaccg tgtggtaccc tctgtggggc ggcatcatgt atatcatctc cggctctctg  300
ctggccgcca cagagaagaa cagcaggaag tgtctggtga agggcaagat gatcatgaat  360
agcctgtccc tgtttgccgc catctctggc atgatcctga gcatcatgga catcctgaac  420
atcaagatca gccacttcct gaagatggag agcctgaact tcatcagagc ccacacccct  480
tacatcaaca tctataattg cgagcctgcc aacccatccg agaagaattc tccaagcaca  540
cagtactgtt attccatcca gtctctgttc ctgggcatcc tgtctgtgat gctgatcttt  600
gccttctttc aggagctggt catcgccggc atcgtggaga acgagtggaa gaggacctgc  660
agccgcccca agtccaatat cgtgctgctg tccgccgagg agaagaagga gcagacaatc  720
gagatcaagg aggaggtggt gggcctgacc gagacatcta gccagcctaa gaatgaggag  780
gatatcgag                                                          789
```

```
SEQ ID NO: 58          moltype = DNA  length = 72
FEATURE                Location/Qualifiers
misc_feature           1..72
                       note = source = /note="Description of Artificial Sequence:
                        Syntheticoligonucleotide"
source                 1..72
                       mol_type = other DNA
                       organism = synthetic construct
SEQUENCE: 58
ctgtgcgcac gcccacgccg cagccccgcc caagaagatg gcaaagtcta catcaacatg  60
ccaggcaggg gc                                                      72
```

```
SEQ ID NO: 59          moltype = AA  length = 24
FEATURE                Location/Qualifiers
REGION                 1..24
                       note = source = /note="Description of Artificial Sequence:
                        Syntheticpeptide"
source                 1..24
                       mol_type = protein
                       organism = synthetic construct
SEQUENCE: 59
LCARPRRSPA QEDGKVYINM PGRG                                          24
```

```
SEQ ID NO: 60          moltype = DNA  length = 156
FEATURE                Location/Qualifiers
misc_feature           1..156
                       note = source = /note="Description of Artificial Sequence:
                        Syntheticpolynucleotide"
source                 1..156
                       mol_type = other DNA
                       organism = synthetic construct
SEQUENCE: 60
tacttcctgg gccggctggt ccctcggggg cgaggggctg cggaggcagc gacccggaaa  60
cagcgtatca ctgagaccga gtcgccttat caggagctcc agggtcagag gtcggatgtc  120
tacagcgacc tcaacacaca gaggccgtat tacaaa                            156
```

```
SEQ ID NO: 61          moltype = AA  length = 52
FEATURE                Location/Qualifiers
REGION                 1..52
                       note = source = /note="Description of Artificial Sequence:
                        Syntheticpolypeptide"
source                 1..52
                       mol_type = protein
                       organism = synthetic construct
SEQUENCE: 61
YFLGRLVPRG RGAAEAATRK QRITETESPY QELQGQRSDV YSDLNTQRPY YK            52
```

```
SEQ ID NO: 62          moltype = AA  length = 12
FEATURE                Location/Qualifiers
REGION                 1..12
                       note = source = /note="Description of Artificial Sequence:
                        Syntheticpeptide"
source                 1..12
                       mol_type = protein
                       organism = synthetic construct
SEQUENCE: 62
ESKYGPPCPP CP                                                       12
```

CD33 SPECIFIC CHIMERIC ANTIGEN RECEPTORS

CROSS-REFERENCE TO RELATED APPLICATIONS

The present application is a continuation of U.S. application Ser. No. 15/616,869, filed Jun. 7, 2017, now U.S. Pat. No. 11,787,848), which in turn claims the priority benefit of U.S. provisional Patent Application No. 62/347,503 filed Jun. 8, 2016, each of which is hereby incorporated by reference in its entirety.

REFERENCE TO SEQUENCE LISTING

The present application contains a Sequence Listing which has been filed electronically in XML format and is hereby incorporated by reference in its entirety. The XML copy, created on Sep. 6, 2023, is named 391665SL.xml is 107,703 bytes in size.

BACKGROUND OF THE DISCLOSURE

Provided herein are compositions and methods for treating cancer in humans. The invention further relates to specific chimeric antigen receptors and vectors for treating myeloid malignancies, for example, acute myelogenous leukemia.

Acute myeloid leukemia (AML) is a type of cancer in which the bone marrow makes abnormal myeloblasts. It is the most common form of acute leukemia in adults (Siegel, R., et al., Cancer Statistics, *CA Cancer J Clin*, 64(1):9-29 (2014)). AML is a rapidly progressive disease with a median age at onset of 65 to 70 years. AML is known by many names, including acute myelocytic leukemia, acute myelogenous leukemia, acute granulocytic leukemia, and acute non-lymphocytic leukemia. "Acute" denotes the aggressive nature of this disease that can progress quickly, and if not treated, is fatal within a few months of diagnosis. The cancer originates in the bone marrow but rapidly spreads via the blood to other anatomical sites. The disease is observed in both children and adults, but is more common in the elderly. The chance of getting AML increases with age, but a person can get AML at any age. About 8 in 10 adults with acute leukemia have AML and about 1 in 6 children with leukemia will have AML. An average of 12,000 new cases of AML is expected on a yearly basis with approximately 30,000 patients living with or experiencing remission currently in the US.

Amongst elderly AML patients (≥65 years of age), median survival is short (ranging from 3.9 months for patients 65 to 74 years of age to 1.4 months for patients ≥85 years of age). Treatment options for AML patients are limited, and outcomes are usually poor with an average 5-year survival rate of 20%, and less than a 5% 5-year survival rate for patients older than 65 (Thein, M. et al., Outcome of older patients with acute myeloid leukemia: an analysis of SEER data over 3 decades, Cancer, 119(15): 2720-7 (2013)). Certain subgroups of AML have a particularly worse outcome such as patients with abnormalities in chromosome 7, complex karyotype, relapsed and/or refractory AML and AML arising from antecedent myelodysplastic syndrome (MDS) or myeloproliferative neoplasms (MPNs). Patients aged 65 years and older with AML are more likely than younger patients to have unfavorable-risk cytogenetics. These cytogenetic factors are associated with resistance to chemotherapy and show considerably lower response rates to therapy. In addition to response rate, older patients with AML are often either not considered candidates for or choose not to receive standard induction chemotherapy because of poor tolerability and treatment outcomes. Induction chemotherapy is associated with high rates of treatment-related mortality and low complete response (CR) rates in this subset of patients. Currently, there are no approved therapies for AML patients who do not receive standard induction chemotherapy. The paucity of therapies and the poor response rates associated cytogenetics make AML an unmet medical need for new agents demonstrating clinical benefit with a favorable safety profile.

Hematopoiesis is characterized by the tissue specific hierarchical differentiation from pluripotent stem cells to more mature differentiated cellular phenotypes. Similar to the homeostatic hematopoiesis, AML is believed to arise form mutations accumulating in this quiescent stem cell population, which gives rise to the leukemic stem cell (LSC). The inability to eliminate this AML LSC population will result in relapse and therapeutic failure.

Although most patients with AML will achieve remission with induction chemotherapy; many will relapse, despite the administration of post-remission consolidation therapies. Relapses may occur weeks to many years later. Up to 10% of patients will be refractory to induction chemotherapy. Both of these groups of patients (relapsed/refractory) constitute a particularly poor risk group. Although an allogeneic stem cell transplant would be considered a recommended approach for most of these patients, it is feasible only in a small number of patients and is associated with significant morbidity and mortality (Hamadani, M., Awan, F. & Copelan, E., Hematopoietic stem cell transplantation in adults with acute myeloid leukemia, *Biol Blood Marrow Transplant*, 5:556-67 (2008)). In addition, outcomes for patients transplanted with refractory disease are poor (Duval, M. et al., Hematopoietic stem-cell transplantation for acute leukemia in relapse or primary induction failure, *J Clin Oncol*, 28(23):3730-8 (2010)) and almost half of patients with relapsed disease are chemorefractory and thus not suitable for transplantation (Hamadani, M., Awan, F. & Copelan, E., Hematopoietic stem cell transplantation in adults with acute myeloid leukemia *Biol Blood Marrow Transplant*, 5:556-67 (2008)), (Estey, E., 2013. Acute myeloid leukemia: 2013 update on risk-stratification and management. *Am J Hematol*, 88(4), pp. 318-27). Many novel drugs and approaches are being investigated for this group of patients. However, the CR rates have been, in general, less than 30% (Litzow, M. et al., Failure of three novel regimens to improve outcome for patients with relapsed or refractory acute myeloid leukaemia: a report from the Eastern Cooperative Oncology Group, *Br J Haemotol*, 148:217-25 (2010)), (Cortes, J. et al., Phase 2 randomized study of p53 antisense oligonucleotide (cenersen) plus idarubicin with or without cytarabine in refractory and relapsed acute myeloid leukemia, *Cancer*, 118(2):418-27 (2012)), (Kirschbaum, M. et al., A phase 1 trial dose-escalation study of tipifarnib on a week-on, week-off schedule in relapsed, refractory or high-risk myeloid leukemia, *Leukemia*, 25(10):1543-7 (2011)).

In AML patients, cytogenetics are important prognostic factors in predicting response to treatment (Grimwade, D. et al., The importance of diagnostic cytogenetics on outcome in AML: analysis of 1,612 patients entered into the MRC AML 10 trial. The Medical Research Council Adult and Children's Leukaemia Working Parties, *Blood*, 92(7):2322-33 (1998)). Patients with AML whose leukemic cells have translocations t(8; 21), t(15; 17), t(16; 16), or inv(16) have a favorable outcome with induction chemotherapy and intensive post-remission consolidation chemotherapy. However, abnormalities of chromosomes 5 or 7,11q23 or complex karyotypes have a very poor outcome with currently available induction and post remission chemotherapy. Patients with a normal karyotype or with trisomy 8 have an intermediate prognosis. Among adults with AML, t(9; 22) or t(4; 11) confer a very poor prognosis. Patients with t(9; 22) AML are rarely, if ever, cured with chemotherapy alone. The immunophenotypic determination of surface antigens expressed on leukemic blast cells may aid in diagnosis and has important implications for treatment and prognosis of myeloid, T, and B lineage leukemias. Given that increases in long-term AML survival have proven elusive using conventional therapies, novel treatment strategies are needed.

SUMMARY OF THE DISCLOSURE

One aspect of the disclosure relates to an isolated nucleic acid encoding a chimeric antigen receptor (CAR), wherein the CAR comprises (a) a CD33 antigen binding domain; (b) a stalk domain; (c) a transmembrane domain; (d) a costimulatory signaling domain comprising at least one of 4-1BB and CD28, or fragments thereof; (e) a CD3 zeta signaling domain; and optionally (f) a truncated epidermal growth factor receptor (HER1t or HER1t-1).

Provided herein is a vector comprising a backbone and a nucleic acid sequence encoding a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain. In certain embodiments is provided a vector further comprising a nucleic acid encoding a truncated epidermal growth factor receptor (HER1t or HER1t-1) or a full length or truncated CD20.

Provided herein is a vector comprising a backbone and a nucleic acid sequence encoding (1) a truncated epidermal growth factor receptor or a functional variant thereof; and (2) a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain.

In certain embodiments is provided a vector comprising a backbone and a nucleic acid sequence encoding (1) full length CD20 and functional variants thereof, and (2) a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain.

In certain embodiments is provided an engineered cell, for instance an immune effector cell comprising a vector comprising a backbone and a nucleic acid sequence encoding a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; (e) a CD3 zeta signaling domain; and (f) at least one of a truncated epidermal growth factor receptor (HER1t, or HER1t-1), a full length CD20 and a truncated CD20 (CD20t-1).

In certain embodiments is provided an engineered cell, for instance an immune effector cell comprising (1) a truncated epidermal growth factor receptor (HER1t or HER1t-1); and (2) a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain.

In certain embodiments is provided an engineered cell, for instance an immune effector cell comprising (1) a cell tag for use as a kill switch, selection marker, a biomarker, or a combination thereof; and (2) a chimeric antigen receptor (CAR), wherein the CAR comprises (a) a CD33 antigen binding domain; (b) a stalk domain; (c) a transmembrane domain; (d) a costimulatory signaling domain; and (e) a CD3 zeta signaling domain. In certain embodiments, the costimulatory signaling domain comprises at least one of 4-1BB and CD28. In embodiments, the cell tag is HER1t, HER1t-1, CD20 or CD20t-1.

Provided herein are methods for stimulating a T cell-mediated immune response to a target cell population or tissue in a human, comprising administering to a human an effective amount of a cell genetically modified to express a CAR, wherein the CAR comprises (a) a CD33 antigen binding domain; (b) a stalk domain; (c) a transmembrane domain; (d) a costimulatory signaling domain comprising 4-1BB or CD28, or both; (e) a CD3 zeta signaling domain; and (f) a truncated epidermal growth factor receptor (HER1t or HER1t-1).

Provided herein is an isolated nucleic acid encoding a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; (e) a CD3 zeta signaling domain.

In some embodiments, the CD33 antigen binding domain comprises at least one of: (a) a polypeptide having at least 90%, 91%, 92%, 93%, 94%, 95%, 96%, 97%, 98%, 99% or 100% identity with the amino acid sequence of SEQ ID NO:8 (hM195scFv); (b) a polypeptide having at least 90%, 91%, 92%, 93%, 94%, 95%, 96%, 97%, 98%, 99% or 100% identity with the amino acid sequence of SEQ ID NOs:9 and 10 (M2H12); (c) a polypeptide having at least 90%, 91%, 92%, 93%, 94%, 95%, 96%, 97%, 98%, 99% or 100% identity with the amino acid sequence of SEQ ID NOs:11 and 12 (DRB2); and (d) a polypeptide having at least 90%, 91%, 92%, 93%, 94%, 95%, 96%, 97%, 98%, 99% or 100% identity with the amino acid sequence of SEQ ID NOs: 13 and 14 (My9-6).

In some cases, the CD33 antigen binding domain is a polypeptide having at least 90%, 91%, 92%, 93%, 94%, 95%, 96%, 97%, 98%, 99% or 100% identity with the amino acid sequence of SEQ ID NO:8 (hM195scFv). In some instances, the stalk domain is a polypeptide having at least 90%, 91%, 92%, 93%, 94%, 95%, 96%, 97%, 98%, 99% or 100% identity with the amino acid sequence of SEQ ID NO:22 (CD8alpha hinge).

In some embodiments, the costimulatory signaling domain comprises 4-1BB. In some cases, the costimulatory signaling domain of 4-1BB comprises a polypeptide having at least 90%, 91%, 92%, 93%, 94%, 95%, 96%, 97%, 98%, 99% or 100% identity with the amino acid sequence of SEQ ID NO:24. In some instances, the costimulatory signaling domain comprises CD28. In some embodiments, the costimulatory signaling domain of CD28 comprises a polypeptide having at least 90%, 91%, 92%, 93%, 94%, 95%, 96%, 97%, 98%, 99% or 100% identity with the amino acid sequence of SEQ ID NO:28.

In some instances, the CD3 zeta signaling domain comprises a polypeptide having at least 90%, 91%, 92%, 93%, 94%, 95%, 96%, 97%, 98%, 99% or 100% identity with the amino acid sequence of SEQ ID NO:26. In some embodiments, the isolated nucleic acid further comprises a truncated epidermal growth factor receptor. In some cases, the truncated epidermal growth factor receptor is HER1t and comprises a polypeptide having at least 90%, 91%, 92%, 93%, 94%, 95%, 96%, 97%, 98%, 99% or 100% identity with the amino acid sequence of SEQ ID NO:32. In some instances, the truncated epidermal growth factor receptor is HER1t-1 and comprises a polypeptide having at least 90%, 91%, 92%, 93%, 94%, 95%, 96%, 97%, 98%, 99% or 100% identity with the amino acid sequence of SEQ ID NO: 54.

In some embodiments, the CAR comprises a polypeptide having at least 90%, 91%, 92%, 93%, 94%, 95%, 96%, 97%, 98%, 99% or 100% identity with an amino acid sequence comprising SEQ ID NOs:39, 41, 43, 45, 47, 49, 51, 53, or 55.

Provided herein is a vector comprising a backbone and a nucleic acid sequence encoding: (1) a truncated epidermal growth factor receptor comprising at least one of HER1t, HER1t-1 or a functional variant thereof; and (2) a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain.

Provided herein is a vector comprising a backbone and a nucleic acid sequence encoding: (1) a full length CD20, a truncated CD20 (CD20t-1) or a functional variant thereof; and (2) a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain.

In some embodiments, the vector is a lentivirus vector, a retroviral vector, or a non-viral vector. In some cases, the truncated epidermal growth factor receptor comprises a polypeptide having at least 90%, 91%, 92%, 93%, 94%, 95%, 96%, 97%, 98%, 99% or 100% identity with the amino acid sequence of SEQ ID NO:32 or SEQ ID NO: 54. In some instances, the vector comprises a nucleotide sequence encoding a truncated CD20 (CD20t-1), or a functional variant thereof wherein said CD20t-1 comprises a polypeptide having at least 90%, 91%, 92%, 93%, 94%, 95%, 96%, 97%, 98%, 99% or 100% identity with the amino acid sequence of SEQ ID NO: 56.

In some embodiments, the full length CD20 comprises a polypeptide having at least 90%, 91%, 92%, 93%, 94%, 95%, 96%, 97%, 98%, 99% or 100% identity with the amino acid sequence of SEQ ID NO:36. In some cases, the vector further comprises a nucleotide sequence encoding a self-cleaving *Thosea asigna* virus (T2A) peptide. In some instances, a backbone of the vector is Sleeping Beauty transposon DNA plasmid or pFUGW.

In some instances, the vector further comprises a promoter. In some cases, the promoter is hEF1a1. In some instances, the CD33 antigen binding domain comprises at least one of: (a) a polypeptide having at least 90%, 91%, 92%, 93%, 94%, 95%, 96%, 97%, 98%, 99% or 100% identity with the amino acid sequence of SEQ ID NO:8 (hM195scFv); (b) a polypeptide having at least 90%, 91%, 92%, 93%, 94%, 95%, 96%, 97%, 98%, 99% or 100% identity with the amino acid sequence of SEQ ID NOs:9 and 10 (M2H12); (c) a polypeptide having at least 90%, 91%, 92%, 93%, 94%, 95%, 96%, 97%, 98%, 99% or 100% identity with the amino acid sequence of SEQ ID NOs:11 and 12 (DRB2); and (d) a polypeptide having at least 90%, 91%, 92%, 93%, 94%, 95%, 96%, 97%, 98%, 99% or 100% identity with the amino acid sequence of SEQ ID NOs: 13 and 14 (My9-6).

In some embodiments, the CD33 antigen binding domain is a polypeptide having at least 90%, 91%, 92%, 93%, 94%, 95%, 96%, 97%, 98%, 99% or 100% identity with the amino acid sequence of SEQ ID NO:8. In some cases, the stalk domain comprises a polypeptide having at least 90%, 91%, 92%, 93%, 94%, 95%, 96%, 97%, 98%, 99% or 100% identity with the amino acid sequence of SEQ ID NO: 22 (CD8alpha hinge). In some instances, the costimulatory signaling domain comprises 4-1BB. In some embodiments, the costimulatory signaling domain of 4-1BB comprises a nucleic acid sequence having at least 90%, 91%, 92%, 93%, 94%, 95%, 96%, 97%, 98%, 99% or 100% identity with the amino acid sequence of SEQ ID NO:24.

In some cases, the costimulatory signaling domain of the vector comprises CD28. In some cases, the costimulatory signaling domain of CD28 comprises a nucleic acid sequence having at least 90%, 91%, 92%, 93%, 94%, 95%, 96%, 97%, 98%, 99% or 100% identity with the amino acid sequence of SEQ ID NO:28. In some instances, the CD3 zeta signaling domain comprises a nucleic acid sequence having at least 90%, 91%, 92%, 93%, 94%, 95%, 96%, 97%, 98%, 99% or 100% identity with the amino acid sequence of SEQ ID NO:26.

In some embodiments, said vector comprises a plasmid. In some cases, each said vector comprises an expression plasmid. In some instances, the non-viral vector is a Sleeping Beauty transposon. In some embodiments, an immune effector cell can comprise a nucleotide disclosed herein.

Provided herein is an immune effector cell comprising a vector comprising a backbone and a nucleic acid sequence encoding (1) a truncated epidermal growth factor receptor (HER1t); and (2) chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain.

Further provided herein is an immune effector cell comprising (1) a cell tag for use as a kill switch, selection marker, a biomarker, or a combination thereof; and (2) a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain.

In some embodiments, the cell tag comprises HER1t, HER1t-1, CD20t-1 or CD20. In some cases, the cell tag comprises HER1t, and said HER1t comprises the polypeptide sequence of SEQ ID NO: 32. In some instances, the cell tag comprises HER1t-1, and said HER1t-1 comprises the polypeptide sequence of SEQ ID NO: 54. In some cases, an immune effector cell comprises a vector disclosed herein. In some embodiments, the cell is a T cell, a Natural Killer (NK) cell, a cytotoxic T lymphocyte (CTL), or a regulatory T cell. In some instances, the cell exhibits an anti-tumor immunity when the CD33 antigen binding domain binds to CD33.

Provided herein is a method for stimulating a T cell-mediated immune response to a target cell population or tissue in a human subject in need thereof, comprising administering to said human subject an effective amount of a cell genetically modified to express a CAR, wherein the CAR comprises (a) a CD33 antigen binding domain; (b) a stalk domain; (c) a transmembrane domain; (d) a costimulatory signaling domain comprising 4-1BB or CD28, or both; (e) a CD3 zeta signaling domain, and (f) a truncated epidermal growth factor receptor (HER1t).

In some embodiments, the human has been diagnosed with acute myeloid leukemia (AML). In some cases, the acute myeloid leukemia is relapsed or refractory AML.

Provided is an isolated nucleic acid encoding a chimeric antigen receptor (CAR), wherein the CAR comprises: (a) a CD33 antigen binding domain with the amino acid sequence of SEQ ID NO:8; (b) a stalk domain with the amino acid sequence of SEQ ID NO:22; (c) a costimulatory signaling domain comprising CD28 with the amino acid sequence of SEQ ID NO:28; (d) a HER1 tag which comprises at least one of HER1t with the amino acid sequence of SEQ ID NO:32 and HER1t-1 with the amino acid sequence of SEQ ID NO: 54; (e) a CD3 zeta signaling domain with the amino acid sequence of SEQ ID NO: 26.

Further provided herein is an isolated nucleic acid encoding a chimeric antigen receptor (CAR), wherein the CAR comprises: (a) a CD33 antigen binding domain with the amino acid sequence of SEQ ID NO:8; (b) a stalk domain with the amino acid sequence of SEQ ID NO:22; (c) a costimulatory signaling domain comprising 4-1BB with the amino acid sequence of SEQ ID NO:24; (d) a HER1 tag which comprises at least one of HER1t with the amino acid sequence of SEQ ID NO:32 and HER1t-1 with the amino acid sequence of SEQ ID NO: 54; (e) a CD3 zeta signaling domain with the amino acid sequence of SEQ ID NO: 26.

In some embodiments, a vector comprises one or more of the polynucleotides disclosed herein. In some cases, said vector is a lentivirus vector, a retroviral vector, or a non-viral vector. In some instances, the non-viral vector is a Sleeping Beauty transposon. In some embodiments, said vector is a plurality of vectors.

Provided is a system for expressing a CAR in an immune effector cell, said system comprising one or more vectors encoding an isolated nucleic acid disclosed herein. In some embodiments, said immune effector cell is a T cell or NK cell. In some cases, said system further comprises a nucleic acid encoding at least one additional gene. In some instances, said additional gene comprises a cytokine. In some embodiments, said cytokine comprises at least one of IL-2, IL-15, IL-12, IL-21, and a fusion of IL-15 and IL-15R□□□□ In some cases, said cytokine is in secreted form. In some embodiments, said cytokine is in membrane bound form.

In some cases, said system comprises one vector. In some instances, said one or more vectors is a lentivirus vector, a retroviral vector, or a non-viral vector. In some embodiments, the non-viral vector is a Sleeping Beauty transposon. In some cases, said system further comprises a Sleeping Beauty transposase. In some instances, the Sleeping Beauty transposase is SB11, SB100X or SB110. In some cases, said immune effector cell is a mammalian cell. In some embodiments, a method of expressing a CAR in an immune effector cell is comprises contacting said immune effector cell with a system disclosed herein.

Provided herein is a method of stimulating the proliferation and/or survival of engineered T-cells comprising: (a) obtaining a sample of cells from a subject, the sample comprising T-cells or T-cell progenitors; (b) transfecting the cells with one or more vectors encoding an isolated nucleic acid encoding a CAR comprising: (i) a CD33 antigen-binding domain, (ii) a stalk domain, (iii) a transmembrane domain, (iv) a 4-1BB costimulatory signaling domain, a CD28 costimulatory signaling domain, or both, and (v) a CD3 zeta signaling domain; and a vector encoding a transposase, to provide a population of engineered CD33 CAR-expressing T-cells; (c) and optionally, culturing the population of CD33CAR T-cells ex vivo for 2 days or less.

In some embodiments, the method further comprises transfecting the cells with a vector encoding a cytokine. In some cases, the cytokine is a fusion protein comprising IL-15 and IL-15Rα. In some instances, said one or more vectors is a lentivirus vector, a retroviral vector, or a non-viral vector. In some embodiments, the non-viral vector is a Sleeping Beauty transposon. In some cases, the method further comprises a Sleeping Beauty transposase. In some instances, the Sleeping Beauty transposase is SB11, SB100X or SB110.

BRIEF DESCRIPTION OF THE FIGURES

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 is a schematic depicting structure of CD33 isoforms.

FIG. 6 demonstrates confirmation of CD33 CAR expression from lentivirally transduced cells by Western Blot.

FIG. 7 shows kinetics of numeric expansion of in vitro cultured CD33 CAR-T cells absolute and fold expansion of total T cell populations from untransduced T cells (UNT) and CD33 CAR-T cells (CD33 CAR LV), following CD3/CD28 beads stimulation.

FIG. 9A shows CD33 surface expression levels in tested cells lines (EL4, EL4/CD33 and MOLM-13) as measured by flow cytometry. The bold shaded line shows staining with isotype control antibody and lighter shaded line shows staining the anti-human CD33 antibody. FIG. 9B shows effector:target (E:T) ratio of 10:1. FIG. 9C shows effector:target (E:T) ratio of 1:1.

FIG. 10A shows IFNγ production. FIG. 10B shows IL-2 production. FIG. 10C shows TNF production.

FIG. 13A is a ventral view. FIG. 13B is a dorsal view.

FIG. 14A shows untransduced sample. FIG. 14B shows blood, bone marrow, and spleen samples.

FIG. 15A shows CD33 CAR expression stained with CD3. FIG. 15B shows CD33 CAR expression stained with HER1t.

FIGS. 16A, 16B and 16C show specificity of the CD33 CAR. FIG. 16A shows graphs depicting flow cytometry results of CD33 expression on various AML cell lines. FIG. 16B shows a graph depicting results of 2 hour europium release assay of various LV CD33 CARs in various CD33 expressing AML cell lines. FIG. 16C shows a graph depicting results of cytokine expression released by T cells upon recognition of various CD33 expressing AML cell lines by LV CD33 CARs.

FIG. 20A provides graphs depicting flow cytometry results of CD33 expression on various AML cell lines. FIG. 20B provides a graph depicting results of 2 hour europium release assay of CAR33-CD8a-CD28m-Z (Sleeping Beauty) in various CD33 expressing AML cell lines.

FIGS. 21A-21O provide a sequence table illustrating sequences of nucleic acid and polypeptide sequences for methods and compositions described herein. FIG. 21A provides a partial representative list of nucleic acid and polypeptide sequences for methods and compositions described herein. FIG. 21B provides a partial representative list of nucleic acid and polypeptide sequences for methods and compositions described herein. FIG. 21C provides a partial representative list of nucleic acid and polypeptide sequences for methods and compositions described herein. FIG. 21D provides a partial representative list of nucleic acid and polypeptide sequences for methods and compositions described herein. FIG. 21E provides a partial representative list of nucleic acid and polypeptide sequences for methods and compositions described herein. FIG. 21F provides a partial representative list of nucleic acid and polypeptide sequences for methods and compositions described herein. FIG. 21G provides a partial representative list of nucleic acid and polypeptide sequences for methods and compositions described herein. FIG. 21H provides a partial representative list of nucleic acid and polypeptide sequences for methods and compositions described herein. FIG. 21I provides a partial representative list of nucleic acid and polypeptide sequences for methods and compositions described herein. FIG. 21J provides a partial representative list of nucleic acid and polypeptide sequences for methods and compositions described herein. FIG. 21K provides a partial representative list of nucleic acid and polypeptide sequences for methods and compositions described herein. FIG. 21L provides a partial representative list of nucleic acid and polypeptide sequences for methods and compositions described herein. FIG. 21M provides a partial representative list of nucleic acid and polypeptide sequences for methods and compositions described herein. FIG. 21N provides a partial representative list of nucleic acid and polypeptide sequences for methods and compositions described herein.

FIG. 21O provides a partial representative list of nucleic acid and polypeptide sequences for methods and compositions described herein.

FIGS. 22A-22E provide effects of compositions described herein upon contact with tumor cells, including in vivo results in mice. FIG. 22A provides graphs depicting cytokine (GM-CSF, IFNγ and TNFα) analysis from the plasma of CAR-T cell administered mice on Study Day 11 (3 days after CAR-T cell administration). FIG. 22B provides graphs depicting cytokine (IL-10, IL-18 and IP-10) analysis from the plasma of CAR-T cell administered mice on Study Day 11 (3 days after CAR-T cell administration). FIGS. 22A and 22B: plasma from mice was collected and the human cytokines were assessed by a multiplex analyte platform. Shown is the mean±SEM of several analytes (GM-CSF, IFNγ, TNFα, IL-10, IL-18 and IP-10) that was measured. N=11-15 mice/group, which included mice that were part of the satellite group for tissue collection at a defined time point. * p<0.05;  p<0.01; * p<0.001; one way analysis of variance (ANOVA) with Tukey's multiple comparison testing of saline, untransduced T cells and CD19-CAR-T cells to the respective treatment groups. FIG. 22B provides graphs depicting representative sampling of blood sample taken from AML tumor bearing mice following treatment with CAR T cells. AML bearing tumor mice were treated on Day 8 with either a single administration of saline, untransduced T cells, CD19-CAR-T cells or with CD33-CAR-T cells. The group marked a 2 doses received a second equivalent dose of CD33-CAR-T cells only on study Day 15. Blood samples were obtained from mice to evaluate the presence and persistence of CAR T cells and for presence of MOLM-13 tumor cells (based upon expression of CD123). Flow cytometry data shown in FIGS. 22C and 22D is gated on FSC/SSC/human CD45+ cells. FIG. 22C shows blood samples taken from mice treated with saline only, untransduced T cells or CD19-CAR-T cells on Day 16, as mice became moribund. FIG. 22D shows blood samples taken from remaining mice treated with CD33-CAR-T cells on Day 18. FIG. 22E is a graph depicting Cytotoxic Activity against ALM Tumor cell lines (THP1 and HL60).

FIG. 23A shows PBMCs from an AML donor phenotypically characterized for CD33 and CD3 expression. FIG. 23B shows T cells isolated from the PBMC fraction using a bead based method and the untouched fraction was characterized for CD33+ tumor cells. FIG. 23C shows T cells transduced with the LV-CD33-CAR construct and CAR expression on Day 14 of the culture. FIG. 23D shows co-culture of the AML donor CD33-CAR-T cells with either MOLM-13 or the AML donor tumor cells is-shewn on Day 0 (upon assay set up) and at Day 3. All cells are gated on FSC/SSC/viable cells. FIG. 23E shows cytokine expression following co-culture of CD33-CAR-T cells from AML patient with CD33 expressing tumor cells. Intracellular cytokine staining was performed following co-culture of CD33-CAR-T cells (derived from an AML donor E261) with designated tumor cells after an 18 hrs time period. T cells were cell surface stained then fixed/permeabilized followed by staining for IFNγ and IL-2 cytokine. Cells are gated based upon FSC/SSC/viable/CD3 T cells. AML E261 cells refer to the patient's autologous CD33 tumor cells present in the sample.

DETAILED DESCRIPTION OF THE INVENTION

Figure 2:
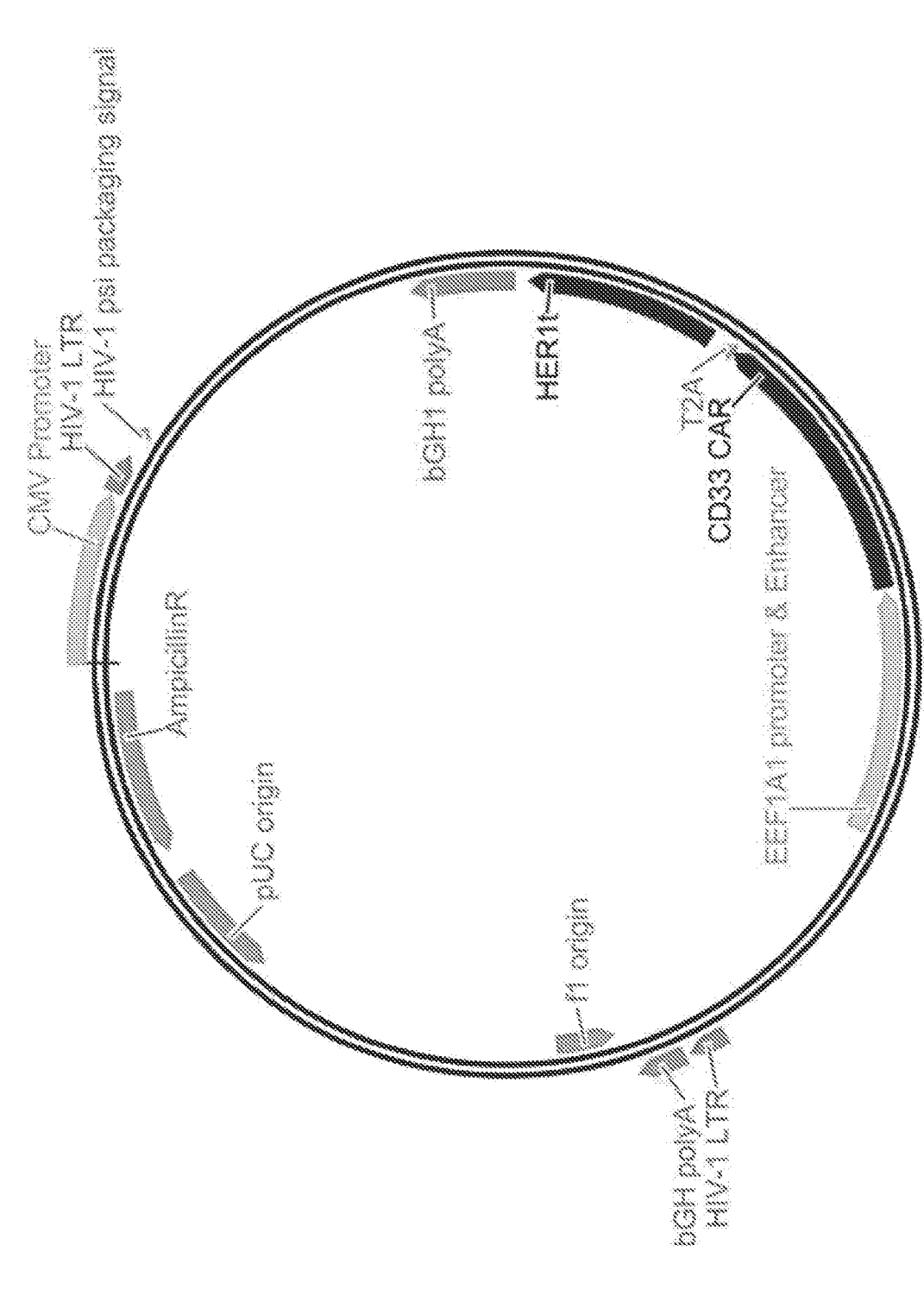
FIG. 2 depicts CD33 CAR lentiviral vector map.

Unless defined otherwise, all technical and scientific terms used herein have the same meaning as commonly understood by one of ordinary skill in the art to which the invention pertains. In describing and claiming the present invention, the following terminology will be used.

Definitions

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

"Synthetic" or "engineered" as used herein refers to compounds formed or expressed through a chemical process and/or by human agency, as opposed to those of natural origin.

By "isolated" is meant the removal of a nucleic acid from its natural environment. By "purified" is meant that a given nucleic acid, whether one that has been removed from nature (including genomic DNA and mRNA) or synthesized (including cDNA) and/or amplified under laboratory conditions, has been increased in purity, wherein "purity" is a relative term, not "absolute purity." It is to be understood, however, that nucleic acids and proteins may be formulated with diluents or adjuvants and still for practical purposes be isolated. For example, nucleic acids typically are mixed with an acceptable carrier or diluent when used for introduction into cells.

"Polynucleotide" or "oligonucleotide" as used herein refers to a polymeric form of nucleotides of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs.

"Polypeptide" is used interchangeably with the terms "polypeptides," "peptide(s)" and "protein(s)", and refers to a polymer of amino acid residues. A "mature protein" is a protein which is full-length and which, optionally, includes glycosylation or other modifications typical for the protein in a given cellular environment.

Nucleic acids and/or nucleic acid sequences are "homologous" when they are derived, naturally or artificially, from a common ancestral nucleic acid or nucleic acid sequence. Proteins and/or protein sequences are homologous when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available.

The terms "identical" or "sequence identity" in the context of two nucleic acid sequences or amino acid sequences of polypeptides refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman, *Adv. Appl. Math.,* 2:482 (1981); by the alignment algorithm of Needleman and Wunsch, *J. Mol. Biol.,* 48:443 (1970); by the search for similarity method of Pearson and Lipman, *Proc. Nat. Acad. Sci U.S.A.,* 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp, *Gene,* 73:237-244 (1988) and Higgins and Sharp, *CABIOS,* 5:151-153 (1989); Corpet et al., *Nucleic Acids Res.,* 16:10881-10890 (1988); Huang et al., *Computer Applications in the Biosciences,* 8:155-165 (1992); and Pearson et al., *Methods in Molecular Biology,*

24:307-331 (1994). Alignment is also often performed by inspection and manual alignment.

In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

The term "substantially identical" as applied to nucleic acid or amino acid sequences means that a nucleic acid or amino acid sequence comprises a sequence that has at least 90% sequence identity or more, at least 95%, at least 98% and at least 99%, compared to a reference sequence using the programs described above, e.g., BLAST, using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1992)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. In embodiments, the substantial identity exists over a region of the sequences that is at least about 50 residues in length, over a region of at least about 100 residues, and in embodiments, the sequences are substantially identical over at least about 150 residues. In embodiments, the sequences are substantially identical over the entire length of the coding regions.

A "functional variant" of a protein disclosed herein can, for example, comprise the amino acid sequence of the reference protein with at least or about 1, 2, 3, 4, 5, 6, 7, 8, 9, 10, 11, 12, 13, 14, 15, 16, 17, 18, 19, or 20 conservative amino acid substitutions. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids may be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge may be maintained; glutamic acid for aspartic acid and vice versa such that a negative charge may be maintained; serine for threonine such that a free —OH can be maintained; and glutamine for asparagine such that a free —$NH_2$ can be maintained.

Alternatively or additionally, the functional variants can comprise the amino acid sequence of the reference protein with at least one non-conservative amino acid substitution. "Non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution may enhance the biological activity of the functional variant, such that the biological activity of the functional variant is increased as compared to the parent CAR.

Proteins disclosed herein (including functional portions and functional variants thereof) may comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

Figure 1:
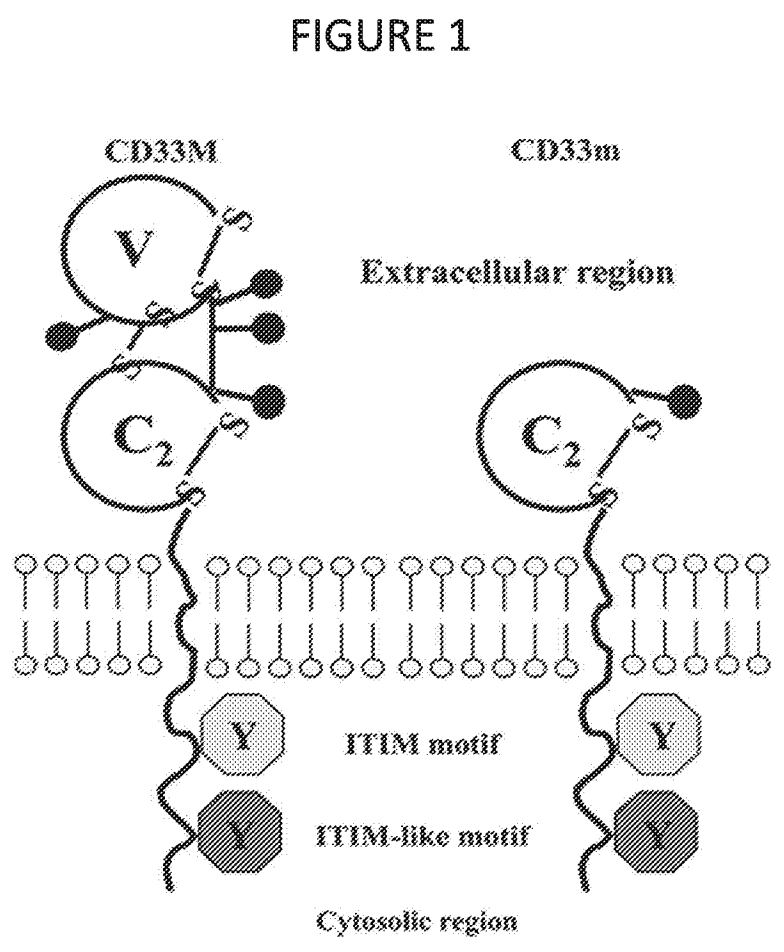

"CD33," is a 67 kDa single pass transmembrane glycoprotein and is a member of the sialic acid-binding immunoglobulin-like lectins (Siglecs) super-family. CD33 is characterized by a V-set Ig-like domain responsible for sialic acid binding and a C2-set Ig-like domain in its extracellular domain. Alternative splicing of CD33 mRNA leads to a shorter isoform (CD33m) lacking the V-set Ig-like domain as well as the disulfide bond linking the V- and C2-set Ig-like domains, as shown in FIG. 1. In healthy subjects, CD33 is primarily expressed as a myeloid differentiation antigen found on normal multipotent myeloid precursors, unipotent colony-forming cells, monocytes and maturing granulocytes. CD33 is expressed on more than 80% of myeloid leukemia cells but not on normal hematopoietic stem cells or mature granulocytes. (Andrews, R. et al., The L4F3 antigen is expressed by unipotent and multipotent colony-forming cells but not by their precursors, *Blood*, 68(5):1030-5 (1986)). CD33 has been reported to be expressed on malignant myeloid cells, activated T cells and activated NK cells and is found on at least a subset of blasts in the vast majority of AML patients (Pollard, J. et al., Correlation of CD33 expression level with disease characteristics and response to gemtuzumab ozogamicin containing chemotherapy in childhood AML, *Blood*, 119(16):3705-11 (2012)). In addition to broad expression on AML blasts, CD33 may be expressed on stem cells underlying AML.

The term "substantially purified" refers to a nucleic acid sequence, polypeptide, protein or other compound which is essentially free, i.e., is more than about 50% free of, more than about 70% free of, more than about 90% free of, the polynucleotides, proteins, polypeptides and other molecules that the nucleic acid, polypeptide, protein or other compound is naturally associated with.

"Coding sequence" as used herein refers to a segment of a polynucleotide that codes for protein. The region or sequence is bounded nearer the 5' end by a start codon and nearer the 3' end with a stop codon. Coding sequences may also be referred to as open reading frames "Operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers may be located upstream, downstream or embedded within the coding regions of the DNA sequence. A DNA for a signal sequence is operably linked to DNA coding for a polypeptide if the signal sequence is expressed as a preprotein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "induction" refers to an increase in nucleic acid sequence transcription, promoter activity and/or expression brought about by a transcriptional regulator, relative to some basal level of transcription.

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter.

The term "promoter activity" refers to the extent of expression of nucleotide sequence that is operably linked to the promoter whose activity is being measured. Promoter activity may be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. In one embodiment, the inducible promoter is part of a genetic switch.

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors may contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors may be capable of directly expressing nucleic acid sequence products encoded therein without ligation or integration of the vector into host cell DNA sequences.

Vector also can comprise a "selectable marker gene." The term "selectable marker gene," as used herein, refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., Proc. Natl. Acad. Sci. USA, 77: 3567 (1980); O'Hare et al., Proc. Natl. Acad. Sci. USA, 78: 1527 (1981); Mulligan &

Berg, Proc. Natl. Acad. Sci. USA, 78: 2072 (1981); Colberre-Garapin et al., J. Mol. Biol., 150:1 (1981); Santerre et al., Gene, 30: 147 (1984); Kent et al., Science, 237: 901-903 (1987); Wigler et al., Cell, 11: 223 (1977); Szybalska & Szybalski, Proc. Natl. Acad. Sci. USA, 48: 2026 (1962); Lowy et al., Cell, 22: 817 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., Gene Therapy, 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

"Transposon" or "transposable element" (TE) is a vector DNA sequence that can change its position within the genome, sometimes creating or reversing mutations and altering the cell's genome size. Transposition often results in duplication of the TE. Class I TEs are copied in two stages: first they are transcribed from DNA to RNA, and the RNA produced is then reverse transcribed to DNA. This copied DNA is then inserted at a new position into the genome. The reverse transcription step is catalyzed by a reverse transcriptase, which may be encoded by the TE itself. The characteristics of retrotransposons are similar to retroviruses, such as HIV. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons may be identified by short direct repeats which may be created by the staggered cut in the target DNA and filling in by DNA polymerase, followed by a series of inverted repeats important for the TE excision by transposase. Cut-and-paste TEs may be duplicated if their transposition takes place during S phase of the cell cycle when a donor site has already been replicated, but a target site has not yet been replicated. Transposition can be classified as either "autonomous" or "non-autonomous" in both Class I and Class II TEs. Autonomous TEs can move by themselves while non-autonomous TEs require the presence of another TE to move. This is often because non-autonomous TEs lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism.

"Sleeping Beauty (SB) Transposon System" refers a synthetic DNA transposon system for to introducing DNA sequences into the chromosomes of vertebrates. Some exemplary embodiments of the system are described, for example, in U.S. Pat. Nos. 6,489,458, 8,227,432, 9,228,180 and WO/2016/145146. The Sleeping Beauty transposon system is composed of a Sleeping Beauty (SB) transposase and a SB transposon. In embodiments, the Sleeping Beauty transposon system can include the SB11 transposon system, the SB100X transposon system, or the SB110 transposon system.

The nucleic acid sequences and vectors disclosed or contemplated herein may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)). Phage or viral vectors can be introduced into host cells, after growth of infectious particles in suitable packaging cells, many of which are commercially available.

"T cell" or "T lymphocyte" as used herein is a type of lymphocyte that plays a central role in cell-mediated immunity. They may be distinguished from other lymphocytes, such as B cells and natural killer cells (NK cells), by the presence of a T-cell receptor (TCR) on the cell surface.

"T helper cells" (TH cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, Th9, or TFH, which secrete different cytokines to facilitate different types of immune responses. Signaling from the APC directs T cells into particular subtypes.

"Cytotoxic T cells" (TC cells, or CTLs) destroy virus-infected cells and tumor cells, and are also implicated in transplant rejection. These cells are also known as CD8+ T cells since they express the CD8 glycoprotein at their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

"Memory T cells" are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells ($T_{CM}$ cells) and two types of effector memory T cells ($T_{EM}$ cells and $T_{EMRA}$ cells). Memory cells may be either CD4+ or CD8+. Memory T cells typically express the cell surface proteins CD45RO, CD45RA and/or CCR7.

"Regulatory T cells" (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

"Natural killer T cells" (NKT cells—not to be confused with natural killer cells of the innate immune system) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both Th and Tc cells (i.e., cytokine production and release of cytolytic/cell killing molecules). They are also able to recognize and eliminate some tumor cells and cells infected with herpes viruses.

"Tumor antigen" as used herein refers to any antigenic substance produced or overexpressed in tumor cells. It may, for example, trigger an immune response in the host. Alternatively, for purposes of this disclosure, tumor antigens may be proteins that are expressed by both healthy and tumor cells but because they identify a certain tumor type, are a suitable therapeutic target. In one embodiment, the tumor antigen is CD33, which is a target for CAR T cell therapies for treating myeloid malignancies, for example, acute myelogenous leukemia (AML).

"AML," as used herein, refers to acute myelogenous leukemia, also known as acute myelocytic leukemia, acute granulocytic leukemia, and acute non-lymphocytic leukemia. AML is differentiated from the other main forms of leukemia because it has eight different subtypes based on the cell type that the leukemia developed from. The term "AML" therefore refers to all subtypes, including myeloblastic (M0) on special analysis, myeloblastic (M1) without maturation, myeloblastic (M2) with maturation, promyelocytic (M3), myelomonocytic (M4), monocytic (M5), erythroleukemia (M6) and megakaryocytic (M7). "AML," as used herein, also refers to acute myeloid leukemia, a cancer in which the bone marrow makes abnormal myeloblasts. It is the most common form of acute leukemia in adults (Siegel, R., Ma, J., Zou, Z. & Jemal, A., *Cancer* statistics, 2014, *CA Cancer J Clin,* 64(1):9-29 (2014)). "Relapsed AML" refers to subjects who have experienced an interval of remission of AML. "Refractory AML" refers to patients whose disease does not respond to the first cycle of initial standard induction therapy (e.g, anthracycline and/or cytarabine-based therapy). In embodiments, "refractory AML" refers to subjects whose disease does not respond to one or two or more cycles of standard induction therapy.

"Adoptive T cell transfer" refers to the isolation and ex vivo expansion of tumor specific T cells to achieve greater number of T cells than what could be obtained by vaccination alone or the patient's natural tumor response. The tumor specific T cells are then infused into patients with cancer in an attempt to give their immune system the ability to overwhelm remaining tumor via T cells which can attack and kill cancer. There are many forms of adoptive T cell therapy being used for cancer treatment; culturing tumor infiltrating lymphocytes or TIL, isolating and expanding one particular T cell or clone, and even using T cells that have been engineered to potently recognize and attack tumors.

"Antigen recognition moiety or domain" refers to a molecule or portion of a molecule that specifically binds to an antigen. In one embodiment, the antigen recognition moiety is an antibody, antibody like molecule or fragment thereof and the antigen is a tumor antigen.

"Antibody" as used herein refers to monoclonal or polyclonal antibodies. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

"Antibody like molecules" may be for example proteins that are members of the Ig-superfamily which are able to selectively bind a partner. MHC molecules and T cell receptors are such molecules. In one embodiment the antibody-like molecule is an TCR. In one embodiment the TCR has been modified to increase its MHC binding affinity.

The terms "fragment of an antibody," "antibody fragment," "functional fragment of an antibody," and "antigen-binding portion" are used interchangeably herein to mean one or more fragments or portions of an antibody that retain the ability to specifically bind to an antigen (see, generally, Holliger et al., Nat. Biotech., 23(9):1126-1129 (2005)). The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., Science, 242: 423-426 (1988); Huston et al., Proc. Natl. Acad. Sci. USA, 85: 5879-5883 (1988); and Osbourn et al., Nat. Biotechnol., 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Patent Application Publication 2009/0093024 A1.

"Chimeric Antigen Receptor" also known as artificial T cell receptors, chimeric T cell receptors, chimeric immunoreceptors. Chimeric antigen receptors (CARs) are engineered receptors, which graft an arbitrary specificity onto an immune effector cell. CARs typically have an extracellular domain (ectodomain), which comprises an antigen-binding domain and a stalk region, a transmembrane domain and an intracellular (endodomain) domain.

A "stalk" region, which encompasses the terms "spacer" or "hinge" region is used to link the antigen-binding domain to the transmembrane domain. As used herein, the term "stalk domain" generally means any oligonucleotide- or polypeptide that functions to link the transmembrane domain to, either the extracellular domain or, the cytoplasmic domain in the polypeptide chain. In embodiments, it is flexible enough to allow the antigen-binding domain to orient in different directions to facilitate antigen recognition. In one embodiment, it is the hinge region from IgG1. Alternatives include but are not limited to the CH2CH3 region of immunoglobulin and portions of CD3. In an embodiment, the stalk region is a CD8alpha hinge (SEQ ID NO:22). The term "functional portion," when used in reference to a CAR, refers to any part or fragment of a CAR described herein, which part or fragment retains the biological activity of the CAR of which it is a part (the parent CAR). In reference to a nucleic acid sequence encoding the parent CAR, a nucleic acid sequence encoding a functional portion of the CAR can encode a protein comprising, for example, about 10%, 25%, 30%, 50%, 68%, 80%, 90%, 95%, or more, of the parent CAR.

The term "functional variant," as used herein, refers to a polypeptide, or a protein having substantial or significant sequence identity or similarity to the reference polypeptide, and retains the biological activity of the reference polypeptide of which it is a variant. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 70% identical, about 75% identical, about 80% identical, about 85% identical, about 90% identical, about 95% identical, or about 99% identical to the nucleic acid sequence encoding the parent CAR.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. The inducible promoter can be part of a genetic switch. The inducible promoter can be a gene switch ligand inducible promoter. In some cases, an inducible promoter can be a small molecule ligand-inducible two polypeptide ecdysone receptor-based gene switch, such as RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/1J52002/005235 (WO 2002/066613); U.S. application Ser. No. 10/468,200 (U.S. Pub. No. 20120167239); PCT/US2002/005706 (WO 2002/066614); U.S. Pat. Nos. 7,531, 326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563, 879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919 each of which is incorporated by reference in its entirety).

"Proliferative disease" as referred to herein means a unifying concept that excessive proliferation of cells and turnover of cellular matrix contribute significantly to the pathogenesis of several diseases, including cancer is presented.

"Patient" as used herein refers to a mammalian subject diagnosed with or suspected of having or developing a proliferative disorder such as cancer. In some embodiments, the term "patient" refers to a mammalian subject with a higher than average likelihood of developing a proliferative disorder such as cancer. Exemplary patients may be humans, apes, dogs, pigs, cattle, cats, horses, goats, sheep, rodents and other mammalians that can benefit from the therapies disclosed herein. Exemplary human patients can be male and/or female.

"Administering" is referred to herein as providing one or more compositions described herein to a patient or a subject. By way of example and not limitation, composition administration, e.g., injection, may be performed by intravenous (i.v.) injection, sub-cutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route. Additionally, administration may also be by surgical deposition of a bolus or pellet of cells, or positioning of a medical device.

"A patient in need thereof" or "a subject in need thereof" is referred to herein as a patient diagnosed with or suspected of having a proliferative disorder such as cancer. In one embodiment, the patient has or is likely to develop leukemias such as but not limited to acute lymphoblastic leukemia (ALL), acute myeloid leukemia (AML), chronic lymphocytic leukemia (CLL) and chronic myeloid leukemia (CML).

In an embodiment, a composition described herein may comprise engineered cells or host cells expressing nucleic acid sequences described herein, or a vector comprising at least one nucleic acid sequence described herein, in an amount that is effective to treat or prevent proliferative disorders. As used herein, the terms "treatment," "treating," and the like refer to obtaining a desired pharmacologic and/or physiologic effect. In embodiments, the effect is therapeutic, i.e., the effect partially or completely cures a disease and/or adverse symptom attributable to the disease. To this end, the inventive method comprises administering a "therapeutically effective amount" of the composition comprising the host cells expressing the inventive nucleic acid sequence, or a vector comprising the inventive nucleic acid sequences.

A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of a composition described herein to elicit a desired response in one or more subjects.

Alternatively, the pharmacologic and/or physiologic effect may be "prophylactic," i.e., the effect completely or partially prevents a disease or symptom thereof.

A "prophylactically effective amount" refers to an amount effective, at dosages and for periods of time necessary, to achieve a desired prophylactic result (e.g., prevention of disease onset).

Chimeric Antigen Receptors

In embodiments described herein, a CAR can comprise an extracellular antibody-derived single-chain variable domain (scFv) for target recognition, wherein the scFv can be connected by a flexible linker to a transmembrane domain and/or an intracellular signaling domain(s) that includes, for instance, CD3ζ for T-cell activation. Normally when T cells are activated in vivo they receive a primary antigen induced TCR signal with secondary costimulatory signaling from CD28 that induces the production of cytokines (i.e., IL-2 and IL-21), which then feed back into the signaling loop in an autocrine/paracrine fashion. With this in mind, CARs can include a signaling domain, for instance, a CD28 cytoplasmic signaling domain or other costimulatory molecule signaling domains such as 4-1BB signaling domain. Chimeric CD28 co-stimulation improves T-cell persistence by up-regulation of anti-apoptotic molecules and production of IL-2, as well as expanding T cells derived from peripheral blood mononuclear cells (PBMC).

In one embodiment, CARs are fusions of single-chain variable fragments (scFv) derived from monoclonal antibodies specific for a tumor associated antigen, CD33 for example, fused to transmembrane domain and CD3-zeta endodomain. Such molecules result in the transmission of a zeta signal in response to recognition by the scFv of its target.

In an embodiment, a CAR may have an ectodomain (extracellular), a transmembrane domain and an endodomain (intracellular). In one embodiment of the CAR ectodomain, a signal peptide directs the nascent protein into the endoplasmic reticulum. This is if the receptor is to be glycosylated and anchored in the cell membrane for example. Any eukaryotic signal peptide sequence is envisaged to be functional. Generally, the signal peptide natively attached to the amino-terminal most component is used (e.g. in a scFv with orientation light chain—linker—heavy chain, the native signal of the light-chain is used). In embodiments, the signal peptide is GM-CSFRa (SEQ ID NO. 16) or IgK (SEQ ID NO. 34). Other signal peptides that can be used include signal peptides from CD8alpha and CD28.

The antigen recognition domain may be a scFv. There may however be alternatives. An antigen recognition domain from native T-cell receptor (TCR) alpha and beta single chains are envisaged, as they have simple ectodomains (e.g. CD4 ectodomain to recognize HIV infected cells) and as well as other recognition components such as a linked e.g., cytokine (which leads to recognition of cells bearing the cytokine receptor). Almost anything that binds a given target, such as e.g., tumor associated antigen, with high affinity can be used as an antigen recognition region.

In general, CARs exist in a dimerized form and are expressed as a fusion protein that links the extracellular scFv (VH linked to VL) region, a stalk domain, a transmembrane domain, and intracellular signaling motifs. The endodomain of the first generation CAR induces T cell activation solely through CD3-ζ signaling. The second generation CAR provides activation signaling through CD3-ζ and CD28, or other endodomains such as 4-1BB or OX40. The 3rd generation CAR activates T cells via a CD3-ζ-containing combination of three signaling motifs such as CD28, 4-1BB, or OX40.

In embodiments, the present invention provides chimeric antigen receptor (CAR) comprising an extracellular domain, a transmembrane domain and an intracellular signaling domain. In embodiments, the extracellular domain comprises a target-specific binding element otherwise referred to as an antigen binding moiety or scFv and a stalk domain. In embodiments, the intracellular signaling domain or otherwise the cytoplasmic signaling domain comprises, a costimulatory signaling region and a zeta chain portion.

The costimulatory signaling region refers to a portion of the CAR comprising the intracellular signaling domain of a costimulatory molecule. Costimulatory molecules are cell surface molecules other than antigens receptors or their ligands that are required for an efficient response of lymphocytes to antigen.

In embodiments, between the extracellular domain and the transmembrane domain of the CAR, there is incorporated a stalk domain. As used herein, the term "stalk domain" generally means any oligonucleotide- or polypeptide that functions to link the transmembrane domain to, either the scFv or, the cytoplasmic domain in the polypeptide chain. A stalk domain can include a flexible hinge such as a Fc hinge and optionally one or two constant domains of Fc.

In some instances, the stalk region comprises the hinge region from IgG1. In alternative instances, the stalk region comprises the CH2CH3 region of immunoglobulin and optionally portions of CD3. In some cases, the stalk region comprises a CD8α hinge region, an IgG4-Fc 12 amino acid hinge region (ESKYGPPCPPCP) (SEQ ID NO: 62) or IgG4 hinge regions as described in WO/2016/073755.

The transmembrane domain can be derived from either a natural or a synthetic source. Where the source is natural, the domain can be derived from any membrane-bound or trans-membrane protein. Suitable transmembrane domains can include the transmembrane region(s) of alpha, beta or zeta chain of the T-cell receptor; or a transmembrane region from CD28, CD3 epsilon, CD3ζ, CD45, CD4, CD5, CD8alpha, CD9, CD16, CD22, CD33, CD37, CD64, CD80, CD86, CD134, CD137 or CD154. Alternatively the transmembrane domain can be synthetic, and can comprise hydrophobic residues such as leucine and valine. In some embodiments, a triplet of phenylalanine, tryptophan and valine is found at one or both termini of a synthetic transmembrane domain. Optionally, a short oligonucleotide or polypeptide linker, in some embodiments, between 2 and 10 amino acids in length may form the linkage between the transmembrane domain and the cytoplasmic signaling domain of a CAR. In some embodiments, the linker is a glycine-serine linker. In some embodiments, the transmembrane domain comprises a CD8α transmembrane domain or a CD3ζ transmembrane domain. In some embodiments, the transmembrane domain comprises a CD8α transmembrane domain. In other embodiments, the transmembrane domain comprises a CD3ζ transmembrane domain.

The intracellular domain can comprise one or more costimulatory domains. Exemplary costimulatory domains include, but are not limited to, CD8, CD27, CD28, 4-1BB (CD137), ICOS, DAP10, DAP12, OX40 (CD134), CD3-zeta or fragment or combination thereof. In some instances, a CAR described herein comprises one or more, or two or more of costimulatory domains selected from CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD27, CD28, 4-1BB (CD137), ICOS, OX40 (CD134) or fragment or combination thereof. In some instances, a CAR described herein comprises one or more, or two or more of costimulatory domains selected from CD8, CD28, 4-1BB (CD137), DAP10, DAP12 or fragment or combination thereof. In some instances, a CAR described herein comprises one or more, or two or more of costimulatory domains selected from CD28, 4-1BB (CD137), or fragment or combination thereof. In some instances, a CAR described herein comprises costimulatory domains CD28 and 4-1BB (CD137) or their respective fragments thereof. In some instances, a CAR described herein comprises costimulatory domains CD28 and OX40 (CD134) or their respective fragments thereof. In some instances, a CAR described herein comprises costimulatory domains CD8 and CD28 or their respective fragments thereof. In some instances, a CAR described herein comprises costimulatory domains CD28 or a fragment thereof. In some instances, a CAR described herein comprises costimulatory domains 4-1BB (CD137) or a fragment thereof. In some instances, a CAR described herein comprises costimulatory domains OX40 (CD134) or a fragment thereof. In some instances, a CAR described herein comprises costimulatory domains CD8 or a fragment thereof. In some instances, a CAR described herein comprises at least one costimulatory domain DAP10 or a fragment thereof. In some instances, a CAR described herein comprises at least one costimulatory domain DAP12 or a fragment thereof.

The intracellular signaling domain, also known as cytoplasmic domain, of the CAR of the present disclosure, is responsible for activation of at least one of the normal effector functions of the immune cell in which the CAR has been placed. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal. In some embodiments, the intracellular domain further comprises a signaling domain for T-cell activation. In some instances, the signaling domain for T-cell activation comprises a domain derived from TCR zeta, FcR gamma, FcR beta, CD3 gamma, CD3 delta, CD3 epsilon, CD5, CD22, CD79a, CD79b or CD66d. In some cases, the signaling domain for T-cell activation comprises a domain derived from CD3ζ.

In embodiments, provided herein is an isolated nucleic acid encoding a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; (e) a CD3 zeta signaling domain; and optionally (f) a truncated epidermal growth factor receptor (HER1t or HER1t-1).

Included in the scope of the invention are nucleic acid sequences that encode functional portions of the CAR described herein. Functional portions encompass, for example, those parts of a CAR that retain the ability to recognize target cells, or detect, treat, or prevent a disease, to a similar extent, the same extent, or to a higher extent, as the parent CAR.

In embodiments, the CAR contains additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity of the CAR, as compared to the biological activity of the parent CAR.

The term "functional variant," as used herein, refers to a CAR, a polypeptide, or a protein having substantial or significant sequence identity or similarity to the CAR encoded by the inventive nucleic acid sequence, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 80% identical, about 90% identical, about 95% identical, or about 99% identical to the nucleic acid sequence encoding the parent CAR.

A CAR described herein include (including functional portions and functional variants thereof) glycosylated, amidated, carboxylated, phosphorylated, esterified, N-acylated, cyclized via, e.g., a disulfide bridge, or converted into an acid addition salt and/or optionally dimerized or polymerized, or conjugated.

Antigen Binding Moiety

In embodiments, a CAR described herein comprises a target-specific binding element otherwise referred to as an antigen-binding moiety. In embodiments, a CAR described herein engineered to target a tumor antigen of interest by way of engineering a desired antigen-binding moiety that specifically binds to an antigen on a tumor cell. In the context of the present invention, "tumor antigen" or "hyperproliferative disorder antigen" or "antigen associated with a hyperproliferative disorder," refers to antigens that are common to specific hyperproliferative disorders such as cancer.

In embodiments, the antigen binding moiety of a CAR described herein is specific to CD33 (CD33 CAR). The CD33-specific CAR, when expressed on the cell surface, redirects the specificity of T cells to human CD33. In embodiments, the antigen binding domain comprises a single chain antibody fragment (scFv) comprising a variable domain light chain (VL) and variable domain heavy chain (VH) of a target antigen specific monoclonal anti-CD33 antibody joined by a flexible linker, such as a glycine-serine linker or a Whitlow linker. In embodiments, the scFv are M195, m2H12, DRB2, and/or My9-6. In embodiments, the scFv is humanized, for example, hM195. In some embodiments, the antigen binding moiety may comprise VH and VL that are directionally linked, for example, from N to C terminus, VH-linker-VL or VL-linker-VH.

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:1 (hM195 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:3 (hM195 VH).

In embodiments, a CAR described herein comprises antigen binding moieties VL (SEQ ID NO:1) and VH (SEQ ID NO:3) of humanized anti-CD33 mAb clone hM195 with Gly-Ser linker (SEQ ID NO:6) or functional variants of the linker.

In embodiments, a CAR described herein comprises an antigen-binding moiety comprising a polypeptide having at least 90%, 91%, 92%, 93%, 94%, 95%, 96%, 97%, 98%, 99% or 100% identity with the amino acid sequence of SEQ ID NO:8 (hM195 VH, VL and linker).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:9 (M2H12 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:10 (M2H12 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:11 (DRB2 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:12 (DRB2 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:13 (My9-6 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:14 (My9-6 VL).

In embodiments, the antigen binding moiety has GM-CSFRa signal peptide having at least 90%, 91%, 92%, 93%, 94%, 95%, 96%, 97%, 98%, 99% or 100% identity with the amino acid sequence of SEQ ID NO:16.

Stalk Domain

In embodiments, the CD33 CAR of the invention comprises a stalk domain that provides a separation between the antigen binding moiety and the T cell membrane. In embodiments, the stalk domain establishes an optimal effector-target inter-membrane distance. In embodiments, the stalk domain provides flexibility for antigen binding domain to reach its target.

In one embodiment, the stalk domain is a CD8alpha hinge domain.

In embodiments, the CD8alpha hinge domain comprises a polypeptide having at least 90%, 91%, 92%, 93%, 94%, 95%, 96%, 97%, 98%, 99% or 100% identity with the amino acid sequence of SEQ ID NO:22.

Transmembrane Domain

In embodiments, the CAR comprises a transmembrane domain that is fused to the extracellular domain of the CAR stalk domain. In one embodiment, the transmembrane domain that naturally is associated with one of the domains in the CAR is used. In embodiments, the transmembrane domain is a hydrophobic alpha helix that spans the membrane.

The transmembrane domain may be derived from either a natural or a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8alpha, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. In embodiments, a triplet of phenylalanine, tryptophan and valine will be found at each end of a synthetic transmembrane domain. Optionally, a short oligonucleotide or polypeptide linker, in embodiments, between 2 and 10 amino acids in length may form the linkage between the transmembrane domain and the cytoplasmic signaling domain of the CAR. In embodiments, the linker is a glycine-serine linker.

In embodiments, the transmembrane domain in a CAR described herein is the CD8alpha transmembrane domain. In embodiments, the CD8alpha transmembrane domain comprises a polypeptide having at least 90%, 91%, 92%, 93%, 94%, 95%, 96%, 97%, 98%, 99% or 100% identity with the amino acid sequence of SEQ ID NO:18.

In embodiments, the transmembrane domain in a CAR described herein is the CD28 transmembrane domain. In embodiments, the CD28 transmembrane domain comprises a polypeptide having at least 90%, 91%, 92%, 93%, 94%, 95%, 96%, 97%, 98%, 99% or 100% identity with the amino acid sequence of SEQ ID NO:20.

Cytoplasmic Domain (Co-Stimulatory Domain and Signaling Domain)

The cytoplasmic domain, also known as the intracellular signaling domain of a CAR described herein, is responsible for activation of at least one of the normal effector functions of the immune cell in which the CAR has been placed. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in a CAR described herein can include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Signals generated through the TCR alone are generally insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM-containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. In embodiments, the cytoplasmic signaling molecule in a CAR described herein comprises a cytoplasmic signaling sequence derived from CD3 zeta.

In embodiments, the cytoplasmic domain of the CAR can be designed to comprise the CD3-zeta signaling domain by itself or combined with any other desired cytoplasmic domain(s) useful in the context of a CAR described herein. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. In embodiments, costimulatory molecules can be used together, e.g., CD28 and 4-1BB or CD28 and OX40. Thus, while the invention in exemplified primarily with 4-1BB and CD28 as the co-stimulatory signaling element, other costimulatory elements are within the scope of the invention.

The cytoplasmic signaling sequences within the cytoplasmic signaling portion of a CAR described herein may be linked to each other in a random or specified order. Optionally, a short oligo- or polypeptide linker, between 2 and 10 amino acids in length may form the linkage. A glycine-serine doublet provides a particularly suitable linker.

In one embodiment, the cytoplasmic domain comprises the signaling domain of CD3-zeta and the signaling domain of CD28. In another embodiment, the cytoplasmic domain comprises the signaling domain of CD3-zeta and the signaling domain of 4-1BB. In yet another embodiment, the cytoplasmic domain is comprises the signaling domain of CD3-zeta and the signaling domains of CD28 and 4-1BB.

In one embodiment, the cytoplasmic domain in a CAR described herein comprises the signaling domain of 4-1BB and the signaling domain of CD3-zeta, wherein the signaling domain of 4-1BB comprises a polypeptide sequence having at least 90%, 91%, 92%, 93%, 94%, 95%, 96%, 97%, 98%, 99% or 100% identity with the polypeptide sequence of SEQ ID NO:24, and the signaling domain of CD3-zeta comprises a polypeptide sequence having at least 90%, 91%, 92%, 93%, 94%, 95%, 96%, 97%, 98%, 99% or 100% identity with the nucleic acid sequence of SEQ ID NO:26.

In one embodiment, the cytoplasmic domain in a CAR described herein is designed to comprise the signaling domain of CD28 and the signaling domain of CD3-zeta, wherein the signaling domain of CD28 comprises a polypeptide sequence having at least 90%, 91%, 92%, 93%, 94%, 95%, 96%, 97%, 98%, 99% or 100% identity with the polypeptide sequence of SEQ ID NO:28, and the signaling domain of CD3-zeta comprises a polypeptide sequence having at least 90%, 91%, 92%, 93%, 94%, 95%, 96%, 97%, 98%, 99% or 100% identity with the polypeptide sequence of SEQ ID NO:26.

In one embodiment, the cytoplasmic domain in a CAR described herein comprises the signaling domain of 4-1BB and the signaling domain of CD3-zeta, wherein the signaling domain of 4-1BB comprises the amino acid sequence set forth in SEQ ID NO:24 and the signaling domain of CD3-zeta comprises the amino acid sequence set forth in SEQ ID NO:26.

Additional Genetic Elements

Although cellular therapies hold great promise for the treatment of human disease, significant toxicities from the cells themselves or from their transgene products have hampered clinical investigation. In embodiments described herein, immune effector cells comprising a CAR described herein that have been infused into a mammalian subject, e.g., a human, can be ablated in order to regulate the effect of such immune effector cells should toxicity arise from their use. Therefore, certain in embodiments, in addition to the therapeutic CD33-specific chimeric antigen receptor described herein, a second gene is also introduced into an engineered immune effector cell described herein. The second gene is effectively a "kill switch" that allows for the depletion of CD33 CAR containing cells. In certain embodiments, the "kill switch" is a HER1 tag or a CD20 tag which comprise a HER1 polypeptide or a CD20 polypeptide which comprises at least an antibody binding epitope of HER1 or CD20 or functional fragment thereof, and optionally a signal polypeptide sequence or fragment thereof.

In certain embodiments, the second gene is a HER1 tag which is Epidermal Growth Factor Receptor (HER1) or a fragment or variant thereof. In embodiments, the second gene is a HER1 tag which is truncated human Epidermal Growth Factor Receptor 1 (for instance HER1t or HER1t-1). In some cases, the second gene is a variant of a truncated human Epidermal Growth Factor Receptor 1. In embodiments, at least one of HER1, HER1t and HER1t-1 provides a safety mechanism by allowing for depletion of infused CAR-T cells through administering FDA approved cetuximab or any antibody that recognizes HER1, HER1t and/or HER1t-1. In embodiments, the HER1t gene comprises a nucleotide sequence having at least 90%, 91%, 92%, 93%, 94%, 95%, 96%, 97%, 98%, 99% or 100% identity with the nucleic acid sequence of SEQ ID NO:32. In embodiments, the HER1t-1 gene comprises a nucleotide sequence having at least 90%, 91%, 92%, 93%, 94%, 95%, 96%, 97%, 98%, 99% or 100% identity with the nucleic acid sequence of SEQ ID NO:54. The truncated HER1 sequence, for instance HER1t and HER1t-1 eliminate the potential for EGF ligand binding, homo- and hetero-dimerization of EGFR, and EGFR mediated signaling while keeping cetuximab binding to the receptor intact (Ferguson, K., 2008. A structure-based view of Epidermal Growth Factor Receptor regulation. *Annu Rev Biophys*, Volume 37, pp. 353-373).

In further embodiments, in addition to the therapeutic CD33-specific chimeric antigen receptor of the invention the second gene introduced is a CD20 tag. In some cases, the CD20 tag is a full-length CD20 polypeptide, or a truncated CD20 polypeptide (CD20t-1). In some cases, the CD20 tag, for instance CD20 or CD20t-1 also provides a safety mechanism by allowing for depletion of infused CAR-T cells through administering FDA-approved rituximab therapy. In certain embodiments, the CD20 tag has a polypeptide sequence having at least 90%, 91%, 92%, 93%, 94%, 95%, 96%, 97%, 98%, 99% or 100% identity with the sequence of SEQ ID NO:36. In certain embodiments, the CD20 tag is a CD20t-1 tag and has a polypeptide sequence having at least 90%, 91%, 92%, 93%, 94%, 95%, 96%, 97%, 98%, 99% or 100% identity with the sequence of SEQ ID NO: 56. In some embodiments, the CD20 tag is encoded by a CD20 gene which comprises a nucleotide sequence having at least 90%, 91%, 92%, 93%, 94%, 95%, 96%, 97%, 98%, 99% or 100% identity with the nucleic acid sequence of SEQ ID NO:35. In some embodiments, the CD20 tag is encoded by a CD20t-1 gene which comprises a nucleotide sequence having at least 90%, 91%, 92%, 93%, 94%, 95%, 96%, 97%, 98%, 99% or 100% identity with the nucleic acid sequence of SEQ ID NO:57.

In embodiments, a CAR vector comprising a CAR described herein further comprises a full length CD20 tag comprising a nucleic acid sequence having at least 90%, 91%, 92%, 93%, 94%, 95%, 96%, 97%, 98%, 99% or 100% identity with the nucleic acid sequence of SEQ ID NO:36.

In embodiments, the gene encoding the kill tag, for instance the HER1t, HER1t-1, CD20 or CD20t-1 tag, is genetically fused to the CD33 CAR at 3' end via in-frame with a self-cleaving peptide, for example but not restricted to *Thosea asigna* virus (T2A) peptide. In embodiments, the T2A peptide has an amino acid sequence having at least 90%, 91%, 92%, 93%, 94%, 95%, 96%, 97%, 98%, 99% or 100% identity with the amino acid sequence of SEQ ID NO:30.

In embodiments, the kill tag gene is cloned into the pFUGW lentiviral plasmid backbone in frame with the CD33 CAR gene. In other embodiments, both genes are cloned into a Sleeping Beauty transposon vector. In other embodiments, the kill tag is cloned into a separate lentiviral vector. In yet other embodiments, the kill tag such as HER1t, HER1t-1, CD20 or CD20t-1 is cloned into a separate Sleeping Beauty transposon vector. In certain embodiments, the kill tags have a signal peptide, for instance, GM-CSFRa signal peptide wherein the GM-CSFRa signal peptide has at least 90%, 91%, 92%, 93%, 94%, 95%, 96%, 97%, 98%, 99% or 100% identity with the amino acid sequence of SEQ ID NO:16. In certain embodiments, the signal peptide is IgK having a sequence at least 90%, 91%, 92%, 93%, 94%, 95%, 96%, 97%, 98%, 99% or 100% identity with the nucleic acid sequence of SEQ ID NO:34. In some cases the signal peptide can be selected from IgE and CD8□□ variants and fragments thereof.

An exemplary vector encoding a CAR and a kill tag as described herein is shown in FIG. 2.
Exemplary CAR Open Reading Frames Exemplary CAR and human CD33 receptor open reading frames encompassed by methods and compositions described herein are in Table 1:

TABLE 1

| CAR ORF |
| --- |
| 1  hM195scFv-CD8a-CD28m-Z (SEQ ID NO: 39) |
| 2  hM195scFv-CD8a-Z (SEQ ID NO: 41) |
| 3  hM195scFv-CD8a-CD28m-Z-T2A-GM-CSFRasp.HER1t ((SEQ ID NO: 43) |
| 4  hM195scFv (SEQ ID NO: 45) |
| 5  hM195scFv-CD8a-4-1BB-Z (SEQ ID NO: 47) |
| 6  hM195scFv-CD8a-4-1BB-Z-T2A-GM-CSFRasp.HER1t (SEQ ID NO: 49) |
| 7  hM195scFv-CD8a-4-1BB-Z-T2A.FL CD20 (SEQ ID NO: 51) |
| 8  human CD33(M1-R287) (SEQ ID NO: 53) |

In embodiments, provided herein is an isolated nucleic acid encoding a CAR, wherein the CAR comprises a polypeptide having at least 90%, 91%, 92%, 93%, 94%, 95%, 96%, 97%, 98%, 99% or 100% identity with an amino acid of SEQ ID NO:39, SEQ ID NO:41, SEQ ID NO:43, SEQ ID NO:45, SEQ ID NO:47, SEQ ID NO:49, SEQ ID NO:51 or SEQ ID NO:53.

In each of the embodiments listed in Table 1 with "hM195scFv," the CAR antigen binding moiety is hM195scFV comprising a polypeptide having at least 90%, 91%, 92%, 93%, 94%, 95%, 96%, 97%, 98%, 99% or 100% identity with the amino acid sequence of SEQ ID NO:8. In embodiments, hM195scFv has GM-CSFRa signal peptide having at least 90%, 91%, 92%, 93%, 94%, 95%, 96%, 97%, 98%, 99% or 100% identity with the amino acid sequence of SEQ ID NO:16.

In each of the embodiments in Table 1 with "CD8a," the transmembrane region of the CAR comprises CD8alpha transmembrane domain comprising a polypeptide having at least 90%, 91%, 92%, 93%, 94%, 95%, 96%, 97%, 98%, 99% or 100% identity with the amino acid sequence of SEQ ID NO:18, and the stalk domain is CD8a comprising a polypeptide having at least 90%, 91%, 92%, 93%, 94%, 95%, 96%, 97%, 98%, 99% or 100% identity with the amino acid sequence of SEQ ID NO:22.

In each of the embodiments in Table 1 with "CD28m," the intracellular domain of the CAR comprises CD28 with an amino acid sequence having at least 90%, 91%, 92%, 93%, 94%, 95%, 96%, 97%, 98%, 99% or 100% identity with the amino acid sequence of SEQ ID NO:28.

In each of the embodiments in Table 1 with "T2A", the CAR ORF comprises a self-cleaving *Thosea asigna* virus (T2A) peptide, which enables the production of multiple gene products from a single vector. In embodiments, the T2A peptide has an amino acid sequence having at least 90%, 91%, 92%, 93%, 94%, 95%, 96%, 97%, 98%, 99% or 100% identity with the amino acid sequence of SEQ ID NO:30.

In the embodiments in Table 1 with "HER1t," the CAR ORF comprises truncated human Epidermal Growth Factor Receptor 1 (HER1t), which provides a safety mechanism by allowing for depletion of infused CAR-T cells through administering FDA approved cetuximab therapy. The HER It gene as described herein can comprise a polypeptide sequence having at least 90%, 91%, 92%, 93%, 94%, 95%, 96%, 97%, 98%, 99% or 100% identity with the amino acid sequence of SEQ ID NO:31. Unless otherwise noted in Table 1, HER1t tags have GM-CSFRa signal peptide ("GM-CSFRsp") (SEQ ID NO:16). In certain embodiments, the HER1t may be substituted with another tag, for instance, HER1t-1 or CD20t-1. In the embodiments in Table 1 with "IgKsp," the signal peptide is IgK having an amino acid sequence at least 90%, 91%, 92%, 93%, 94%, 95%, 96%, 97%, 98%, 99% or 100% identity with the amino acid sequence of SEQ ID NO:34.

In embodiments in Table 1 with "4-1BB," the CAR ORF comprises costimulatory molecule having a polypeptide sequence having at least 90%, 91%, 92%, 93%, 94%, 95%, 96%, 97%, 98%, 99% or 100% identity with the amino acid sequence of SEQ ID NO:24. In embodiments in Table 1 with "FL CD20," the CAR ORF comprises a full length CD20 tag comprising a polypeptide sequence having at least 90%, 91%, 92%, 93%, 94%, 95%, 96%, 97%, 98%, 99% or 100% identity with the amino acid sequence of SEQ ID NO:36. CD20 provides a safety mechanism by allowing for depletion of infused CAR-T cells through administering FDA-approved rituximab therapy. In certain embodiments in Table 1, the CAR ORF can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

Cytokines

In some embodiments, a CAR described herein of the is administered to a subject with one or more additional therapeutic agents that include but are not limited to cytokines. In some cases, the cytokine comprises at least one chemokine, interferon, interleukin, lymphokine, tumor necrosis factor, or variant or combination thereof. In some cases, the cytokine is an interleukin. In some cases the interleukin is at least one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33 and functional variants and fragments thereof. In some embodiments, the cytokines can be membrane bound or secreted. In embodiments, the cytokine is soluble IL-15, soluble IL-15/IL-15R□ complex (e.g., ALT-803). In certain cases, the interleukin can comprise membrane bound IL-15 (mbIL-15) or a fusion of IL-15 and IL-15R□□□ In some embodiments, a mbIL-15 is a membrane-bound chimeric IL-15 which can be co-expressed with a modified immune effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15RU through a linker. In some instances, the mbIL-15 is as described in Hurton et al., "Tethered IL-15 augments antitumor activity and promotes a stein-cell memory subset in tumor-specific T cells," PNAS 2016. In some cases, the cytokine is expressed in the same immune effector cell as the CAR. In some embodiments, the cytokines described above can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In further embodiments, an immune effector cell expressing a CAR described herein expresses membrane-bound IL-15 ("mIL-15 or mbIL-15"). In aspects of the invention, the mbIL-15 comprises a fusion protein between IL-15 and IL-15R□. In further embodiments, the mbIL-15 comprises an amino acid sequence having at least 90%, 91%, 92%, 93%, 94%, 95%, 96%, 97%, 98%, 99% or 100% identity with the amino acid sequence of SEQ ID NO:37

In some embodiments, the mbIL-15 is expressed with a cell tag such as HER1t, HER-It-1, CD20t-1 or CD20 as described herein. The mbIL-15 may be expressed in-frame with HER1t, HER-It-1, CD20t-1 or CD20.

In some embodiments, the mbIL-15 can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

Viral Based Delivery Systems

The present invention also provides delivery systems, such as viral-based systems, in which a nucleic acid of the present invention is inserted. Representative viral expression vectors include, but are not limited to, the adenovirus-based vectors (e.g., the adenovirus-based Per.C6 system available from Crucell, Inc. (Leiden, The Netherlands)), lentivirus-based vectors (e.g., the lentiviral-based pLPI from Life Technologies (Carlsbad, Calif.)) and retroviral vectors (e.g., the pFB-ERV plus pCFB-EGSH), herpes viruses. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In general, and in embodiments, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In embodiments, provided is a lentiviral vector comprising a backbone and a nucleic acid sequence encoding a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; (e) a CD3 zeta signaling domain. Optionally, the vector further comprises a nucleic acid encoding a truncated epidermal growth factor receptor (HER1t or HER1t-1), CD20t-1 or a full length CD20.

In some cases is provided a vector comprising a backbone and a nucleic acid sequence encoding (1) a truncated epidermal growth factor receptor for instance HER1t or HERt-1 or a functional variant thereof; and (2) a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain.

In some cases is provided a vector comprising a backbone and a nucleic acid sequence encoding (1) full length CD20, truncated CD20 or functional variants thereof, and (2) a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain.

In embodiments, the nucleic acid encoding the CD33 specific CAR is cloned into a vector comprising lentiviral backbone components. Exemplary backbone components include, but are not limited to, pFUGW, and pSMPUW. The pFUGW lentiviral vector backbone is a self inactivating (SIN) lentiviral vector backbone and has unnecessary HIV-1 viral sequences removed resulting in reduced potential for the development of neoplasia, harmful mutations, and regeneration of infectious particles. In embodiments, the vector encoding the CD33 CAR also encodes mbIL-15 in a single construct. In embodiments, the CD33 CAR and mbIL-15 are encoded on two separate lentiviral vectors. In some embodiments, the mbIL-15 is expressed with a truncated epidermal growth factor receptor tag. In embodiments, the CD33 CAR can be co-expressed with mbIL-15 and the cell tag from a single lentiviral vector. In further embodiments, the CD33 CAR can be under the control of an inducible promoter. In another embodiment, the mbIL-15 can be under the control of an inducible promoter. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In one embodiment, a CD33 CAR described herein comprises anti-CD33 scFv, human CD8 hinge and transmembrane domain, and human 4-1BB and CD3zeta signaling domains. In another embodiment, the CD33 CAR of the invention comprises anti-CD33 scFv, human CD8 hinge and transmembrane domain, human 4-1BB and CD3zeta signaling domains and optionally, a truncated epidermal growth factor receptor (HER1t or HER1t-1) tag. Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto.

Another example of a suitable promoter is human elongation growth factor 1 alpha 1 (hEF1a1). In embodiments, the vector construct comprising a CAR described herein comprises hEF1a1 functional variants.

However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR described herein or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker can be carried on a separate piece of DNA and used in a co-transfection procedure. Both selectable markers and reporter genes can be flanked with appropriate regulatory sequences to enable expression in the host cells. Useful selectable markers include, for example, antibiotic-resistance genes, such as neomycin resistance gene (neo) and ampicillin resistance gene and the like. In some embodiments, a truncated epidermal growth factor receptor (HER1t or HER1t-1) tag can be used as a selectable marker gene.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes include genes encoding luciferase, beta-galactosidase, chloramphenicol acetyl transferase, secreted alkaline phosphatase, or the green fluorescent protein gene (e.g., Ui-Tei et al., FEBS Letters 479: 79-82 (2000)). Suitable expression systems are well known and can be prepared using known techniques or obtained commercially. In general, the construct with the minimal 5' flanking region showing the highest level of expression of reporter gene is identified as the promoter. Such promoter regions can be linked to a reporter gene and used to evaluate agents for the ability to modulate promoter-driven transcription.

In embodiments, a vector described herein can comprise a hEF1a1 promoter to drive expression of transgenes, a bovine growth hormone polyA sequence to enhance transcription, a woodchuck hepatitis virus posttranscriptional regulatory element (WPRE), as well as LTR sequences derived from the pFUGW plasmid.

Methods of introducing and expressing genes into a cell are well known. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell, for instance an immune effector cell, include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection.

Biological methods for introducing a polynucleotide of interest into a host cell, for instance an immune effector cell, include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a viral delivery system is utilized, an exemplary delivery vehicle is a liposome. Lipid formulations can be used for the introduction of the nucleic acids into a host cell (in vitro, ex vivo or in vivo). In another aspect, the nucleic acid may be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They can also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5: 505-10 (1991)). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Non-Viral Based Delivery Systems

Figure 3:
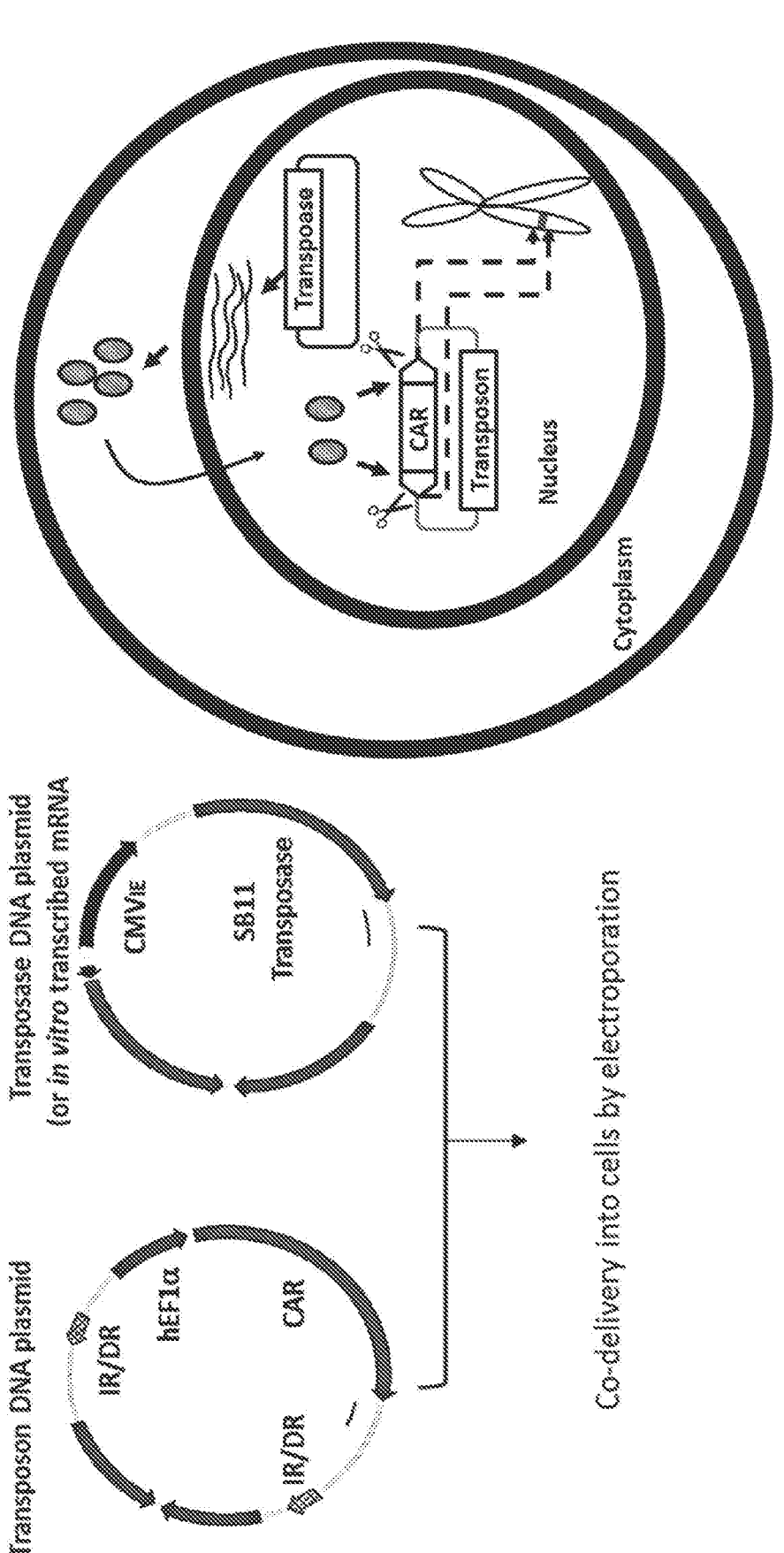
FIG. 3 is an exemplary schematic of Sleeping Beauty Transposon System

A nucleic acid encoding a CAR described invention can also be introduced into immune effector cells using non-viral based delivery systems, such as the "Sleeping Beauty (SB) Transposon System," which refers a synthetic DNA transposon system for introducing DNA sequences into the chromosomes of vertebrates. An exemplary SB transposon system is described for example, in U.S. Pat. Nos. 6,489,458 and 8,227,432, and is illustrated in FIG. 3. The Sleeping Beauty transposon system is composed of a Sleeping Beauty (SB) transposase and a SB transposon.

DNA transposons translocate from one DNA site to another in a simple, cut-and-paste manner. Transposition is a precise process in which a defined DNA segment is excised from one DNA molecule and moved to another site in the same or different DNA molecule or genome. As do other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, in which case the transposon becomes a non-autonomous element. Non-autonomous transposons are most useful as genetic tools because after insertion they cannot independently continue to excise and re-insert. SB transposons envisaged to be used as non-viral vectors for introduction of genes into genomes of vertebrate animals and for gene therapy. Briefly, the Sleeping Beauty (SB) system (Hackett et al., Mol Ther 18:674-83, (2010)) was adapted to genetically modify the T cells (Cooper et al., Blood 105:1622-31, (2005)). This involved two steps: (i) the electro-transfer of DNA plasmids expressing a SB transposon [i.e., chimeric antigen receptor (CAR) to redirect T-cell specificity (Jin et al., Gene Ther 18:849-56, (2011); Kebriaei et al., Hum Gene Ther 23:444-50, (2012)) and SB transposase and (ii) the propagation and expansion of T cells stably expressing integrants on designer artificial antigen-presenting cells (AaPC) derived from the K562 cell line (also known as AaPCs (Activating and Propagating Cells). In one embodiment, the SB transposon system includes coding sequence encoding tdIL-15, an IL-21 and/or a chimeric antigen receptor. Such systems are described for example in Singh et al., Cancer Res (8):68 (2008). Apr. 15, 2008 and Maiti et al., J Immunother. 36(2): 112-123 (2013), incorporated herein by reference in their entireties.

In certain embodiments, a CD33 CAR described herein and mbIL-15 are encoded in a transposon DNA plasmid vector, and the SB transposase is encoded in a separate vector. In certain embodiments, a CD33 CAR described herein is encoded in a transposon DNA plasmid vector, mb-IL15 is encoded in a second transposon DNA plasmid vector, and the SB transposase is encoded in a third DNA plasmid vector. In some embodiments, the mbIL-15 is encoded with a kill tag, for instance, HER1t, HRt-1, CD20 or CD20t-1.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In embodiments, the CD33 CARs and other genetic elements are delivered to a cell using the SB11 transposon system, the SB100X transposon system, the SB110 transposon system, the piggyBac transposon system (see, e.g., Wilson et al, "PiggyBac Transposon-mediated Gene Transfer in Human Cells," Molecular Therapy 15:139-145 (2007), incorporated herein by reference in its entirety) and/or the piggyBat transposon system (see, e.g., Mitra et al., "Functional characterization of piggyBat from the bat *Myotis lucifugus* unveils an active mammalian DNA transposon," Proc. Natl. Acad. Sci USA 110:234-239 (2013). Additional transposases and transposon systems are provided in U.S. Pat. Nos. 7,148,203; 8,227,432; U.S. Patent Publn. No. 2011/0117072; Mates et al., *Nat Genet,* 41(6):753-61 (2009). doi: 10.1038/ng.343. Epub 2009 May 3, *Gene Ther.,* 18(9):849-56 (2011). doi: 10.1038/gt.2011.40. Epub 2011 Mar. 31 and in Ivics et al., Cell. 91(4):501-10, (1997), each of which is incorporated herein by reference in their entirety.

In other embodiments, the CD33 CAR and other genetic elements such as cytokines, mbIL-15 and/or HER1t/HER1t-1/CD20/CD20t-1 tag, can be integrated into the immune effector cell's DNA through a recombinase and integrating expression vectors. Such vectors may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. In some embodiments, targeted integration is promoted by the presence of sequences on the donor polynucleotide that are homologous to sequences flanking the integration site. For example, targeted integration using the donor polynucleotides described herein may be achieved following conventional transfection techniques, e.g. techniques used to create gene knockouts or knockins by homologous recombination. In other embodiments, targeted integration is promoted both by the presence of sequences on the donor polynucleotide that are homologous to sequences flanking the integration site, and by contacting the cells with donor polynucleotide in the presence of a site-specific recombinase. By a site-specific recombinase, or simply a recombinase, it is meant is a polypeptide that catalyzes conservative site-specific recombination between its compatible recombination sites. As used herein, a site-specific recombinase includes native polypeptides as well as derivatives, variants and/or fragments that retain activity, and native polynucleotides, derivatives, variants, and/or fragments that encode a recombinase that retains activity.

The recombinases can be introduced into a target cell before, concurrently with, or after the introduction of a targeting vector. The recombinase can be directly introduced into a cell as a protein, for example, using liposomes, coated particles, or microinjection. Alternately, a polynucleotide, either DNA or messenger RNA, encoding the recombinase can be introduced into the cell using a suitable expression vector. The targeting vector components described above are useful in the construction of expression cassettes containing sequences encoding a recombinase of interest. However, expression of the recombinase can be regulated in other ways, for example, by placing the expression of the recombinase under the control of a regulatable promoter (i.e., a promoter whose expression can be selectively induced or repressed).

A recombinase can be from the Integrase or Resolvase families. The Integrase family of recombinases has over one hundred members and includes, for example, FLP, Cre, and lambda integrase. The Integrase family, also referred to as the tyrosine family or the lambda integrase family, uses the catalytic tyrosine's hydroxyl group for a nucleophilic attack on the phosphodiester bond of the DNA. Typically, members of the tyrosine family initially nick the DNA, which later forms a double strand break. Examples of tyrosine family integrases include Cre, FLP, SSV1, and lambda ($\lambda$) integrase. In the resolvase family, also known as the serine recombinase family, a conserved serine residue forms a covalent link to the DNA target site (Grindley, et al., (2006) Ann Rev Biochem 16:16).

In one embodiment, the recombinase is an isolated polynucleotide sequence comprising a nucleic acid sequence that encodes a recombinase selecting from the group consisting of a SP$\beta$c2 recombinase, a SF370.1 recombinase, a Bxb1 recombinase, an A118 recombinase and a $\Phi$Rv1 recombinase. Examples of serine recombinases are described in detail in U.S. Pat. No. 9,034,652, hereby incorporated by reference in its entirety.

Recombinases for use in the practice of the present invention can be produced recombinantly or purified as previously described. Polypeptides having the desired recombinase activity can be purified to a desired degree of purity by methods known in the art of protein ammonium sulfate precipitation, purification, including, but not limited to, size fractionation, affinity chromatography, HPLC, ion exchange chromatography, heparin agarose affinity chromatography (e.g., Thorpe & Smith, Proc. Nat. Acad. Sci. 95:5505-5510, 1998.)

In one embodiment, the recombinases can be introduced into the eukaryotic cells that contain the recombination attachment sites at which recombination is desired by any suitable method. Methods of introducing functional proteins, e.g., by microinjection or other methods, into cells are well known in the art. Introduction of purified recombinase protein ensures a transient presence of the protein and its function, which is often a preferred embodiment. Alternatively, a gene encoding the recombinase can be included in an expression vector used to transform the cell, in which the recombinase-encoding polynucleotide is operably linked to a promoter which mediates expression of the polynucleotide in the eukaryotic cell. The recombinase polypeptide can also be introduced into the eukaryotic cell by messenger RNA that encodes the recombinase polypeptide. It is generally preferred that the recombinase be present for only such time as is necessary for insertion of the nucleic acid fragments into the genome being modified. Thus, the lack of permanence associated with most expression vectors is not expected to be detrimental. One can introduce the recombinase gene into the cell before, after, or simultaneously with, the introduction of the exogenous polynucleotide of interest. In one embodiment, the recombinase gene is present within the vector that carries the polynucleotide that is to be inserted; the recombinase gene can even be included within the polynucleotide.

In one embodiment, a method for site-specific recombination comprises providing a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB Further embodiments provide for the introduction of a site-specific recombinase into a cell whose genome is to be modified. One embodiment relates to a method for obtaining site-specific recombination in an eukaryotic cell comprises providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP) or a bacterial genomic recombination attachment site (attB), the second recombination attachment site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB. In an embodiment the recombinase is selected from the group consisting of an A118 recombinase, a SF370.1 recombinase, a SPβc2 recombinase, a ΦRv1 recombinase, and a Bxb1 recombinase. In one embodiment the recombination results in integration.

Cells Comprising CD33 CARs and Vectors

Provided herein are engineered cells expressing a CAR described herein. In certain embodiments, an engineered cell described herein is an immune effector cell. In embodiments, provided herein is an immune effector cell comprising a vector comprising a backbone and a nucleic acid sequence encoding (1) a truncated epidermal growth factor receptor (HER1t or HER1t-1) and (2) a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and e) a CD3 zeta signaling domain.

In certain embodiments is an immune effector cell comprising a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; e) a CD3 zeta signaling domain; and (f) a truncated epidermal growth factor receptor (HER1t or HER1t-1).

In embodiments, provided herein is an immune effector cell comprising (1) a cell tag for use as a kill switch, selection marker, a biomarker, or a combination thereof, and (2) a chimeric antigen receptor (CAR), wherein the CAR comprises (a) a CD33 antigen binding domain; (b) a stalk domain; (c) a transmembrane domain; (d) a costimulatory signaling domain comprising 4-1BB or CD28, or both; and (e) a CD3 zeta signaling domain. In embodiments, the cell tag is HER1t, HER1t-1, CD20t-1 or CD20.

In embodiments, an immune effector cell is a T cell, a Natural Killer (NK) cell, a cytotoxic T lymphocyte (CTL), and a regulatory T cell. In embodiments, the cell exhibits an anti-tumor immunity when the CD33 antigen binding domain binds to CD33.

Modified Immune Effector Cells

Provided are immune effector cells modified to express one or more heterologous genes or polypeptides described herein. Provided are immune effector cells modified to express a CD33 CAR described herein and at least one of a HER1t, HER1t-1, CD20 and CD20t-1 tag. In some cases is provided an immune effector cell modified to express CD33 CAR, mbIL-15 and at least one of a HER1t, HER1t-1, CD20 and CD20t-1 tag disclosed herein.

"T cell" or "T lymphocyte" as used herein is a type of lymphocyte that plays a central role in cell-mediated immunity. They may be distinguished from other lymphocytes, such as B cells and natural killer cells (NK cells), by the presence of a T-cell receptor (TCR) on the cell surface.

In some embodiments, modified immune effector cells are modified immune cells that comprise T cells and/or natural killer cells. T cells or T lymphocytes are a subtype of white blood cells that are involved in cell-mediated immunity. Exemplary T cells include T helper cells, cytotoxic T cells, TH17 cells, stem memory T cells (TSCM), naïve T cells, memory T cells, effector T cells, regulatory T cells, or natural killer T cells.

T helper cells (TH cells) assist other white blood cells in immunologic processes, including maturation of B cells into plasma cells and memory B cells, and activation of cytotoxic T cells and macrophages. In some instances, TH cells are known as CD4+ T cells due to expression of the CD4 glycoprotein on the cell surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, Th9, or TFH, which secrete different cytokines to facilitate different types of immune responses. Signaling from the APC directs T cells into particular subtypes.

Cytotoxic T cells (TC cells or CTLs) destroy virus-infected cells and tumor cells, and are also implicated in transplant rejection. These cells are also known as CD8+ T cells since they express the CD8 glycoprotein on their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise subtypes: stem memory T cells (TSCM), central memory T cells (TCM cells) and two types of effector memory T cells (TEM cells and TEMRA cells). Memory cells may be either CD4+ or CD8+. Memory T cells may express the cell surface proteins CD45RO, CD45RA and/or CCR7.

Regulatory T cells (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

Natural killer T cells (NKT cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both Th and Tc cells (i.e., cytokine production and release of cytolytic/cell killing molecules). They are also able to recognize and eliminate some tumor cells and cells infected with herpes viruses.

Natural killer (NK) cells are a type of cytotoxic lymphocyte of the innate immune system. In some instances, NK cells provide a first line defense against viral infections and/or tumor formation. NK cells can detect MHC presented on infected or cancerous cells, triggering cytokine release, and subsequently induce lysis and apoptosis. NK cells can further detect stressed cells in the absence of antibodies and/or MHC, thereby allowing a rapid immune response.

Modified Immune Effector Cell Doses

In some embodiments, an amount of modified immune effector cells is administered to a subject in need thereof and the amount is determined based on the efficacy and the potential of inducing a cytokine-associated toxicity. In some cases, an amount of modified immune effector cells comprises about $10^5$ to about $10^9$ modified immune effector cells/kg. In some cases, an amount of modified immune effector cells comprises about $10^5$ to about $10^8$ modified immune effector cells/kg. In some cases, an amount of modified immune effector cells comprises about $10^5$ to about $10^7$ modified immune effector cells/kg. In some cases, an amount of modified immune effector cells comprises about $10^6$ to about $10^9$ modified immune effector cells/kg. In some cases, an amount of modified immune effector cells comprises about $10^6$ to about $10^8$ modified immune effector cells/kg. In some cases, an amount of modified immune effector cells comprises about $10^7$ to about $10^9$ modified immune effector cells/kg. In some cases, an amount of modified immune effector cells comprises about $10^5$ to about $10^6$ modified immune effector cells/kg. In some cases, an amount of modified immune effector cells comprises about $10^6$ to about $10^7$ modified immune effector cells/kg. In some cases, an amount of modified immune effector cells comprises about $10^7$ to about $10^8$ modified immune effector cells/kg. In some cases, an amount of modified immune effector cells comprises about $10^8$ to about $10^9$ modified immune effector cells/kg. In some instances, an amount of modified immune effector cells comprises about $10^9$ modified immune effector cells/kg. In some instances, an amount of modified immune effector cells comprises about $10^8$ modified immune effector cells/kg. In some instances, an amount of modified immune effector cells comprises about $10^7$ modified immune effector cells/kg. In some instances, an amount of modified immune effector cells comprises about $10^6$ modified immune effector cells/kg. In some instances, an amount of modified immune effector cells comprises about $10^5$ modified immune effector cells/kg.

In some embodiments, are CAR-T cells which are CD33-specific CAR-T cells. In some cases, an amount of CD33-specific CAR-T cells comprises about $10^5$ to about $10^9$ CAR-T cells/kg. In some cases, an amount of CD33-specific CAR-T cells comprises about $10^5$ to about $10^8$ CAR-T cells/kg. In some cases, an amount of CD33-specific CAR-T cells comprises about $10^5$ to about $10^7$ CAR-T cells/kg. In some cases, an amount of CD33-specific CAR-T cells comprises about $10^6$ to about $10^9$ CAR-T cells/kg. In some cases, an amount of CD33-specific CAR-T cells comprises about $10^6$ to about $10^8$ CAR-T cells/kg. In some cases, an amount of CD33-specific CAR-T cells comprises about $10^7$ to about $10^9$ CAR-T cells/kg. In some cases, an amount of CD33-specific CAR-T cells comprises about $10^5$ to about $10^6$ CAR-T cells/kg. In some cases, an amount of CD33-specific CAR-T cells comprises about $10^6$ to about $10^7$ CAR-T cells/kg. In some cases, an amount of CD33-specific CAR-T cells comprises about $10^7$ to about $10^8$ CAR-T cells/kg. In some cases, an amount of CD33-specific CAR-T cells comprises about $10^8$ to about $10^9$ CAR-T cells/kg. In some instances, an amount of CD33-specific CAR-T cells comprises about $10^9$ CAR-T cells/kg. In some instances, an amount of CD33-specific CAR-T cells comprises about $10^8$ CAR-T cells/kg. In some instances, an amount of CD33-specific CAR-T cells comprises about $10^7$ CAR-T cells/kg. In some instances, an amount of CD33-specific CAR-T cells comprises about $10^6$ CAR-T cells/kg. In some instances, an amount of CD33-specific CAR-T cells comprises about $10^5$ CAR-T cells/kg.

Immune Effector Cell Sources

In certain aspects, the embodiments described herein include methods of making and/or expanding the antigen-specific redirected immune effector cells (e.g., T-cells, NK-cell or NK T-cells) that comprises transfecting the cells with an expression vector containing a DNA (or RNA) construct encoding the CAR, then, optionally, stimulating the cells with feeder cells, recombinant antigen, or an antibody to the receptor to cause the cells to proliferate. In certain aspects, the cell (or cell population) engineered to express a CAR is a stem cell, iPS cell, immune effector cell or a precursor of these cells.

Sources of immune effector cells can include both allogeneic and autologous sources. In some cases immune effector cells may be differentiated from stem cells or induced pluripotent stem cells (iPSCs). Thus, cell for engineering according to the embodiments can be isolated from umbilical cord blood, peripheral blood, human embryonic stem cells, or iPSCs. For example, allogeneic T cells can be modified to include a chimeric antigen receptor (and optionally, to lack functional TCR). In some aspects, the immune effector cells are primary human T cells such as T cells derived from human peripheral blood mononuclear cells (PBMC). PBMCs can be collected from the peripheral blood or after stimulation with G-CSF (Granulocyte colony stimulating factor) from the bone marrow, or umbilical cord blood. Following transfection or transduction (e.g., with a CAR expression construct), the cells may be immediately infused or may be cryo-preserved. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric antigen receptor is expanded ex vivo. The clone selected for expansion demonstrates the capacity to specifically recognize and lyse antigen-expressing target cells. The recombinant T cells may be expanded by stimulation with IL-2, or other cytokines that bind the common gamma-chain (e.g., IL-7, IL-12, IL-15, IL-21, and others). The recombinant T cells may be expanded by stimulation with artificial antigen presenting cells. The recombinant T cells may be expanded on artificial antigen presenting cell or with an antibody, such as OKT3, which cross links CD3 on the T cell surface. Subsets of the recombinant T cells may be further selected with the use of magnetic bead based isolation methods and/or fluorescence activated cell sorting technology and further cultured with the AaPCs. In a further aspect, the genetically modified cells may be cryopreserved.

T cells can also be obtained from a number of sources, including bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll® separation. In embodiments, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL® gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also provided in certain embodiments is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., *Cell* 66:807-815, (1991); Henderson et al., *Immun* 73:316-321, (1991); Bierer et al., *Curr. Opin. Immun* 5:763-773, (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after engineering of the T cells to express a CAR described herein, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells described herein are expanded by contact with a surface having attached thereto an agent that stimulates a CD3/TCR complex associated signal and a ligand that stimulates a co-stimulatory molecule on the surface of the T cells. In particular, T cell populations can be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, (1998); Haanen et al., *J. Exp. Med.* 190(9):13191328, (1999); Garland et al., *J. Immunol Meth.* 227(1-2):53-63, (1999)).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In embodiments, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one ratio being at least 1:1 particles per T cell. In one embodiment, a ratio of particles to cells of 1:1 or less is used. In one particular embodiment, the particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments described herein, the immune effector cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1, or MACS® MicroBeads from Miltenyi Biotec) are combined in a buffer, for example, PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment described herein, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-.gamma., IL-4, IL-7, GM-CSF, IL-10, IL-12, IL-15, TGFbeta, and TNF-alpha or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, alpha-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population (Tc, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of Tc cells. Accordingly, depending on the purpose of treatment, infusing a subject with a T cell population comprising predominately of $T_H$ cells may be advantageous. Similarly, if an antigen-specific subset of Tc cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some cases, immune effector cells of the embodiments (e.g., T-cells) are co-cultured with activating and propagating cells (AaPCs), to aid in cell expansion. AaPCs can also be referred to as artificial Antigen Presenting cells (aAPCs). For example, antigen presenting cells (APCs) are useful in preparing therapeutic compositions and cell therapy products of the embodiments. In one aspect, the AaPCs may be transgenic K562 cells. For general guidance regarding the preparation and use of antigen-presenting systems, see, e.g., U.S. Pat. Nos. 6,225,042, 6,355,479, 6,362,001 and 6,790, 662; U.S. Patent Application Publication Nos. 2009/0017000 and 2009/0004142; and International Publication No. WO2007/103009, each of which is incorporated by reference. In yet a further aspect of the embodiments, culturing the transgenic CAR cells comprises culturing the transgenic CAR cells in the presence of dendritic cells or activating and propagating cells (AaPCs) that stimulate expansion of the CAR-expressing immune effector cells. In still further aspects, the AaPCs comprise a CAR-binding antibody or fragment thereof expressed on the surface of the AaPCs. The AaPCs may comprise additional molecules that activate or co-stimulate T-cells in some cases. The additional molecules may, in some cases, comprise membrane-bound C7 cytokines. In yet still further aspects, the AaPCs are inactivated or irradiated, or have been tested for and confirmed to be free of infectious material. In still further aspects, culturing the transgenic CAR cells in the presence of AaPCs comprises culturing the transgenic CAR cells in a medium comprising soluble cytokines, such as IL-15, IL-21 and/or IL-2. The cells may be cultured at a ratio of about 10:1 to about 1:10; about 3:1 to about 1:5; about 1:1 to about 1:3 (immune effector cells to AaPCs); or any range derivable therein. For example, the co-culture of T cells and AaPCs can be at a ratio of about 1:1, about 1:2 or about 1:3.

In one aspect, the AaPCs may express CD137L. In other aspects, the AaPCs may further express CD19, CD64, CD86, or mIL15. In certain aspects, the AaPCs may express at least one anti-CD3 antibody clone, such as, for example, OKT3 and/or UCHT1. In one aspect, the AaPCs may be inactivated (e.g., irradiated). In one aspect, the AaPCs may have been tested for and confirmed to be free of infectious material. Methods for producing such AaPCs are known in the art. In one aspect, culturing the CAR-modified T cell population with AaPCs may comprise culturing the cells at a ratio of about 10:1 to about 1:10; about 3:1 to about 1:5; about 1:1 to about 1:3 (T cells to AaPCs); or any range derivable therein. For example, the co-culture of T cells and AaPCs can be at a ratio of about 1:1, about 1:2 or about 1:3. In one aspect, the culturing step may further comprise culturing with an aminobisphosphonate (e.g., zoledronic acid).

In a further aspect, the population of transgenic CAR cells is cultured and/or stimulated for no more than 7, 14, 21, 28, 35 42 days, 49, 56, 63 or 70 days. In an embodiment, a stimulation includes the co-culture of the transgenic CAR T cells with AaPCs to promote the growth of CAR positive T cells. In another aspect, the population of transgenic CAR cells is stimulated for not more than: 1× stimulation, 2× stimulation, 3× stimulation, 4× stimulation, 5× stimulation, 5× stimulation, 6× stimulation, 7× stimulation, 8× stimulation, 9× stimulation or 10× stimulation. In some instances, the transgenic cells are not cultured ex vivo in the presence of AaPCs. In some specific instances, the method of the embodiment further comprises enriching the cell population for CAR-expressing immune effector cells (e.g., T-cells) after the transfection and/or culturing step. The enriching may comprise fluorescence-activated cell sorting (FACS)

and sorting for CAR-expressing cells. In a further aspect, the sorting for CAR-expressing cells comprises use of a CAR-binding antibody. The enriching may also comprise depletion of CD56+ cells. In yet still a further aspect of the embodiment, the method further comprises cryopreserving a sample of the population of transgenic CAR cells.

In some cases, AaPCs are incubated with a peptide of an optimal length that allows for direct binding of the peptide to the MHC molecule without additional processing. Alternatively, the cells can express an antigen of interest (i.e., in the case of MHC-independent antigen recognition). Furthermore, in some cases, APCs can express an antibody that binds to either a specific CAR polypeptide or to CAR polypeptides in general (e.g., a universal activating and propagating cell (uAPC). Such methods are disclosed in WO/2014/190273, which is incorporated herein by reference. In addition to peptide-MHC molecules or antigens of interest, the AaPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001, incorporated herein by reference.

Cells selected to become AaPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become AaPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, AaPCs preferably retain the deficiencies and poikilothermic properties that were possessed by the cells prior to their modification to generate the AaPCs. Exemplary AaPCs either constitute or are derived from a transporter associated with antigen processing (TAP)-deficient cell line, such as an insect cell line. An exemplary poikilothermic insect cells line is a *Drosophila* cell line, such as a Schneider 2 cell line (see, e.g., Schneider 1972 Illustrative methods for the preparation, growth, and culture of Schneider 2 cells, are provided in U.S. Pat. Nos. 6,225,042, 6,355,479, and 6,362,001.

In one embodiment, AaPCs are also subjected to a freeze-thaw cycle. In an exemplary freeze-thaw cycle, the AaPCs may be frozen by contacting a suitable receptacle containing the AaPCs with an appropriate amount of liquid nitrogen, solid carbon dioxide (i.e., dry ice), or similar low-temperature material, such that freezing occurs rapidly. The frozen APCs are then thawed, either by removal of the AaPCs from the low-temperature material and exposure to ambient room temperature conditions, or by a facilitated thawing process in which a lukewarm water bath or warm hand is employed to facilitate a shorter thawing time. Additionally, AaPCs may be frozen and stored for an extended period of time prior to thawing. Frozen AaPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing AaPCs that undergo the freeze-thaw cycle, or are essentially removed, such as by transfer of AaPCs to media that is essentially devoid of such preservatives.

In further embodiments, xenogenic nucleic acid and nucleic acid endogenous to the AaPCs, may be inactivated by crosslinking, so that essentially no cell growth, replication or expression of nucleic acid occurs after the inactivation. In one embodiment, AaPCs are inactivated at a point subsequent to the expression of exogenous MHC and assisting molecules, presentation of such molecules on the surface of the AaPCs, and loading of presented MHC molecules with selected peptide or peptides. Accordingly, such inactivated and selected peptide loaded AaPCs, while rendered essentially incapable of proliferating or replicating, retain selected peptide presentation function. Preferably, the crosslinking also yields AaPCs that are essentially free of contaminating microorganisms, such as bacteria and viruses, without substantially decreasing the antigen-presenting cell function of the AaPCs. Thus crosslinking maintains the important AaPC functions of while helping to alleviate concerns about safety of a cell therapy product developed using the AaPCs. For methods related to crosslinking and AaPCs, see for example, U.S. Patent Application Publication No. 20090017000, which is incorporated herein by reference.

In certain embodiments there are further provided an engineered antigen presenting cell (APC). Such cells may be used, for example, as described above, to propagate immune effector cells ex vivo. In further aspects, engineered APCs may, themselves be administered to a patient and thereby stimulate expansion of immune effector cells in vivo. Engineered APCs of the embodiments may, themselves, be used as a therapeutic agent. In other embodiments, the engineered APCs can used as a therapeutic agent that can stimulate activation of endogenous immune effector cells specific for a target antigen and/or to increase the activity or persistence of adoptively transferred immune effector cells specific to a target antigen.

As used herein the term "engineered APC" refers to cell(s) that comprises at least a first transgene, wherein the first transgene encodes a HLA. Such engineered APCs may further comprise a second transgene for expression of an antigen, such that the antigen is presented at the surface on the APC in complex with the HLA. In some aspects, the engineered APC can be a cell type that presented antigens (e.g., a dendritic cell). In further aspects, engineered APC can be produced from a cell type that does not normally present antigens, such a T-cell or T-cell progenitor (referred to as "T-APC"). Thus, in some aspects, an engineered APC of the embodiments comprises a first transgene encoding a target antigen and a second transgene encoding a human leukocyte antigen (HLA), such that the HLA is expressed on the surface of the engineered APC in complex with an epitope of the target antigen. In certain specific aspects, the HLA expressed in the engineered APC is HLA-A2.

In some aspects, an engineered APC of the embodiments may further comprise at least a third transgene encoding co-stimulatory molecule. The co-stimulatory molecule may be a co-stimulatory cytokine that may be a membrane-bound C7 cytokine. In certain aspects, the co-stimulatory cytokine is IL-15, such as membrane-bound IL-15. In some further aspects, an engineered APC may comprise an edited (or deleted) gene. For example, an inhibitory gene, such as PD-1, LIM-3, CTLA-4 or a TCR, can be edited to reduce or eliminate expression of the gene. An engineered APC of the embodiments may further comprise a transgene encoding any target antigen of interest. For example, the target antigen can be an infectious disease antigen or a tumor-associated antigen (TAA).

In one embodiment of the present disclosure, immune effector cells described herein are modified at a point-of-care site. In some cases, the point-of-care site is at a hospital or at a facility (e.g., a medical facility) near a subject. In some cases, the immune effector cells are modified by engineering/introducing a chimeric receptor and/or cytokine into the immune effector cells and then rapidly infused into a subject. In some embodiments, such immune effectors cells are modified by the vectors as described herein through electroporation. In other embodiments, the vector is a non-viral or viral vector. In one case, the non-viral vector includes a Sleeping Beauty transposon system. In some cases, the modified immune effector cells do not undergo a propagation and activation step. In some cases, the modified immune effector cells do not undergo an incubation or culturing step. In other cases, the immune effector cells are modified by engineering/introducing a chimeric receptor and a cytokine into said immune effector cells and then rapidly infused into a subject. In other cases, the immune effector cells are modified by engineering/introducing a chimeric receptor and a cytokine into said cells and then infused within at least: 0, 0.5, 1, 2, 3, 4, 5, 6, 7, 8, 9, 10, 11, 12, 13, 14, 15, 16, 17, 18, 19, 20, 21, 22, 23 or 24 hours into a subject. In other cases, the NK or T cells are modified by engineering/introducing a chimeric receptor and a cytokine into the cells and then infused in 0 days, <1 day, <2 days, <3 days, <4 days, <5 days, <6 days or <7 days into a subject. In some cases, the sources of immune effector cells can include both allogeneic and autologous sources. In one case, the immune effector cells can be T cells or NK cells. In one case, the chimeric receptor can be a CD33 CAR. In another case, the cytokine can be mbIL-15. In another case, an immune effector cell expressing a CD33 CAR can include a HER1t or HER1t-1 tag. In another case, the HER1t tag can comprise SEQ ID NO: 32 or 54 or variant or fragment thereof. In one case, the mbIL-15 is of SEQ ID NO: 37, or variant or fragment thereof. In another case, the mbIl-15 can also comprise a HER1t or HER1t-1tag. In yet another case, expression of CD33 CAR and/or mbIL-15 is modulated by gene-switch expression systems described herein.

Therapeutic Applications

In embodiments described herein, is an immune effector cell (e.g., T cell) transduced with a lentiviral vector (LV). For example, the LV encodes a CAR that combines an antigen recognition domain of CD33 with a stalk domain of CD8 alpha hinge and variants thereof, an intracellular domain of CD3-zeta, CD28, 4-1BB, or any combinations thereof and the intracellular domain CD3zeta. Therefore, in some instances, the transduced T cell can elicit a CAR-mediated T-cell response.

In embodiments described herein, is provided the use of a CAR to redirect the specificity of a primary T cell to a CD33 tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with CD33, a stalk domain, a zeta chain portion comprising for example the intracellular domain of human CD3zeta, and a costimulatory signaling region.

In one embodiment, the present disclosure includes a type of cellular therapy where T cells are genetically modified to express the CD33-specific CARs of the invention and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In one embodiment, the CAR T cells described herein can undergo robust in vivo T cell expansion and can persist for an extended amount of time. In another embodiment, the CAR T cells of the invention evolve into specific memory T cells that can be reactivated to inhibit any additional tumor formation or growth.

The CAR-modified T cells described herein may also serve as a type of vaccine for ex vivo immunization and/or in vivo therapy in a mammal. In embodiments, the mammal is a human. With respect to ex vivo immunization, at least one of the following occurs in vitro prior to administering the immune effector cell into a mammal: i) expansion of the cells, ii) introducing a nucleic acid encoding a CAR to the cells, and/or iii) cryopreservation of the cells.

Ex vivo procedures are well known and are discussed more fully below. Briefly, cells are isolated from a mammal (for example, a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of myeloid malignancies, such as for example, acute myeloid leukemia (AML). In certain embodiments, the cells of the invention are used in the treatment of patients at risk for developing AML. Thus, the present invention provides methods for the treatment or prevention of AML comprising administering to a subject in need thereof, a therapeutically effective amount of the CAR-modified T cells of the invention. In embodiments, the cells activated and expanded as described herein may be utilized in the treatment of relapsed or refractory AML.

Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In embodiments, compositions of the present invention are formulated for intravenous administration.

Pharmaceutical compositions described herein may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, (1988)). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells. In another embodiment, it may be desired to administer activated T cells of the subject composition following lymphodepletion of the patient, either via radiation or chemotherapy.

The administration of compositions described herein may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are administered by i.v. injection. The compositions of T cells may be injected directly into a tumor, lymph node, or site of infection.

The dosage of the above treatments to be administered to a patient will vary with the precise nature of the condition being treated and the recipient of the treatment. The scaling of dosages for human administration can be performed according to art-accepted practices. For example, the dose of the above treatment can be in the range of $1 \times 10^4$ CAR+ cells/kg to $5 \times 10^6$ CAR+ cells/kg. Exemplary doses can belx$10^4$ CAR+ cells/kg, $1 \times 10^5$ CAR+ cells/kg, $3 \times 10^5$ CAR+ cells/kg, $1 \times 10^6$ CAR+ cells/kg or $5 \times 10^6$ CAR+ cells/kg. The appropriate dose can be adjusted accordingly for an adult or a pediatric patient.

Alternatively, a typical amount of immune effector cells administered to a mammal (e.g., a human) can be, for example, in the range of one million to 100 billion cells; however, amounts below or above this exemplary range are within the scope of the invention. For example, the dose of inventive host cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising the immune effector cells expressing the disclosed nucleic acid sequences, or a vector comprising the those nucleic acid sequences, can be administered with one or more additional therapeutic agents, which can be co-administered to the mammal. By "co-administering" is meant administering one or more additional therapeutic agents and the composition comprising the inventive host cells or the inventive vector sufficiently close in time to enhance the effect of one or more additional therapeutic agents, or vice versa. In this regard, the composition comprising the immune effector cells described herein or a vector described herein can be administered simultaneously with one or more additional therapeutic agents, or first, and the one or more additional therapeutic agents can be administered second, or vice versa. Alternatively, the composition comprising the disclosed immune effector cells or the vectors described herein and the one or more additional therapeutic agents can be administered simultaneously.

An example of a therapeutic agents that can be included in or co-administered with the composition (or included in kits) comprising the inventive host cells and/or the inventive vectors are interleukins, cytokines, interferons, adjuvants and chemotherapeutic agents. In embodiments, the additional therapeutic agents are IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, and TLR10.

Bcl-2, STAT3 or STAT5 inhibitors may also be included in or co-administered with the composition (or included in kits). Cancer cells may overexpress anti-apoptotic proteins such as Bcl-2 or possess persistently activated pathways (i.e., STAT5 and STAT3) that result in aberrantly high resistance to natural apoptotic mediators or pharmacologic agents. Combining the approaches of drugs and immunotherapy to utilize more than one apoptotic pathway is envisaged to increase tumor cell death and decrease therapeutic resistance. The use of small molecule inhibitors may shift the balance enough between the pro- and anti-apoptotic molecules within tumor cells to sensitize them toward death or decrease resistance to killing during encounter with tumor-specific T cells. Elevated Bcl-2 expression has been found in hematologic malignancies such as acute myelogenous leukemia (AML) and chronic lymphocytic leukemia (CLL), and solid tumors (i.e., melanoma, breast and ovarian cancer). Persistently activated STAT3 or STAT5 has been observed in AML, CLL, chronic myelogenous leukemia, large granular lymphocytic leukemia, and leukemia cell lines. It is envisaged that small molecule inhibitors targeting Bcl-2, STAT3, or STAT5 are included in, co-administered with and/or co-cultured with the compositions of the invention. One bcl-2 inhibitor is ABT-737. This compound is part of a group of BH3 mimetic small molecule inhibitors (SMI), which target these Bcl-2 family proteins, but not A1 or Mcl-1. ABT-737 is different to previous BCL-2 inhibitors because this compound ostensibly has higher affinity for Bcl-2, Bcl-xL, and Bcl-w. ABT-199, a so-called BH3-mimetic drug designed to block the function of the Bcl-2 protein, on patients with chronic lymphocytic leukemia.

STAT3 and STAT5 inhibitors include but are not limited to those described in Fagard et al., STAT3 inhibitors for cancer therapy, JAK-STAT, 2:1 (2013), e22882, DOI: 10.4161/jkst.22882 and Furqan, et al., Journal of Hematology & Oncology 2013, 6:90 doi:10.1186/1756-8722-6-90. In addition to JAK/STAT pathway effectors, there are three major classes of negative regulator: SOCS (suppressors of cytokine signaling), PIAS (protein inhibitors of activated stats) and PTPs. Tyrosine phosphatases reverse the activity of the JAKs. The best characterized of these is SHP-1, the product of the mouse motheaten gene. SHP-1 contains two SH2 domains and can bind to either phosphorylated JAKs or phosphorylated receptors to facilitate dephosphorylation of these activated signaling molecules. Other tyrosine phosphatases, such as CD45, appear to have a role in regulating JAK/STAT signaling through a subset of receptors. As such, the JAK/STAT pathway is an envisaged to be a drug target for the compositions of the disclosure.

"Antifoaming agents" reduce foaming during processing which can result in coagulation of aqueous dispersions, bubbles in the finished film, or generally impair processing. Exemplary anti-foaming agents include silicon emulsions or sorbitan sesquioleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropyl-methyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan mono-laurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits and Compositions

One aspect of the disclosure relates to kits and compositions including a first vector including coding regions that encode the CD33-specific CARs of the invention and optionally genes included for safety reasons, e.g., HER1t or HER1t-1 and functional variants thereof, or CD20 or CD20t-1, and functional variants thereof. These kits and compositions can include multiple vectors each encoding different proteins or subsets of proteins. These vectors can be viral, non-viral, episomal, or integrating. In some embodiments, the vectors are transposons, e.g., sleeping beauty transposons.

In some embodiments, the kits and compositions include not only vectors but also cells and agents such as inter-leukins, cytokines, interleukins and chemotherapeutics, adjuvants, wetting agents, or emulsifying agents. In one embodiment the cells are T cells. In one embodiment the kits and composition includes IL-2. In one embodiment, the kits and compositions include IL-21. In one embodiment, the kits and compositions include Bcl-2, STAT3 or STAT5 inhibitors. In embodiments, the kit includes IL-15, or mbIL-15.

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain pack-aging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include CAR-T cells (e.g., CD33-specific CAR-T cells described herein), and option-ally in addition with cytokines and/or chemotherapeutic agents disclosed herein. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Sequences

Provided in Table 2 is a representative list of certain sequences included in embodiments provided herein.

| Sequence Name | SEQ ID NO | Sequence |
|---|---|---|
| hM195 VL (aa) | 1 | DIQMTQSPSSLSASVGDRVTITCRASESVDNYGISFMNWFQQKPGKAPKLL IYAASNQGSGVPSRFSGSGSGTDFTLTISSLQPDDFATYYCQQSKEVPWTF GQGTKVEIK |
| hM195 VL (nt) | 2 | Gacattcagatgacccagtctccgagctctctgtccgcatcagtaggagac agggtcaccatcacatgcagagccagcgaaagtgtcgacaattatggcatt agctttatgaactggttccaacagaaacccgggaaggctcctaagcttctg atttacgctgcatccaaccaaggctccggggtaccctctcgcttctcaggc agtggatctgggacagacttcactctcaccatttcatctctgcagcctgat gacttcgcaacctattactgtcagcaaagtaaggaggttccgtggacgttc ggtcaagggaccaaggtggagatcaaa |
| hM195 VH (aa) | 3 | QVQLVQSGAEVKKPGSSVKVSCKASGYTFTDYNMHWVRQAPGQGLEWIGYI YPYNGGTGYNQKFKSKATITADESTNTAYMELSSLRSEDTAVYYCARGRPA MDYWGQGTLVTVSS |
| hM195 VH (nt) | 4 | Caggttcagctggtgcagtctggagctgaggtgaagaagcctgggagctca gtgaaggtttcctgcaaagcttctggctacaccttcactgactacaacatg cactgggtgaggcaggctcctggccaaggcctggaatggattggatatatt tatccttacaatggtggtaccggctacaaccagaagttcaagagcaaggcc acaattacagcagacgagagtactaacacagcctacatggaactctccagc ctgaggtctgaggacactgcagtctattactgcgcaagagggcgccccgct atggactactggggccaagggactctggtcactgtctcttca |
| (G4S)3 Linker (nt) | 5 | Ggtggcggtggctcgggcggtggtgggtcgggtggcggcggatct |

| Sequence Name | SEQ ID NO | Sequence |
|---|---|---|
| (G4S)3 Linker (aa) | 6 | GGGGSGGGGSGGGGS |
| hM195 scFv with linker (nt) | 7 | Gacattcagatgacccagtctccgagctctctgtccgcatcagtaggagac agggtcaccatcacatgcagagccagcgaaagtgtcgacaattatggcatt agctttatgaactggttccaacagaaacccgggaaggctcctaagcttctg atttacgctgcatccaaccaaggctccgggggtaccctctcgcttctcaggc agtggatctgggacagacttcactctcaccatttcatctctgcagcctgat gacttcgcaacctattactgtcagcaaagtaaggaggttccgtggacgttc ggtcaagggaccaaggtggagatcaaaGgtggcggtggctcgggcggtggt gggtcgggtggcggcggcgatctcaggttcagctggtgcagtctggagctgag gtgaagaagcctgggagctcagtgaaggtttcctgcaaagcttctggctac accttcactgactacaacatgcactgggtgaggcaggctcctggccaaggc ctggaatggattggatatatttatccttacaatggtggtaccggctacaac cagaagttcaagagcaaggccacaattacagcagacgagagtactaacaca gcctacatggaactctccagcctgaggtctgaggacactgcagtctattac tgcgcaagagggcgccccgctatggactactgggggccaagggactctggtc actgtctcttca |
| hM195 scFv with linker (aa) | 8 | DIQMTQSPSSLSASVGDRVTITCRASESVDNYGISFMNWFQQKPGKAPKLL IYAASNQGSGVPSRFSGSGSGTDFTLTISSLQPDDFATYYCQQSKEVPWTF GQTKVEIKGGGGSGGGGSGGGGSQVQLVQSGAEVKKPGSSVKVSCKASGYT FTDYNMHWVRQAPGQGLEWIGYIYPYNGGTGYNQKFKSKATITADESTNTA YMELSSLRSEDTAVYYCARGRPAMDYWGQGTLVTVSS |
| M2H12 VH (aa) | 9 | QVQLQQSGPELVRPGTFVKISCKASGYTFTNYDINWVNQRPGQGLEWIGWI YPGDGSTKYNEKFKAKATLTADKSSSTAYLQLNNLTSENSAVYFCASGYED AMDYWGQGTSVTVSS |
| M2H12 VL (aa) | 10 | DIKMTQSPSSMYASLGERVIINCKASQDINSYLSWFQQKPGKSPKTLIYRA NRLVDGVPSRFSGSGSGQDYSLTISSLEYEDMGIYYCLQYDEFPLTFGAGT KLELKR |
| DRB2 VH (aa) | 11 | EVKLQESGPELVKPGASVKMSCKASGYKFTDYVVHWLKQKPGQGLEWIGYI NPYNDGTKYNEKFKGKATLTSDKSSSTAYMEVSSLTSEDSAVYYCARDYRY EVYGMDYWGQGTSVTVSS |
| DRB2 VL (aa) | 12 | DIVLTQSPTIMSASPGERVTMTCTASSSVNYIHWYQQKSGDSPLRSIFDTS KVASGVPARFSGSGSGTSYSLTISTMEAEDAATYYCQQWRSYPLTFGDGTR LELKRADAAPTVS |
| My9-6 VH (aa) | 13 | QVQLQQPGAEVVKPGASVKMSCKASGYTFTSYYIHWIKQTPGQGLEWVGVI YPGNDDISYNQKFKGKATLTADKSSTTAYMQLSSLTSEDSAVYYCAREVRL RYFDVWGAGTTVTVSS |
| My9-6 VL (aa) | 14 | NIMLTQSPSSLAVSAGEKVTMSCKSSQSVFFSSSQKNYLAWYQQIPGQSPK LLIYWASTRESGVPDRFTGSGSGTDFTLTISSVQSEDLAIYYCHQYLSSRT FGGGTKLEIKR |
| GM-CSFRa signal peptide (nt) | 15 | Atgcttctgctggtgaccagcctgctgctgtgtgagctgccccacccccgcc tttctgctgatcccc |
| GM-CSFRa signal peptide (aa) | 16 | MLLLVTSLLLCELPHPAFLLIP |
| CD8alpha TM (nt) | 17 | Atctacatctgggcccctctggccggcacctgtggcgtgctgctgctgagc ctggtcatcaccctgtactgcaaccaccggaat |
| CD8alpha TM (aa) | 18 | IYIWAPLAGTCGVLLLSLVITLYCNHRN |
| CD28 TM (nt) | 19 | Ttttgggtgctggtggtggttggtggagtcctggcttgctatagcttgcta gtaacagtggcctttattattttctgggtg |
| CD28 TM (aa) | 20 | FWVLVVVGGVLACYSLLVTVAFIIFWV |
| CD8alpha hinge (nt) | 21 | Aagcccaccaccacccctgccctagacctccaaccccagcccctacaatc gccagccagcccctgagcctgaggcccgaagcctgtagacctgccgctggc ggagccgtgcacaccagaggcctggatttcgcctgcgac |
| CD8alpha hinge (aa) | 22 | KPTTTPAPRPPTPAPTIASQPLSLRPEACRPAAGGAVHTRGLDFACD |

-continued

| Sequence Name | SEQ ID NO | Sequence |
|---|---|---|
| 4-1BB signaling domain (nt) | 23 | Aagagaggccggaagaaactgctgtacatcttcaagcagcccttcatgcgg cccgtgcagaccacccaggaagaggacggctgcagctgccggttccccgag gaagaggaaggcggctgcgaactg |
| 4-1BB signaling domain (aa) | 24 | KRGRKKLLYIFKQPFMRPVQTTQEEDGCSCRFPEEEEGGCEL |
| CD3ζ signaling domain (nt) | 25 | Cgggtgaagttcagccggagcgccgacgcccctgcctaccagcagggccag aaccagctgtacaacgagctgaacctgggccggagggaggagtacgacgtg ctggacaagcggagaggccgggaccctgagatgggcggcaagcccggaga aagaaccctcaggagggcctgtataacgaactgcagaaagacaagatggcc gaggcctacagcgagatcggcatgaagggcgagcggcggaggggcaagggc cacgacggcctgtaccagggcctgagcaccgccaccaaggatacctacgac gccctgcacatgcaggccctgccccccaga |
| CD3ζ signaling domain (aa) | 26 | RVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYD ALHMQALPPR |
| CD28 signaling domain (nt) | 27 | Aggagcaagcggagcagaggcggccacagcgactacatgaacatgaccccc cggaggcctggccccacccggaagcactaccagcccctacgcccctcccagg gacttcgccgcctaccggagc |
| CD28 signaling domain (aa) | 28 | RSKRSRGGHSDYMNMTPRRPGPTRKHYQPYAPPRDFAAYRS |
| T2A (nt) | 29 | GAGGGCAGAGGAAGTCTTCTAACATGCGGTGACGTGGAGGAGAATCCCGGC CCT |
| T2A (aa) | 30 | EGRGSLLTCGDVEENPGP |
| HER1t (nt) | 31 | Cgcaaagtgtgtaacggaataggtattggtgaatttaaagactcactctcc ataaatgctacgaatattaaacactttcaaaaactgcacctccatcagtggc gatctccacatcctgccggtggcatttaggggtgactccttcacacatact cctcctctggatccacaggaactggatattctgaaaaccgtaaaggaaatc acagggtttttgctgattcaggcttggcctgaaaacaggacggacctccat gcctttgagaacctagaaatcatacgcggcaggaccaagcaacatggtcag tttctcttgcagtcgtcagcctgaacataacatccttgggattacgctcc ctcaaggagataagtgatggagatgtgataatttcaggaaacaaaaatttg tgctatgcaaatacaataaactggaaaaaactgtttgggacctccggtcag aaaaccaaaattataagcaacagaggtgaaaacagctgcaaggccacaggc caggtctgccatgccttgtgctccccgagggctgctgggcccggagccc agggactgcgtctcttgccggaatgtcagccgaggcagggaatgcgtggac aagtgcaaccttctggagggtgagccaagggagtttgtggagaactctgag tgcatacagtgccacccagagtgcctgcctcaggccatgaacatcacctgc acaggacgggggaccagacaactgtatccagtgtgcccactacattgacgtgc ccccactgcgtcaagacctgcccggcaggagtcatgggagaaaacaacacc ctggtctggaagtacgcagacgccggccatgtgtgccacctgtgccatcca aactgcacctacggatgcactgggccaggtcttgaaggctgtccaacgaat gggcctaagatcccgtccatcgccactgggatggtgggggccctcctcttg ctgctggtggtggcccctggggatcggcctcttcatg |
| HER1t (aa) | 32 | RKVCNGIGIGEFKDSLSINATNIKHFKNCTSISGDLHILPVAFRGDSFTHT PPLDPQELDILKTVKEITGFLLIQAWPENRTDLHAFENLEIIRGRTKQHGQ FSLAVVSLNITSLGLRSLKEISDGDVIISGNKNLCYANTINWKKLFGTSGQ KTKIISNRGENSCKATGQVCHALCSPEGCWGPEPRDCVSCRNVSRGRECVD KCNLLEGEPREFVENSECIQCHPECLPQAMNITCTGRGPDNCIQCAHYIDG PHCVKTCPAGVMGENNTLVWKYADAGHVCHLCHPNCTYGCTGPGLEGCPTN GPKIPSIATGMVGALLLLLVVALGIGLFM |
| IgK signal peptide (nt) | 33 | Atgaggctccctgctcagctcctggggctgctaatgctctgggtcccagga tccagtggg |
| IgK signal peptide (aa) | 34 | MRLPAQLLGLLMLWVPGSSG |
| FL CD20 (nt) | 35 | Atgacaacacccagaaattcagtaaatgggactttcccggcagagccaatg aaaggccctattgctatgcaatctggtccaaaaccactcttcaggaggatg tcttcactggtgggccccacgcaaagcttcttcatgagggaatctaagact ttggggggctgtccagattatgaatgggctcttccacattgccctgggggt cttctgatgatcccagcagggatctatgcacccatctgtgtgactgtgtgg taccctctctgggggaggcattatgtatattatttccggatcactcctggca gcaacggagaaaaactccaggaagtgtttggtcaaaggaaaaatgataatg aattcattgagcctctttgctgccatttctggaatgattcttccaatcatg |

-continued

| Sequence Name | SEQ ID NO | Sequence |
|---|---|---|
| | | gacatacttaatattaaaatttcccattttttaaaaatggagagtctgaat |
| | | tttattagagctcacacaccatatattaacatatacaactgtgaaccagct |
| | | aatccctctgagaaaaactccccatctacccaatactgttacagcatacaa |
| | | tctctgttcttgggcattttgtcagtgatgctgatctttgccttcttccag |
| | | gaacttgtaatagctggcatcgttgagaatgaatggaaaagaacgtgctcc |
| | | agacccaaatctaacatagttctcctgtcagcagaagaaaaaaagaacag |
| | | actattgaaataaaagaagaagtggttgggctaactgaaacatcttcccaa |
| | | ccaaagaatgaagaagacgaactttccaatccaagaagaggaagaa |
| | | gaagaaacagagacgaacttccagaacctccccaagatcaggaatcctca |
| | | ccaatagaaaatgacagctctcct |
| FL CD20 (aa) | 36 | MTTPRNSVNGTFPAEPMKGPIAMQSGPKPLFRRMSSLVGPTQSFFMRESKT |
| | | LGAVQIMNGLFHIALGGLLMIPAGIYAPICVTVWYPLWGGIMYIISGSLLA |
| | | ATEKNSRKCLVKGKMIMNSLSLFAAISGMILSIMDILNIKISHFLMKMESL |
| | | NFIRAHTPYINIYNCEPANPSEKNSPSTQYCYSIQSLFLGILSVMLIFAFF |
| | | QELVIAGIVENEWKRTCSRPKSNIVLLSAEEKKEQTIEIKEEVVGLTETSS |
| | | QPKNEEDIEIIPIQEEEEEETETNFPEPPQDQESSPIENDSSP |
| mbIL-15 (aa) | 37 | MDWTWILFLVAAATRVHSNWVNVISDLKKIEDLIQSMHIDATLYTESDVHP |
| | | SCKVTAMKCFLLELQVISLESGDASIHDTVENLIILANNSLSSNGNVTESG |
| | | CKECEELEEKNIKEFLQSFVHIVQMFINTSSGGGSGGGGSGGGGSGGGGSG |
| | | GGSLQITCPPPMSVEHADIWVKSYSLYSRERYICNSGFKRKAGTSSLTECV |
| | | LNKATNVAHWTTPSLKCIRDPALVHQRPAPPSTVTTAGVTPQPESLSPSGK |
| | | EPAASSPSSNNTAATTAAIVPGSQLMPSKSPSTGTTEISSHESSHGTPSQT |
| | | TAKNWELTASASHQPPGVYPQGHSDTTVAISTSTVLLCGLSAVSLLACYLK |
| | | SRQTPPLASVEMEAMEALPVTWGTSSRDEDLENCSHHL |
| hM195scFv-CD8a-CD28m-Z | 38 | atgctgctgctggtgaccagcctgctgctgtgtgagctgccccaccccgcc |
| | | tttctgctgatccccgacattcagatgacccagtctccgagctctctgtcc |
| | | gcatcagtaggagacagggtcaccatcacatgcagagccagcgaaagtgtc |
| | | gacaattatggcattagctttatgaactggttccaacagaaacccgggaag |
| | | gctcctaagcttctgatttacgctgcatccaaccaaggctccgggggtaccc |
| | | tctcgcttctcaggcagtggatctgggacagacttcactctcaccatttca |
| | | tctctgcagcctgatgacttcgcaacctattactgtcagcaaagtaaggag |
| | | gttccgtggacgttcggtcaagggaccaaggtggagatcaaaggtggcggt |
| | | ggctcgggcggtggtgggtcgggtggcggcggatctcaggttcagctggtg |
| | | cagtctggagctgaggtgaagaagcctgggagctcagtgaaggtttcctgc |
| | | aaagcttctggctacaccttcactgactacaacatgcactgggtgaggcag |
| | | gctcctggccaaggcctggaatggattggatatatttatccttacaatggt |
| | | ggtaccggctacaaccagaagttcaagagcaaggccacaattacagcagac |
| | | gagagtactaacacagcctacatggaactctccagcctgaggtctgaggac |
| | | actgcagtctattactgcgcaagagggcgccccgctatggactactgggc |
| | | caagggactctggtcactgtctcttcaaagcccaccaccacccctgcccct |
| | | agacctccaaccccagcccctacaatcgccagccagcccctgagcctgagg |
| | | cccgaagcctgtagacctgccgctggcggagccgtgcacaccagaggcctg |
| | | gatttcgcctgcgacatctacatctgggcccctctggccggcacctgtggc |
| | | gtgctgctgctgagcctggtcatcaccctgtactgcaaccaccggaatagg |
| | | agcaagcggagcagaggcggccacagcgactacatgaacatgacccccgg |
| | | aggcctggccccacccggaagcactaccagccctacgcccctcccagggac |
| | | ttcgccgcctaccggagccgggtgaagttcagccggagcgccgacgcccct |
| | | gcctaccagcagggccagaaccagctgtacaacgagctgaacctgggccgg |
| | | agggaggagtacgacgtgctggacaagcggagaggccgggaccctgagatg |
| | | ggcggcaagccccgagaaagaaccctcaggagggcctgtataacgaactg |
| | | cagaaagacaagatggccgaggcctacagcgagatcggcatgaagggcgag |
| | | cggcggaggggcaagggccacgacggcctgtaccagggcctgagcaccgcc |
| | | accaaggatacctacgacgccctgcacatgcaggccctgcccccagga |
| hM195scFv-CD8a-CD28m-Z | 39 | MLLLVTSLLLCELPHPAFLLIPDQIMTQSPSSLSASVGDRVTITCRASESV |
| | | DNYGISFMNWFQQKPGKAPKLLIYAASNQGSGVPSRFSGSGSGTDFTLTIS |
| | | SLQPDDFATYYCQQSKEVPWTFGQGTKVEIKGGGGSGGGGSGGGGSQVQLV |
| | | QSGAEVKKPGSSVKVSCKASGYTFTDYNMHWVRQAPGQGLEWIGYIYPYNG |
| | | GTGYNQKFKSKATITADESTNTAYMELSSLRSEDTAVYYCARGRPAMDYWG |
| | | QGTLVTVSSKPTTTPAPRPPTPAPTIASQPLSLRPEACRPAAGGAVHTRGL |
| | | DFACDIYIWAPLAGTCGVLLLSLVITLYCNHRNRSKRSRGGHSDYMNMTPR |
| | | RPGPTRKHYQPYAPPRDFAAYRSRVKFSRSADAPAYQQGQNQLYNELNLGR |
| | | REEYDVLDKRRGRDPEMGGKPRRKNPQEGLYNELQKDKMAEAYSEIGMKGE |
| | | RRRGKGHDGLYQGLSTATKDTYDALHMQALPPR |
| hM195scFv-CD8a-Z | 40 | atgctgctgctggtgaccagcctgctgctgtgtgagctgccccaccccgcc |
| | | tttctgctgatccccgacattcagatgacccagtctccgagctctctgtcc |
| | | gcatcagtaggagacagggtcaccatcacatgcagagccagcgaaagtgtc |
| | | gacaattatggcattagctttatgaactggttccaacagaaacccgggaag |
| | | gctcctaagcttctgatttacgctgcatccaaccaaggctccgggggtaccc |
| | | tctcgcttctcaggcagtggatctgggacagacttcactctcaccatttca |
| | | tctctgcagcctgatgacttcgcaacctattactgtcagcaaagtaaggag |
| | | gttccgtggacgttcggtcaagggaccaaggtggagatcaaaggtggcggt |
| | | ggctcgggcggtggtgggtcgggtggcggcggatctcaggttcagctggtg |

-continued

| Sequence Name | SEQ ID NO | Sequence |
|---|---|---|
| | | cagtctggagctgaggtgaagaagcctgggagctcagtgaaggtttcctgc<br>aaagcttctggctacaccttcactgactacaacatgcactgggtgaggcag<br>gctcctggccaaggcctggaatggattggatatatttatccttacaatggt<br>ggtaccggctacaaccagaagttcaagagcaaggccacaattacagcagac<br>gagagtactaacacagcctacatggaactctccagcctgaggtctgaggac<br>actgcagtctattactgcgcaagagggcgccccgctatggactactgggc<br>caagggactctggtcactgtctcttcaaagcccaccaccacccctgcccct<br>agacctccaaccccagcccctacaatcgccagcagcccctgagcctgagg<br>cccgaagcctgtagacctgccgctggcggagccgtgcacaccagaggcctg<br>gatttcgcctgcgacatctacatctgggcccctctggccggcacctgtggc<br>gtgctgctgctgagcctggtcatcaccctgtactgcaaccaccggaatcgg<br>gtgaagttcagccggagcgccgacgcccctgcctaccagcagggccagaac<br>cagctgtacaacgagctgaacctgggccggagggaggagtacgacgtgctg<br>gacaagcggagaggccgggaccctgagatgggcggcaagccccgggagaag<br>aaccctcaggagggcctgtataacgacctgcagaaagacaagatggccgag<br>gcctacagcgagatcggcatgaagggcgagcggcggaggggcaagggccac<br>gacggcctgtaccagggcctgagcaccgccaccaaggatacctacgacgcc<br>ctgcacatgcaggccctgccccccaga |
| hM195scFv-<br>CD8a-Z | 41 | MLLLVTSLLLCELPHPAFLLIPDIQMTQSPSSLSASVGDRVTITCRASESV<br>DNYGISFMNWFQQKPGKAPKLLIYAASNQGSGVPSRFSGSGSGTDFTLTIS<br>SLQPDDFATYYCQQSKEVPWTFGQGTKVEIKGGGGSGGGGSGGGGSQVQLV<br>QSGAEVKKPGSSVKVSCKASGYTFTDYNMHWVRQAPGQGLEWIGYIYPYNG<br>GTGYNQKFKSKATITADESTNTAYMELSSLRSEDTAVYYCARGRPAMDYWG<br>QGTLVTVSSKPTTTPAPRPPTPAPTIASQPLSLRPEACRPAAGGAVHTRGL<br>DFACDIYIWAPLAGTCGVLLLSLVITLYCNHRNRVKFSRSADAPAYQQGQN<br>QLYNELNLGRREEYDVLDKRRGRDPEMGGKPRRKNPQEGLYNELQKDKMAE<br>AYSEIGMKGERRRGKGHDGLYQGLSTATKDTYDALHMQALPPR |
| hM195scFv-<br>CD8a-<br>CD28m-Z-<br>T2A-GM-<br>CSFRasp.H<br>ER1t | 42 | ATGCTGCTGCTGGTGACCAGCCTGCTGCTGTGTGAGCTGCCCCACCCCGCC<br>TTTCTGCTGATCCCCGACATTCAGATGACCCAGTCTCCGAGCTCTCTGTCC<br>GCATCAGTAGGAGACAGGGTCACCATCACATGCAGAGCCAGCGAAAGTGTC<br>GACAATTATGGCATTAGCTTTATGAACTGGTTCCAACAGAAACCCGGGAAG<br>GCTCCTAAGCTTCTGATTTACGCTGCATCCAACCAAGGCTCCGGGGGTACCC<br>TCTCGCTTCTCAGGCAGTGGATCTGGGACAGACTTCACTCTCACCATTTCA<br>TCTCTGCAGCCTGATGACTTCGCAACCTATTACTGTCAGCAAAGTAAGGAG<br>GTTCCGTGGACGTTCGGTCAAGGGACCAAGGTGGAGATCAAAGGTGGCGGT<br>GGCTCGGGCGGTGGTGGGTCGGGTGGCGGCGGATCTCAGGTTCAGCTGGTG<br>CAGTCTGGAGCTGAGGTGAAGAAGCCTGGGAGCTCAGTGAAGGTTTCCTGC<br>AAAGCTTCTGGCTACACCTTCACTGACTACAACATGCACTGGGTGAGGCAG<br>GCTCCTGGCCAAGGCCTGGAATGGATTGGATATATTTATCCTTACAATGGT<br>GGTACCGGCTACAACCAGAAGTTCAAGAGCAAGGCCACAATTACAGCAGAC<br>GAGAGTACTAACACAGCCTACATGGAACTCTCCAGCTGAGGTCTGAGGAC<br>ACTGCAGTCTATTACTGCGCAAGAGGGCGCCCCGTATGGACTACTGGGGC<br>CAAGGGACTCTGGTCACTGTCTCTTCAAAGCCCACCACCACCCCTGCCCCT<br>AGACCTCCAACCCCAGCCCCTACAATCGCCAGCAGCCCCTGAGCCTGAGG<br>CCCGAAGCCTGTAGACCTGCCGCTGGCGGAGCCGTGCACACCAGAGGCCTG<br>GATTTCGCCTGCGACATCTACATCTGGGCCCCTCTGGCCGGCACCTGTGGC<br>GTGCTGCTGCTGAGCCTGGTCATCACCCTGTACTGCAACCACCGGAATAGG<br>AGCAAGCGGAGCAGAGGCGGCCACAGCGACTACATGAACATGACCCCCCCGG<br>AGGCCTGGCCCCACCCGGAAGCACTACCAGCCCTACGCCCCTCCCAGGGAC<br>TTCGCCGCCTACCGGAGCCGGGTGAAGTTCAGCCGGAGCGCCGACGCCCCT<br>GCCTACCAGCAGGGCCAGAACCAGCTGTACAACGAGCTGAACCTGGGCCGG<br>AGGGAGGAGTACGACGTGCTGGACAAGCGGAGAGGCCGGGACCCTGAGATG<br>GGCGGCAAGCCCCGGAGAAAGAACCCTCAGGAGGGCCTGTATAACGAACTG<br>CAGAAAGACAAGATGGCCGAGGCCTACAGCGAGATCGGCATGAAGGGCGAG<br>CGGCGGAGGGGCAAGGGCCACGACGGCCTGTACCAGGGCCTGAGCACCGCC<br>ACCAAGGATACCTACGACGCCCTGCACATGCAGGCCCTGCCCCCCAGACTC<br>GAGGGCGGCGGAGAGGGCAGAGGAAGTCTTCTAACATGCGGTGACGTGGAG<br>GAGAATCCCGGCCCTAGGATGCTTCTCCTGGTGACAAGCCTTCTGCTCTGT<br>GAGTTACCACACCCAGCATTCCTCCTGATCCCACGCAAAGTGTGTAACGGA<br>ATAGGTATTGGTGAATTTAAAGACTCACTCTCCATAAATGCTACGAATATT<br>AAACACTTCAAAAACTGCACCTCCATCAGTGGCGATCTCCACATCCTGCCG<br>GTGGCATTTAGGGGTGACTCCTTCACACATACTCCTCCTCTGGATCCACAG<br>GAACTGGATATTCTGAAAACCGTAAAGGAAATCACAGGGTTTTTGCTGATT<br>CAGGCTTGGCCTGAAAACAGGACGGACCTCCATGCCTTTGAGAACCTAGAA<br>ATCATACGCGGCAGGACCAAGCAACATGGTCAGTTTTCTCTTGCAGTCGTC<br>AGCCTGAACATAACATCCTTGGGATTACGCTCCCTCAAGGAGATAAGTGAT<br>GGGAGATGTGATAATTTCAGGAAACAAAAATTTGTGCTATGCAAATACAATA<br>AACTGGAAAAAACTGTTTGGGACCTCCGGTCAGAAAACCAAAATTATAAGC<br>AACAGAGGTGAAAACAGCTGCAAGGCCACAGGCCAGGTCTGCCATGCCTTG<br>TGCTCCCCCGAGGGCTGCTGGGGCCCGGAGCCCAGGGACTGCGTCTCTTGC<br>CGGAATGTCAGCCGAGGCAGGGAATGCGTGGACAAGTGCAACCTTCTGGAG<br>GGTGAGCCAAGGGGAGTTTGTGGAGAACTCTGAGTGCATACAGTGCCACCCA<br>GAGTGCCTGCCTCAGGCCATGAACATCACCTGCACAGGACGGGGACCAGAC<br>AACTGTATCCAGTGTGCCCACTACATTGACGGCCCCCACTGCGTCAAGACC<br>TGCCCGGCAGGAGTCATGGGAGAAAACAACACCCTGGTCTGGAAGTACGCA |

| Sequence Name | SEQ ID NO | Sequence |
|---|---|---|
| | | GACGCCGGCCATGTGTGCCACCTGTGCCATCCAAACTGCACCTACGGATGC<br>ACTGGGCCAGGTCTTGAAGGCTGTCCAACGAATGGGCCTAAGATCCCGTCC<br>ATCGCCACTGGGATGGTGGGGGCCCTCCTCTTGCTGCTGGTGGTGGCCCTG<br>GGGATCGGCCTCTTCATG |
| hM195scFv-<br>CD8a-<br>CD28m-Z-<br>T2A-GM-<br>CSFRasp.H<br>ER1t | 43 | MLLLVTSLLLCELPHPAFLLIPDIQMTQSPSSLSASVGDRVTITCRASESV<br>DNYGISFMNWFQQKPGKAPKLLIYAASNQGSGVPSRFSGSGSGTDFTLTIS<br>SLQPDDFATYYCQQSKEVPWTFGQGTKVEIKGGGGSGGGGSGGGGSQVQLV<br>QSGAEVKKPGSSVKVSCKASGYTFTDYNMHWVRQAPGQGLEWIGYIYPYNG<br>GTGYNQKFKSKATITADESTNTAYMELSSLRSEDTACYYCARGRPAMDYWG<br>QGTLVTVSSKPTTTPAPRPPTPAPTIASQPLSLRPEACRPAAGGAVHTRGL<br>DFACDIYIWAPLAGTCGVLLLSLVITLYCNHRNRSKRSRGGHSDYMNMTPR<br>RPGPTRKHYQPYAPPRDFAAYRSRVKFSRSADAPAYQQGQNQLYNELNLGR<br>REEYDVLDKRRGRDPEMGGKPRRKNPQEGLYNELQKDKMAEAYSEIGMKGE<br>RRGKGHDGLYQGLSTATKDTYDALHMQALPPRLEGGGEGRGSLLTCGDVEE<br>NPGPRMLLLVTSLLLCELPHPAFLLIPRKVCNGIGIGEFKDSLSINATNIK<br>HFKNCTSISGDLHILPVAFRGDSFTHTPPLDPQELDILKTVKEITGFLLIQ<br>AWPENRTDLHAFENLEIIRGRTKQHGQFSLAVVSLNITSLGLRSLKEISDG<br>DVIISGNKNLCYANTINWKKLFGTSGQKTKIISNRGENSCKATGQVCHALC<br>SPEGCWGPEPRDCVSCRNVSRGRECVDKCNLLEGEPREFVENSECIQCHPE<br>CLPQAMNITCTGRGPDNCIQCAHYIDGPHCVKTCPAGVMGENNTLVWKYAD<br>AGHVCHLCHPNCTYGCTGPGLEGCPTNGPKIPSIATGMVGALLLLLVVALG<br>IGLFM |
| hM195scFv | 44 | Atgctgctgctggtgaccagcctgctgctgtgtgagctgccccacccccgcc<br>tttctgctgatccccgacattcagatgacccagtctccgagctctctgtcc<br>gcatcagtaggagacagggtcaccatcacatgcagagccagcgaaagtgtc<br>gacaattatggcattagctttatgaactggttccaacagaaacccgggaag<br>gctcctaagcttctgatttacgctgcatccaaccaaggctccggggtaccc<br>tctcgcttctcaggcagtggatctgggacagacttcactctcaccatttca<br>tctctgcagcctgatgacttcgcaacctattactgtcagcaaagtaaggag<br>gttccgtggacgttcggtcaagggaccaaggtggagatcaaaggtggcggt<br>ggctcgggcggtggtgggtcgggtggcggcggatctcaggttcagctggtg<br>cagtctggagctgaggtgaagaagcctgggagctcagtgaaggtttcctgc<br>aaagcttctggctacacctttcactgactacaacatgcactgggtgaggcag<br>gctcctggccaaggcctggaatggattggatatatttatccttacaatggt<br>ggtaccggctacaaccagaagttcaagagcaaggccacaattacagcagac<br>gagagtactaacacagcctacatggaactctccagcctgaggtctgaggac<br>actgcagtctattactgcgcaagagggcgccccgctatggactactggggc<br>caagggactctggtcactgtctcttca |
| hM195scFv | 45 | MLLLVTSLLLCELPHPAFLLIPDIQMTQSPSSLSASVFDRVTITCRASESV<br>DNYGISFMNWFQQKPGKAPKLLIYAASNQGSGVPSRFSGSGSGTDFTLTIS<br>SLQPDDFATYYCQQSKEVPWTFGQGTKVEIKGGGGSGGGGSGGGGSQVQLV<br>QSGAEVKKPGSSVKVSCKASGYTFTDYNMHWVRQAPGQGLEWIGYIYPYNG<br>GTGYNQKFKSKATITADESTNTAYMELSSLRSEDTAVYYCARGRPAMDYWG<br>QGTLVTVSS |
| hM195scFv-<br>CD8a-4-<br>1BB-Z | 46 | atgctgctgctggtgaccagcctgctgctgtgtgagctgccccacccccgcc<br>tttctgctgatccccgacattcagatgacccagtctccgagctctctgtcc<br>gcatcagtaggagacagggtcaccatcacatgcagagccagcgaaagtgtc<br>gacaattatggcattagctttatgaactggttccaacagaaacccgggaag<br>gctcctaagcttctgatttacgctgcatccaaccaaggctccggggtaccc<br>tctcgcttctcaggcagtggatctgggacagacttcactctcaccatttca<br>tctctgcagcctgatgacttcgcaacctattactgtcagcaaagtaaggag<br>gttccgtggacgttcggtcaagggaccaaggtggagatcaaaggtggcggt<br>ggctcgggcggtggtgggtcgggtggcggcggatctcaggttcagctggtg<br>cagtctggagctgaggtgaagaagcctgggagctcagtgaaggtttcctgc<br>aaagcttctggctacacctttcactgactacaacatgcactgggtgaggcag<br>gctcctggccaaggcctggaatggattggatatatttatccttacaatggt<br>ggtaccggctacaaccagaagttcaagagcaaggccacaattacagcagac<br>gagagtactaacacagcctacatggaactctccagcctgaggtctgaggac<br>actgcagtctattactgcgcaagagggcgccccgctatggactactggggc<br>caagggactctggtcactgtctcttcaaaagcccaccaccacccctgcccct<br>agacctccaaccccagcccctacaatcgccagccagcccctgagcctgagg<br>cccgaagcctgtagacctgccgctggcggagccgtgcacaccagaggcctg<br>gatttcgcctgcgacatctacatctgggcccctctggccggcacctgtggc<br>gtgctgctgctgagcctggtcatcaccctgtactgcaaccaccggaataag<br>agaggccggaagaaactgctgtacatcttcaagcagcccttcatgcggccc<br>gtgcagaccacccaggaagaggacggctgcagctgccggttccccgaggaa<br>gaggaaggcggctgcgaactgcgggtgaagttcagccggagcgccgacgcc<br>cctgcctaccagcaggggcagaaccagctgtacaacgagctgaacctgggc<br>cggagggaggagtacgacgtgctggacaagcggagaggccgggaccctgag<br>atgggcggcaagcccggagaaagaaccctcaggagggcctgtataacgaa<br>ctgcagaaagacaagatggccgaggcctacagcgagatcggcatgaagggc<br>gagcggcggagggggcaagggccacgacggcctgtaccagggcctgagcacc<br>gccaccaaggatacctacgacgccctgcacatgcaggccctgcccccccaga |

-continued

| Sequence Name | SEQ ID NO | Sequence |
|---|---|---|
| hM195scFv-CD8a-4-1BB-Z | 47 | MLLLVTSLLLCELPHPAFLLIPDIQMTQSPSSLSASVGDRVTITCRASESV<br>DNYGISFMNWFQQKPGKAPKLLIYAASNQGSGVPSRFSGSGSGTDFTLTIS<br>SLQPDDFATYYCQQSKEVPWTFGQGTKVEIKGGGGSGGGGSGGGGSQVQLV<br>QSGAEVKKPGSSVKVSCKASGYTFTDYNMHWVRQAPGQGLEWIGYIYPYNG<br>GTFYNQKFKSKATITADESTNTAYMELSSLRSEDTAVYYCARGRPAMDYWG<br>QGTLVTVSSKPTTTPAPRPPTPAPTIASQPLSLRPEACRPAAGGAVHTRGL<br>DFACDIYIWAPLAGTCGVLLLSLVITLYCNHRNKRGRKKLLYIFKQPFMRP<br>VQTTQEEDGCSCRFPEEEEGGCELRVKFSRSADAPAYQQGQNQLYNELNLG<br>RREEYDVLDKRRGRDPEMGGKPRRKNPQEGLYNELQKDKMAEAYSEIGMKG<br>ERRRGKGHDGLYQGLSTATKDTYDALHMQALPPR |
| hM195scFv-CD8a-4-1BB-Z-T2A-GM-CSFRasp.HER1t | 48 | atgctgctgctggtgaccagcctgctgctgtgtgagctgccccacccccgcc<br>tttctgctgatccccgacattcagatgacccagtctccgagctctctgtcc<br>gcatcagtaggagacagggtcaccatcacatgcagagccagcgaaagtgtc<br>gacaattatggcattagctttatgaactggttccaacagaaacccgggaag<br>gctcctaagcttctgatttacgctgcatccaaccaaggctccgggtaccc<br>tctcgcttctcaggcagtggatctgggacagacttcactctcaccatttca<br>tctctgcagcctgatgacttcgcaacctattactgtcagcaaagtaaggag<br>gttccgtggacgttcggtcaagggaccaaggtggagatcaaaggtggcggt<br>ggctcgggcggtggtgggtcgggtggcggcggatctcaggttcagctggtg<br>cagtctggagctgaggtgaagaagcctgggagctcagtgaaggtttcctgc<br>aaagcttctggctacaccttcactgactacaacatgcactgggtgaggcag<br>gctcctggccaaggcctggaatggattggatatatttatccttacaatggt<br>ggtaccggctacaaccagaagttcaagagcaaggccacaattacagcagac<br>gagagtactaacacagcctacatggaactctccagcctgaggtctgaggac<br>actgcagtctattactgcgcaagagggcgccccgctatggactactgggc<br>caagggactctggtcactgtctcttcaaagcccaccaccaccccctgcccct<br>agacctccaaccccagcccctacaatcgccagccagcccctgagcctgagg<br>cccgaagcctgtagacctgccgctggcggagccgtgcacaccagaggcctg<br>gatttcgcctgcgacatctacatctgggcccctctggccggcacctgtggc<br>gtgctgctgctgagcctggtcatcaccctgtactgcaaccaccggaataag<br>agaggccggaagaaactgctgtacatcttcaagcagcccttcatgcggccc<br>gtgcagaccacccaggaagaggacggctgcagctgccggttccccgaggaa<br>gaggaaggcggctgcgaactgcgggtgaagttcagccggagcgccgacgcc<br>cctgcctaccagcaggggccagaaccagctgtacaacgagctgaacctgggc<br>cggagggaggagtacgacgtgctggacaagcggagaggccggaccctgag<br>atgggcggcaagcccccggagaaagaaccctcaggagggcctgtataacgaa<br>ctgcagaaagacaagatggccgaggcctacagcgagatcggcatgaagggc<br>gagcggcggagggcaagggccacgacggcctgtaccagggcctgagcacc<br>gccaccaaggataccacgacgccctgcacatgcaggcccctgcccccccaga<br>ctcgagggcggcggagagggcagaggaagtcttctaacatgcggtgacgtg<br>gaggagaatcccggccctaggatgcttctcctggtgacaagccttctgctc<br>tgtgagttaccacacccagcattcctcctgatcccacgcaaagtgtgtaac<br>ggaataaggtattggtgaatttaaagactcactctccataaatgctacgaat<br>attaaacacttcaaaaactgcacctccatcagtggcgatctccacatcctg<br>ccggtggcatttaggggtgactccttcacacatactcctcctctggatcca<br>caggaactggatattctgaaaaccgtaaaggaaatcacagggttttttgctg<br>attcaggcttggcctgaaaacaggacgacctccatgcctttgagaaccta<br>gaaatcatacgcggcaggaccaagcaacatggtcagttttctcttgcagtc<br>gtcagcctgaacataacatcctgggattacgctccctcaaggagataagt<br>gatggagatgtgataatttcaggaaacaaaaatttgtgctatgcaaataca<br>ataaactggaaaaaactgtttgggacctccggtcagaaaaccaaaattata<br>agcaacagaggtgaaaacagctgcaaggccacaggccaggtctgccatgcc<br>ttgtgctcccccgagggctgctggggcccggagcccaggactgcgtctct<br>tgccggaatgtcagccgaggcagggaatgcgtggacaagtgcaaccttctg<br>gagggtgagccaagggagtttgtggagaactctgagtgcatacagtgccac<br>ccagagtgcctgcctcaggccatgaacatcacctgcacaggacggggacca<br>gacaactgtatccagtgtgcccactacattgacggcccccactgcgtcaag<br>acctgcccggcaggagtcatgggagaaaacaacaccctggtctggaagtac<br>gcagacgccggccatgtgtgccacctgtgccatccaaactgcacctacgga<br>tgcactgggccaggtcttgaaggctgtccaacgaatgggcctaagatcccg<br>tccatcgccactgggatggtgggggccctcctcttgctgctggtggtggcc<br>ctggggatcggcctcttcatg |
| hM195scFv-CD8a-4-1BB-Z-T2A-GM-CSFRasp.HER1t | 49 | MLLLVTSLLLCELPHPAFLLIPDIQMTQSPSSLSASVGDRVTITCRASESV<br>DNYGISFMNWFQQKPGKAPKLLIYAASNQGSGVPSRFSGSGSGTDFTLTIS<br>SLQPDDFATYYCQQSKEVPWTFGQGTKVEIKGGGGSGGGGSGGGGSQVQLV<br>QSGAEVKKPGSSVKVSCKASGYTFTDYNMHWVRQAPGQGLEWIGYIYPYNG<br>GTFYNQKFKSKATITADESTNTAYMELSSLRSEDTAVYYCARGRPAMDYWG<br>QGTLVTVSSKPTTTPAPRPPTPAPTIASQPLSLRPEACRPAAGGAVHTRGL<br>DFACDIYIWAPLAGTCGVLLLSLVITLYCNHRNKRGRKKLLYIFKQPFMRP<br>VQTTQEEDGCSCRFPEEEEGGCELRVKFSRSADAPAYQQGQNQLYNELNLG<br>RREEYDVLDKRRGRDPEMGGKPRRKNPQEGLYNELQKDKMAEAYSEIGMKG<br>ERRRGKGHDGLYQGLSTATKDTYDALHMQALPPRLEGGGEGRGSLLTCGDV<br>EENPGPRMLLLVTSLLLCELPHPAFLLIPRKVCNGIGIGEFKDSLSINATN<br>IKHFKNCTSISGDLHILPVAFRGDSFTHTPPLDPQELDILKTVKEITGFLL |

| Sequence Name | SEQ ID NO | Sequence |
|---|---|---|
| | | IQAWPENRTDLHAFENLEIIRGRTKQHGQFSLAVVSLNITSLGLRSLKEIS<br>DGDVIISGNKNLCYANTINWKKLFGTSGQKTKIISNRGENSCKATGQVCHA<br>LCSPEGCWGPEPRDCVSCRNVSRGRECVDKCNLLEGEPREFVENSECIQCH<br>PECLPQAMNITCTGRGPDNCIQCAHYIDGPHCVKTCPAGVMGENNTLVWKY<br>ADAGHVCHLCHPNCTYGCTGPGLEGCPTNGPKIPSIATGMVGALLLLLVVA<br>LGIGLFM |
| hM195scFv-<br>CD8a-4-<br>1BB-Z-<br>T2A.FL<br>CD20 | 50 | ATGCTGCTGCTGGTGACCAGCCTGCTGCTGTGTGAGCTGCCCCACCCCGCC<br>TTTCTGCTGATCCCCGACATTCAGATGACCCAGTCTCCGAGCTCTCTGTCC<br>GCATCAGTAGGAGACAGGGTCACCATCACATGCAGAGCCAGCGAAAGTGTC<br>GACAATTATGGCATTAGCTTTATGAACTGGTTCCAACAGAAACCCGGGAAG<br>GCTCCTAAGCTTCTGATTTACGCTGCATCCAACCAAGGCTCCGGGGTACCC<br>TCTCGCTTCTCAGGCAGTGGATCTGGGACAGACTTCACTCTCACCATTTCA<br>TCTCTGCAGCCTGATGACTTCGCAACCTATTACTGTCAGCAAAGTAAGGAG<br>GTTCCGTGGACGTTCGGTCAAGGGACCAAGGTGGAGATCAAAGGTGGCGGT<br>GGCTCGGGCGGTGGTGGGTCGGGTGGCGGCGGATCTCAGGTTCAGCTGGTG<br>CAGTCTGGAGCTGAGGTGAAGAAGCCTGGGAGCTCAGTGAAGGTTTCCTGC<br>AAAGCTTCTGGCTACACCTTCACTGACTACAACATGCACTGGGTGAGGCAG<br>GCTCCTGGCCAAGGCCTGGAATGGATTGGATATATTTATCCTTACAATGGT<br>GGTACCGGCTACAACCAGAAGTTCAAGAGCAAGGCCACAATTACAGCAGAC<br>GAGAGTACTAACACAGCCTACATGGAACTCTCCAGCCTGAGGTCTGAGGAC<br>ACTGCAGTCTATTACTGCGCAAGAGGGCGCCCCGCTATGGACTACTGGGGC<br>CAAGGGACTCTGGTCACTGTCTCTTCAAAGCCCACCACCACCCCTGCCCCT<br>AGACCTCCAACCCCAGCCCCTACAATCGCCAGCCAGCCCCTGAGCCTGAGG<br>CCCGAAGCCTGTAGACCTGCCGCTGGCGGAGCCGTGCACACCAGAGGCCTG<br>GATTTCGCCTGCGACATCTACATCTGGGCCCCTCTGGCCGGCACCTGTGGC<br>GTGCTGCTGCTGAGCCTGGTCATCACCCTGTACTGCAACCACCGGAATAAG<br>AGAGGCCGGAAGAAACTGCTGTACATCTTCAAGCAGCCCTTCATGCGGCCC<br>GTGCAGACCACCCAGGAAGAGGACGGCTGCAGCTGCCGGTTCCCCGAGGAA<br>GAGGAAGGCGGCTGCGAACTGCGGGTGAAGTTCAGCCGGAGCGCCGACGCC<br>CCTGCCTACCAGCAGGGCCAGAACCAGCTGTACAACGAGCTGAACCTGGGC<br>CGGAGGGAGGAGTACGACGTGCTGGACAAGCGGAGAGGCCGGGACCCTGAG<br>ATGGGCGGCAAGCCCCGGAGAAAGAACCCTCAGGAGGGCCTGTATAACGAA<br>CTGCAGAAAGACAAGATGGCCGAGGCCTACAGCGAGATCGGCATGAAGGGC<br>GAGCGGCGGAGGGGCAAGGGCCACGACGGCCTGTACCAGGGCCTGAGCACC<br>GCCACCAAGGATACCTACGACGCCCTGCACATGCAGGCCCTGCCCCCCAGA<br>CTCGAGGGCGGCGGAGAGGGCAGAGGAAGTCTTCTAACATGCGGTGACGTG<br>GAGGAGAATCCCGGCCCTAGGATGACAACACCCAGAATTCAGTAAATGGG<br>ACTTTCCCGGCAGAGCCAATGAAAGGCCCTATTGCTATGCAATCTGGTCCA<br>AAACCACTCTTCAGGAGGATGTCTTCACTGGTGGGCCCCACGCAAAGCTTC<br>TTCATGAGGGAATCTAAGACTTTGGGGGCTGTCCAGATTATGAATGGGCTC<br>TTCCACATTGCCCTGGGGGGTCTTCTGATGATCCCAGCAGGGATCTATGCA<br>CCCATCTGTGTGACTGTGTGGTACCCTCTCTGGGGAGGCATTATGTATATT<br>ATTTCCGGATCACTCCTGGCAGCAACGGAGAAAAACTCCAGGAAGTGTTTG<br>GTCAAAGGAAAAATGATAATGAATTCATTGAGCCTCTTTGCTGCCATTTCT<br>GGAATGATTCTTTCAATCATGGACATACTTAATATTAAAATTTCCCATTTT<br>TTAAAAATGGAGAGTCTGAATTTTATTAGAGCTCACACACCATATATTAAC<br>ATATACAACTGTGAACCAGCTAATCCCTCTGAGAAAAACTCCCCATCTACC<br>CAATACTGTTACAGCACATACAATCTCTGTTCTTGGGCATTTTGTCAGTGATG<br>CTGATCTTTGCCTTCTTCCAGGAACTTGTAATAGCTGGCATCGTTGAGAAT<br>GAATGGAAAAGAACGTGCTCCAGACCCAAATCTAACATAGTTCTCCTGTCA<br>GCAGAAGAAAAAAAGAACAGACTATTGAAATAAAAGAAGAAGTGGTTGGG<br>CTAACTGAAACATCTTCCCAACCAAAGAATGAAGAAGACATTGAAATTATT<br>CCAATCCAAGAAGAGGAAGAAGAAGAAACAGAGACGAACTTTCCAGAACCT<br>CCCCAAGATCAGGAATCCTCACCAATAGAAAATGACAGCTCTCCT |
| hM195scFv-<br>CD8a-4-<br>1BB-Z-<br>T2A.FL<br>CD20 | 51 | MLLLVTSLLLCELPHPAFLLIPDIQMTQSPSSLSASVGDRVTITCRASESV<br>DNYGISFMNWFQQKPGKAPKLLIYAASNQGSGVPSRFSGSGSGTDFTLTIS<br>SLQPDDFATYYCQQSKEVPWTFGQGTKVEIKGGGGSGGGGSGGGGSQVQLV<br>QSGAEVKKPGSSVKVSCKASGYTFTDYNMHWVRWAPGQGLEWIGYIYPYNG<br>GTGYNQFKSKATITADESTNTAYMELSSLRSEDTAVYYCARGRPAMDYWG<br>QGTLVTVSSKPTTTPAPRPPTPAPTIASQPLSLRPEACRPAAGGAVHTRGL<br>DFACDIYIWAPLAGTCGVLLLSLVITLYCNHRNKRGRKKLLYIFKQPFMRP<br>VQTTQEEDGCSCRFPEEEEGGCELRVKFSRSADAPAYQQGQNQLYNELNLG<br>RREEYDVLDKRRGRDPEMGGKPRRKNPQEGLYNELQKDKMAEAYSEIGMKG<br>ERRRGKGHDGLYQGLSTATKDTYDALHMQALPPRLEGGGEGRGSLLTCGDV<br>EENPGPRMTTPRNSVNGTFPAEPMKGPIAMQSGPKPLFRRMSSLVGPTQSF<br>FMRESKTLGAVQIMNGLFHIALGGLLMIPAGIYAPICVTVWYPLWGGIMYI<br>ISGSLLAATEKNSRKCLVKGKMIMNSLSLFAAISGMILSIMDILNIKISHF<br>LKMESLNFIRAHTPYINIYNCEPANPSEKNSPSTQYCYSIQSLFLGILSVM<br>LIFAFFQELVIAGIVENEWKRTCSRPKSNIVLLSAEEKKEQTIEIKEEVVG<br>LTETSSQPKNEEDIEIIPIQEEEEETNFPEPPQDQESSPIENDSSP |
| human<br>CD33(M1-R287) | 52 | Atgccgctgctgctactgctgcccctgctgtgggcaggggccctggctatg<br>gatccaaatttctggctgcaagtgcaggagtcagtgacggtacaggagggt<br>ttgtgcgtcctcgtgccctgcactttcttccatcccataccctactacgac<br>aagaactccccagttcatggttactggttccgggaaggagccattatatcc |

-continued

| Sequence Name | SEQ ID NO | Sequence |
|---|---|---|
| | | agggactctccagtggccacaaacaagctagatcaagaagtacaggaggag |
| | | actcagggcagattccgcctccttggggatcccagtaggaacaactgctcc |
| | | ctgagcatcgtagacgccaggaggagggataatggttcatacttctttcgg |
| | | atggagagaggaagtaccaaatacagttacaaatctccccagctctctgtg |
| | | catgtgacagacttgacccacaggcccaaaatcctcatccctggcactcta |
| | | gaacccggccactccaaaaacctgacctgctctgtgtcctgggcctgtgag |
| | | cagggaacaccccgatcttctcctggttgtcagctgcccccacctccctg |
| | | ggccccaggactactcactcctcggtgctcataatcaccccacggcccag |
| | | gaccacggcaccaacctgacctgtcaggtgaagttcgctggagctggtgtg |
| | | actacggagagaaccatccagctcaacgtcacctatgttccacagaaccca |
| | | acaactggtatctttccaggagatggctcagggaaacaagagaccagagca |
| | | ggagtggttcatggggccattggaggagctggtgttacagccctgctcgct |
| | | ctttgtctctgcctcatcttcttcatagtgaagacccacaggagg |
| human CD33(M1-R287) | 53 | MPLLLLLPLLWAGALAMDPNFWLQVQESVTVQEGLCVLVPCTFFHPIPYYD |
| | | KNSPVHGYWFREGAIISRDSPVATNKLDQEVQEETQGRFRLLGDPSRNNCS |
| | | LSIVDARRRDNGSYFFRMERGSTKYSYKSPQLSVHVTDLTHRPKILIPGTL |
| | | EPGHSKNLTCSVSWACEQGTPPIFSWLSAAPTSLGPRTTHSSVLIITPRPQ |
| | | DHGTNLTCQVKFAGAGVTTERTIQLNVTYVPQNPTTGIFPGDGSGKQETRA |
| | | GVVHGAIGGAGVTALLALCLCLIFFIVKTHRR |
| HER1t-1 | 54 | RKVCNGIGIGEFKDSLSINATNIKHFKNCTSISGDLHILPVAFRGDSFTHT |
| | | PPLDPQELDILKTVKEITGFLLIQAWPENRTDLHAFENLEIIRGRTKQHGQ |
| | | FSLAVVSLNITSLGLRSLKEISDGDVIISGNKNLCYANTINWKKLFGTSGQ |
| | | KTKIISNRGENSCKATGQVCHALCSPEGCWGPEPRDCVSGGGGSGGGGSGG |
| | | GGSGGGGSFWVLVVVGGVLACYSLLVTVAFIIFWVRSKRS |
| HER1t-1 | 55 | cgcaaagtgtgtaacggaataggtattggtgaatttaaagactcactctcc |
| | | ataaatgctacgaatattaaacacttcaaaaactgcacctccatcagtggc |
| | | gatctccacatcctgccggtggcatttaggggtgactccttcacacatact |
| | | cctcctctggatccacaggaactggatattctgaaaaccgtaaaggaaatc |
| | | acagggttttttgctgattcaggcttggcctgaaaacaggacggacctccat |
| | | gcctttgagaacctagaaatcatacgcggcaggaccaagcaacatggtcag |
| | | tttctcttgcagtcgtcagcctgaacataacatcctgggattacgctcc |
| | | ctcaaggagataagtgatggagatgtgataatttcaggaaacaaaaatttg |
| | | tgctatgcaaatacaataaactggaaaaaactgtttgggacctccggtcag |
| | | aaaaccaaaattataagcaacagaggtgaaaacagctgcaaggccacaggc |
| | | caggtctgccatgccttgtgctcccccgagggctgctggggcccggagccc |
| | | agggactgcgtctctggtggcggtggctcgggcggtggtgggtcgggtggc |
| | | ggcggatctggtggcggtggctcgtttttgggtgctggtggtggtggtgga |
| | | gtcctggcttgctatagcttgctagtaacagtggcctttattattttctgg |
| | | gtgaggagtaagaggagc |
| CD20t-1 | 56 | MTTPRNSVNGTFPAEPMKGPIAMQSGPKPLFRRMSSLVGPTQSFFMRESKT |
| | | LGAVQIMNGLFHIALGGLLMIPAGIYAPICVTVWYPLWGGIMYIISGSLLA |
| | | ATEKNSRKCLVKGKMIMNSLSLFAAISGMILSIMDILNIKISHFLKMESLN |
| | | FIRAHTPYINIYNCEPANPSEKNSPSTQYCYSIQSLFLGILSVMLIFAFFQ |
| | | ELVIAGIVENEWKRTCSRPKSNIVLLSAEEKKEQTIEIKEEVVGLTETSSQ |
| | | PKNEEDIE |
| Cd20t-1 | 57 | atgaccacaccacggaactctgtgaatggcacctttcccagcagagccaatg |
| | | aagggaccaatcgcaatgcagagcggacccaagcctctgtttcggagaatg |
| | | agctccctggtgggcccaacccagtccttctttatgagagagtctaagaca |
| | | ctgggcgccgtgcagatcatgaacggactgttccacatcgccctgggagga |
| | | ctgctgatgatcccagccggcatctacgccctatctgcgtgaccgtgtgg |
| | | taccctctgtggggcggcatcatgtatatcatctccggctctctgctggcc |
| | | gccacagagaagaacagcaggaagtgtctggtgaagggcaagatgatcatg |
| | | aatagcctgtccctgtttgccgccatctctggcatgatcctgagcatcatg |
| | | gacatcctgaacatcaagatcagccacttcctgaagatggagagcctgaac |
| | | ttcatcagagcccacacccttacatcaacatctataattgcgagcctgcc |
| | | aacccatccgagaagaattctccaagcacacagtactgttattccatccag |
| | | tctctgttcctgggcatcctgtctgtgatgctgatctttgccttcttcag |
| | | gagctggtcatcgccggcatcgtggagaacgagtggaagaggacctgcagc |
| | | cgccccaagtccaatatcgtgctgctgtccgccgaggagaagaaggagcag |
| | | acaatcgagatcaaggaggaggtggtgggcctgaccgagacatctagccag |
| | | cctaagaatgaggaggatatcgag |
| DNAX-activation protein 10 (DAP 10) Signaling Domain | 58 | ctgtgcgcacgcccacgccgcagccccgcccaagaagatggcaaagtctac |
| | | atcaacatgccaggcaggggc |

-continued

| Sequence Name | SEQ ID NO | Sequence |
|---|---|---|
| DNAX-activation protein 10 (DAP10) Signaling Domain | 59 | LCARPRRSPAQEDGKVYINMPGRG |
| DNAX-activation protein 12 (DAP12) Signaling Domain | 60 | tacttcctgggccggctggtccctcgggggcgagggctgcggaggcagcg acccggaaacagcgtatcactgagaccgagtcgccttatcaggagctccag ggtcagaggtcggatgtctacagcgacctcaacacacagaggccgtattac aaa |
| DNAX-activation protein 12 (DAP12) Signaling Domain | 61 | YFLGRLVPRGRGAAEAATRKQRITETESPYQELQGQRSDVYSDLNTQRPYY K |

EXAMPLES

These examples are provided for illustrative purposes only and not to limit the scope of the claims provided herein.

Example 1

Delivery of CD33 CAR via Lentiviral Vector. CD33 CAR lentiviral vector was constructed based on a HIV-1 derived vector backbone. The HER1t gene was genetically fused to the CD33 CAR at 3' end via in-frame self-cleaving *Thosea asigna* virus 2A peptide (T2A). Both genes were cloned into the pFUGW lentiviral plasmid backbone as described below.

For CD33 CAR lentivirus, VSV-G (glycoprotein of the vesicular stomatitis virus (VSV-G)) was used as a substitute for the HIV-1 envelope proteins resulting in improved vector stability, target cell tropism, and transduction efficiency (Cronin, J., Zhang, X. & Reiser, J., Altering the tropism of lentiviral vectors through pseudotyping, *Curr Gene Ther,* 5(4):387-98 (2005)).

During production, CD33 CAR viral particles assembled and bud out from the surface of transfected HEK293T cells. The VSV-G protein was provided by the pMND-VSVG helper plasmid, the vector core and enzyme proteins were provided by the pA8.9 so (GagPol) helper plasmid, and the Rev protein, which is needed for efficient RNA genome transport and packaging into the viral particle, was provided by the pRSV-Rev plasmid. All the other HIV-1 accessory proteins including Vpu, Vif, Vpr, Nef, and Tat, were deleted from the CD33 CAR vector.

The pFUGW lentiviral vector backbone is a SIN lentiviral vector backbone.

Regulatory Elements

The LV-CD33 CAR vector contained a human elongation factor 1 alpha 1 (EF1A1) promoter and bovine growth hormone polyA sequence to drive expression of transgenes, and a Kozak ribosomal initiation sequence. The vector used woodchuck hepatitis virus posttranscriptional regulatory element (WPRE) as well as LTR sequences derived from the pFUGW plasmid. The origin of replication was based on the pUC19 plasmid. FIG. 2 is the lentiviral vector map of CD33 CAR.

Example 2

Methods of Making CD33 CAR Vector

LV-CD33 CAR vector was assembled from three sources:
(1) The following were obtained from a previously constructed vector, digested with restriction enzymes PacI and BlpI:
  (a) pFUGW backbone components
  (b) A human elongation factor 1 alpha 1 promoter (EF1A1) promoter and enhancer driving the anti-CD33 scFv with GM-CSFR alpha signal peptide
  (c) The CD8α hinge and transmembrane regions.
(2) The 4-1BB signaling domain module was obtained as synthetic gene.
(3) A region containing CD3ζ, T2A transcription linker, GM-CSFR alpha signal peptide, HER1t depletion marker, bovine growth hormone polyA, and flanking cloning sites was amplified by PCR.

The three DNA cassettes were annealed together in an in vitro assembly reaction, using homology regions provided to each cassette. Resulting lentiviral vector contained transgenes of interest (CD33 CAR and HER1t) in the reverse orientation with respect to lentiviral genome. Following transformation into the Stb14 *E. coli* strain, positive colonies were identified by colony PCR and the three-piece insert was verified by Sanger sequencing. The entire plasmid sequence was verified by Illumina Next Generation Sequencing.

The vector was generated in HEK-293T cells in DMEM with 10% FBS, using calcium phosphate precipitation transfection of 4 plasmids, LV-CD33 CAR vector plasmid and 3 helper plasmids, pA8.9 so (GagPol); pMND-VSVG; and pRSV-Rev.

Approximately 18 hours post plasmid transfection, a complete medium exchange was carried out with culture medium containing Benzonase (50 U/mL). Approximately 24 hours post media change, the vector containing culture supernatant was harvested, which was labeled as Harvest #1. The cells were refed with fresh medium and returned to the incubator. The Harvest 1 supernatant was clarified using a filter and stored overnight between 2-8° C.

The following day, the cells were examined microscopically and vector containing supernatant was harvested again as Harvest #2, which is filtered as before. Harvest 1 supernatant was combined with the filtered Harvest 2 supernatant and the pooled supernatant was further clarified through a 0.45 m filter. The clarified vector harvest was purified using anion exchange membrane chromatography, and concentrated and diafiltered into the medium of choice using a hollow fiber device. The purified LV-CD33 CAR vector was filled and stored frozen at <−80° C.

Example 3

Delivery System Efficiency

Figure 4:
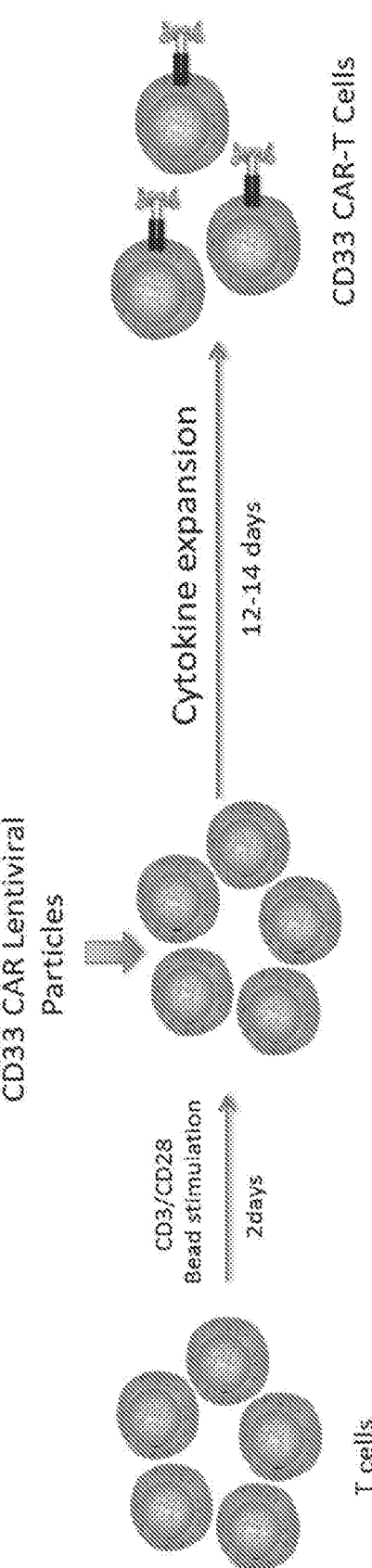
FIG. 4 is an exemplary schematic of lentiviral transduction to generate CAR-T cells.
Figure 5:
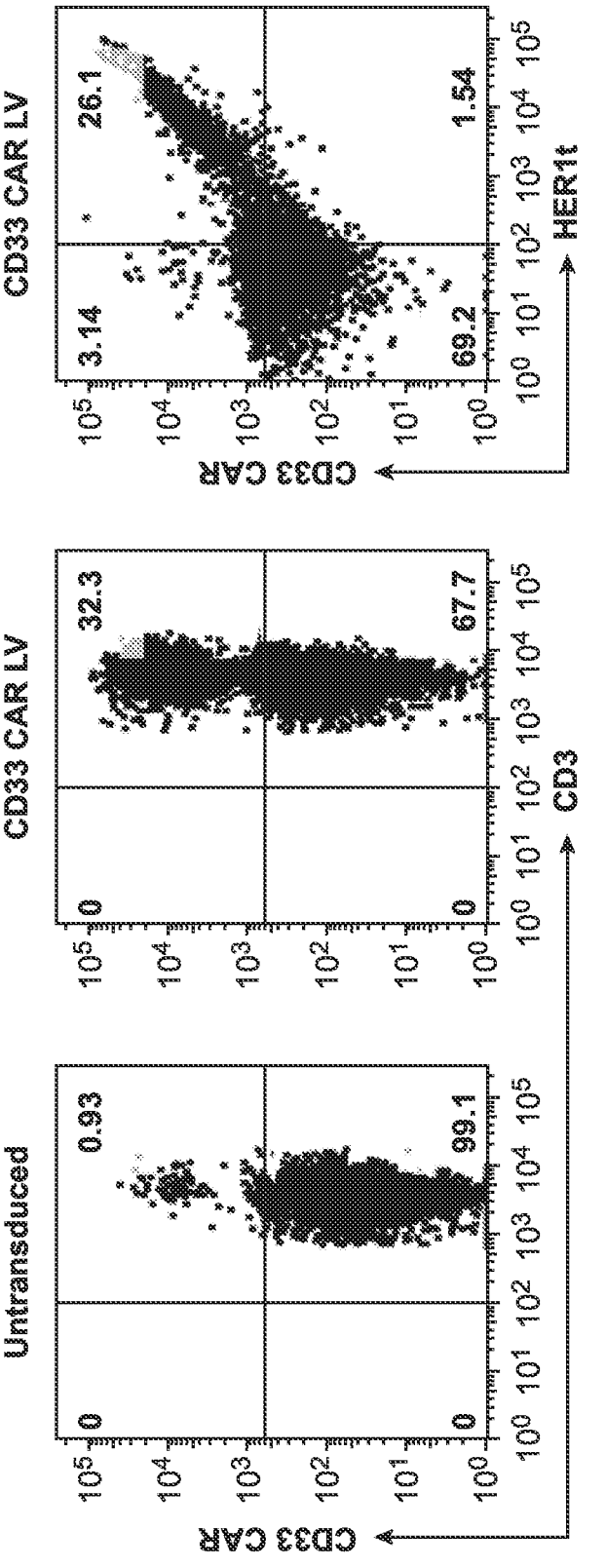
FIG. 5 depicts expression of CD33 CAR and HER1t on adoptively transferred T-cells.

Transduction of T cells from healthy donors with LV-CD33 CAR lentiviral vector typically resulted in 25-50% cells stably co-expressing CD33 CAR and HER1t at 12-14 days post transduction. FIG. 4 describes typical lentiviral transduction schematic for generation of CAR-T cells. FIG. 5 shows representative data of CD33 CAR and HER1t expression at 12 days post lentiviral transduction from one healthy donor T cells. Purified human CD3+ T cells were activated using Dynabeads® Human T-Activator CD3/CD28 beads prior to transduction with CD33 CAR lentiviral vector at a multiplicity of infection (MOI) of 5. Cells were grown in medium containing IL-2 for 12 days post transduction. Flow cytometric analysis was performed 12 days post transduction to assess CD33 CAR and HER1t expression as measured by protein L and cetuximab mAb, respectively.

FIG. 6 confirms CD33 CAR expression from lentivirally transduced cells by Western Blot. Expanded untransduced or lentivirally transduced CD33 CAR-T cells were cultured and cell lysates were generated using RIPA buffer with protease inhibitors. A BCA assay was also performed to on the donor generated samples to normalize the amount of protein loaded onto the gel with reducing conditions. Following the protein transfer, the membrane was blocked then probed with the anti-CD3ζ antibody (Clone 8D3) at 1 μg/ml followed by a goat anti-mouse horse radish peroxidase detection antibody. Bands were detected by chemiluminescence and captured on a digital imaging system. The 16 kDa band represents the endogenously expressed CD3ζ while the 60 kDa band represents the CD33 CAR that expresses a CD3ζ signaling moiety. Only the CD33 CAR-T cells show the 60 kDa band in addition to the endogenous CD3ζ band whereas untransduced cells and Jurkat T cells only have the endogenous CD3ζ present.

FIG. 7 shows ex vivo growth of CD33 CAR-T cells in culture post lentiviral vector transduction. Starting cell population was $2.5 \times 10^5$ and data shown is the mean±SEM from four independent T cell donors. CD33 CAR-T cells were efficiently transduced and expanded ex vivo to levels that translates to achieving clinically relevant doses.

Example 4

Genetic Material Integration

Figure 8:
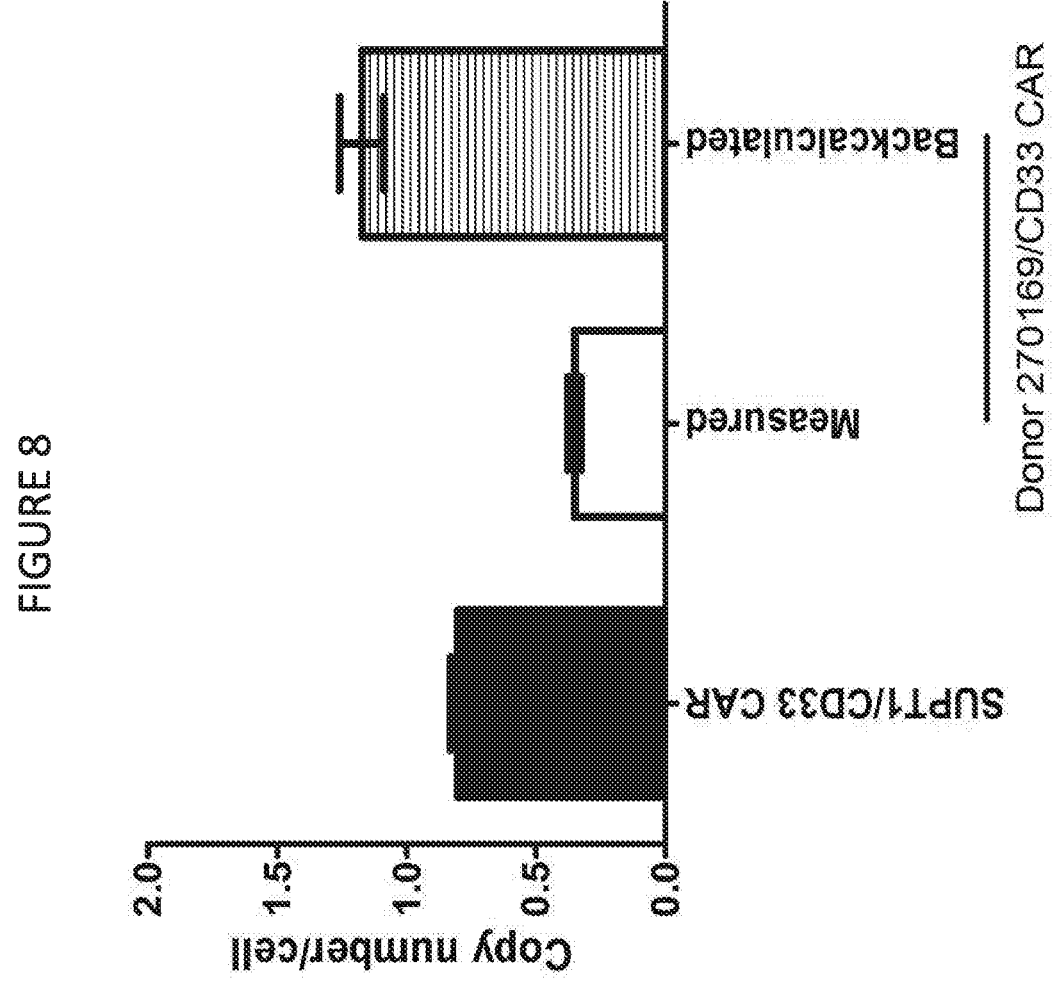
FIG. 8 provides copy number assessment of CD33 CAR-T cells following lentiviral transduction.

The delivered genetic material was integrated in the form of proviral genome. Transgene introduced in T cells using lentiviral transduction was stable for the length of time studied. FIG. 8 is a copy number assessment of CD33-CAR-T cells following lentiviral transduction. Droplet digital PCR (ddPCR) was utilized to determine the number of gene copies integrated into the host genome following lentiviral transductions of either human SUPT1 T cells or T cells from healthy Donor 270169 (D270169), using a MOI of 5. Genomic DNA (gDNA) was obtained after at least 14 days post transduction. The ddPCR reaction was set up using Bio-Rad's ddPCR system (QX200TM AutoDG ddPCR system) with Taqman based primer and probes set for the detection of CD33 CAR. RNaseP was used as the normalizing reference gene for the assessment of copy number variant (CNV), based on the assumption that every cell will have 2 copies of the RNaseP gene. CD33 CAR expression on SUPT1/CD33 CAR and D270169/CD33 CAR-T cells was confirmed by flow cytometry and reported to be ~80% and ~30% respectively (data not shown). For D270169/CD33 CAR-T cells, the sample measured in the assay (designated as measured) is from a mixed population and additional calculation performed to determine the copy number insert for the CAR expressing T cells (referred to as Backcalculated). Data shown is the mean copy number±SD per cell from two experiments.

Example 5

Animal and Cultured Cell Models to Assess Efficacy of Gene Transfer System

The efficiency of lentiviral mediated gene transfer as measured by expression of transferred genes was evaluated by flow cytometry of transduced cells (FIG. 5). Expansion of transduced T cells was carried out ex vivo in culture medium over 12-14 days post transduction to achieve relevant doses (FIG. 7).

Figure 12:
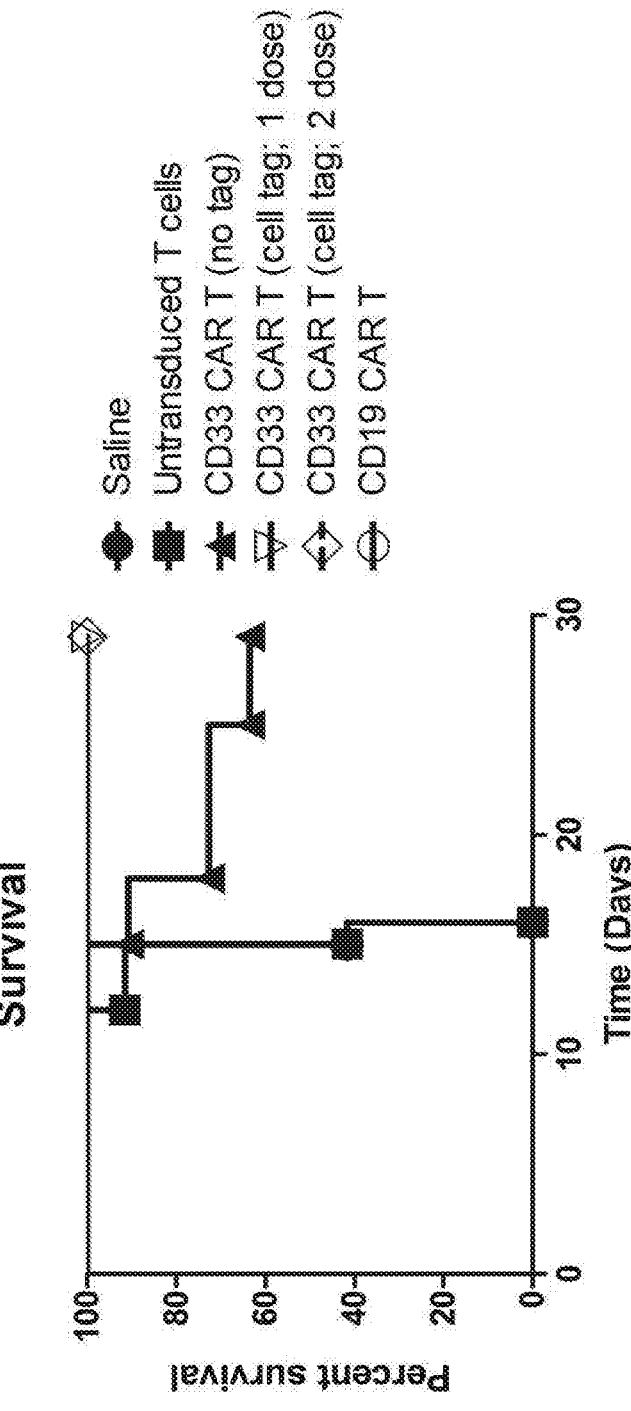
FIG. 12 demonstrates NSG Mice Survival Curves for Treatment Groups in an AML tumor model.

Levels of CD33 CAR observed on T cell surface with lentiviral transduction (FIG. 8) during preclinical analysis were sufficient to efficiently and specifically eliminate different CD33 positive target tumor cell lines in vitro (FIG. 9) as well as enhance survival of CD33 positive tumor bearing mice to statistically significant levels over control groups (FIG. 12). See also FIGS. 5 and 6 for further supporting data.

The functional capability of CD33 CAR-T cells was tested in both in vitro and in vivo models.

In vitro testing of CD33 CAR-T cells included cytotoxicity of AML cell line expressing CD33 as well as mouse EL4 cell line transduced to express human CD33 on surface, and secretion of IFN-γ, IL-2 and TNF-α cytokines upon co-culture with CD33 positive target cells. CD33 CAR-T cells co-expressed HER1t protein to allow for depletion of infused CAR-T cells by administration of cetuximab. Ability of cetuximab to eliminate CD33 CAR-T cells by ADCC was also assessed in vitro.

Figures 9A, 9B:
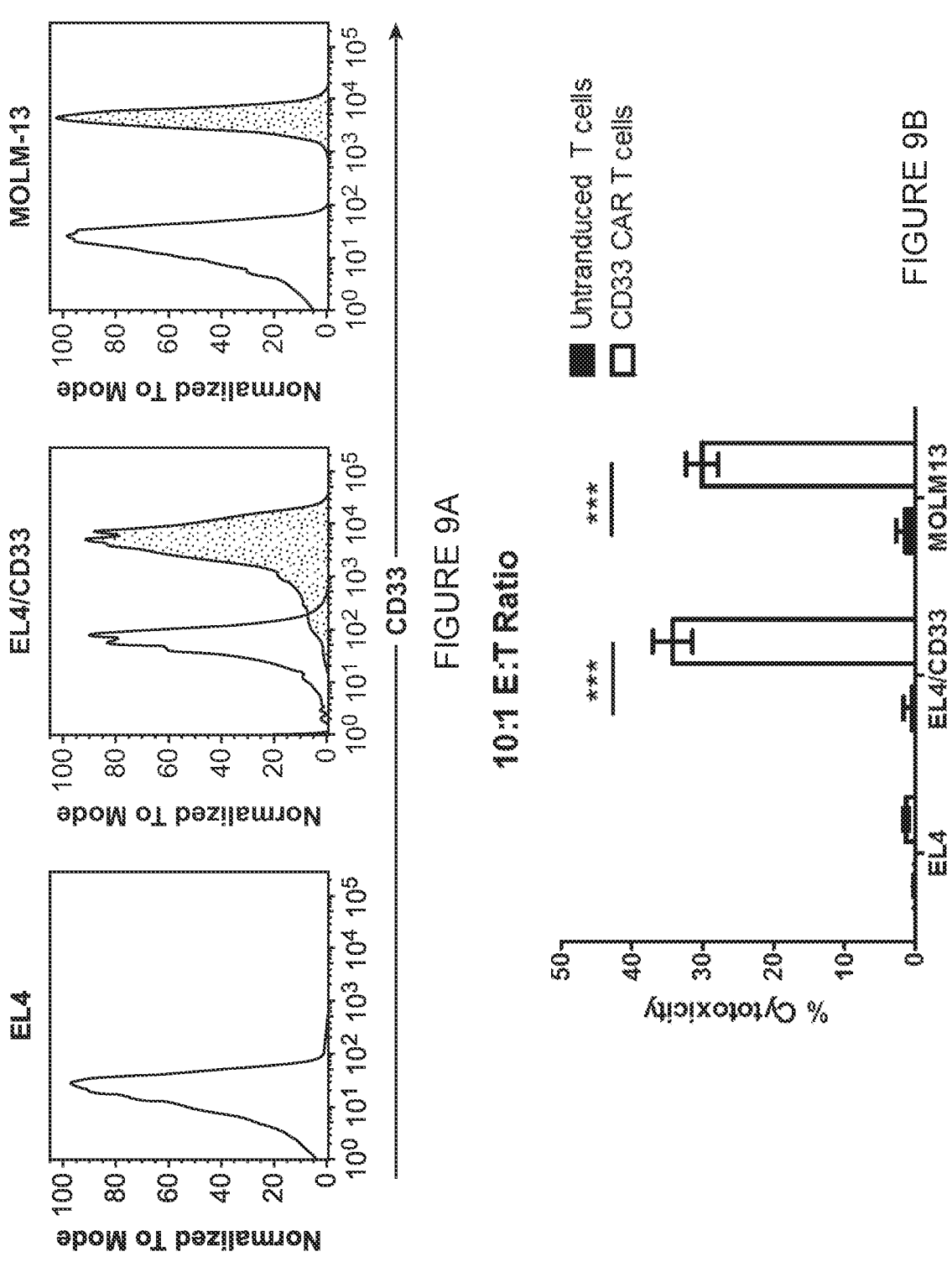
FIGS. 9A, 9B and 9C demonstrate Target Specific in vitro Cytotoxicity of CD33 CAR-T Cells. CD33 specific cytotoxicity was measured from Europium labeled target cells.
Figure 9C:
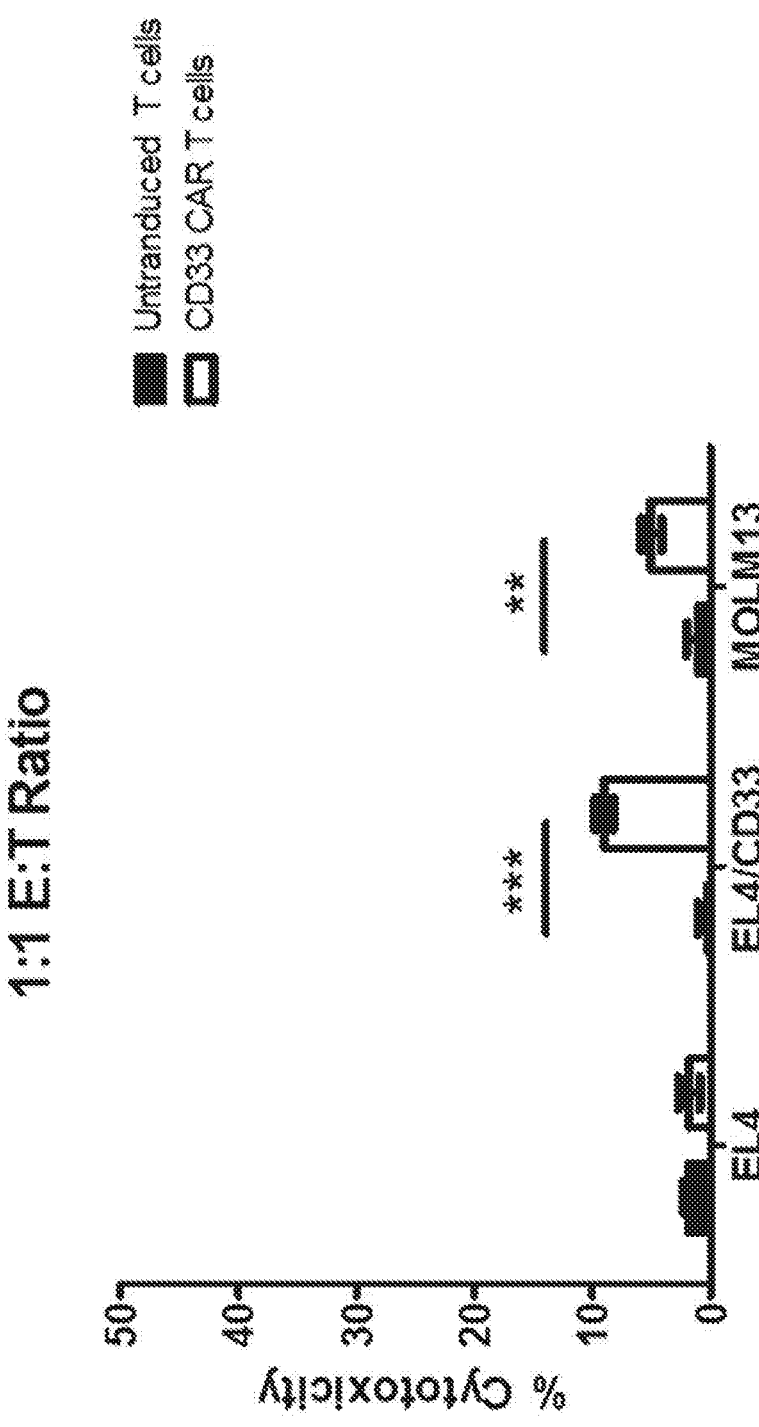

CD33 CAR-T cells were specifically cytotoxic to target cells in dose dependent manner (FIG. 9). Cytotoxicity of CD33 CAR-T cells at effector:target (E:T) ratio of 10:1 (B) and E:T ratio of 1:1 (B) as measured by 2 hr Europium release assay. A dose dependent cytotoxicity of target cells by CD33 CAR-T cells was observed between E:T ratio of 10:1 versus the 1:1 ratio; however, significant cytotoxicity was observed only when target cells expressed CD33 on surface. Untransduced T cells did not show significant cytotoxicity of any target cells tested. Data shown in the graphs is the mean±SEM from 4 different donors,  p values<0.01 and * p values<0.001.

Figure 10A:
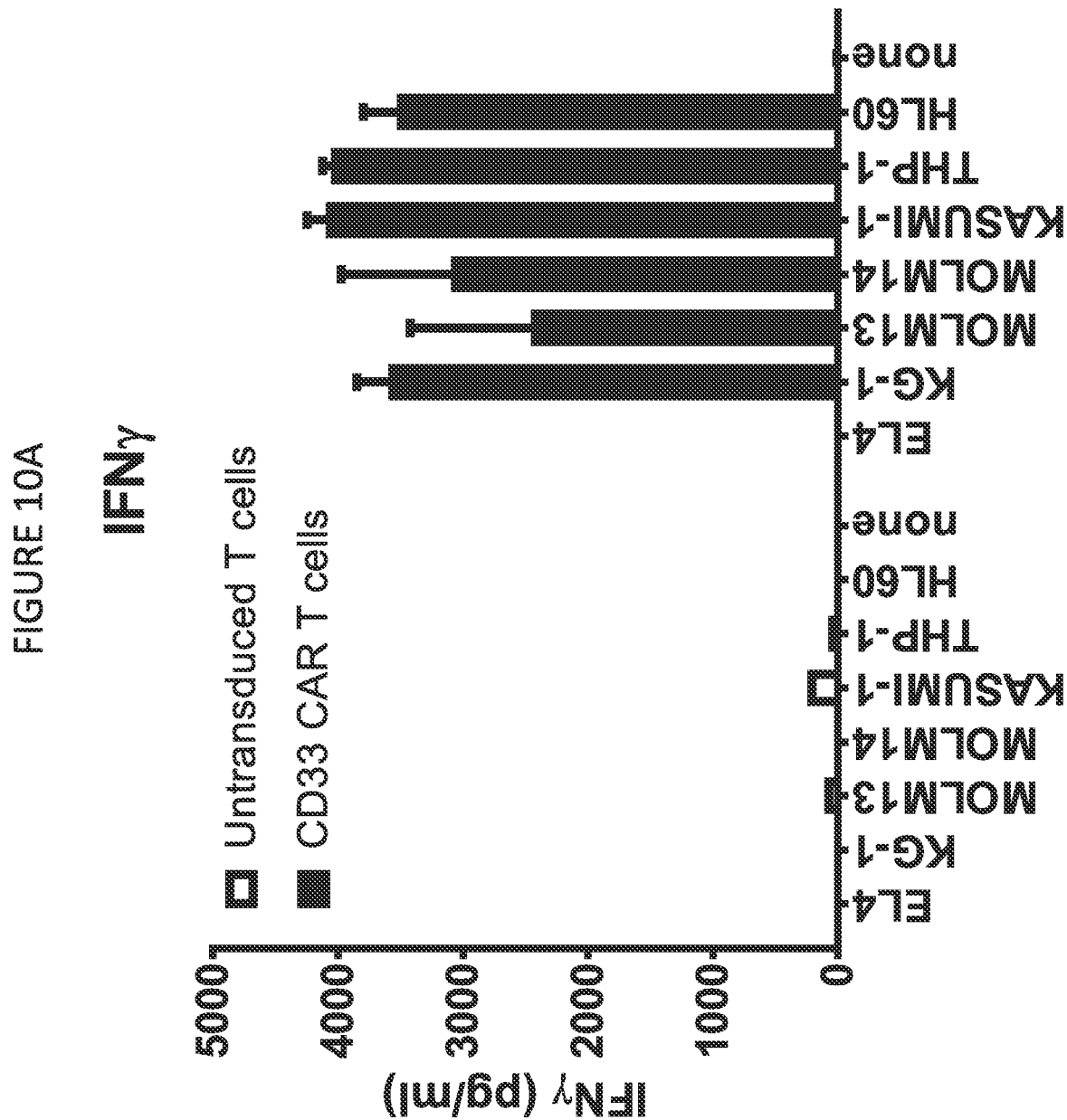
FIGS. 10A, 10B and 10C demonstrate Cytokine Production from ex vivo Expanded CD33 CAR-T Cells.
Figure 10B:
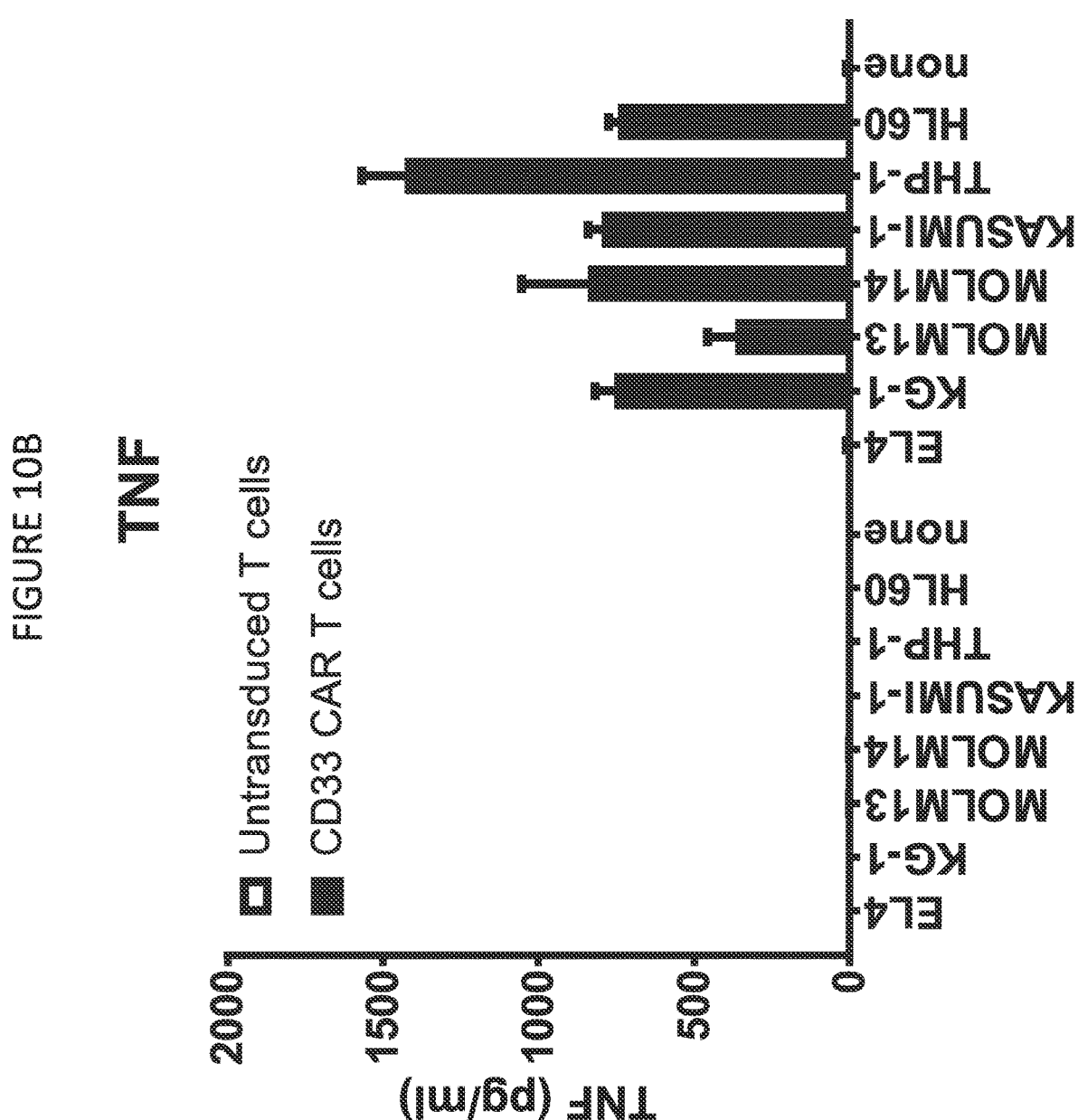
Figure 10C:
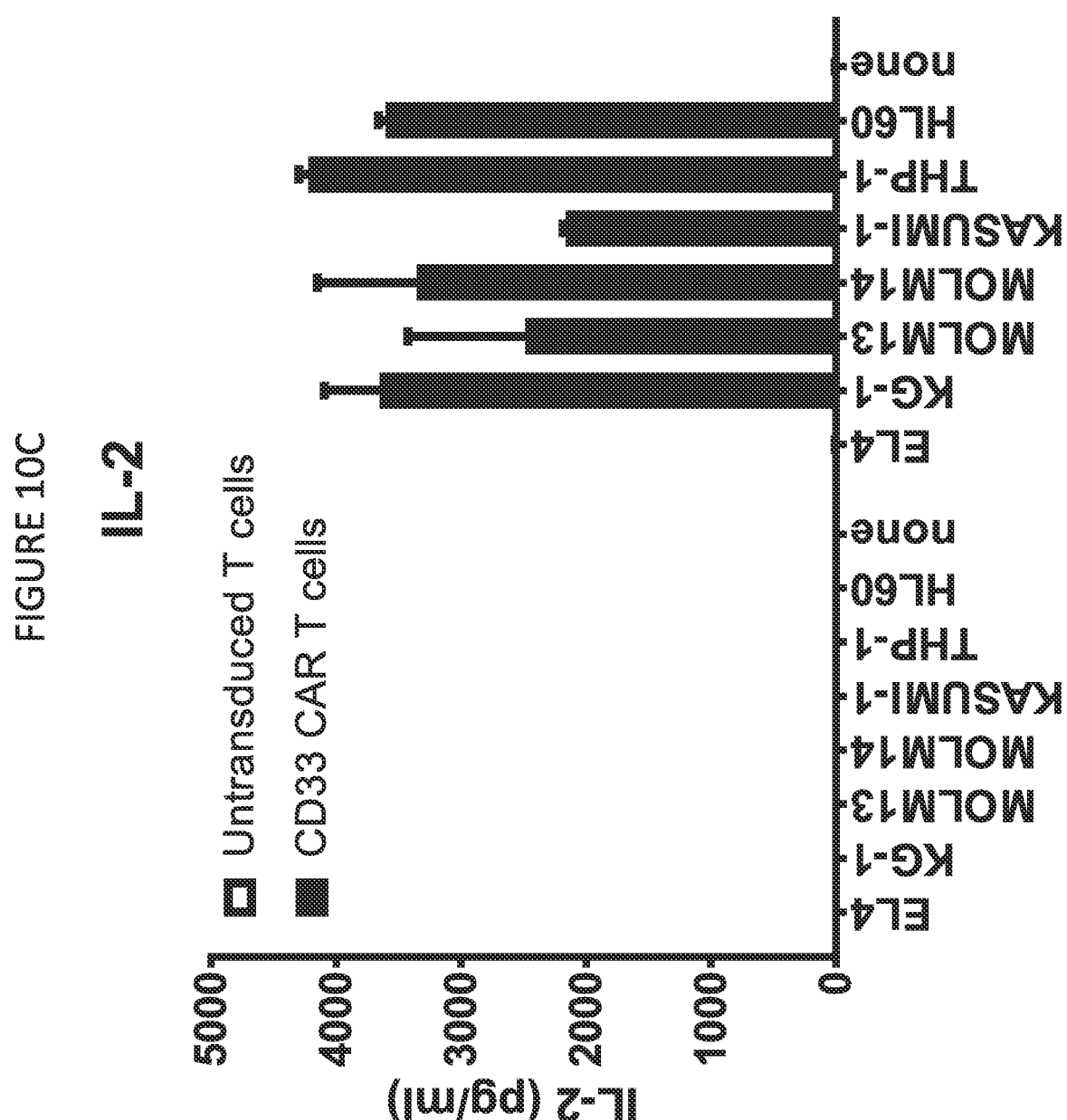

CD33 CAR-T cells specifically secreted elevated levels of various cytokines upon co-culture with different target cell lines as compared to untransduced T cells (FIG. 10). An assessment of cytokine production from untransduced T cells and CD33 CAR-T cells following co-culture with various target AML cell lines that express CD33. The murine EL4 cell line was used as a negative control for human CD33 expression. T cells were co-cultured with at a effector: target (E:T) ratio of 10:1 overnight and culture supernatants were collected for multiplex cytokine analysis using the QBeads (Intellicyt). The multiplex analysis was assayed for expression of human IFNγ, IL-2 and TNF secretion into the culture media. High levels of IFNγ, IL-2 and TNF cytokines were detected following co-cultures of CD33 CAR-T cells with target cells that expressed CD33, when compared to the basal expression levels of the untransduced T cells with the same target cells. Values plotted represent mean±SD of samples tested in duplicates.

Figure 11:
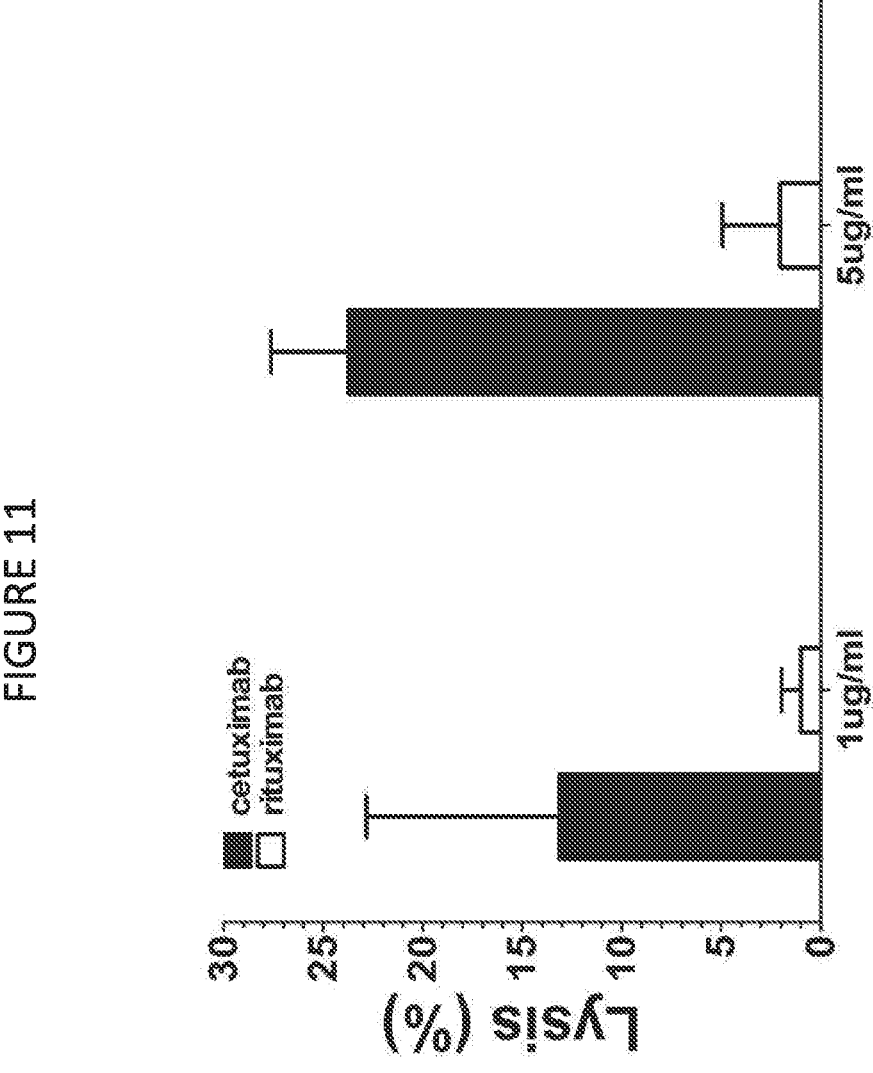
FIG. 11 shows Cetuximab Induced Antibody Dependent Cell-Mediated Cytotoxicity (ADCC) of CD33 CAR-T Cells Expressing HER1t.

Cetuximab was capable of eliminating CD33 CAR-T cells expressing HER1t on the surface in dose dependent manner (FIG. 11). ADCC was determined by flow cytometric analysis of 7-AAD uptake using PKH26 labeled target cells co-incubated with purified effector NK cells at an E:T ratio of 5:1 for 24 hours. Specific dose dependent ADCC of CD33 CAR-T cells was observed with cetuximab. Values plotted represent mean±SD of samples tested in duplicates.

Ability of CD33 CAR-T cells to specifically reduce tumor burden was also tested in an in vivo xenograft model in immunodeficient NSG (NOD.Cg-PrkdcscidIL2rgtm1Wjl/SzJ, NOD scid gamma) mice using AML cell line MOLM-13 transduced to express fLUC (MOLM-13/fLUC) to monitoring tumor burden by bioluminescent imaging. Details of study design are depicted in Table 2. Administration of CD33 CAR-T cells in MOLM-13/fLUC tumor bearing NSG mice reduced the tumor burden and increased the mean survival to statistically significant level (P<0.001) when compared to control treatment groups consisting of saline, untransduced T cells and non-specific CD19 CAR-T cells Tumor bearing mice were confirmed by bioluminescence expression via IVIS imaging on day 7 then randomized into the different treatment groups. On day 8, mice were treated with either saline only, untransduced T cells ($10^7$ total T cells/mouse), CD33 CAR-T cells with no cell tag or with the HER1t cell tag ($10^7$ CD33 CAR-T cells/mouse) or with CD19 CAR T cells ($10^7$ CD19 CAR-T cells/mouse) by IV injection. In addition, another group of mice received a second dose of CD33 CAR T cells with the HER1t cell tag ($10^7$ CD33 CAR+ T cells/mouse) on Day 15. Overall tumor burden was evaluated by fLUC expression using bioluminescence imaging over the course of the study. Survival curves from different treatment groups are shown in FIG. 12. The median survival time for mice in the saline, untransduced T cells and CD19 CAR-T cells was day 15. Mice treated with the CD33 CAR T cells containing no cell tag had an enhanced survival while all mice treated with CD33 CAR-T cells (1 or 2 doses) had complete survival up to Day 29.

Figures 13A, 13B:
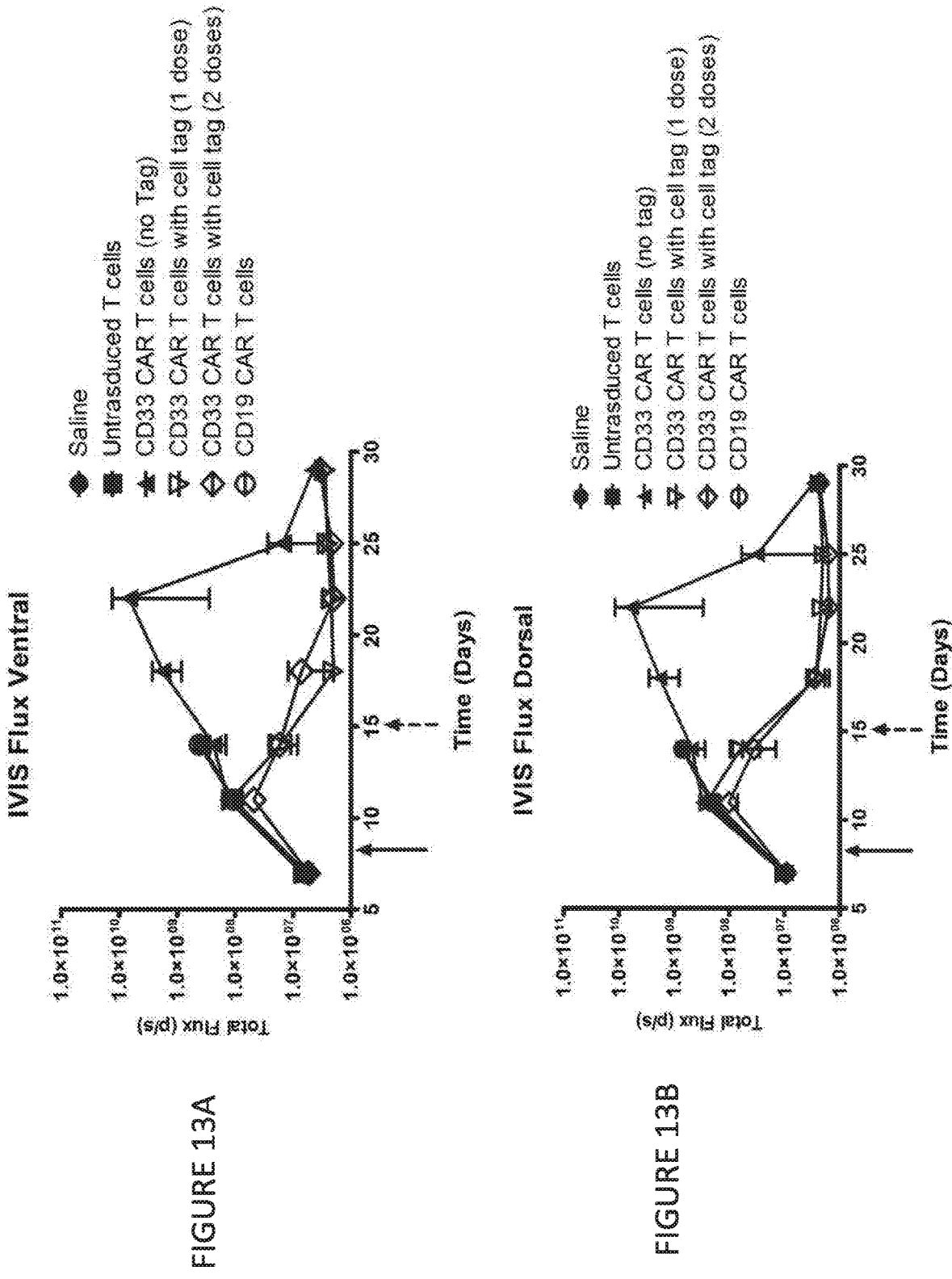
FIGS. 13A and 13B provide Quantitative Analysis of Tumor Burden as Measured by fLUC Bioluminescence.

Mean flux values from ventral and dorsal views are plotted in FIG. 13 for different treatment groups. Values shown are total flux values expressed as photons/see with the average±SEM shown for each group. Solid upward arrow indicate day of CAR-T dosing for each group, dotted upward arrow on day 15 indicate second CD33 CAR-T dose for 2 dose group.

TABLE 3

Figure 14A:
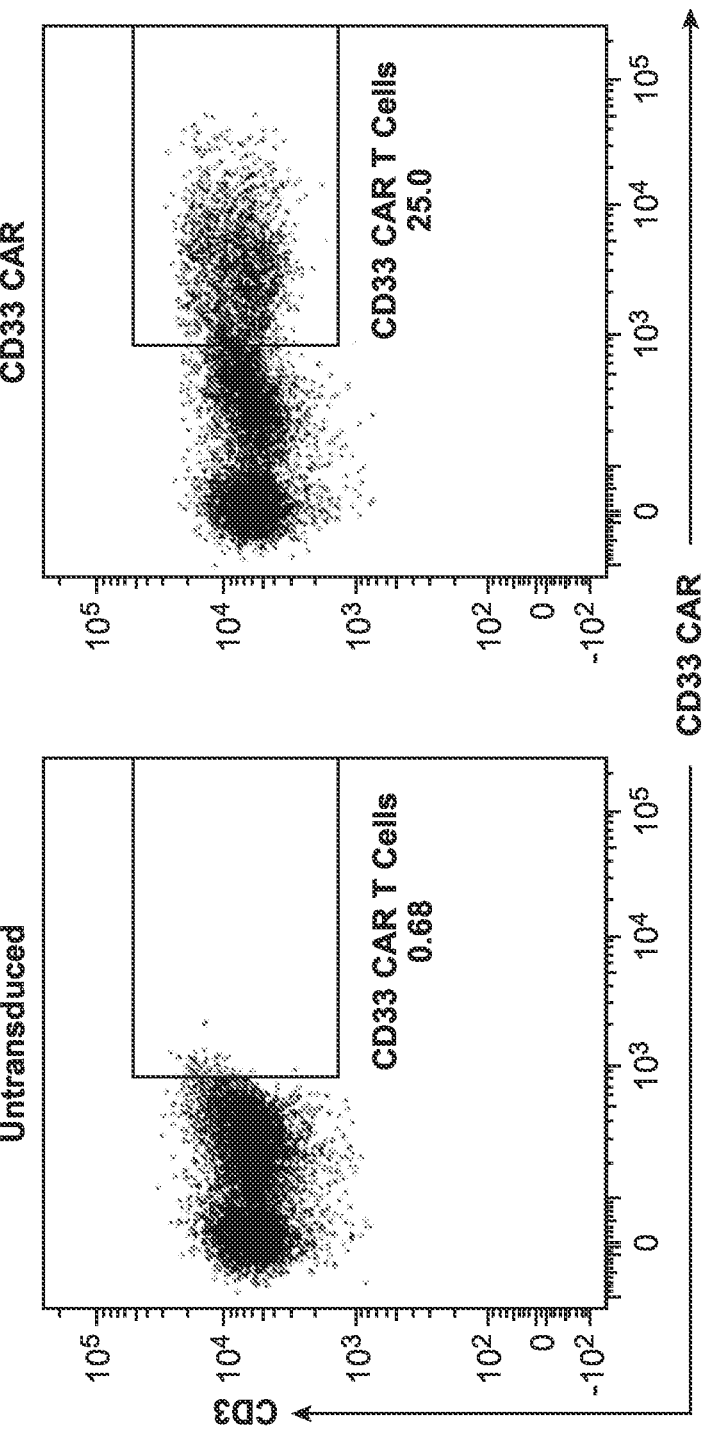
FIGS. 14A and 14B provide Flow cytometry Analysis of Blood, Bone Marrow and Spleen Samples From CD33 CAR-T cell Treated NSG Mice.
Figure 14B:
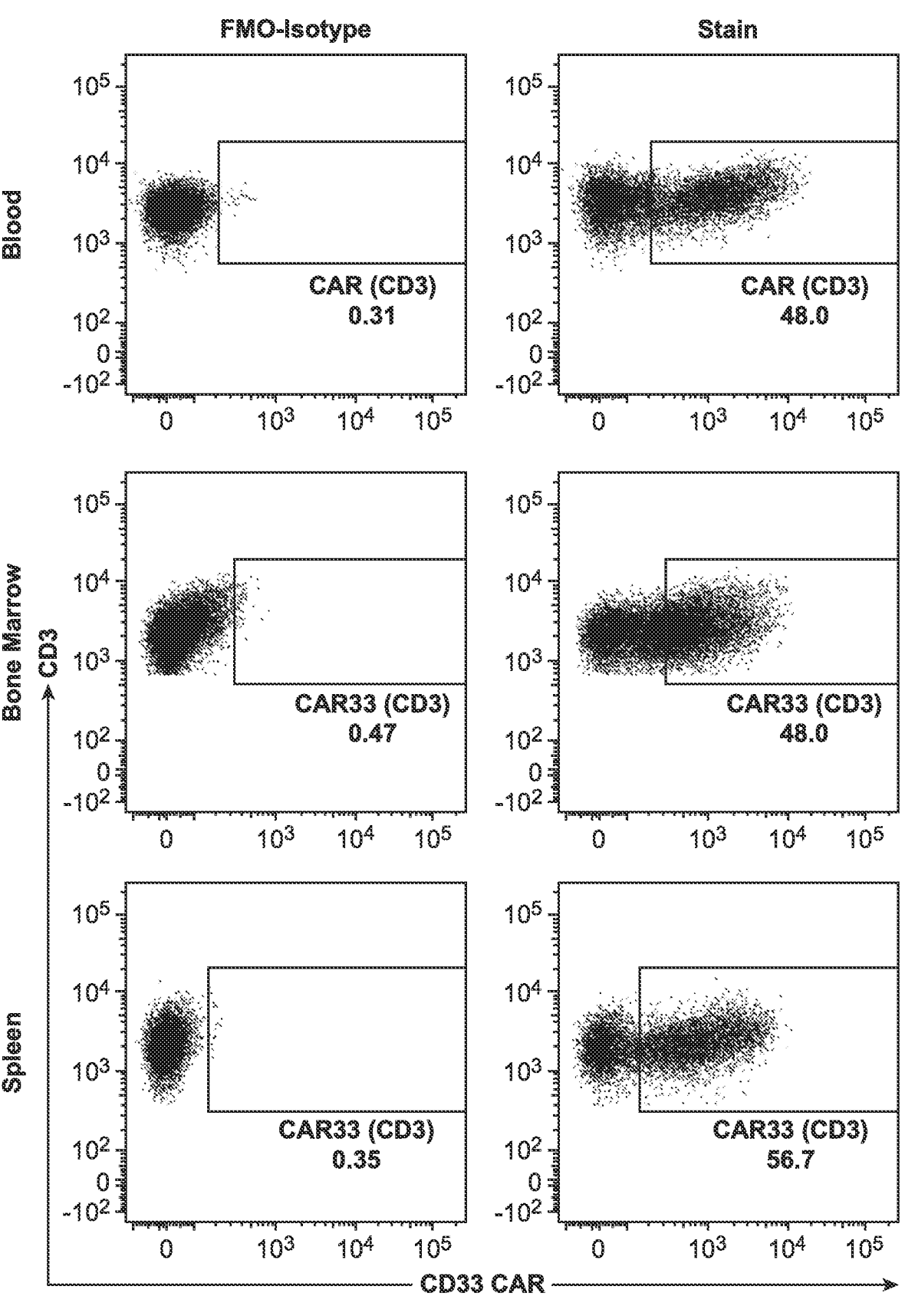

| | | | | | |
|---|---|---|---|---|---|
| Study Design to Evaluate in vivo Efficacy of CD33 CAR-T cells in NSG Mice | | | | | |
| N | Tumor Cell Line | Tumor Cell Dose on Day 0 (route of administration) | Treatment | Dose per animal (no. of cells) | CAR T cell Dose Administration (Day) |
| 12 | MOLM-13/fLUC | $5 \times 10^5$ cells (IV) | Saline | N/A | D8 |
| 12 | MOLM-13/fLUC | $5 \times 10^5$ cells (IV) | Non-transduced T cells | $10^7$ | D8 |
| 11 | MOLM-13/fLUC | $5 \times 10^5$ cells (IV) | CD33 CAR-T (no cell tag) | $10^7$ | D8 |
| 11 | MOLM-13/fLUC | $5 \times 10^5$ cells (IV) | CD33 CAR-T with cell tag (1 dose) | $10^7$ | D8 |
| 11 | MOLM-13/fLUC | $5 \times 10^5$ cells (IV) | CD33 CAR-T with cell tag (2 doses) | $10^7$ per each dose | D8 and D15 |
| 12 | MOLM-13/fLUC | $5 \times 10^5$ cells (IV) | CD19 CAR-T | $10^7$ | D8 | generated from same healthy T cell donor as CD33 CAR-T cells. CD33 CAR-T cells proliferated in vivo in tumor bearing mice (FIG. 14). Flow cytometric analysis of CD33 CAR-T cells prior to injection in NSG mice and the detection of the CD33 CAR-T cells in various tissues in treated mice were carried out to document persistence and expansion of CAR-T cells in vivo. (FIG. 14A) Healthy donor T cells were transduced with the CD33 CAR lentivirus and expanded ex vivo. Prior to injection of the CD33 CAR-T cells for treatment, flow cytometric analysis was performed to assess CD33 CAR expression level. Population shown was gated on FSC/SSC/viable/CD3+ cells. (FIG. 14B). Flow cytometric analysis was performed on Day 18 (10 days after CD33 CAR-T cell injection by systemic IV injection into the tail vein) on the blood, bone marrow and spleen sample recovered from a MOLM-13 tumor bearing, CD33 CAR-T treated mice to detect the presence of the CD33 CAR-T cells. Data from one representative mouse with the populations gated based on FSC/SSC/hCD45/hCD3 expression.

Immune deficient NSG mice were injected intravenously (IV) with $5 \times 10^5$ MOLM-13 cell line modified to express firefly luciferase (fLUC) gene (MOLM-13/fLUC) on Day 0.

Example 6

Cytokine Analysis: Plasma samples from mice were collected at specific time points in the protocol or when mice became moribund and were euthanized for humane reasons. To obtain the plasma, blood was collected in EDTA collection tubes then spun at 5,000×g for 15 min at room temperature then the resulting plasma transferred to a clean collection tube. The plasma was frozen and stored at −80° C. until assayed. The ProcartaPlex® Human cytokine/chemokine/growth factor Panel 1 kit (eBioscience) is a 45-plex magnetic bead based kit for the multiplex detection of the following analytes: brain-derived neurotrophic factor (BDNF), epidermal growth factor (EGF), eotaxin, Fibroblast growth factor-2 (FGF-2), granulocyte/macrophage-colony stimulating factor (GM-CSF), GRO alpha (CXCL1), hepatocyte growth factor (HGF), Interferon (IFN) alpha, IFN-gamma (IFNγ), Interleukin (IL)-1Receptor alpha (IL-1RA), IL-1 alpha, IL-1 beta, IL-2, IL-4, IL-5, IL-6, IL-7, IL-8, IL-9, IL-10, IL-12p70, IL-13, IL-15, IL-17A, IL-18, IL-21, IL-22, IL-23, IL-27, IL-31, Interferon gamma-induced protein 10 (IP-10; also known as CXCL10), leukemia inhibitory factor (LIF), monocyte chemotactic protein-1 (MCP-1, known as CCL2), macrophage inflammatory protein-1 alpha (MIP-1 alpha; also known as CCL3), MIP-1 beta (also known as CCL4), beta-nerve growth factor (NGF beta), Regulated upon Activation Normal T cell Expressed and Secreted (RANTES, also known as CCL5), platelet derived growth factor-BB (PDGF-BB), placental growth factor-1 (PlGF-1), stem cell factor (SCF), stromal derived factor-1 alpha (SDF-1 alpha, also known as CXCL12 alpha), tumor necrosis factor alpha (TNF alpha), TNF beta (also known as lymphotoxin alpha), vascular endothelial growth factor-alpha (VEGF-A) and vascular endothelial growth factor-D (VEGF-D). The assay was performed according to the manufacturer's specific protocol. Data was collected on a Bio-Rad Bio-Plex® 200 instrument (Bio-Rad, Hercules, CA), running the Bio-Plex Manager software version 6.1.

Figure 22A:
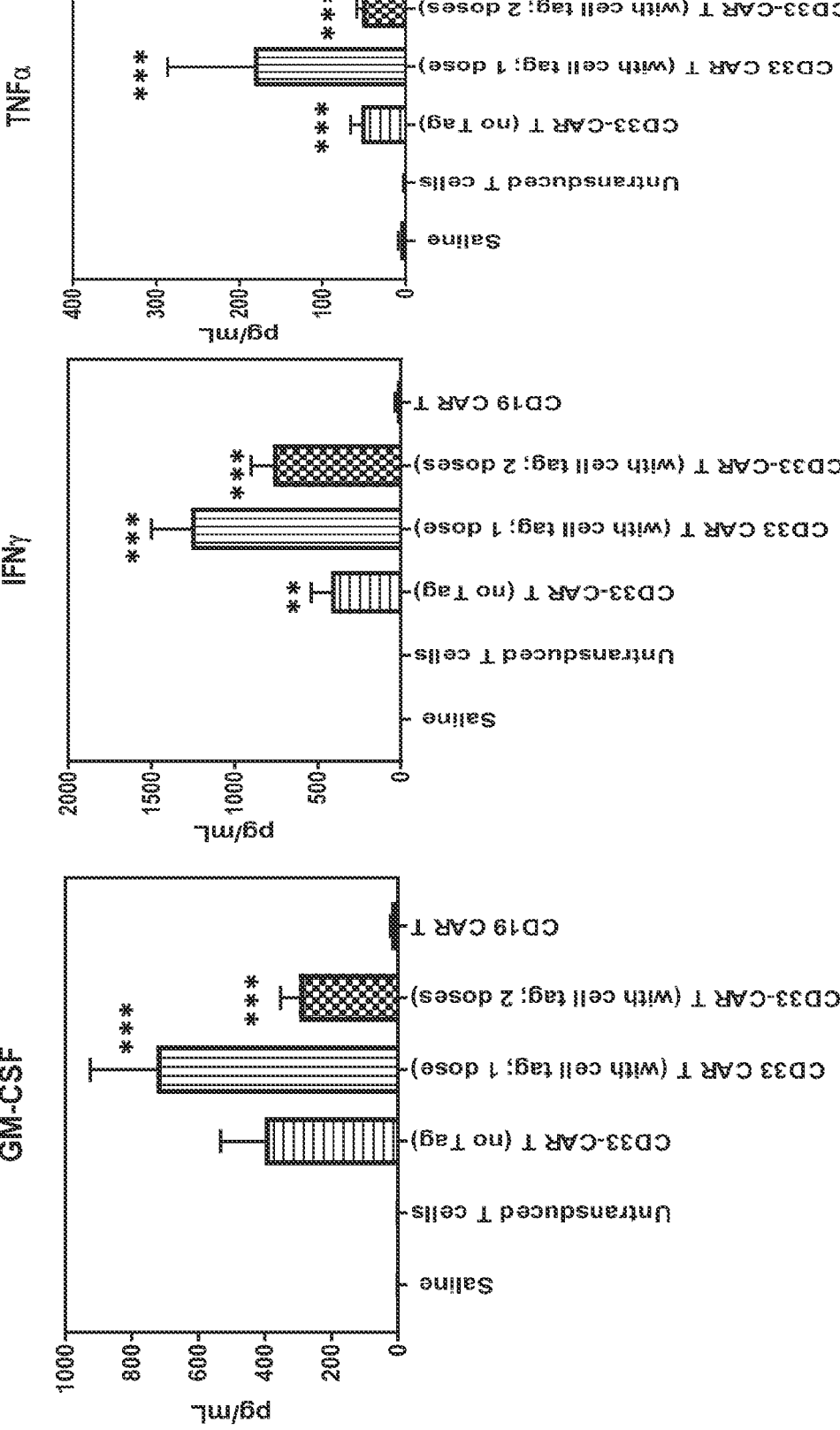

Human cytokine and growth factor expression was assessed using the plasma taken from the mice on Day 11. See FIG. 22A. As MOLM-13 and the transferred T cells into the NSG mice are of human origin, the measurement of human cytokines allowed for further examining details into the mechanism of action for the CAR-T cells acting upon the tumor cells. In the MOLM-13 tumor bearing mice that received only saline treatment, there were some human systemic cytokines detected such as MCP-1 and MIP1-beta (data not shown) as well as several other growth factors, but the levels of cytokines such as IFNγ and TNFα were below the range of detection (FIG. 22A). The MOLM-13 tumor bearing mice treated with untransduced T cells also continued to show a similar pattern of cytokine and growth factor expression as compared to the saline only treated group. The cytokine and growth factor levels seen in the untransduced T cell group provides the baseline values with the mixture of human T cells and tumor cells in this mouse model system. The analysis of cytokine expression data from the CD33-CAR-T cells (regardless of whether the CAR T cells co-expressed the cell tag) showed significant levels of IFNγ and TNF production in addition with GM-CSF, IL-10, IL-18 and IP-10. In contrast, administration of the CD19-CAR-T cells to the MOLM-13 tumor bearing mice showed a slightly elevated level for cytokines such GM-CSF, IFNγ, IL-18 in comparison to saline only or untransduced T cell group of mice; however the expression levels of these cytokines were not as significantly elevated when compared to the levels of the same cytokines detected in mice administered the CD33-CAR-T (no cell tag) or CD33-CAR-T (with cell tag) or the CD33-CAR-T (with cell tag, 2 doses).

Blood samples were taken at specified times in the study to evaluate the presence of the tumor cells as well as the adoptively transferred T cells by flow cytometry. The presence of MOLM-13/fLUC cells could be detected in the peripheral blood of mice on Day 16, as shown in FIG. 22B. To avoid underestimation or the potential for CD33 antigen loss in MOLM-13 cells, CD123 antibody was utilized to identify the tumor cells. MOLM-13 tumor cells were detected in the peripheral blood samples obtained from mice administered saline only, untransduced T cells or CD19-CAR-T cells. In addition, the transferred T cells from the mice given untransduced T cells or CD19-CAR-T cells were detected in the blood at Day 16 and as early as Day 11, when cellular analysis of the blood was initiated. The blood from mice administered the CD33-CAR-T cells showed little to no MOLM-13 tumor cell presence, while the T cell population was clearly present.

Figure 22C:
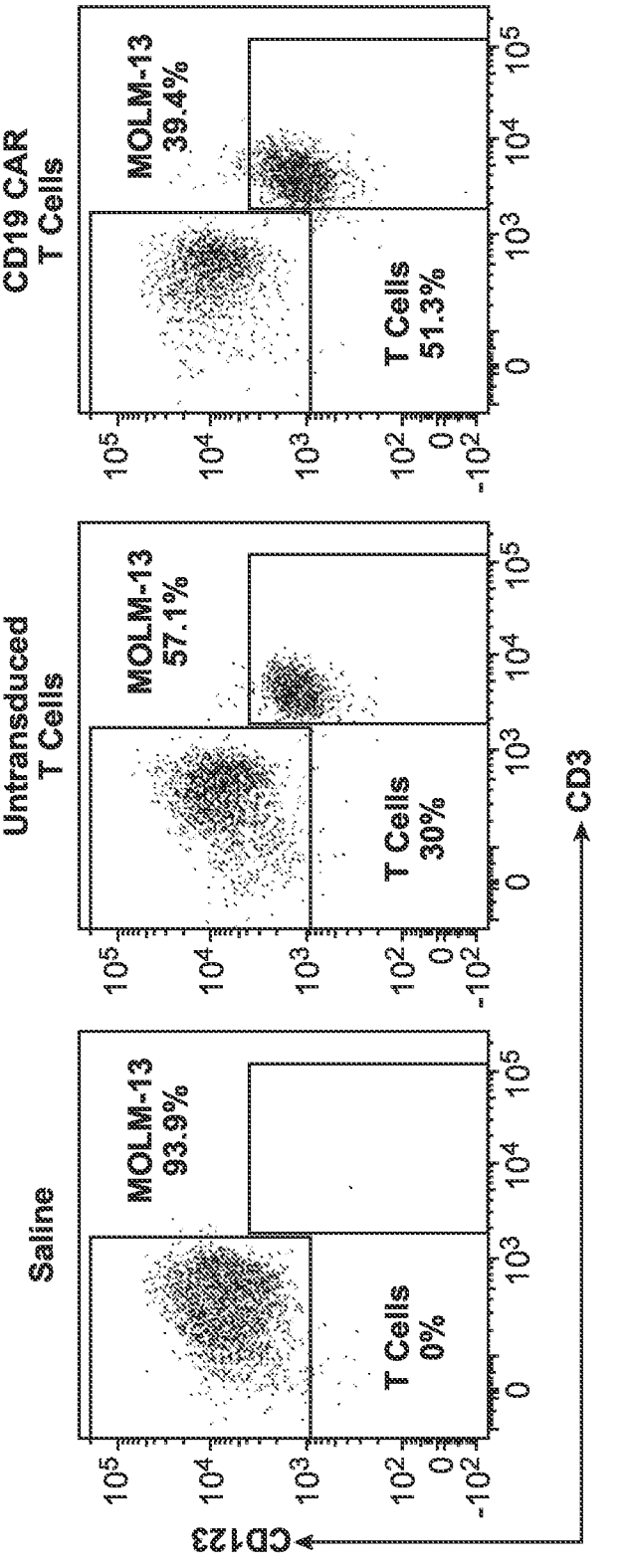
Figure 22D:
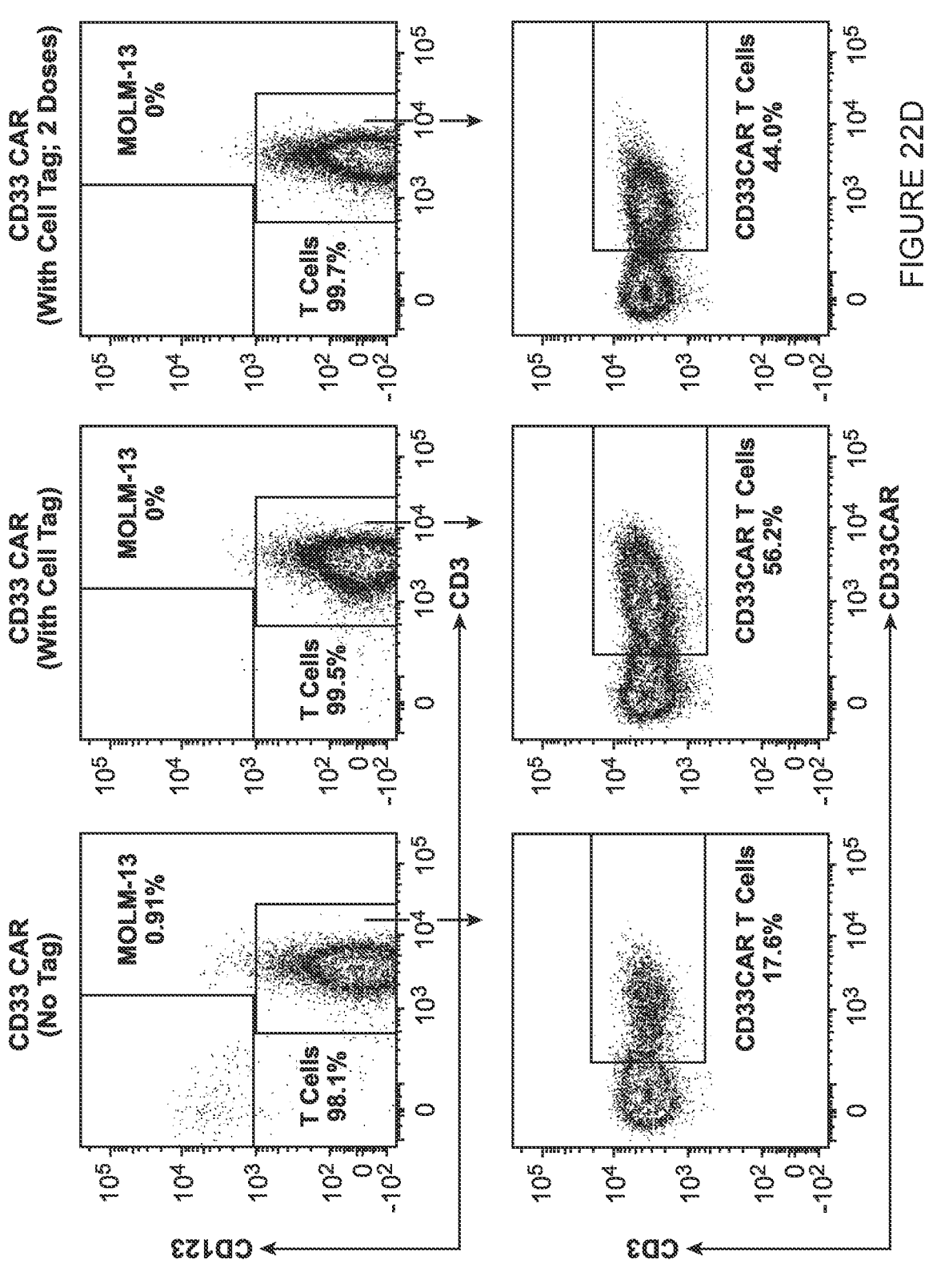
Figure 22E:
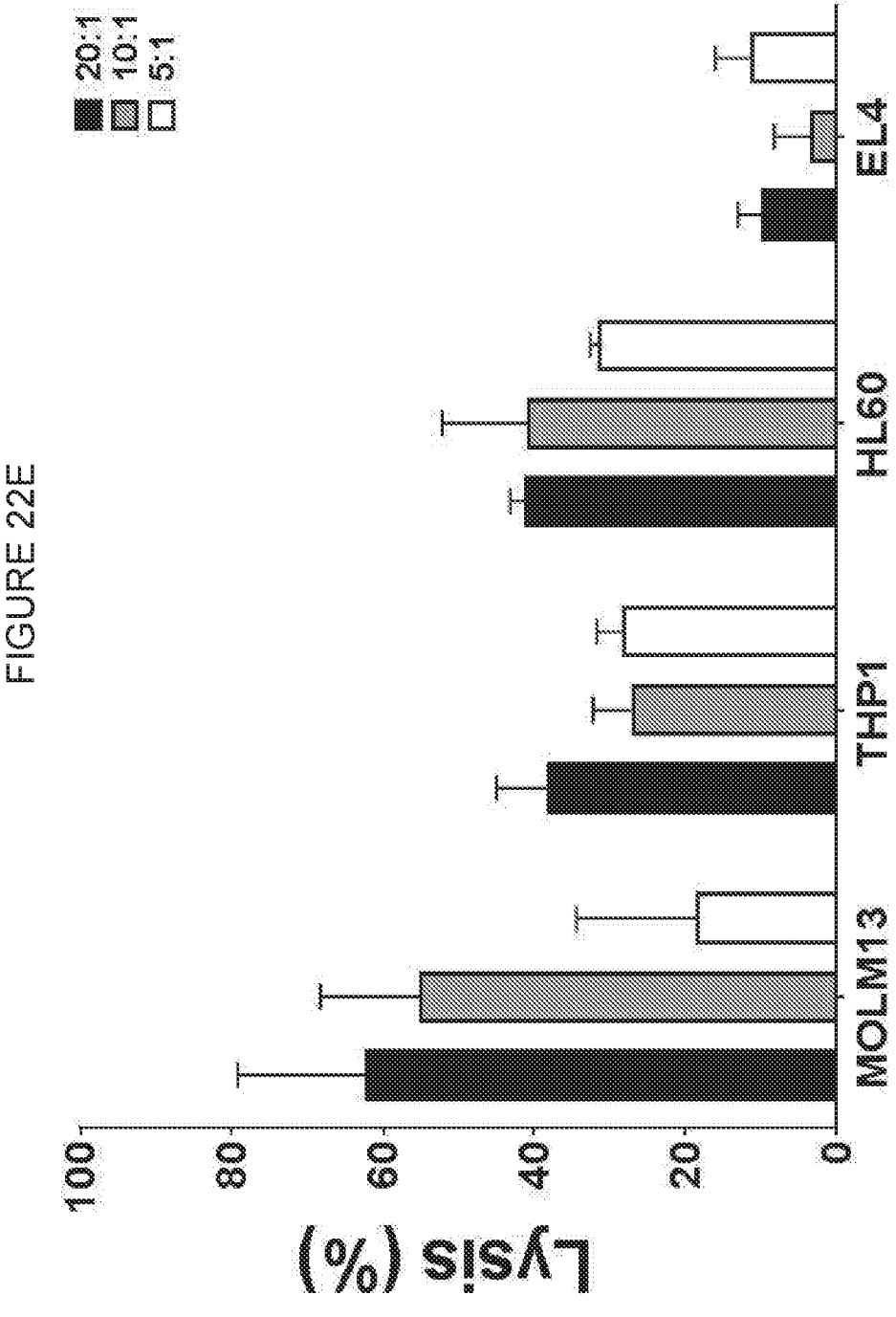

FIG. 22C demonstrates cytotoxic activity against additional AML Tumor cell lines (THP1 and HL60). Additional evidence for the redirected cytotoxic functions of CD33-

Figures 23A, 23B, 23C:
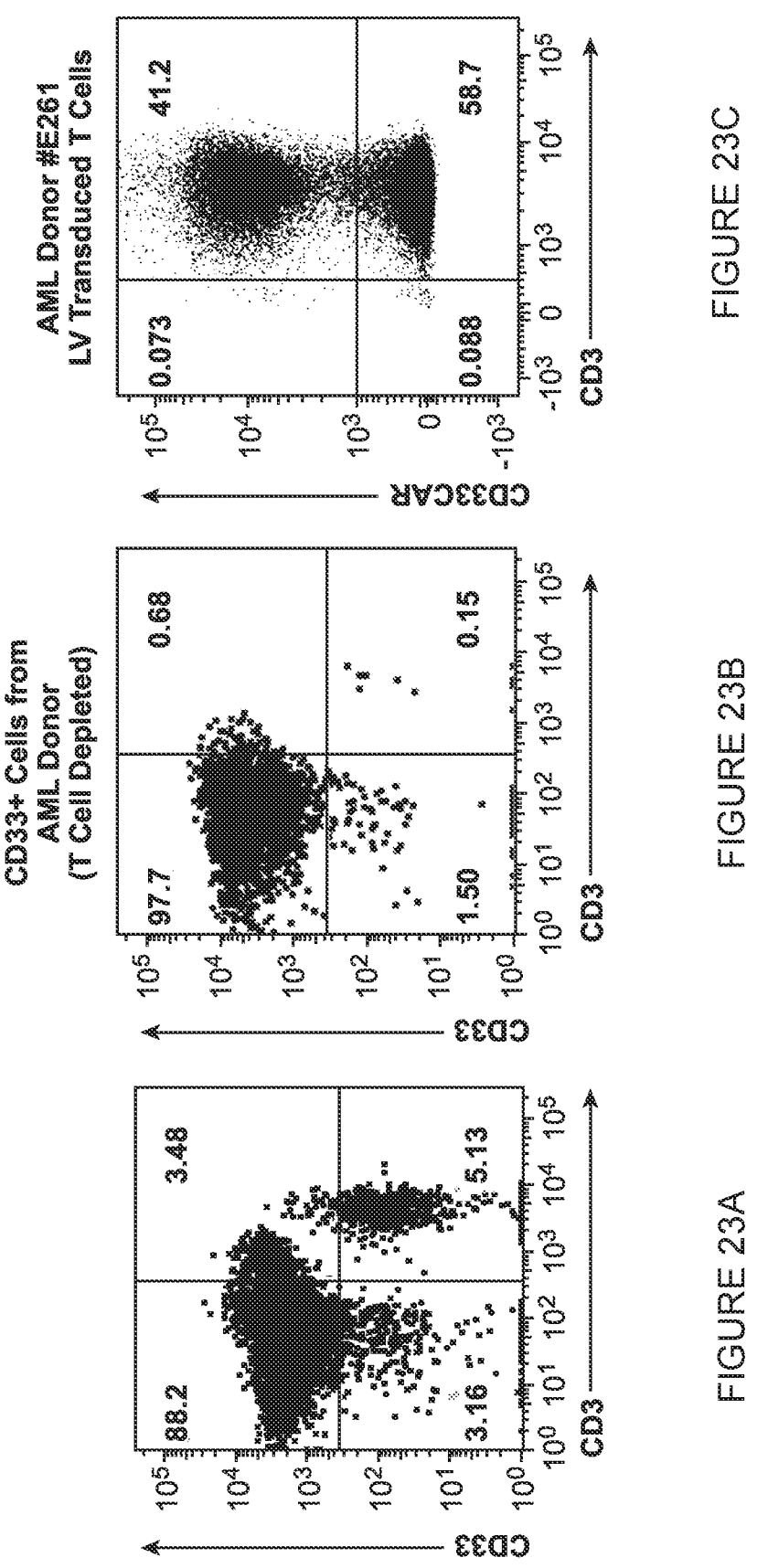
FIG. 23A-E describe generation of CD33-CAR-T cells from T cells an AML patient and demonstrating cytotoxicity activity to AML tumor cells.
Figure 23D:
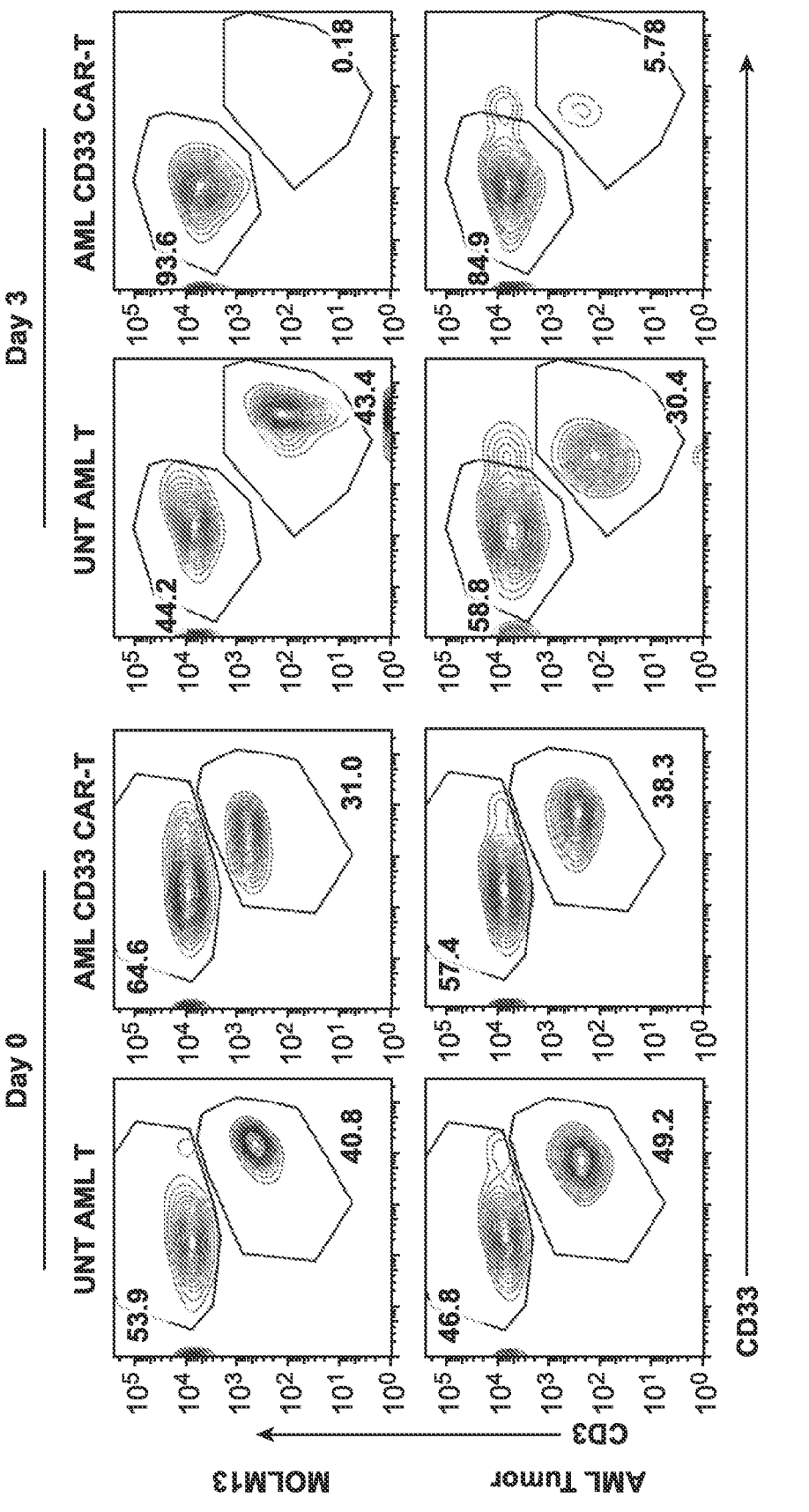
Figure 23E:
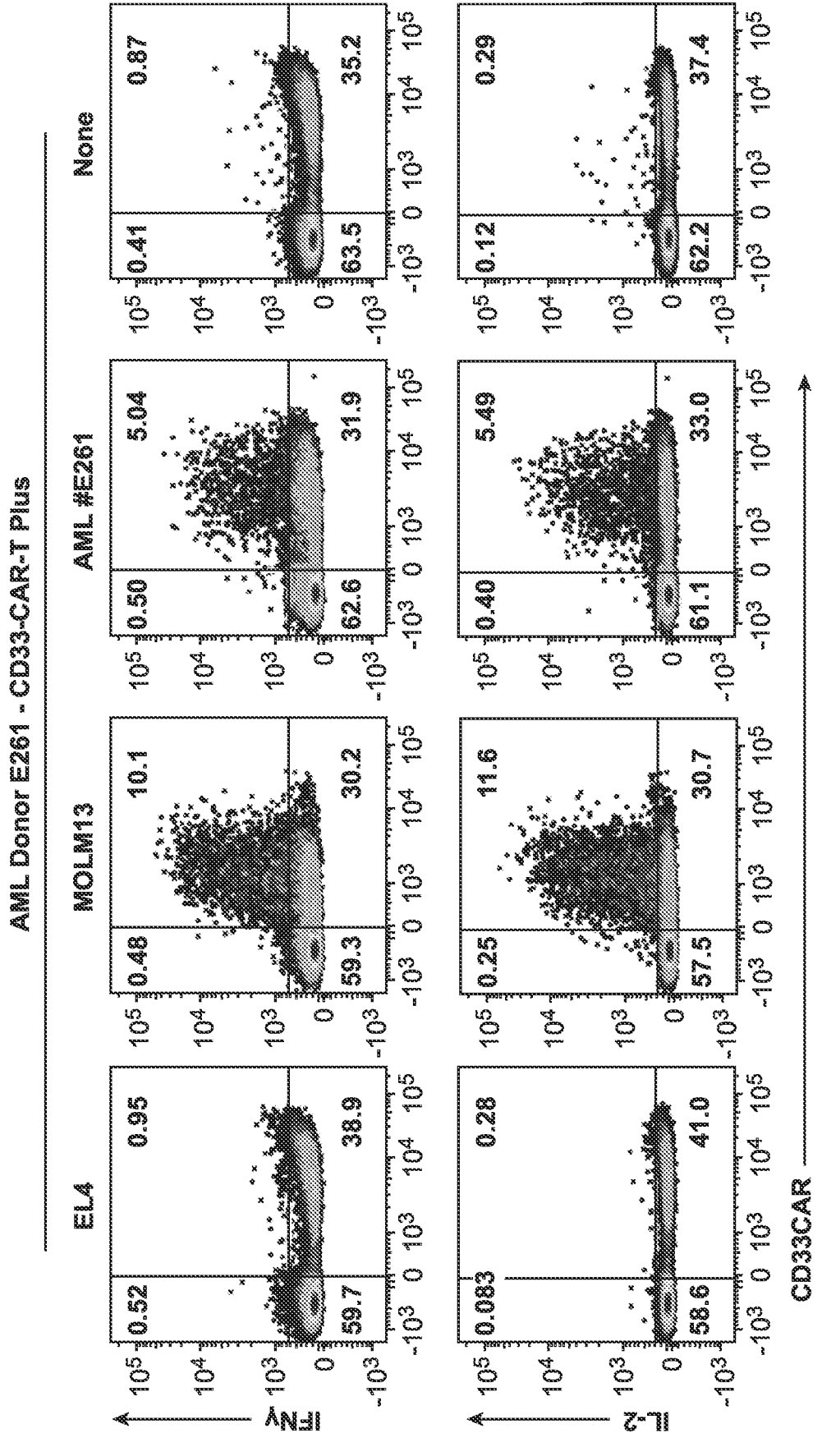
Figure 24:
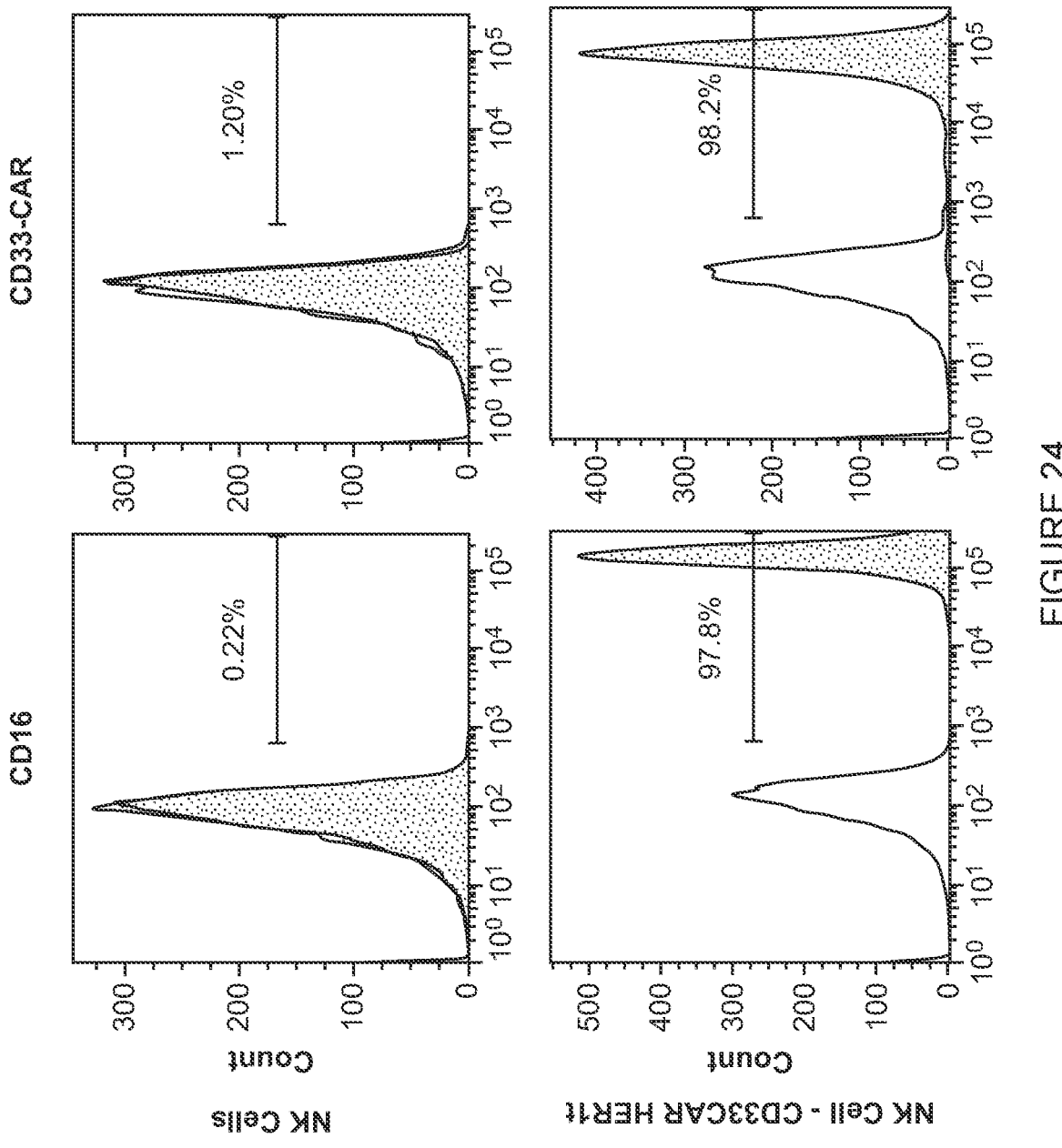
FIG. 24 describes expression of CD33 CAR and HER1t on NK cells.

CAR-T cells was provided by examining cytokine expression by the immune effector cells upon co-culture with CD33 tumor cells. Several CD33 expressing tumor cell lines were assessed for induction of IFNγ, TNF (also referred to as TNFα) and IL-2 expression, following co-culture with the CD33-CAR-T cells. Co-culture of the CD33-CAR-T cells with the CD33 expressing tumor cells caused a marked increase in expression of IFNγ, TNF, and IL-2 (FIG. 10), compared to untransduced T cells from the same donor. Furthermore, no cytokine expression was detected from the parental EL4 cell line, which served as the negative tumor target control. Intracellular cytokine staining (ICS) was performed as additional confirmation for target specificity. CD33-CAR-T cells demonstrated both IFNγ and IL-2 expression at the cellular level following overnight co-culture with MOLM-13, THP-1, or HL-60 tumor cells which express CD33, while co-culture with murine EL4 cells did not show any significant cytokine expression above the levels seen with the T cells only (FIG. 23E).

CD33-CAR-T cells were generated from cells obtained from an AML patient (Donor E261) with relapsed AML disease. Briefly, cryopreserved PBMCs from the AML donor were thawed and T cells were selected and expanded using anti-CD3/anti-CD28 beads. T cells were transduced with the CD33-CAR LV particles and T cells expanded in culture. Characterization of the thawed PMBC sample revealed from this donor a low frequency of T cells present in the PBMC sample and consisted of mainly CD33+ cells (FIG. 23A). The T cells were isolated, activated and expanded for LV transduction to generate the CD33-CAR-T cells. Remaining cells following T cell isolation were CD33+(Figure E-B) and maintained in culture with the use of granulocyte-macrophage colony stimulating factor (GM-CSF) cytokine. For this AML donor, ~41% of the T cells expressed CD33-CAR on the cell surface, as assessed after 12 days of culture following LV transduction (FIG. 23C). Cytotoxic activity was demonstrated in a flow cytometric based co-culture assay of CD33-CAR-T cells from this donor, with either MOLM-13 tumor cells or with the patient's own CD33 expressing tumor cells. Assessment of the remaining cell populations at the time points examined (Day 0 and Day 3) by staining for CD3 (T cells) and CD33 expression (tumor) on cells, only co-cultures with the CD33-CAR-T cells were able to eliminate the CD33 expressing tumor cells, whereas no cell killing was observed in the co-cultures set up with the untransduced (UNT) T cells (FIG. 23D).

Additionally, the CD33-CAR-T cells generated from an AML donor also induced IFNγ and IL-2 expression, as assessed by flow cytometry using intracellular cytokine staining. Intracellular cytokine staining was performed following co-culture of CD33-CAR-T cells (derived from an AML donor E261) with designated tumor cells after an 18 hrs time period. T cells were cell surface stained then fixed/permeabilized followed by staining for IFNγ and IL-2 cytokine. Cells are gated based upon FSC/SSC/viable/CD3 T cells. Co-culture of the CD33-CAR-T cells, alone or with the murine EL4 tumor cells, did not show any expression of IFNγ or IL-2; whereas increased expression of both cytokines was observed following co-culture with MOLM-13 or with the tumor cells from the particular donor cells (FIG. 23E). In addition, the cytokine expression was induced specifically from cells that expressed CD33-CAR, whereas T cells that do not express the CAR showed no cytokine expression.

Example 7

Figures 15A, 15B:
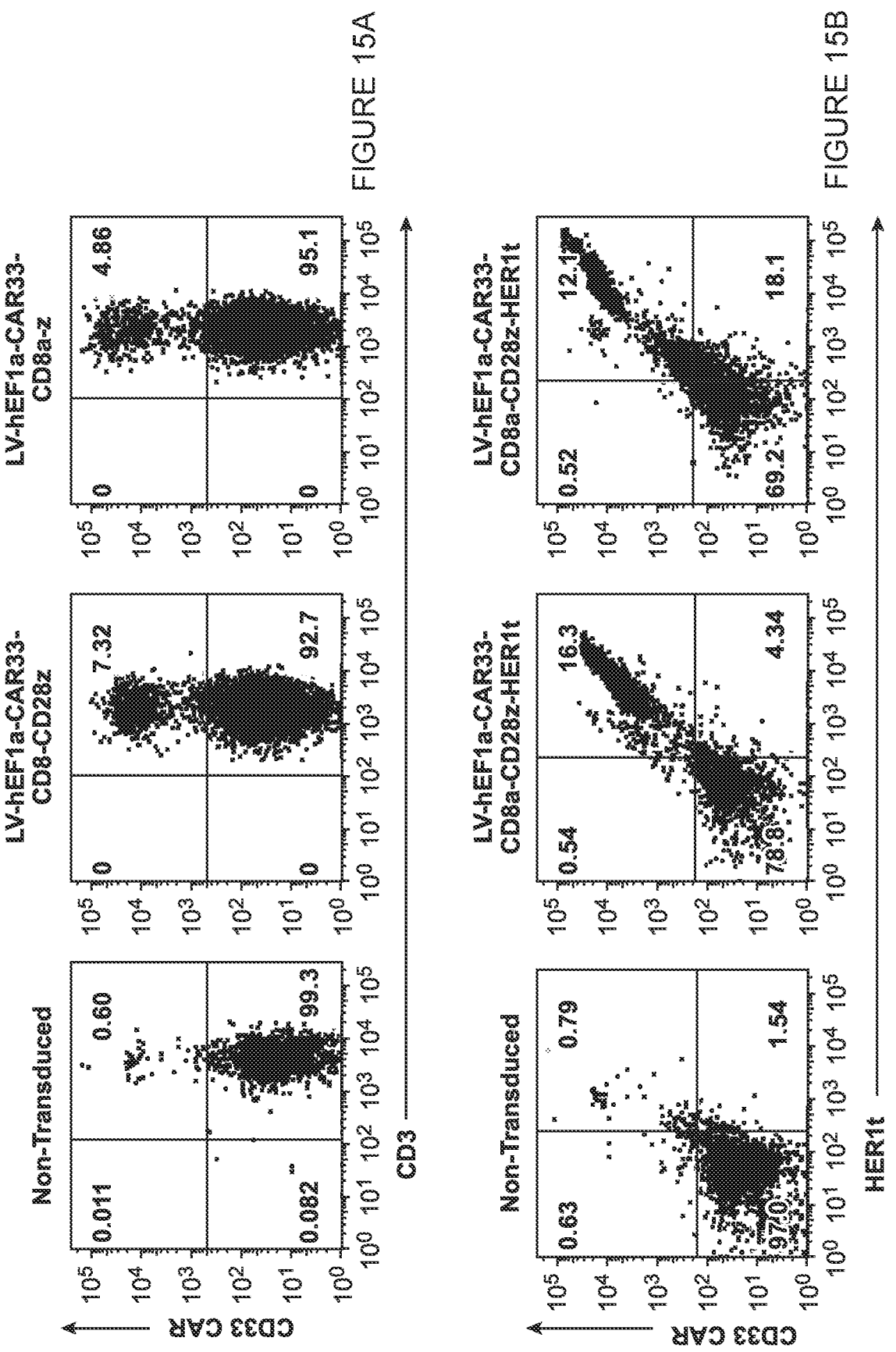
FIGS. 15A and 15B demonstrate expression of CD33 CARs and HER1t on various LV transduced human T-cells.

Lentiviral CD33 CAR with various signaling domains were constructed and tested for expression. Lentiviral particles with the CD33 CAR with a CD3ζ signaling domain only, a CD33 CAR with a CD28-CD3z (referred to as CD28z) signaling domain, or with a CD33 CAR with a CD28-CD3z domain with co-expression of HER1t were transduced into pre-activated human T cells following the schematic as outlined in FIG. 4. Flow cytometric analysis was performed on T cells after 12-14 days post transduction. CD33 CAR expression was detected via Protein L staining and HER1t was detected via cetuximab staining (FIGS. 15A and B).

Figure 16A:
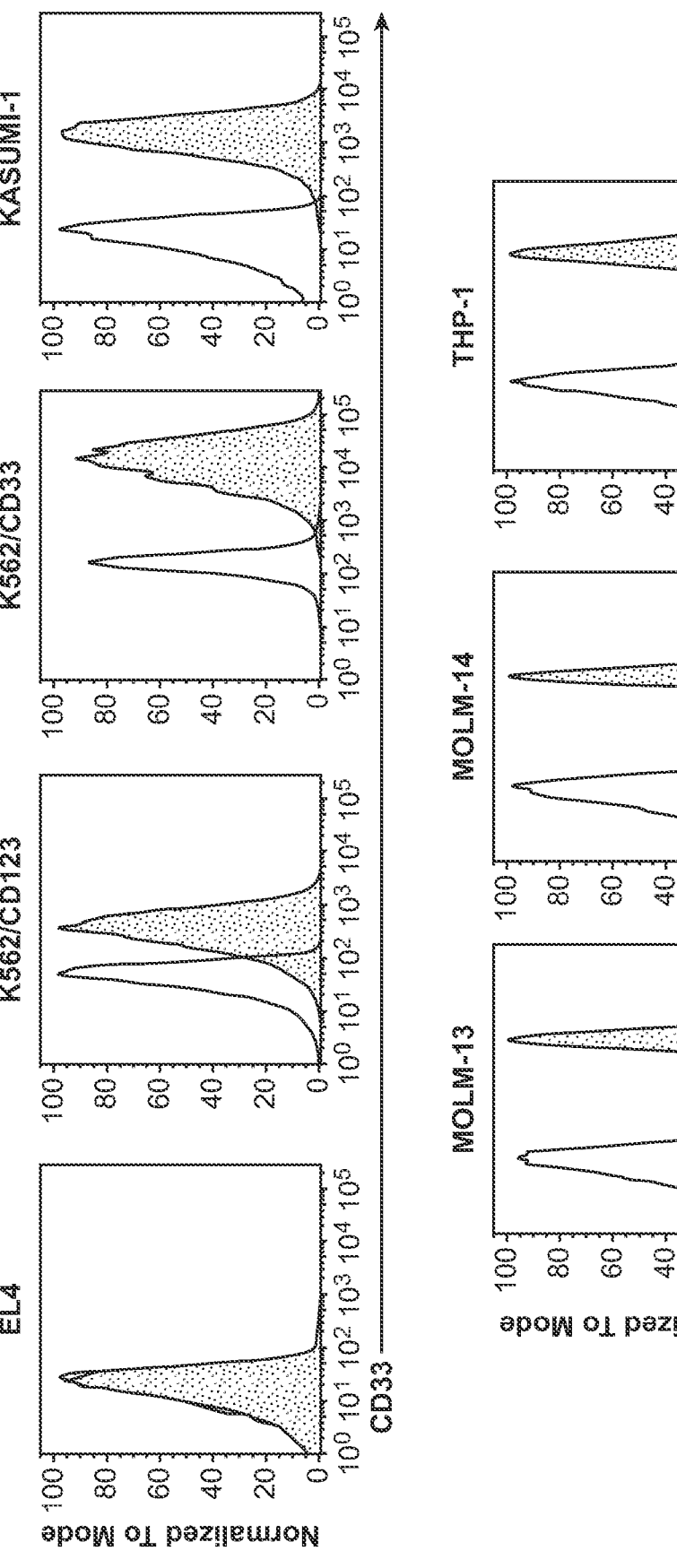
Figure 16B:
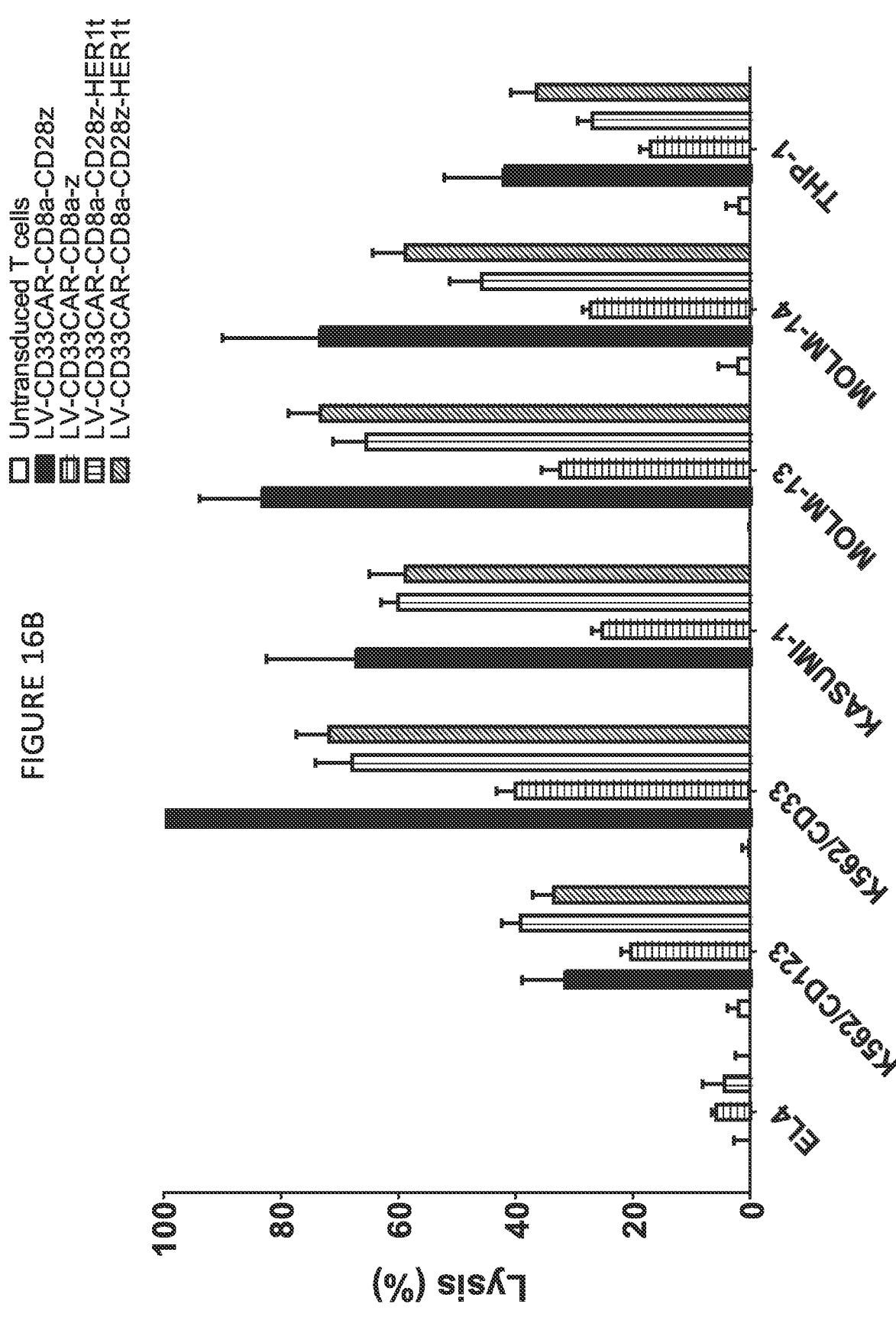

To demonstrate the specificity of the CD33 CAR (with the different signaling domains) to recognize its target, co-culture assays were performed against various tumor cell lines. CD33 expression was displayed on the cell lines tested (FIG. 16A). Note that K562 cell endogenously express CD33 thus expression is observed in K562/CD123; the K562/CD33 line was transduced to overexpress CD33. EL4 is a murine cell line that does not express human CD33. Cytotoxicity was determined by labeling the various tumor target cell lines using the DELFIA BATDA reagent (DEL-FIA EuTDA Cytotoxicity assay; Perkin Elmer) then co-culturing the CD33 CAR T cells or untransduced T cell (UNT) with the labeled tumor cells at a ratio of 20:1 effector:target (E:T) ratios. After 2 hrs, supernatant from the assay was harvested and developed with addition of the DELFIA Europium assay and read on a time-resolved fluorescence instrument. (FIG. 16B) Robust IFNγ production with co-cultures of CD33 CAR T cells with tumor cells that express CD33, utilizing a 20:1 Effector:Target (E:T) ratio and incubated for 18 hrs, Culture supernatant were harvested and assayed for IFNγ production by ELISA according to manufacturer's instructions. Untransduced T cells (UNT) had little to no IFNγ detected in the co-culture (FIG. 16C).

Lentiviral transduction of T cells derived from cryopre-served PBMC sample of a patient diagnosed with AML was performed similar to the process outlined above for trans-duction of T cells from healthy donor T cells. Briefly, isolated T cells from PBMC samples were activated using anti-CD3/CD28 beads followed by lentiviral transduction with CD33 CAR-41BBz-T2A-HER1t at varying MOIs. The transduced T cell cultures were expanded over a 14 day culture period. CAR expression, as determined by Protein L staining, was evaluated throughout the culture expansion period. Levels of CD33 CAR were observed on the T cell surface (data not shown). Cytotoxic activity of the CD33 CAR T cells was demonstrated utilizing the donor's autolo-gous CD33+ expressing tumor cells as well as AML tumor cell lines. In one instance, a co-culture was set up using low E:T ratio. Flow cytometric analysis was performed at dif-ferent time points to determine the presence and frequency of T cells and CD33 expressing tumor cells present in the co-culture at various time points were assessed. The co-culture of CD33 CAR-T cells with autologous CD33 expressing tumor cells demonstrated cytotoxic activity as determined by the decrease or absence of CD33+ tumor cells (data not shown). Similar findings were observed with known AML tumor cell line tested such as MOLM-13.

Example 8

Sleeping Beauty CD33 CARs

Different CD33 CAR constructs were constructed and generated in the Sleeping Beauty Transposase-Transposon System (FIG. 3). For example, CD33-CD8a-CD28TM-CD3z constructs were made with various EF1a promoter lengths (short, medium and long). CD33 CAR constructs with HER1t cell tags were also made and tested.

CAR constructs were introduced into cells via electropo-ration, using a Sleeping Beauty-based transposon system to mediate genomic integration of the constructs. On day 0, 20 million PBMC were resuspended in 100 μL of Amaxa Human T cell Nucleofector solution (Cat. no. VPA-1002; Lonza, Basel, Switzerland) mixed with 15 μg of transposon and 5 μg of transposase (pKan-CMV-SB11) and electropo-rated using Program U-14. The following day (day 1) cells were counted, surface stained for CAR expression by Pro-tein L and HER1t staining using cetuximab. Cells were stimulated with either 7-irradiated (100 Gy) or mitomycin C treated AaPCs at a 1:1 ratio. The AaPC cells used were K562-AaPC expressing CD64-CD86-41BBL-CD19-mbIL-15/IL15Ra-ROR1 antigen with endogenously expressed CD33. CAR T cells were stimulated with the AaPCs at a 1:1 ratio. Cultures were supplemented with IL-21 (30 ng/ml) only for the first round of stimulation and subsequently with recombinant human IL-2 (50 IU/ml) and IL-21 (30 ng/ml) (Pepro Tech) for remaining stimulations. T cell cultures were phenotyped at the end of each stimulation cycle, which typically lasted 7 days. The cultures were phenotyped for CAR expression, utilizing either Protein L staining or with recombinant CD33/Fc protein staining as detected by multi-parameter flow cytometry. Cultures were also closely moni-tored for the outgrowth of NK cells (defined as CD3negCD56+ population) and were removed from the CAR T cell cultures when the percentage exceeded 10% of total cell populations using magnetic beads for CD56 (Stem Cell Technologies and/or Miltenyi Biotec), according to the manufacturer's instructions. CD33 CAR expression from multiple donor PBMCs following stimulation with AaPCs was examined using flow cytometry.

Figure 17:
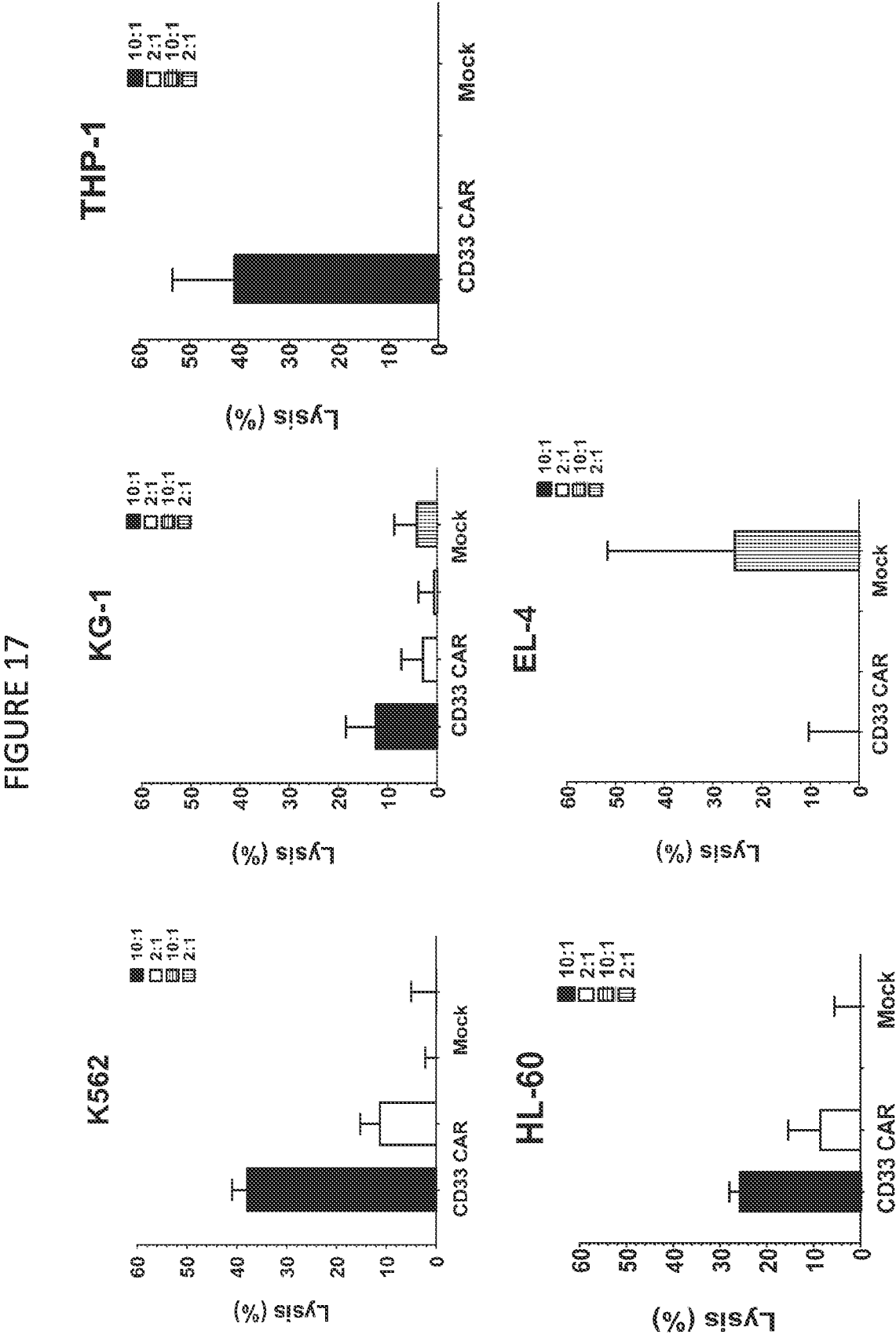
FIG. 17 provides graphs depicting CAR33-CD8a-CD28m-Z (Sleeping Beauty) T cell lysis with CD33 expressing leukemia cell lines.

To demonstrate the specificity of the CD33 CAR (with the different signaling domains) to recognize its target, co-culture assays were performed against various tumor cell lines. Note that K562 cell endogenously express CD33 and EL4 is a murine cell line that does not express human CD33. Cytotoxicity was determined by labeling the various tumor target cell lines using the DELFIA BATDA reagent (DEL-FIA EuTDA Cytotoxicity assay; Perkin Elmer) then co-culturing the CD33 CAR T cells or untransduced T cell (UNT) with the labeled tumor cells at a ratio of 10:1 effector:target (E:T) and 2:1 E:T ratios. After 2 hrs, super-natant from the assay is harvested and developed with addition of the DELFIA Europium assay and read on a time-resolved fluorescence instrument. (FIG. 17).

Degranulation Assay and IFNγ Intracellular Cytokine Stain-ing.

Figure 18:
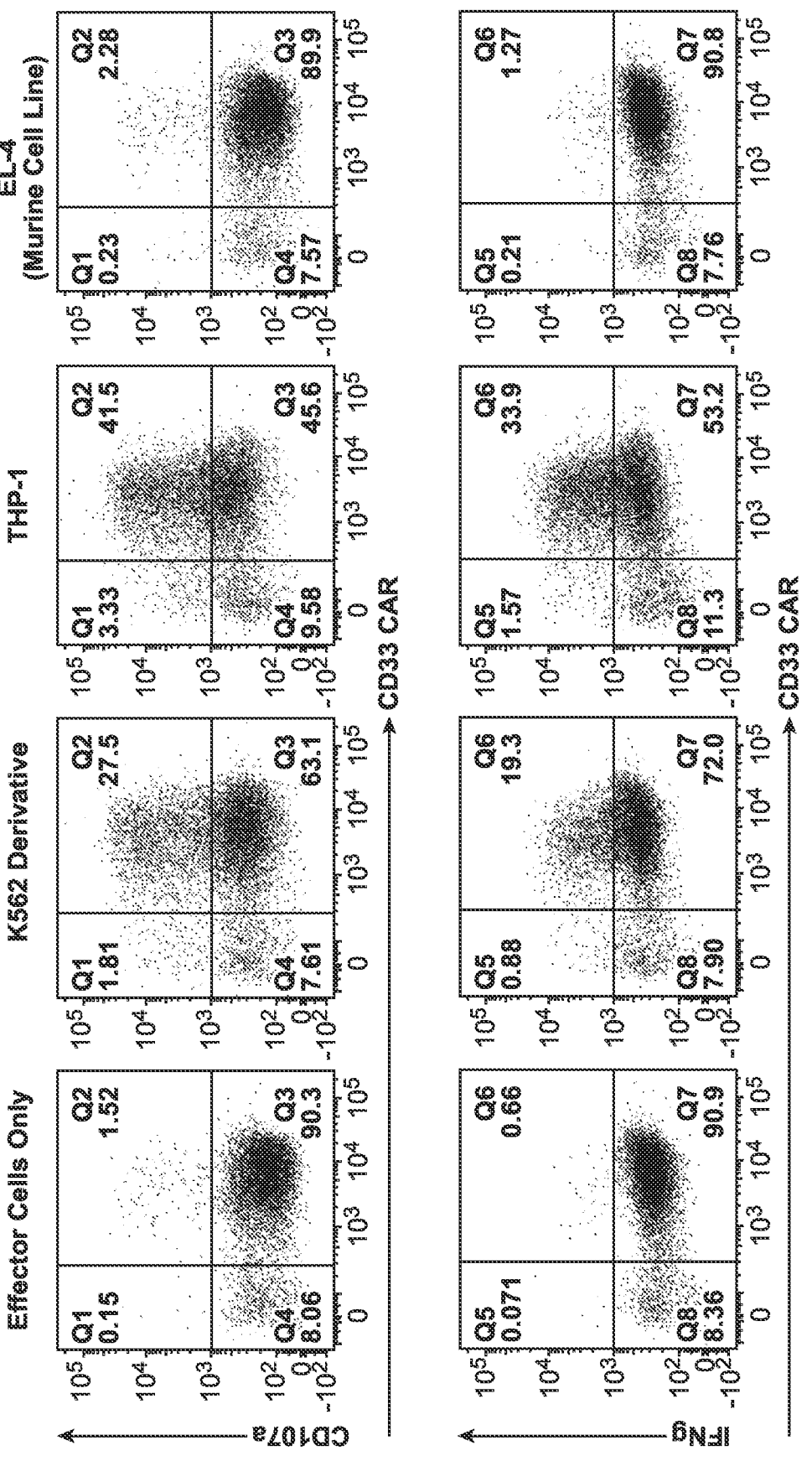
FIG. 18 provides graphs depicting flow cytometry results demonstrating the effects of CAR33-CD8a-CD28m-Z (Sleeping Beauty) T cells on CD107a degranulation and IFNγ production in the presence of CD33 expressing target cells.

CD107a, also known as lysosomal-associate membrane protein-1 (LAMP-1), is constitutively expressed in the late endosomes-lysosomes of cells but transiently expressed on the cell surface of degranulating cells. The degranulation assay was established to assess the capability of the CD33 CAR T to recognize different target cells with or without CD33 expression with concurrent intracellular IFNγ detec-tion on a per cell basis. Briefly, CD33 CAR T cells were co-cultured with target cells at a 10:1 E:T ratio in a 96 well plate. Target cell included K562/CD19 (having endogenous CD33 expression), THP-1 and EL-4 (murine cell line). At the start of the co-culture, the fluorescently conjugated CD107a or isotype antibody was added along with the Transport Inhibitor Cocktail (containing monensin and brefeldin, 1×; eBioscience) and incubated at 37° C. for 4 hrs. At the end of the incubation period, cells were pelleted in the plate and cell surface antigens were stained for detection of CAR expression and T cell markers. Following cell surface staining, cells were also stained with the Fixable Cell viability dye (eBioscience) according to the manufacturer's instructions then washed followed by fixation with Fix/Perm Solution (BD Biosciences). After fixing the samples, cells were washed in a Perm/Wash solution (BD Biosciences) then intracellularly stained with the fluorescently conjugated anti-human IFNγ antibody. Samples were washed then resuspended in appropriate staining buffer with data acquired on a LSR II flow cytometer (BD Biosciences). As shown in FIG. 18, significant expression of CD107a degranulation was observed only in the K562 derivative and THP-1 cell line that expresses CD33 while immune effector cells only and co-culture with EL-4 had minimal degranulation observed. Similar pattern was observed for intracellular IFNγ expression.

Example 9

Figure 19:
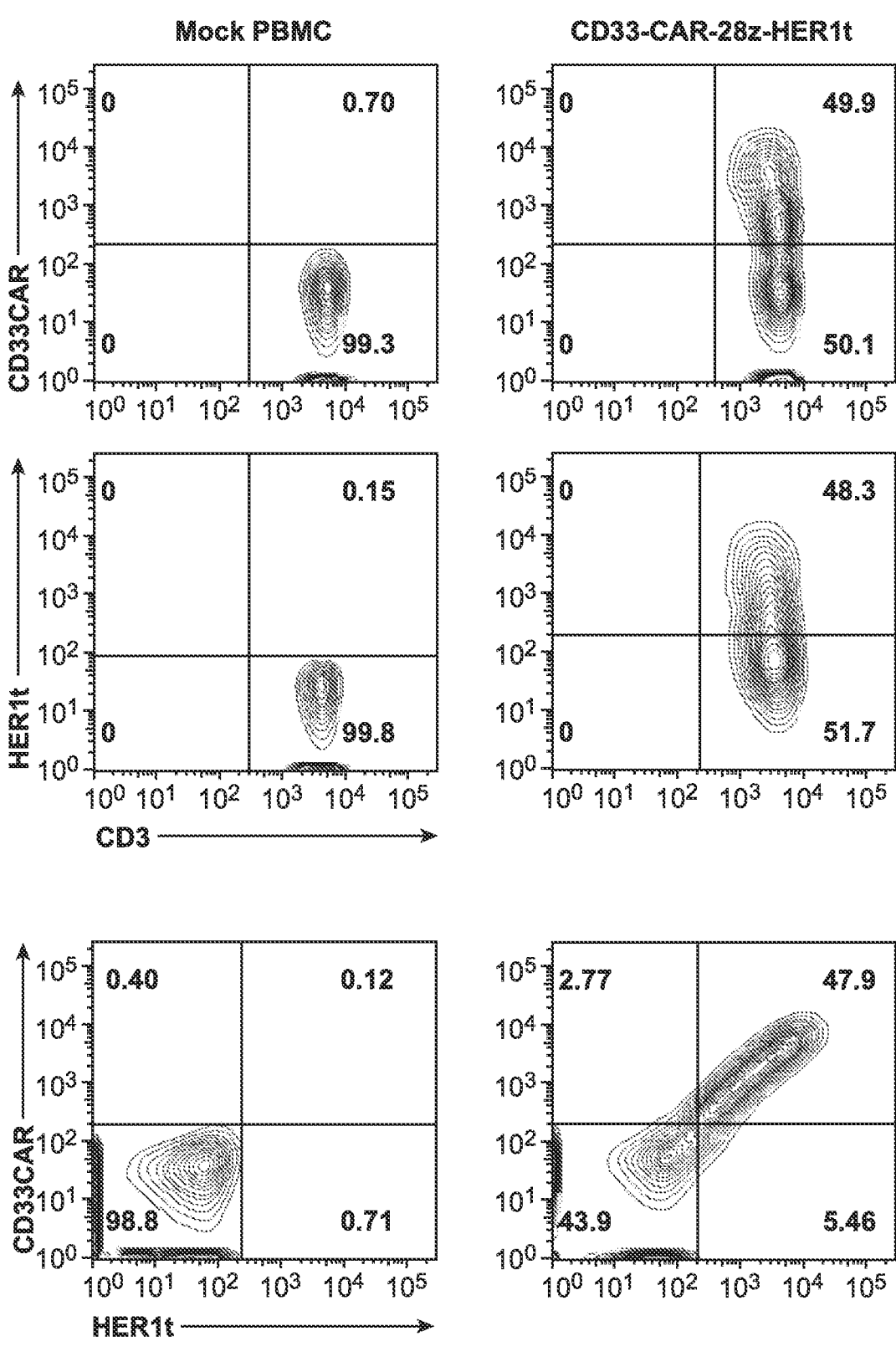
FIG. 19 provides graphs depicting flow cytometry results demonstrating expression of CD33 CAR (Sleeping Beauty) and HER1t on gene modified T-cells.
Figure 20A:
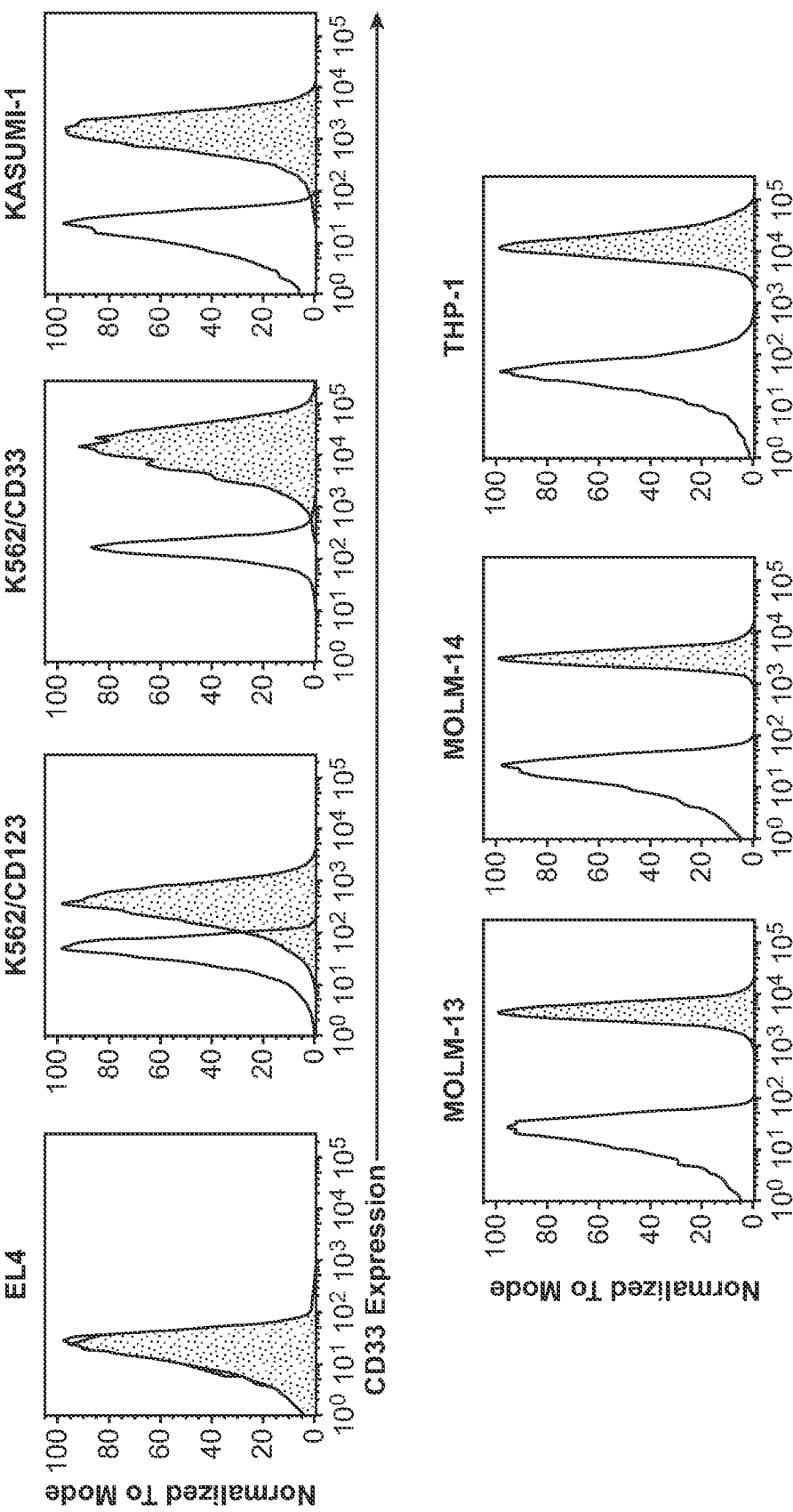
FIGS. 20A-20B depict effects of a CAR described herein in CD33 expressing AML cells.
Figure 20B:
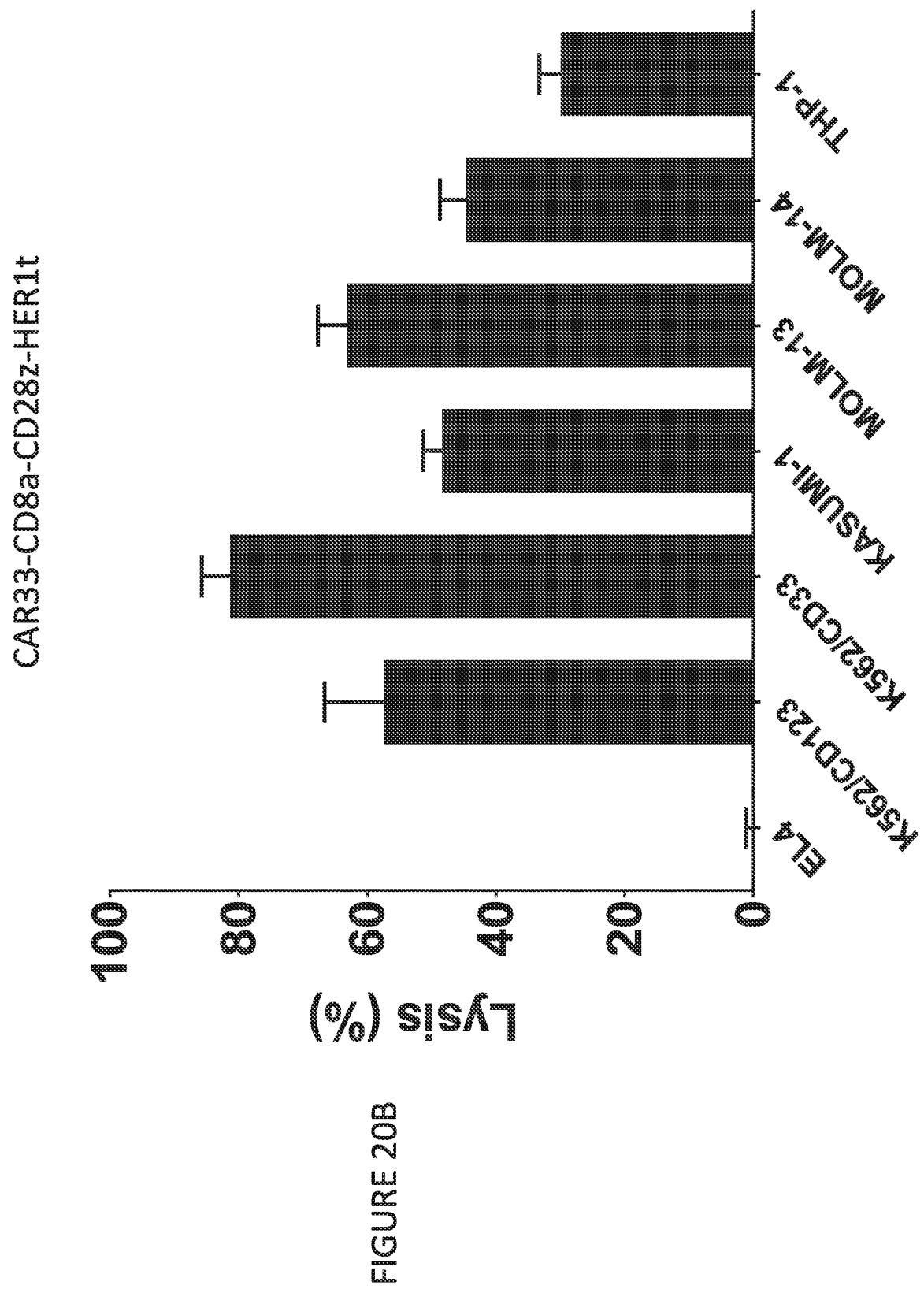

CAR constructs were introduced into cells via electroporation, using a Sleeping Beauty-based transposon system to mediate genomic integration of the constructs. On day 0, 20 million PBMC were resuspended in 100 μL of Amaxa Human T cell Nucleofector solution (Cat. no. VPA-1002; Lonza, Basel, Switzerland) mixed with 15 μg of transposon (for CD33 CAR-CD8-CD28z) and 5 μg of transposase (pKan-CMV-SB11) and electroporated using Program U-14. The following day (day 1) cells were counted, surface stained for CAR expression by Protein L and HER1t staining using cetuximab. Cells were stimulated with either γ-irradiated (100 Gy) or mitomycin C treated AaPCs at a 1:1 ratio. The AaPC cells used were K562-AaPC expressing CD64-CD8641BBL-CD19-mbIL-15/IL15Ra-ROR1 antigen. CAR T cells were stimulated with the AaPCs at a 1:1 ratio. Cultures were supplemented with IL-21 (30 ng/ml) only for the first round of stimulation and subsequently with recombinant human IL-2 (50 IU/ml) and IL-21 (30 ng/ml) (PeproTech) for remaining stimulations. T cell cultures were phenotyped at the end of each stimulation cycle, which typically lasted 7 days. The cultures were phenotyped for CAR T cell expression, utilizing either Protein L staining or with recombinant CD33/Fc protein staining as detected by multi-parameter flow cytometry. Cultures were also closely monitored for the outgrowth of NK cells (defined as CD3negCD56+ population) and were removed from the CAR T cell cultures when the percentage exceeded 10% of total cell populations using magnetic beads for CD56 (Stem Cell Technologies and/or Miltenyi Biotec), according to the manufacturer's instructions. CD33 CAR expression from various donor PBMCs following stimulation with AaPCs was examined using flow cytometry. Data from representative donors is summarized in Table 3 for CD33 CAR-CD8-CD28z) and in Table 4 for CD33-CAR-CD8-4-1BBz with or without the HER1t cell tag. FIG. 19 further demonstrates expression of Sleeping Beauty CD33 CAR-CD28z construct with HER1t tag.

TABLE 4 demonstrates an exemplary Sleeping Beauty CD33-CD8a-CD28z CAR expression in different PBMC donors.

| PBMC Donor | CD33 CAR (CAR33-CD8a-CD8m-Z) expression | | | | |
| --- | --- | --- | --- | --- | --- |
| | Day 1 | Day 7 | Day 14 | Day 21 | Day 28 |
| #205 | 4% | 22% | 79% | 96% | 99% |
| #309 | 11% | 61% | 90% | 98% | 99% |
| #309R | 15% | 52% | 89% | 94% | 94% |

TABLE 5 demonstrates exemplary Sleeping Beauty CD33-CD8-41BBz CARs with and without HER1t tag expression in different PBMC donors.

| PBMC Donor | Day 1 | Day 7 | Day 14 | Day 21 | Day 28 |
| --- | --- | --- | --- | --- | --- |
| | CD33 CAR (CAR33-CD8-41BBz) Expression | | | | |
| Donor 309 | 68.9 | 78.1 | 79.5 | 91.2 | 95 |
| Donor 270169 | 60.1 | 65.4 | 76.2 | 84.2 | 94.3 |
| Donor 6507 | 64.1 | 52.5 | 26.8 | 26.1 | 40.4 |
| Donor 163890 | 47.4 | 63.9 | 64.2 | 7022 | 95.3 |
| | CD33 CAR/Her1t (CAR33-CD8-41BBz-HER1t) Expression | | | | |
| Donor 309 | 46.7 | 78.6 | 86.9 | 92.4 | 98.5 |
| Donor 270169 | 35.7 | 80.5 | 89.4 | 92.4 | 88.9 |
| Donor 6507 | 36.7 | 80.1 | 79.2 | 89.1 | 83.7 |
| Donor 163890 | 39.7 | 77.3 | 85.5 | 92.8 | 86.9 |

Example 10

Figure 25:
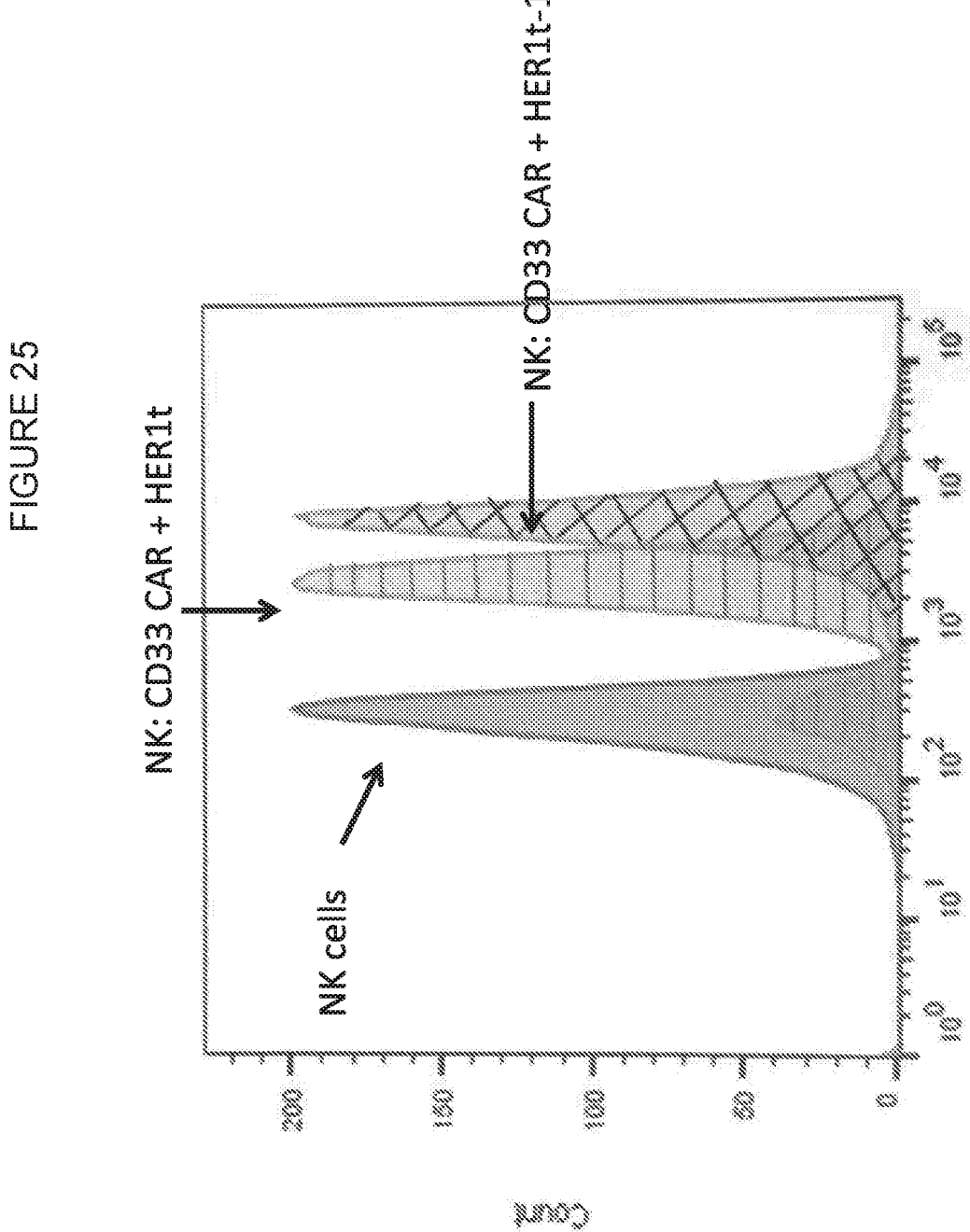
FIG. 25 describes expression of HER1t and HER1t-1 tags on CD33CAR NK cells.
Figure 26:
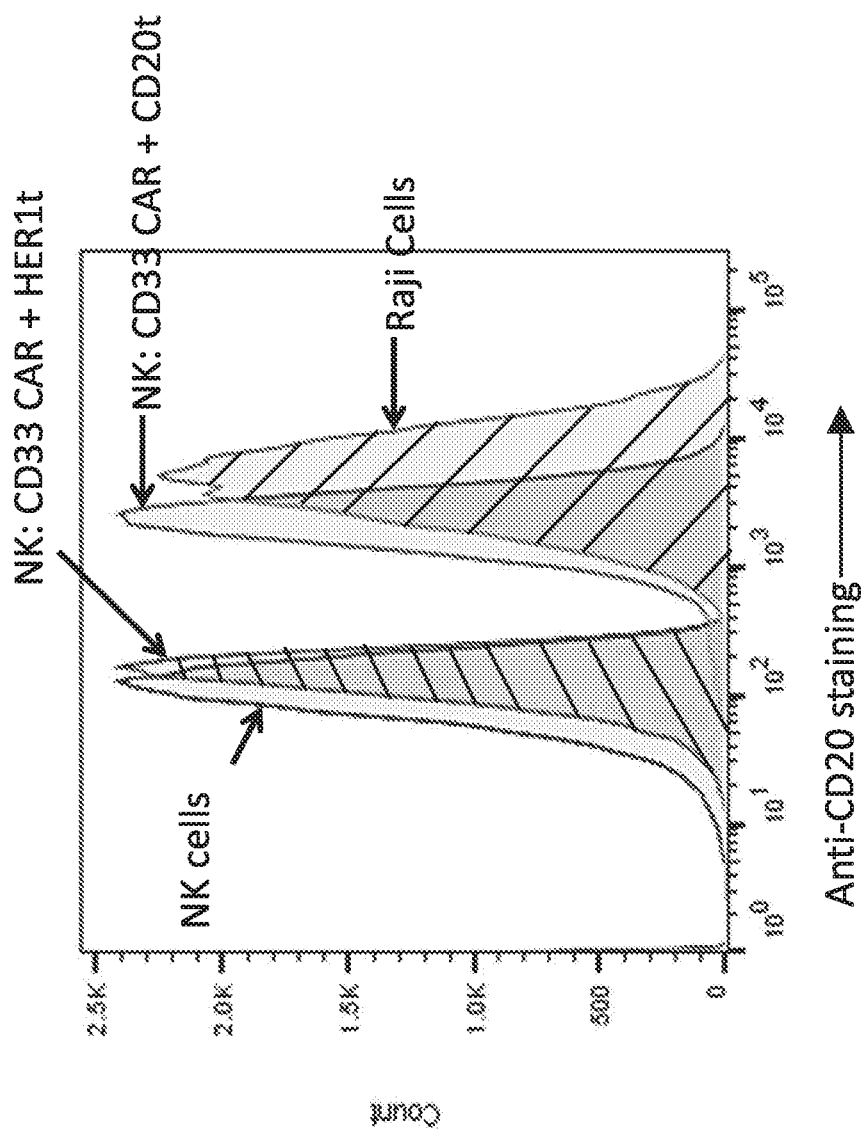
FIG. 26 discloses expression of CD20t-1 tag on CD33CAR NK cells.
Figure 27:
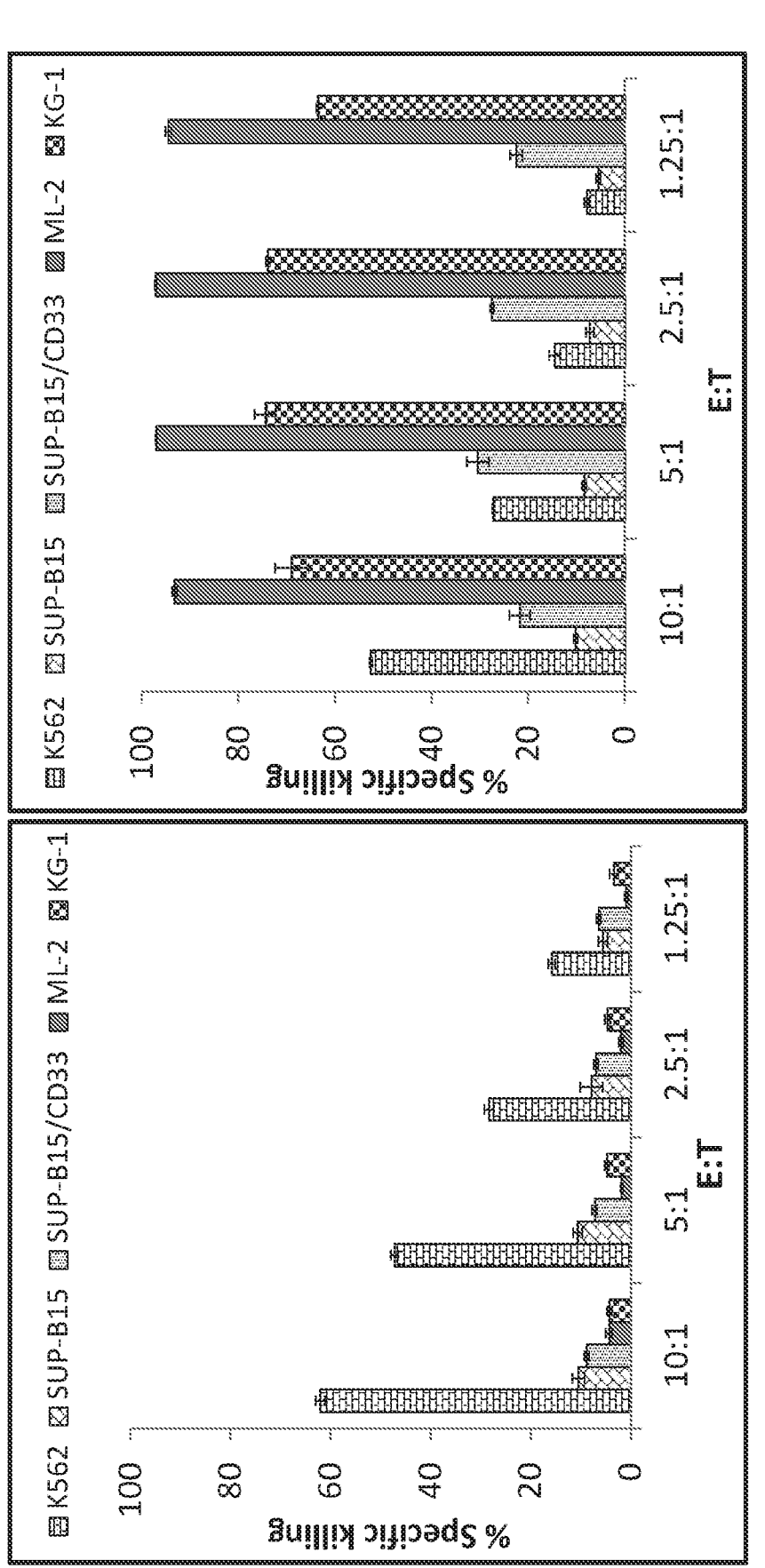
FIG. 27 demonstrates CD33-CAR NK cells efficiently lyse NK resistant CD33+ AML cells (ML-2, KG-1).
Figure 28:
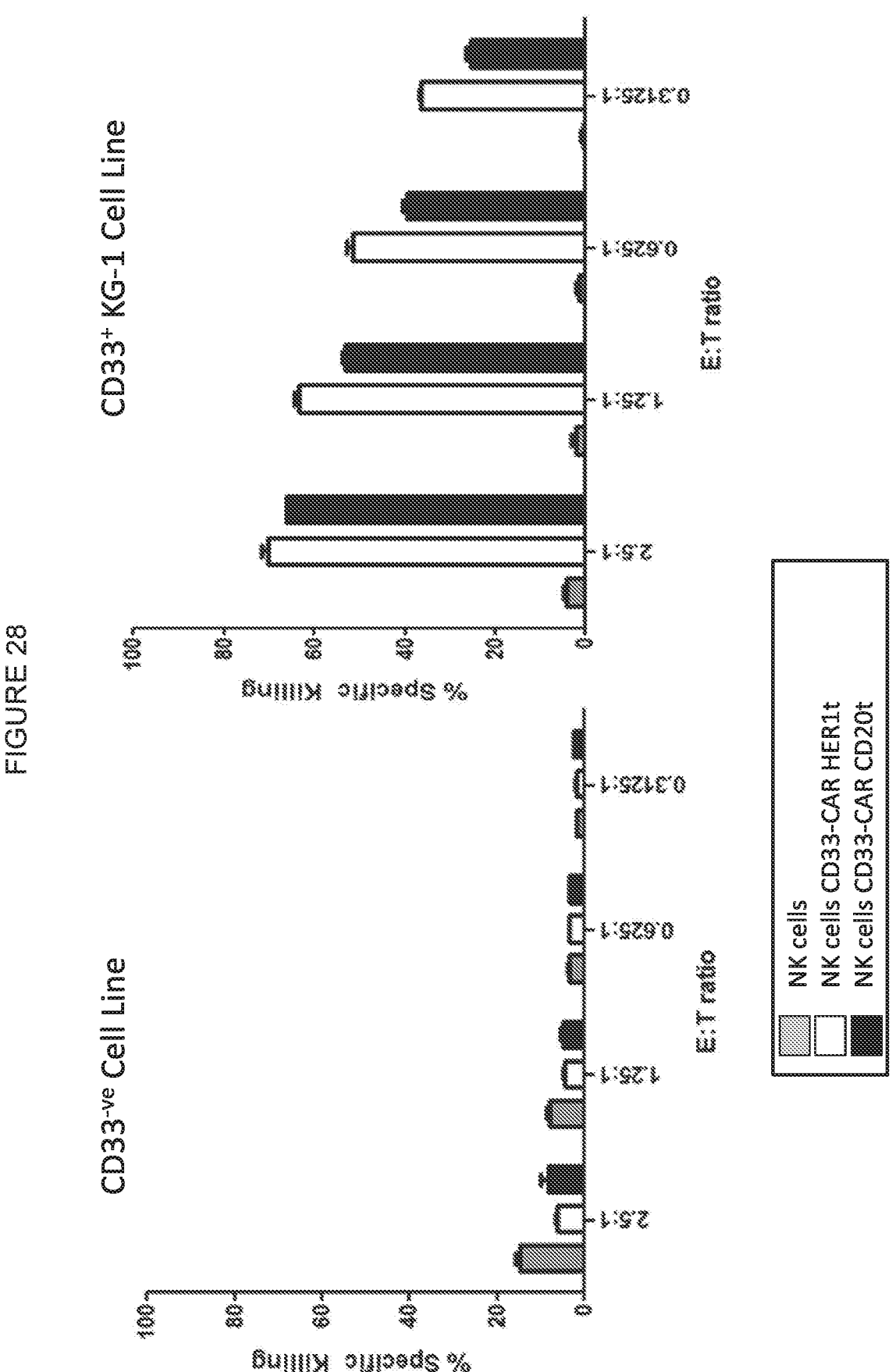
FIG. 28 demonstrates CD33-CAR NK cells efficiently lyse NK resistant AML cell line (KG-1) at low E:T ratio.

Lentiviral transduction of NK cells was also performed with CD33CAR coupled to various HER1t tags (SEQ ID NOs: 32 and 54) and C20t tag. FIGS. 25-27 demonstrate the expression of CD33 CAR and HER1t and CD20t-1 tags on NK cells. FIG. 28-29 also demonstrates that CD33 CAR NK cells efficiently lysed NK resistant CD33+AML cells at different E:T ratios. Cytokines (e.g. IFNγ, TNF-α, IL-6, RANTES, GM-CSF, IL-10, MIP-1a and MIP-1b) were produced by CD33CAR NK cells when cocultured with different target cells (data not shown)

Unless defined otherwise, all technical and scientific terms and any acronyms used herein have the same meanings as commonly understood by one of ordinary skill in the art in the field of this invention.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein, or combinations of one or more of these embodiments or aspects described therein may be employed in practicing the present disclosure. It is intended that the following claims define the scope of the present disclosure and that methods and structures within the scope of these claims and their equivalents be covered thereby.

What is claimed is:

1. A vector comprising a backbone and a nucleic acid sequence encoding:

(a) a polypeptide having the amino acid sequence of SEQ ID NO: 36 or 56; and (b) a chimeric antigen receptor (CAR) comprising a CD33 antigen-binding domain, a transmembrane domain, and an intracellular signaling domain; wherein the CD33 antigen binding domain comprises either:

(i) a polypeptide having the amino acid sequence of SEQ ID NO: 1 and a polypeptide having the amino acid sequence of SEQ ID NO: 3;

(ii) a polypeptide having the amino acid sequence of SEQ ID NO: 9 and a polypeptide having the amino acid sequence of SEQ ID NO: 10;

(iii) a polypeptide having the amino acid sequence of SEQ ID NO: 11 and a polypeptide having the amino acid sequence of SEQ ID NO: 12; or (iv) a polypeptide having the amino acid sequence of SEQ ID NO: 13 and a polypeptide having the amino acid sequence of SEQ ID NO: 14.

2. The vector of claim 1, wherein the vector is a lentivirus vector, a retroviral vector, or a non-viral vector.

3. The vector of claim 1, further comprising an hEF1a1 promoter.

4. The vector of claim 1, wherein:

the CAR further comprises a stalk domain comprising a polypeptide having at least 90% identity to the amino acid sequence of SEQ ID NO: 22; and the intracellular signaling domain comprises: (i) a costimulatory signaling domain comprising a polypeptide having at least 90% identity to the amino acid sequence of SEQ ID NO: 24 or 28; and (ii) a CD3 zeta signaling domain comprising a polypeptide having at least 90% identity to the amino acid sequence of SEQ ID NO: 26.

5. An immune effector cell comprising the vector of claim 1.

6. The immune effector cell of claim 5, wherein the cell is a T cell, a Natural Killer (NK) cell, a cytotoxic T lymphocyte (CTL), or a regulatory T cell.

7. A composition comprising the vector of claim 1.

8. A kit comprising the vector of claim 1.

9. The vector of claim 1, wherein the nucleic acid encodes a polypeptide having the amino acid sequence of SEQ ID NO: 56.

10. The vector of claim 1, wherein the CD33 antigen binding domain comprises: (1) a polypeptide having the amino acid sequence of SEQ ID NO: 1; and (ii) a polypeptide having the amino acid sequence of SEQ ID NO: 3.

11. The vector of claim 1, wherein the CD33 antigen binding domain comprises a polypeptide having the amino acid sequence of SEQ ID NO: 8.

* * * * *